(12) United States Patent
Hamblin et al.

(10) Patent No.: US 8,524,751 B2
(45) Date of Patent: Sep. 3, 2013

(54) 4-OXADIAZOL-2-YL-INDAZOLES AS INHIBITORS OF P13 KINASES

(75) Inventors: Julie Nicole Hamblin, Stevenage (GB); Zoe Alicia Harrison, Stevenage (GB); Paul Spencer Jones, Stevenage (GB); Suzanne Elaine Keeling, Stevenage (GB); Joelle Le, Stevenage (GB); Christopher James Lunniss, Stevenage (GB); Nigel James Parr, Stevenage (GB)

(73) Assignee: GlaxoSmithKline Intellecutual Property Development, Brentford, Middlesex (GB)

( * ) Notice: Subject to any disclaimer, the term of this patent is extended or adjusted under 35 U.S.C. 154(b) by 5 days.

(21) Appl. No.: 13/254,034

(22) PCT Filed: Mar. 5, 2010

(86) PCT No.: PCT/EP2010/052835
§ 371 (c)(1),
(2), (4) Date: Nov. 8, 2011

(87) PCT Pub. No.: WO2010/102958
PCT Pub. Date: Sep. 16, 2010

(65) Prior Publication Data
US 2012/0053166 A1  Mar. 1, 2012

Related U.S. Application Data

(60) Provisional application No. 61/158,428, filed on Mar. 9, 2009, provisional application No. 61/266,355, filed on Dec. 3, 2009.

(51) Int. Cl.
*A61K 31/4245* (2006.01)
*A61K 31/416* (2006.01)
*C07D 271/10* (2006.01)
*C07D 231/56* (2006.01)

(52) U.S. Cl.
USPC ......... 514/364; 514/405; 548/143; 548/361.1

(58) Field of Classification Search
USPC .................. 514/364, 405; 548/143, 361.1
See application file for complete search history.

(56) References Cited

U.S. PATENT DOCUMENTS

| | | |
|---|---|---|
| 8,076,326 B2 | 12/2011 | Haupt et al. |
| 8,114,868 B2 | 2/2012 | Himmelsbach |
| 8,138,178 B2 | 3/2012 | Claremon et al. |
| 8,163,743 B2 | 4/2012 | Baldwin et al. |
| 8,242,111 B2 | 8/2012 | Claremon et al. |
| 2004/0009968 A1 | 1/2004 | Binch et al. |
| 2005/0090529 A1 | 4/2005 | McAlpine et al. |
| 2005/0288286 A1 | 12/2005 | Flynn et al. |
| 2006/0135540 A1 | 6/2006 | Lin et al. |
| 2006/0264433 A1 | 11/2006 | Backes et al. |
| 2007/0037820 A1 | 2/2007 | Edwards et al. |
| 2008/0032960 A1 | 2/2008 | Knight et al. |
| 2008/0200523 A1 | 8/2008 | Murthi et al. |
| 2009/0203690 A1 | 8/2009 | Akritopoulou-Zanze et al. |
| 2010/0216792 A1 | 8/2010 | Gorgens et al. |
| 2010/0256363 A1 | 10/2010 | Xu |
| 2010/0280014 A1 | 11/2010 | Haupt et al. |
| 2010/0280029 A1 | 11/2010 | Hamblin et al. |
| 2010/0280045 A1 | 11/2010 | Hamblin et al. |
| 2010/0331320 A1 | 12/2010 | Renz et al. |
| 2011/0009402 A1 | 1/2011 | Himmelsbach |
| 2011/0015157 A1 | 1/2011 | Claremon et al. |
| 2011/0021512 A1 | 1/2011 | Claremon et al. |
| 2011/0067448 A1 | 3/2011 | Matsumoto et al. |
| 2011/0118246 A1 | 5/2011 | Baldwin et al. |
| 2011/0124635 A1 | 5/2011 | Claremon et al. |
| 2011/0178063 A1 | 7/2011 | Baldwin et al. |
| 2011/0183973 A1 | 7/2011 | Baldwin et al. |
| 2011/0263583 A1 | 10/2011 | Claremon et al. |
| 2011/0263584 A1 | 10/2011 | Claremon et al. |
| 2012/0040969 A1 | 2/2012 | Haupt et al. |
| 2012/0108579 A1 | 5/2012 | Renz et al. |
| 2012/0129854 A1 | 5/2012 | Mihara et al. |
| 2012/0178746 A1 | 7/2012 | Claremon et al. |
| 2012/0184549 A1 | 7/2012 | Himmelsbach |

(Continued)

FOREIGN PATENT DOCUMENTS

| | | |
|---|---|---|
| EP | 1679308 A1 | 7/2006 |
| WO | 98/03487 A1 | 1/1998 |

(Continued)

OTHER PUBLICATIONS

Schafer et al. Drug Discovery Today, 2008, 13 (21/22), 913-916.*

(Continued)

*Primary Examiner* — Yong Chu
(74) *Attorney, Agent, or Firm* — Robert J. Smith

(57) ABSTRACT

The invention is directed to certain novel compounds. Specifically, the invention is directed to compounds of formula (I):

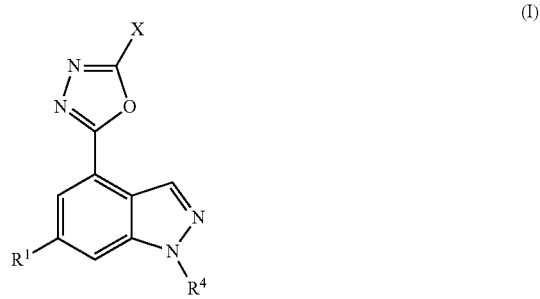

and salts thereof. The compounds of the invention are inhibitors of kinase activity, in particular PI3-kinase activity.

9 Claims, No Drawings

(56) References Cited

U.S. PATENT DOCUMENTS

| | | |
|---|---|---|
| 2012/0238559 A1 | 9/2012 | Baldwin et al. |
| 2012/0238571 A1 | 9/2012 | Baldwin et al. |
| 2012/0245171 A1 | 9/2012 | Baldwin et al. |

FOREIGN PATENT DOCUMENTS

| | | |
|---|---|---|
| WO | 02/067683 A1 | 9/2002 |
| WO | 2002067683 A1 | 9/2002 |
| WO | 02/083111 A2 | 10/2002 |
| WO | 0283111 A2 | 10/2002 |
| WO | 03/000257 A1 | 1/2003 |
| WO | 2003000257 A1 | 1/2003 |
| WO | 2003/051847 A1 | 6/2003 |
| WO | 03/064397 A1 | 8/2003 |
| WO | 2004/002480 A1 | 1/2004 |
| WO | 2004002480 A1 | 1/2004 |
| WO | 2004/014370 A2 | 2/2004 |
| WO | 2004/014881 A2 | 2/2004 |
| WO | 2004/014902 A2 | 2/2004 |
| WO | 2004014370 A2 | 2/2004 |
| WO | 2004014881 A2 | 2/2004 |
| WO | 2004014902 A2 | 2/2004 |
| WO | 2005/016245 A1 | 2/2005 |
| WO | 2005/075482 A1 | 8/2005 |
| WO | 2005/077345 A1 | 8/2005 |
| WO | 2005/077368 A2 | 8/2005 |
| WO | 2005/077373 A2 | 8/2005 |
| WO | 2005075482 A1 | 8/2005 |
| WO | 2005077345 A1 | 8/2005 |
| WO | 2005077368 A2 | 8/2005 |
| WO | 2005077373 A2 | 8/2005 |
| WO | 2005/082889 A1 | 9/2005 |
| WO | 2005082889 A1 | 9/2005 |
| WO | 2006/012226 A2 | 2/2006 |
| WO | 2006/014290 A2 | 2/2006 |
| WO | 2006012226 A2 | 2/2006 |
| WO | 2006014290 A2 | 2/2006 |
| WO | 2006/055752 A2 | 5/2006 |
| WO | 2006055752 A2 | 5/2006 |
| WO | 2006/060535 A2 | 6/2006 |
| WO | 2006060535 A2 | 6/2006 |
| WO | 2006/089076 A2 | 8/2006 |
| WO | 2006089076 A2 | 8/2006 |
| WO | 2006/135383 A1 | 12/2006 |
| WO | 2007/017759 A2 | 2/2007 |
| WO | 2007/021573 A1 | 2/2007 |
| WO | 2007/022371 A2 | 2/2007 |
| WO | 2007017759 A2 | 2/2007 |
| WO | 2007021573 A1 | 2/2007 |
| WO | 2007022371 A2 | 2/2007 |
| WO | 2007/105637 A1 | 9/2007 |
| WO | 2007105637 A1 | 9/2007 |
| WO | 2007/126841 A2 | 11/2007 |
| WO | 2007/132171 A1 | 11/2007 |
| WO | 2008/016123 A1 | 2/2008 |
| WO | 2008/020229 A2 | 2/2008 |
| WO | 2008/024945 A1 | 2/2008 |
| WO | 2008016123 A1 | 2/2008 |
| WO | 2008020229 A2 | 2/2008 |
| WO | 2008/037477 A1 | 4/2008 |
| WO | 2008/038136 A2 | 4/2008 |
| WO | 2008038136 A2 | 4/2008 |
| WO | 2008/057938 A1 | 5/2008 |
| WO | 2008057938 A1 | 5/2008 |
| WO | 2008/090382 A1 | 7/2008 |
| WO | 2008090382 A1 | 7/2008 |
| WO | 2008/139161 A1 | 11/2008 |
| WO | 2009/000832 A1 | 12/2008 |
| WO | 2009/017664 A1 | 2/2009 |
| WO | 2009/134400 A1 | 11/2009 |
| WO | 2009/147187 A1 | 12/2009 |
| WO | 2009/147188 A1 | 12/2009 |
| WO | 2009/147189 A1 | 12/2009 |
| WO | 2009/147190 A1 | 12/2009 |
| WO | 2010/011314 A1 | 1/2010 |
| WO | 2010/043315 A1 | 4/2010 |
| WO | 2010/068287 A2 | 6/2010 |
| WO | 2010068287 A2 | 6/2010 |
| WO | 2010/083163 A1 | 7/2010 |
| WO | 2010/102958 A1 | 9/2010 |
| WO | 2010/125082 A1 | 11/2010 |
| WO | 2010/125134 A1 | 11/2010 |
| WO | 2010/127237 A2 | 11/2010 |
| WO | 2010125082 A1 | 11/2010 |
| WO | 2011/067364 A1 | 6/2011 |
| WO | 2012/032065 A1 | 3/2012 |
| WO | 2012/032067 A1 | 3/2012 |
| WO | 2012/055846 A1 | 5/2012 |

OTHER PUBLICATIONS

Horig et al. Journal of Translational Medicine 2004, 2(44), p. 1-8.*
U.S. Appl. No. 12/266,254, filed Oct. 26, 2011.
Verheijen, et al., "Phosphatidylinositol 3-kinase (PI3K) inhibitors as anticancer drugs" Drugs of the Future, Prous Science; 2007; vol. 32 (6); pp. 537-547.
Ameriks, et al., "Small Molecule Inhibitors of Phosphoinositide 3-Kinase (PI3K) delta and gamma" Current Topics in Medicinal Chemistry; 2009; vol. 9 (8); pp. 738-753.
Finan, at al. "PI3-kinase inhibition: a therapeutic target for respiratory disease," Biochemical Society Transactions; 2004; vol. 32, part 2; pp. 378-382.
Folkes, et al. "The Identification of 2-(1H-indazol-4-yl)-6-(4-methaneaulfonyl-piperazin-1-ylmethyl)-4-morpholin-4-yl-thieno [3,2-d] pyrimidine (GDC-0941) as a Potent Selective, Orally Bioavailable inhibitor of class I PI3 kinase for the treatment of cancer" Journal of Medicinal Chemistry; 2008; vol. 51(18); pp. 5522-5532.
Ameriks, et al., "Small Molecule inhibitors of Phosphoinositide 3-kinase (PI3k) delta and gamma" Current Topics in Medicinal Chemistry; 2009; vol. 9(8); pp. 738-753.
Horig, et al., "From bench to clinic and back: Perspective on the 1st IQPC Translational Research Conference"; Journal of Translational Medicine; 2004; vol. 2(44); pp. 1-8.
Schafer, et al., "Failure is an option: learning from unsuccessful proof-of-concept trials" Drug Discovery Today; 2008; vol. 13 (21/22); pp. 913-916.
Verheijen, et al., "Phosphatidylinositol 3-kinase (PI3) inhibitors as anticancer drugs" Drugs of the Future, Prous Science; 2007; vol. 32(6); pp. 537-547.
Centers for Disease Control and Prevention. Public Health Strategic Framework for COPD Prevention. Atlanta, GA: Centers for Disease Control and Prevention; 2011; URL.
Voskoglou-Nomikos, et al., "Clinical Predictive Value of the in Vitro Cell Line, Human Xenograft, and Mouse Allograft Preclinical" Clinical Cancer Research, vol. 9, pp. 4227-4239, 2003.
Jaworska, et al., SAR applicability domain, ptcl.chem.ox.ac.uk/MSDS structure activity relationship; pp. 1-8; 2004.
Lala, et al., "Role of nitric oxide in tumor progression: Lessons from experimental tumors", Cancer and Metastasis Reviews (1998), vol. 17, Issue 1, pp. 91-106.
Golub, et al., "Molecular Classification of Cancer: Class Discovery and Class Prediction by Gene Expression Monitoring", Science, 1999, vol. 286, pp. 531-537.
U.S. Appl. No. 12/768,775, filed Apr. 28, 2010.
U.S. Appl. No. 12/768,777, filed Apr. 28, 2010.
U.S. Appl. No. 13/266,254, filed Oct. 26, 2011.
Shin, et al., Effect of the phosphatidylinositol 3-kinase/Akt pathway on influenza A virus propagation Journal of General Virology, 2007, vol. 88, pp. 942-950.

* cited by examiner

4-OXADIAZOL-2-YL-INDAZOLES AS INHIBITORS OF PI3 KINASES

This application is filed pursuant to 35 U.S.C. §371 as a United States National Phase Application of International Application No. PCT/EP2010/052835 filed Mar. 5, 2010, which claims priority from U.S. Provisional 61/158,428 filed Mar. 9, 2009 and U.S. Provisional 61/266,355 filed Dec. 3, 2009.

FIELD OF THE INVENTION

The present invention is directed to certain novel compounds which are inhibitors of activity or function of the phosphoinositide 3'OH kinase family (hereinafter PI3-kinases), processes for their preparation, pharmaceutical compositions comprising the compounds, and the use of the compounds or the compositions in the treatment of various disorders. More specifically, the compounds of the invention are inhibitors of the activity or function of, for example, PI3Kδ, PI3Kα, PI3Kβ and/or PI3Kγ. Compounds which are inhibitors of the activity or function of PI3-kinases may be useful in the treatment of disorders such as respiratory diseases including asthma and chronic obstructive pulmonary disease (COPD); allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; cystic fibrosis; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trama), trigeminal neuralgia and central pain.

BACKGROUND OF THE INVENTION

Cellular membranes represent a large store of second messengers that can be enlisted in a variety of signal transduction pathways. In relation to function and regulation of effector enzymes in phospholipids signaling pathways, class I PI3-kinases (e.g. PI3 Kdelta) generate second messengers from the membrane phospholipid pools. Class I PI3Ks convert the membrane phospholipid $PI(4,5)P_2$ into $PI(3,4,5)P_3$, which functions as a second messenger. PI and PI(4)P are also substrates of PI3K and can be phosphorylated and converted into PI3P and $PI(3,4)P_2$, respectively. In addition, these phosphoinositides can be converted into other phosphoinositides by 5'-specific and 3'-specific phophatases. Thus, PI3K enzymatic activity results either directly or indirectly in the generation of two 3'-phosphoinositide subtypes which function as second messengers in intracellular signal transduction pathways (Trends Biochem. Sci. 22(7) p. 267-72 (1997) by Vanhaesebroeck et al.; Chem. Rev. 101(8) p. 2365-80 (2001) by Leslie et al.; Annu. Rev. Cell Dev. Biol. 17 p. 615-75 (2001) by Katso et al.; and Cell. Mol. Life. Sci. 59(5) p. 761-79 (2002) by Toker). To date, eight mammalian PI3Ks have been identified, divided into three main classes (I, II, and III) on the basis of sequence homology, structure, binding partners, mode of activation, and substrate preference. In vitro, class I PI3Ks can phosphorylate phosphatidylinositol (PI), phosphatidylinositol-4-phosphate (PI4P), and phosphatidylinositol-4,5-bisphosphate $(PI(4,5)P_2)$ to produce phosphatidylinositol-3-phosphate (PI3P), phosphatidylinositol-3,4-bisphosphate $(PI(3,4)P_2)$, and phosphatidylinositol-3,4,5-trisphosphate $(PI(3,4,5)P_3)$, respectively. Class II PI3Ks can phosphorylate PI and PI4P. Class III PI3Ks can only phosphorylate PI (Vanhaesebrokeck et al. (1997), above; Vanhaesebroeck et al., Exp. Cell Res. 253(1) p. 239-54 (1999); and Leslie et al. (2001), above).

Class I PI3K is a heterodimer consisting of a p110 catalytic subunit and a regulatory subunit, and the family is further divided into class Ia and class Ib enzymes on the basis of regulatory partners and mechanism of regulation. Class Ia enzymes consist of three distinct catalytic subunits (p110α, p110β, and p110δ) that dimerise with five distinct regulatory subunits (p85α, p55α, p50α, p85β, and p55γ), with all catalytic subunits being able to interact with all regulatory subunits to form a variety of heterodimers. Class Ia PI3K are generally activated in response to growth factor-stimulation of receptor tyrosine kinases, via interaction of the regulatory subunit SH2 domains with specific phospho-tyrosine residues of the activated receptor or adaptor proteins such as IRS-1. Small GTPases (ras as an example) are also involved in the activation of PI3K in conjunction with receptor tyrosine kinase activation. Both p110α and p110β are constitutively expressed in all cell types, whereas p110δ expression is more restricted to leukocyte populations and some epithelial cells. In contrast, the single Class Ib enzyme consists of a p110γ catalytic subunit that interacts with a p101 regulatory subunit. Furthermore, the class Ib enzyme is activated in response to G-protein coupled receptor (GPCR) systems and its expression appears to be limited to leukocytes.

Scheme A: Conversion of $Pl(4,5)P_2$ to $Pl(3,4,5)P_3$

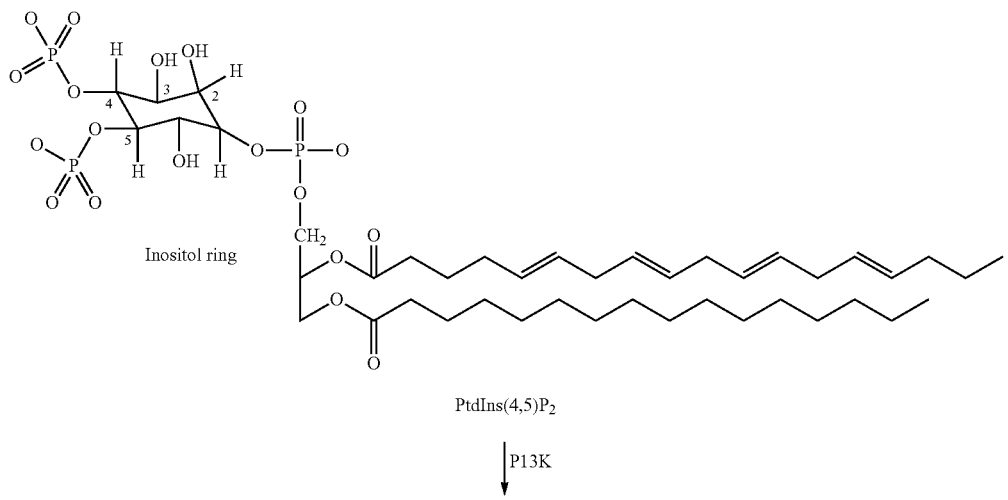

PtdIns(4,5)P$_2$

↓ PI3K

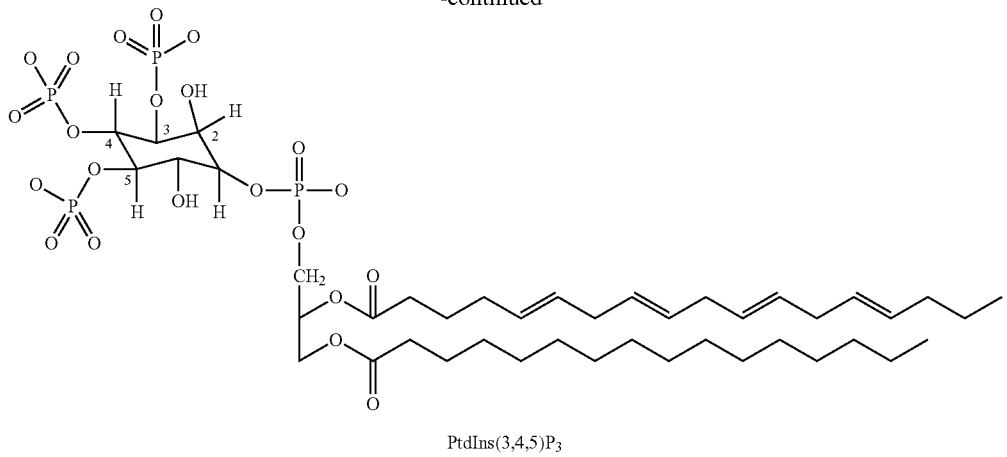

PtdIns(3,4,5)P$_3$

As illustrated in Scheme A above, phosphoinositide 3-kinases (PI3Ks) phosphorylate the hydroxyl of the third carbon of the inositol ring. The phosphorylation of phosphoinositides to generate PtdIns(3,4,5)P$_3$, PtdIns(3,4)P$_2$ and PtdIns(3) P, produces second messengers for a variety of signal transduction pathways, including those essential to cell proliferation, cell differentiation, cell growth, cell size, cell survival, apoptosis, adhesion, cell motility, cell migration, chemotaxis, invasion, cytoskeletal rearrangement, cell shape changes, vesicle trafficking and metabolic pathway (Katso et al. (2001), above; and Mol. Med. Today 6(9) p. 347-57 (2000) by Stein et al.).

The activity of PI3-kinases responsible for generating these phosphorylated signalling products was originally identified as being associated with viral oncoproteins and growth factor receptor tyrosine kinases that phosphorylate phosphatidylinositol (PI) and its phosphorylated derivatives at the 3'-hydroxyl of the inositol ring (Panayotou et al. Trends Cell Biol. 2 p. 358-60 (1992)). However, more recent biochemical studies have revealed that class I PI3-kinases (e.g. class IA isoform PI3Kδ) are dual-specific kinase enzymes, meaning they display both lipid kinase (phosphorylation of phosphoinositides) as well as protein kinase activity, and are capable of phosphorylation of other protein as substrates, including auto-phosphorylation as an intramolecular regulatory mechanism (EMBO J. 18(5) p. 1292-302 (1999) by Vanhaesebroeck et al.). Cellular processes in which PI3Ks play an essential role include suppression of apoptosis, reorganization of the actin skeleton, cardiac myocyte growth, glycogen synthase stimulation by insulin, TNFα-mediated neutrophil priming and superoxide generation, and leukocyte migration and adhesion to endothelial cells.

PI3-kinase activation is believed to be involved in a wide range of cellular responses including cell growth, differentiation, and apoptosis (Parker, Current Biology, 5(6) p. 577-99 (1995); and Yao et al. Science 267(5206) p. 2003-05 (1995)). PI3-kinase appears to be involved in a number of aspects of leukocyte activation. A p85-associated PI3-kinase has been shown to physically associate with the cytoplasmic domain of CD28, which is an important costimulatory molecule for the activation of T-cells in response to antigen (Pages et al. Nature 369 p. 327-29 (1994); and Rudd, Immunity 4 p. 527-34 (1996)). Activation of T cells through CD28 lowers the threshold for activation by antigen and increases the magnitude and duration of the proliferative response. These effects are linked to increases in the transcription of a number of genes including interleukin-2 (IL2), an important T cell growth factor (Fraser et al. Science 251(4991) p. 313-16 (1991)).

PI3Kγ has been identified as a mediator of G beta-gamma-dependent regulation of JNK activity, and G beta-gamma are subunits of heterotrimeric G proteins (Lopez-Ilasaca et al. J. Biol. Chem. 273(5) p. 2505-8 (1998)). Recently, (Laffargue et al. Immunity 16(3) p. 441-51 (2002)) it has been described that PI3Kγ relays inflammatory signals through various G(i)-coupled receptors and is central to mast cell function, stimuli in the context of leukocytes, and immunology including cytokines, chemokines, adenosines, antibodies, integrins, aggregation factors, growth factors, viruses or hormones for example (J. Cell Sci. 114 (Pt 16) p. 2903-10 (2001) by Lawlor et al.; Laffargue et al. (2002), above; and Curr. Opinion Cell Biol. 14(2) p. 203-13 (2002) by Stephens et al.).

Specific inhibitors against individual members of a family of enzymes provide invaluable tools for deciphering functions of each enzyme. Two compounds, LY294002 and wortmannin (hereinafter), have been widely used as PI3-kinase inhibitors. These compounds are non-specific PI3K inhibitors, as they do not distinguish among the four members of Class I PI3-kinases. For example, the IC$_{50}$ values of wortmannin against each of the various Class I PI3-kinases are in the range of 1-10 nM. Similarly, the IC$_{50}$ values for LY294002 against each of these PI3-kinases is about 15-20 µM (Fruman et al. Ann. Rev. Biochem. 67 p. 481-507 (1998)), also 5-10 microM on CK2 protein kinase and some inhibitory activity on phospholipases. Wortmannin is a fungal metabolite which irreversibly inhibits PI3K activity by binding covalently to the catalytic domain of this enzyme. Inhibition of PI3K activity by wortmannin eliminates subsequent cellular response to the extracellular factor. For example, neutrophils respond to the chemokine fMet-Leu-Phe (fMLP) by stimulating PI3K and synthesizing PtdIns (3, 4, 5)P$_3$. This synthesis correlates with activation of the respiratory burst involved in neutrophil destruction of invading microorganisms. Treatment of neutrophils with wortmannin prevents the fMLP-induced respiratory burst response (Thelen et al. Proc. Natl. Acad. Sci. USA 91 p. 4960-64 (1994)). Indeed, these experiments with wortmannin, as well as other experimental evidence, show that PI3K activity in cells of hematopoietic lineage, particularly neutrophils, monocytes, and other types of leukocytes, is involved in many of the non-memory immune response associated with acute and chronic inflammation.

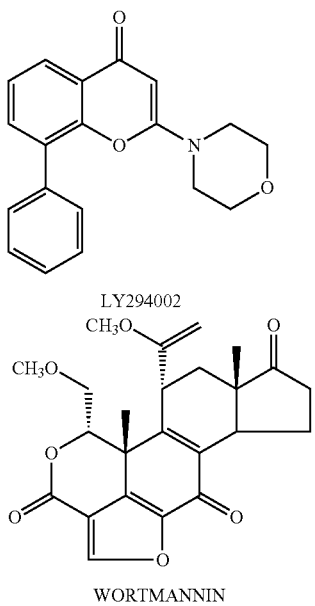

LY294002

WORTMANNIN

Based on studies using wortmannin, there is evidence that PI3-kinase function is also required for some aspects of leukocyte signaling through G-protein coupled receptors (Thelen et al. (1994), above). Moreover, it has been shown that wortmannin and LY294002 block neutrophil migration and superoxide release.

It is now well understood that deregulation of oncogenes and tumour suppressor genes contributes to the formation of malignant tumours, for example by way of increased cell growth and proliferation or increased cell survival. It is also now known that signaling pathways mediated by the PI3K family have a central role in a number of cell processes including proliferation and survival, and deregulation of these pathways is a causative factor a wide spectrum of human cancers and other diseases (Katso et al. Annual Rev. Cell Dev. Biol. (2001) 17 p. 615-617 and Foster et al. J. Cell Science (2003) 116(15) p. 3037-3040). PI3K effector proteins initiate signalling pathways and networks by translocating to the plasma membrane through a conserved Pleckstrin Homology (PH) domain, which specifically interacts with PtdIns(3,4,5)P3 (Vanhaesebroeck et al. Annu. Rev. Biochem. (2001) 70 p. 535-602). The effector proteins signalling through PtdIns(3,4,5)P3 and PH domains include Serine/Threonine (Ser/Thr) kinases, Tyrosine kinases, Rac or Arf GEFs (Guanine nucleotide exchange factors) and Arf GAPs (GTPase activating proteins).

In B and T cells PI3Ks have an important role through activation of the Tec family of protein tyrosine kinases which include Bruton's tyrosine kinase (BTK) in B cells and Interleukin-2-inducible T-cell kinase (ITK) in T cells. Upon PI3K activation, BTK or ITK translocate to the plasma membrane where they are subsequently phosphorylated by Src kinases. One of the major targets of activated ITK is phospholipase C-gamma (PLCγ1), which hydrolyses PtdIns(4,5)P2 into Ins (3,4,5)P3 and initiates an intracellular increase in calcium levels and diacylglycerol (DAG) which can activate Protein Kinases C in activated T cells.

Unlike the Class IA p110α and p110β, p110δ is expressed in a tissue restricted fashion. Its high expression level in lymphocytes and lymphoid tissues suggests a role in PI3K-mediated signalling in the immune system. The p110δ kinase dead knock-in mice are also viable and their phenotype is restricted to defects in immune signalling (Okkenhaug et al., Science (2002) 297 p. 1031-4). These transgenic mice have offered insight into the function of PI3Kδ in B-cell and T-cell signalling. In particular, p110δ is required for PtdIns(3,4,5) P3 formation downstream of CD28 and/or T cell Receptor (TCR) signalling. A key effect of PI3K signalling downstream of TCR is the activation of Akt, which phosphorylates anti-apoptotic factors as well as various transcription factors for cytokine production. As a consequence, T cells with inactive p110δ have defects in proliferation and Th1 and Th2 cytokine secretion. Activation of T cells through CD28 lowers the threshold for TCR activation by antigen and increases the magnitude and duration of the proliferative response. These effects are mediated by the PI3Kδ-dependent increase in the transcription of a number of genes including IL2, an important T cell growth factor.

Therefore, PI3K inhibitors are anticipated to provide therapeutic benefit via its role in modulating T-cell mediated inflammatory responses associated to respiratory diseases such as asthma, COPD and cystic fibrosis. In addition, there is indication that T-cell directed therapies may provide corticosteroid sparing properties (Alexander et al. Lancet (1992) 339 p. 324-8) suggesting that it may provide a useful therapy either as a standalone or in combination with inhaled or oral glucocorticosteroids in respiratory diseases. A PI3K inhibitor might also be used alongside other conventional therapies such as a long acting beta-agonists (LABA) in asthma.

In the vasculature, PI3Kδ is expressed by endothelial cells and participates in neutrophil trafficking by modulating the proadhesive state of these cells in response to TNFalpha (Puri et al. Blood (2004) 103(9) p. 3448-56.). A role for PI3Kδ in TNFalpha-induced signalling of endothelial cells is demonstrated by the pharmacological inhibition of Akt phosphorylation and PDK1 activity. In addition, PI3Kδ is implicated in vascular permeability and airway tissue edema through the VEGF pathway (Lee et al. J. Allergy Clin. Immunol. (2006) 118(2) p. 403-9). These observations suggest additional benefits of PI3Kδ inhibition in asthma by the combined reduction of leukocyte extravasation and vascular permeability associated with asthma. In addition, PI3Kδ activity is required for mast cell function both in vitro and in vivo (Ali et al. Nature (2004) 431 p. 1007-11; and Ali et al. J Immunol. (2008) 180(4) p. 2538-44) further suggesting that PI3K inhibition should be of therapeutical benefit for allergic indications such asthma, allergic rhinitis and atopic dermatitis.

The role of PI3Kδ in B cell proliferation, antibody secretion, B-cell antigen and IL-4 receptor signalling, B-cell antigen presenting function is also well established (Okkenhaug et al. (2002), above; Al-Alwan et al. J. Immunol. (2007) 178(4) p. 2328-35; and Bilancio et al. Blood (2006) 107(2) p. 642-50) and indicates a role in autoimmune diseases such as rheumatoid arthritis or systemic lupus erythematosus. Therefore PI3K inhibitors may also be of benefit for these indications.

Pharmacological inhibition of PI3Kδ inhibits fMLP-dependent neutrophil chemotaxis on an ICAM coated agarose matrix integrin-dependent biased system (Sadhu et al. J. Immunol. (2003) 170(5) p. 2647-54). Inhibition of PI3Kδ regulates neutrophil activation, adhesion and migration without affecting neutrophil mediated phagocytosis and bactericidal activity over *Staphylococcus aureus* (Sadhu et al. Biochem. Biophys. Res. Commun. (2003) 308(4) p. 764-9.). Overall, the data suggest that PI3Kδ inhibition should not globally inhibit neutrophil functions required for innate immune defence. PI3Kδ's role in neutrophils offers further scope for treating inflammatory diseases involving tissue remodeling such as COPD or rheumatoid arthritis.

In addition, there is also good evidence that class Ia PI3K enzymes also contribute to tumourigenesis in a wide variety of human cancers, either directly or indirectly (Vivanco and Sawyers, Nature Reviews Cancer (2002) 2(7) p. 489-501). For example, inhibition of PI3Kδ may have a therapeutic role for the treatment of malignant haematological disorders such as acute myeloid leukaemia (Billottet et al. Oncogene (2006) 25(50) p. 6648-59). Moreover, activating mutations within p110α (PIK3CA gene) have been associated with various other tumors such as those of the colon and of the breast and lung (Samuels et al. Science (2004) 304(5670) p. 554).

It has also been shown that PI3K is involved in the establishment of central sensitization in painful inflammatory conditions (Pezet et al. The J. of Neuroscience (2008) 28 (16) p. 4261-4270).

Attempts have been made to prepare compounds which inhibit PI3-kinase activity and a number of such compounds have been disclosed in the art. However, in view of the number of pathological responses which are mediated by PI3-kinases, there remains a continuing need for inhibitors of PI3-kinase which can be used in the treatment of a variety of conditions.

The present inventors have discovered novel compounds which are inhibitors of kinase activity, in particular PI3-kinase activity. Compounds which are PI3-kinase inhibitors may be useful in the treatment of disorders associated with inappropriate kinase activity, in particular inappropriate PI3-kinase activity, for example in the treatment and prevention of disorders mediated by PI3-kinase mechanisms. Such disorders include respiratory diseases including asthma and chronic obstructive pulmonary disease (COPD); allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; cystic fibrosis; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trama), trigeminal neuralgia and Central pain.

In one embodiment, compounds of the invention may show selectivity for PI3-kinases over other kinases.

In one embodiment, compounds of the invention may show selectivity for PI3Kδ over other PI3-kinases.

SUMMARY OF THE INVENTION

The invention is directed to certain novel compounds. Specifically, in one embodiment, the invention is directed to compounds of formula (I)

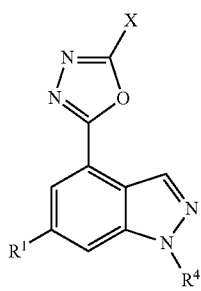

(I)

wherein $R^1$, X and $R^4$ are as defined below for compounds of formula (I), and salts thereof.

In a further embodiment, the invention is directed to compounds of formula (IB)

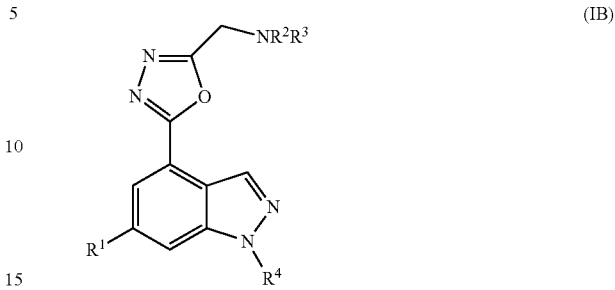

(IB)

wherein $R^1$, $R^2$, $R^3$ and $R^4$ are as defined below for compounds of formula (IB), and salts thereof.

The compounds are inhibitors of kinase activity, in particular PI3-kinase activity. Compounds which are PI3-kinase inhibitors may be useful in the treatment of disorders associated with inappropriate PI3-kinase activity, such as asthma and chronic obstructive pulmonary disease (COPD). Accordingly, the invention is further directed to pharmaceutical compositions comprising a compound of formula (I) or a pharmaceutically acceptable salt thereof. The invention is still further directed to methods of inhibiting PI3-kinase activity and treatment of disorders associated therewith using a compound of formula (I) or a pharmaceutically acceptable salt thereof, or a pharmaceutical composition comprising a compound of formula (I) or a pharmaceutically acceptable salt thereof. The invention is yet further directed towards processes for the preparation of the compounds of the invention.

DETAILED DESCRIPTION OF THE INVENTION

In one embodiment, the invention is directed to compounds of formula (I)

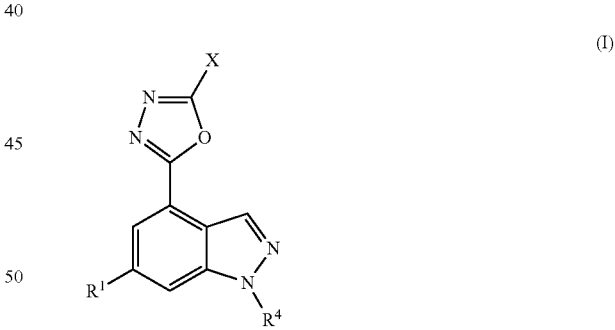

(I)

wherein
$R^1$ is 9- or 10-membered bicyclic heteroaryl wherein the 9- or 10-membered bicyclic heteroaryl contains from one to three heteroatoms independently selected from oxygen and nitrogen and is optionally substituted by $C_{1-6}$alkyl, $C_{3-6}$cycloalkyl, halo, —CN or —NHSO$_2$R$^5$, or
pyridinyl optionally substituted by one or two substituents independently selected from $C_{1-6}$alkyl, —OR$^6$, halo and —NHSO$_2$R$^7$;
X is —CH$_2$NR$^2$R$^3$, $C_{1-6}$alkyl, —CH$_2$phenyl, —(CH$_2$)$_n$OR$^{10}$, —CH$_2$SO$_2$R$^{11}$ or —(CH$_2$)$_p$C$_{3-6}$cycloalkyl;
$R^2$ and $R^3$, together with the nitrogen atom to which they are attached, are linked to form a 6- or 7-membered heterocyclyl or a 9- or 10-membered bicyclic heterocyclyl wherein the 6- or 7-membered heterocyclyl or the 9- or 10-membered bicyclic heterocyclyl optionally contains an oxygen atom, a sulphur atom or a further nitrogen atom and is optionally substituted by from one to three substituents independently selected from oxo, $C_{1-6}$alkyl, —$(CH_2)_m NR^8 R^6$, phenyl optionally substituted by halo, and 6-membered heteroaryl wherein the 6-membered heteroaryl contains one or two nitrogen atoms, a 7-membered bridged heterocyclyl wherein the 7-membered bridged heterocyclyl optionally contains a further nitrogen atom and is optionally substituted by from one to three substituents independently selected from $C_{1-6}$alkyl, or a 10-membered spiro bicyclic heterocyclyl wherein the 10-membered spiro bicyclic heterocyclyl optionally contains an oxygen atom, or $R^2$ is hydrogen and $R^3$ is $C_{1-6}$alkyl optionally substituted by one or two substituents independently selected from —$OR^{12}$ and —$NR^{13}R^{14}$;

$R^4$ is hydrogen or methyl;

$R^6$, $R^{12}$ and $R^{15}$ are each independently hydrogen or $C_{1-4}$alkyl;

$R^5$ and $R^7$ are each independently $C_{1-6}$alkyl or phenyl wherein the phenyl is optionally substituted by one or two substituents independently selected from halo and —$OR^{15}$;

$R^8$ and $R^9$, together with the nitrogen atom to which they are attached, are linked to form a 5- or 6-membered heterocyclyl optionally containing an oxygen atom;

$R^{10}$ is hydrogen, $C_{1-6}$alkyl, —$(CH_2)_q$phenyl or $C_{3-6}$cycloalkyl wherein the $C_{3-6}$cycloalkyl is optionally substituted by one or two substituents independently selected from $C_{1-6}$alkyl;

$R^{11}$ is $C_{1-6}$alkyl or phenyl;

$R^{13}$ and $R^{14}$, together with the nitrogen atom to which they are attached, are linked to form a 6-membered heterocyclyl optionally containing an oxygen atom;

m, p and q are each independently 0, 1 or 2; and n is 1 or 2;

and salts thereof (hereinafter "compounds of the invention").

In another embodiment, the invention is directed to compounds of formula (IA)

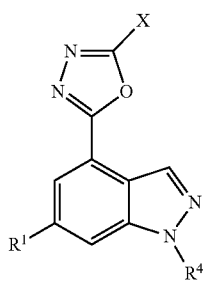

(IA)

wherein $R^1$ is 9- or 10-membered bicyclic heteroaryl wherein the 9- or 10-membered bicyclic heteroaryl contains from one to three heteroatoms independently selected from oxygen and nitrogen and is optionally substituted by $C_{1-6}$alkyl, $C_{3-6}$cycloalkyl, halo, —CN or —$NHSO_2R^5$, or pyridinyl optionally substituted by one or two substituents independently selected from $C_{1-6}$alkyl, —$OR^6$, halo and —$NHSO_2R^7$;

X is —$CH_2NR^2R^3$, $C_{1-6}$alkyl, —$CH_2$phenyl, —$(CH_2)_n OR^{10}$, —$CH_2SO_2R^{11}$ or —$(CH_2)_p C_{3-6}$cycloalkyl;

$R^2$ and $R^3$, together with the nitrogen atom to which they are attached, are linked to form a 6- or 7-membered heterocyclyl or a 9- or 10-membered bicyclic heterocyclyl wherein the 6- or 7-membered heterocyclyl or the 9- or 10-membered bicyclic heterocyclyl optionally contains an oxygen atom, a sulphur atom or a further nitrogen atom and is optionally substituted by from one to three substituents independently selected from oxo, $C_{1-6}$alkyl, —$(CH_2)_m NR^8 R^9$, phenyl optionally substituted by halo, and 6-membered heteroaryl wherein the 6-membered heteroaryl contains one or two nitrogen atoms, a 7-membered bridged heterocyclyl wherein the 7-membered bridged heterocyclyl optionally contains a further nitrogen atom and is optionally substituted by from one to three substituents independently selected from $C_{1-6}$alkyl, or a 10-membered Spiro bicyclic heterocyclyl wherein the 10-membered Spiro bicyclic heterocyclyl optionally contains an oxygen atom, or $R^2$ is hydrogen and $R^3$ is $C_{1-6}$alkyl optionally substituted by one or two substituents independently selected from —$OR^{12}$ and —$NR^{13}R^{14}$;

$R^4$ is hydrogen or methyl;

$R^6$, $R^{12}$ and $R^{15}$ are each independently hydrogen or $C_{1-4}$alkyl;

$R^5$ and $R^7$ are each independently $C_{1-6}$alkyl or phenyl wherein the phenyl is optionally substituted by one or two substituents independently selected from halo and —$OR^{15}$;

$R^8$ and $R^9$, together with the nitrogen atom to which they are attached, are linked to form a 5- or 6-membered heterocyclyl optionally containing an oxygen atom;

$R^{10}$ is hydrogen, $C_{1-6}$alkyl, —$(CH_2)_q$phenyl or $C_{3-6}$cycloalkyl wherein the $C_{3-6}$cycloalkyl is optionally substituted by one or two $C_{1-6}$alkyl substituents;

$R^{11}$ is $C_{1-6}$alkyl or phenyl;

$R^{13}$ and $R^{14}$, together with the nitrogen atom to which they are attached, are linked to form a 6-membered heterocyclyl optionally containing an oxygen atom;

m, p and q are each independently 0, 1 or 2; and n is 1 or 2;

and salts thereof.

In a further embodiment, the invention is directed to compounds of formula (IB)

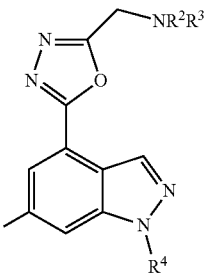

(IB)

wherein $R^1$ is 9- or 10-membered bicyclic heteroaryl wherein the 9- or 10-membered bicyclic heteroaryl contains from one to three heteroatoms independently selected from oxygen and nitrogen and is optionally substituted by $C_{1-6}$alkyl, $C_{3-6}$cycloalkyl, halo, —CN or —$NHSO_2R^5$, or pyridinyl optionally substituted by one or two substituents independently selected from $C_{1-6}$alkyl, —$OR^6$, halo and —$NHSO_2R^7$;

R² and R³, together with the nitrogen atom to which they are attached, are linked to form a 6-membered heterocyclyl or a 10-membered bicyclic heterocyclyl wherein the 6-membered heterocyclyl or the 10-membered bicyclic heterocyclyl optionally contains an oxygen atom or a further nitrogen atom and is optionally substituted by one or two substituents independently selected from $C_{1-6}$alkyl, $—(CH_2)_m NR^8 R^9$, phenyl optionally substituted by halo, and 6-membered heteroaryl wherein the 6-membered heteroaryl contains one or two nitrogen atoms, or a 7-membered bridged heterocyclyl wherein the 7-membered bridged heterocyclyl optionally contains a further nitrogen atom and is optionally substituted by from one to three substituents independently selected from $C_{1-6}$alkyl;

$R^4$ is hydrogen or methyl;

$R^6$ is hydrogen or $C_{1-4}$alkyl;

$R^5$ and $R^7$ are each independently $C_{1-6}$alkyl, or phenyl optionally substituted by one or two substituents independently selected from halo;

$R^8$ and $R^9$, together with the nitrogen atom to which they are attached, are linked to form a 5- or 6-membered heterocyclyl optionally containing an oxygen atom; and m is 1 or 2;

and salts thereof.

In one embodiment, $R^1$ is 9- or 10-membered bicyclic heteroaryl wherein the 9- or 10-membered bicyclic heteroaryl contains one or two nitrogen atoms and is optionally substituted by $C_{1-6}$alkyl or halo, or pyridinyl optionally substituted by one or two substituents independently selected from $C_{1-6}$alkyl, $—OR^6$, halo and $—NHSO_2R^7$. In another embodiment, $R^1$ is 9- or 10-membered bicyclic heteroaryl wherein the 9- or 10-membered bicyclic heteroaryl contains one or two nitrogen atoms and is optionally substituted by $C_{1-6}$alkyl or halo. In another embodiment, $R^1$ is indolyl. In another embodiment, $R^1$ is pyridinyl optionally substituted by one or two substituents independently selected from $C_{1-6}$alkyl, $—OR^6$, halo and $—NHSO_2R^7$. In another embodiment, $R^1$ is pyridinyl optionally substituted by one or two substituents independently selected from $—OR^6$, halo and $—NHSO_2R^7$. In another embodiment, $R^1$ is pyridinyl substituted two substituents independently selected from halo and $—NHSO_2R^7$. In a further embodiment, $R^1$ is pyridinyl optionally substituted by one or two substituents independently selected from $—OR^6$ and $—NHSO_2R^7$.

In one embodiment, X is $—CH_2NR^2R^3$ or $C_{1-6}$alkyl. In a further embodiment, X is $—CH_2NR^2R^3$.

In one embodiment, $R^2$ and $R^3$, together with the nitrogen atom to which they are attached, are linked to form a 6-membered heterocyclyl or a 10-membered bicyclic heterocyclyl wherein the 6-membered heterocyclyl or the 10-membered bicyclic heterocyclyl optionally contains an oxygen atom or a further nitrogen atom and is optionally substituted by one or two substituents independently selected from $C_{1-6}$alkyl, $—(CH_2)_m NR^8 R^9$, phenyl optionally substituted by halo, and 6-membered heteroaryl wherein the 6-membered heteroaryl contains one or two nitrogen atoms, or a 7-membered bridged heterocyclyl wherein the 7-membered bridged heterocyclyl optionally contains a further nitrogen atom and is optionally substituted by from one to three substituents independently selected from $C_{1-6}$alkyl. In another embodiment, $R^2$ and $R^3$, together with the nitrogen atom to which they are attached, are linked to form a 6- or 7-membered heterocyclyl or a 9- or 10-membered bicyclic heterocyclyl wherein the 6- or 7-membered heterocyclyl or the 9- or 10-membered bicyclic heterocyclyl optionally contains an oxygen atom, a sulphur atom or a further nitrogen atom and is optionally substituted by from one to three substituents independently selected from oxo, $C_{1-6}$alkyl, $—(CH_2)_m NR^8 R^9$, phenyl optionally substituted by halo, and 6-membered heteroaryl wherein the 6-membered heteroaryl contains one or two nitrogen atoms, or a 10-membered spiro bicyclic heterocyclyl wherein the 10-membered spiro bicyclic heterocyclyl optionally contains an oxygen atom, or $R^2$ is hydrogen and $R^3$ is $C_{1-6}$alkyl optionally substituted by one or two substituents independently selected from $—OR^{12}$ and $—NR^{13}R^{14}$. In another embodiment, $R^2$ and $R^3$, together with the nitrogen atom to which they are attached, are linked to form a 6-membered heterocyclyl wherein the 6-membered heterocyclyl optionally contains an oxygen atom or a further nitrogen atom and is optionally substituted by one or two substituents independently selected from $C_{1-6}$alkyl, $—(CH_2)_m NR^8 R^9$ and phenyl optionally substituted by halo. In a another embodiment, $R^2$ and $R^3$, together with the nitrogen atom to which they are attached, are linked to form a 6-membered heterocyclyl wherein the 6-membered heterocyclyl optionally contains an oxygen atom or a further nitrogen atom and is optionally substituted by one or two substituents independently selected from $C_{1-4}$alkyl. In a further embodiment, $R^2$ and $R^3$, together with the nitrogen atom to which they are attached, are linked to form a 6-membered heterocyclyl wherein the 6-membered heterocyclyl optionally contains an oxygen atom and is optionally substituted by one or two substituents independently selected from $C_{1-4}$alkyl.

In one embodiment, $R^4$ is hydrogen. In a further embodiment, $R^4$ is methyl.

In one embodiment, $R^5$ is $C_{1-6}$alkyl, or phenyl optionally substituted by one or two substituents independently selected from halo. In a further embodiment, $R^5$ is $C_{1-4}$alkyl such as methyl.

In one embodiment, $R^6$ is $C_{1-4}$alkyl such as methyl.

In one embodiment, $R^7$ is $C_{1-6}$alkyl, or phenyl optionally substituted by one or two substituents independently selected from halo. In another embodiment, $R^7$ is $C_{1-4}$alkyl such as methyl. In a further embodiment, $R^7$ is phenyl optionally substituted by one or two substituents independently selected from halo.

In one embodiment, $R^8$ and $R^9$, together with the nitrogen atom to which they are attached, are linked to form pyrrolidinyl or morpholinyl. In another embodiment, $R^8$ and $R^9$, together with the nitrogen atom to which they are attached, are linked to form pyrrolidinyl. In a further embodiment, $R^8$ and $R^9$, together with the nitrogen atom to which they are attached, are linked to form morpholinyl.

In one embodiment, $R^{10}$ is hydrogen, $C_{1-6}$alkyl, $—(CH_2)_q$phenyl or $C_{3-6}$cycloalkyl wherein the $C_{3-6}$cycloalkyl is optionally substituted by one or two $C_{1-6}$alkyl substituents. In a further embodiment, $R^{10}$ is hydrogen, $C_{1-4}$alkyl, $—(CH_2)_q$phenyl or $C_{3-6}$cycloalkyl wherein the $C_{3-6}$cycloalkyl is optionally substituted by one or two $C_{1-4}$alkyl substituents.

In one embodiment, $R^{11}$ is $C_{1-4}$alkyl such as methyl, or phenyl.

In one embodiment, $R^{12}$ is hydrogen.

In one embodiment, $R^{13}$ and $R^{14}$, together with the nitrogen atom to which they are attached, are linked to form 4-morpholinyl.

In one embodiment, $R^{15}$ is $C_{1-4}$alkyl such as methyl.

In one embodiment, m is 1 or 2. In another embodiment, m is 1. In a further embodiment, m is 2.

In one embodiment, n is 1. In a further embodiment, n is 2.

In one embodiment, p is 0 or 1. In another embodiment, p is 0. In a further embodiment, p is 1.

In one embodiment, q is 1.

It is to be understood that the present invention covers all combinations of substituent groups described hereinabove.

Compounds of the invention include the compounds of Examples 1 to 62 and salts thereof.

In one embodiment, the compound of the invention is:

6-(1H-indol-4-yl)-4-[5-(4-morpholinylmethyl)-1,3,4-oxadiazol-2-yl]-1H-indazole;

N-(2-chloro-5-{4-[5-(4-morpholinylmethyl)-1,3,4-oxadiazol-2-yl]-1H-indazol-6-yl}-3-pyridinyl)methanesulfonamide;

4-(5-{[(2R,6S)-2,6-dimethyl-4-morpholinyl]methyl}-1,3,4-oxadiazol-2-yl)-6-(1H-indol-4-yl)-1H-indazole;

6-(1H-indol-4-yl)-4-(5-{[4-(2-pyrimidinyl)-1-piperazinyl]methyl}-1,3,4-oxadiazol-2-yl)-1H-indazole;

4-{5-[(4,4-dimethyl-1-piperidinyl)methyl]-1,3,4-oxadiazol-2-yl}-6-(1H-indol-4-yl)-1H-indazole;

6-(1H-indol-4-yl)-4-(5-{[4-(2-methylpropyl)-1-piperazinyl]methyl}-1,3,4-oxadiazol-2-yl)-1H-indazole;

6-(1H-indol-4-yl)-4-(5-{[4-(1-methylethyl)-1-piperidinyl]methyl}-1,3,4-oxadiazol-2-yl)-1H-indazole;

6-(1H-indol-4-yl)-4-(5-{[2-(1-pyrrolidinylmethyl)-1-piperidinyl]methyl}-1,3,4-oxadiazol-2-yl)-1H-indazole;

4-(5-{[4-(4-fluorophenyl)-1-piperazinyl]methyl}-1,3,4-oxadiazol-2-yl)-6-(1H-indol-4-yl)-1H-indazole;

6-(1H-indol-4-yl)-4-(5-{[(1R,4R)-1,4,5-trimethyl-2,5-diazabicyclo[2.2.1]hept-2-yl]methyl}-1,3,4-oxadiazol-2-yl)-1H-indazole;

6-(1H-indol-4-yl)-4-(5-{[2-(1-pyrrolidinylmethyl)-4-morpholinyl]methyl}-1,3,4-oxadiazol-2-yl)-1H-indazole;

6-(1H-indol-4-yl)-4-[5-({4-[2-(4-morpholinyl)ethyl]-1-piperazinyl}methyl)-1,3,4-oxadiazol-2-yl]-1H-indazole;

6-(1H-indol-4-yl)-4-(5-{[4-(1-methylethyl)-1-piperazinyl]methyl}-1,3,4-oxadiazol-2-yl)-1H-indazole;

4-(5-{[(2R,6S)-2,6-dimethyl-1-piperidinyl]methyl}-1,3,4-oxadiazol-2-yl)-6-(1H-indol-4-yl)-1H-indazole;

4-(5-{[(1S,4S)-1,4-dimethyl-7-azabicyclo[2.2.1]hept-7-yl]methyl}-1,3,4-oxadiazol-2-yl)-6-(1H-indol-4-yl)-1H-indazole;

4-({5-[6-(1H-indol-4-yl)-1H-indazol-4-yl]-1,3,4-oxadiazol-2-yl}methyl)octahydro-2H-1,4-benzoxazine;

6-(1H-indol-4-yl)-4-(5-{[2-(2-methylpropyl)-4-morpholinyl]methyl}-1,3,4-oxadiazol-2-yl)-1H-indazole;

N-{2-chloro-5-[4-(5-{[4-(1-methylethyl)-1-piperazinyl]methyl}-1,3,4-oxadiazol-2-yl)-1H-indazol-6-yl]-3-pyridinyl}methanesulfonamide;

N-{2-chloro-5-[4-(5-{[(2R,6S)-2,6-dimethyl-4-morpholinyl]methyl}-1,3,4-oxadiazol-2-yl)-1H-indazol-6-yl]-3-pyridinyl}methanesulfonamide;

N-(2-chloro-5-{4-[5-(4-morpholinylmethyl)-1,3,4-oxadiazol-2-yl]-1H-indazol-6-yl}-3-pyridinyl)methanesulfonamide;

N-[5-[4-(5-{[(2R,6S)-2,6-dimethyl-4-morpholinyl]methyl}-1,3,4-oxadiazol-2-yl)-1H-indazol-6-yl]-2-(methyloxy)-3-pyridinyl]methanesulfonamide;

N-[5-[4-(5-{[4-(1-methylethyl)-1-piperazinyl]methyl}-1,3,4-oxadiazol-2-yl)-1H-indazol-6-yl]-2-(methyloxy)-3-pyridinyl]methanesulfonamide;

4-(5-{[(2R,6S)-2,6-dimethyl-4-morpholinyl]methyl}-1,3,4-oxadiazol-2-yl)-6-(1H-indol-4-yl)-1-methyl-1H-indazole;

6-(1H-indol-4-yl)-1-methyl-4-(5-{[4-(1-methylethyl)-1-piperazinyl]methyl}-1,3,4-oxadiazol-2-yl)-1H-indazole;

N-[5-[1-methyl-4-(5-{[4-(1-methylethyl)-1-piperazinyl]methyl}-1,3,4-oxadiazol-2-yl)-1H-indazol-6-yl]-2-(methyloxy)-3-pyridinyl]methanesulfonamide;

N-[5-[4-(5-{[(2R,6S)-2,6-dimethyl-4-morpholinyl]methyl}-1,3,4-oxadiazol-2-yl)-1-methyl-1H-indazol-6-yl]-2-(methyloxy)-3-pyridinyl]methanesulfonamide;

N-[5-[4-(5-{[(2R,6S)-2,6-dimethyl-4-morpholinyl]methyl}-1,3,4-oxadiazol-2-yl)-1H-indazol-6-yl]-2-(m ethyloxy)-3-pyridinyl]-2,4-difluorobenzenesulfonamide;

N-[5-(4-{5-[(2,2-dimethyl-4-morpholinyl)methyl]-1,3,4-oxadiazol-2-yl}-1H-indazol-6-yl)-2-(methyloxy)-3-pyridinyl]methanesulfonamide;

6-(1H-indol-4-yl)-4-[5-(1-methylethyl)-1,3,4-oxadiazol-2-yl]-1H-indazole;

4-(5-cyclohexyl-1,3,4-oxadiazol-2-yl)-6-(1H-indol-4-yl)-1H-indazole;

4-[5-(cyclohexylmethyl)-1,3,4-oxadiazol-2-yl]-6-(1H-indol-4-yl)-1H-indazole;

6-(1H-indol-4-yl)-4-[5-(phenylmethyl)-1,3,4-oxadiazol-2-yl]-1H-indazole;

6-(1H-indol-4-yl)-4-{5-[2-(methyloxy)ethyl]-1,3,4-oxadiazol-2-yl}-1H-indazole;

6-(1H-indol-4-yl)-4-(5-{[(phenylmethyl)oxy]methyl}-1,3,4-oxadiazol-2-yl)-1H-indazole;

6-(1H-indol-4-yl)-4-[5-({[(1R,2S,5R)-5-methyl-2-(1-methylethyl)cyclohexyl]oxy}methyl)-1,3,4-oxadiazol-2-yl]-1H-indazole;

{5-[6-(1H-indol-4-yl)-1H-indazol-4-yl]-1,3,4-oxadiazol-2-yl}methanol;

6-(1H-indol-4-yl)-4-{5-[(methyloxy)methyl]-1,3,4-oxadiazol-2-yl}-1H-indazole;

6-(1H-indol-4-yl)-4-(5-methyl-1,3,4-oxadiazol-2-yl)-1H-indazole;

N-{2-chloro-5-[4-(5-methyl-1,3,4-oxadiazol-2-yl)-1H-indazol-6-yl]-3-pyridinyl}methanesulfonamide;

6-(1H-indol-4-yl)-4-{5-[(methylsulfonyl)methyl]-1,3,4-oxadiazol-2-yl}-1H-indazole;

6-(1H-indol-4-yl)-4-{5-[(phenylsulfonyl)methyl]-1,3,4-oxadiazol-2-yl}-1H-indazole;

N-(2-(methyloxy)-5-{4-[5-(6-oxa-9-azaspiro[4.5]dec-9-ylmethyl)-1,3,4-oxadiazol-2-yl]-1H-indazol-6-yl}-3-pyridinyl)methanesulfonamide;

2-[({5-[6-(1H-indol-4-yl)-1H-indazol-4-yl]-1,3,4-oxadiazol-2-yl}methyl)amino]ethanol;

1-[({5-[6-(1H-indol-4-yl)-1H-indazol-4-yl]-1,3,4-oxadiazol-2-yl}methyl)amino]-3-(4-morpholinyl)-2-propanol;

N-[5-[4-(5-{[(3R,5S)-3,5-dimethyl-4-(1-methylethyl)-1-piperazinyl]methyl}-1,3,4-oxadiazol-2-yl)-1H-indazol-6-yl]-2-(methyloxy)-3-pyridinyl]methanesulfonamide;

N-[5-(4-{5-[(1,1-dioxido-4-thiomorpholinyl)methyl]-1,3,4-oxadiazol-2-yl}-1H-indazol-6-yl)-2-(methyloxy)-3-pyridinyl]methanesulfonamide;

N-[5-(4-{5-[(2-ethyl-4-morpholinyl)methyl]-1,3,4-oxadiazol-2-yl}-1H-indazol-6-yl)-2-(methyloxy)-3-pyridinyl]methanesulfonamide;

9-({5-[6-(1H-indol-4-yl)-1H-indazol-4-yl]-1,3,4-oxadiazol-2-yl}methyl)-6-oxa-9-azaspiro[4.5]decane;

4-{5-[(2,2-dimethyl-4-morpholinyl)methyl]-1,3,4-oxadiazol-2-yl}-6-(1H-indol-4-yl)-1H-indazole;

N-[5-[4-(5-{[(3R,5S)-3,5-dimethyl-4-(1-methylethyl)-1-piperazinyl]methyl}-1,3,4-oxadiazol-2-yl)-1H-indazol-6-yl]-2-(methyloxy)-3-pyridinyl]-2,4-difluorobenzenesulfonamide;

2,4-difluoro-N-[5-[4-(5-{[4-(1-methylethyl)-1-piperazinyl]methyl}-1,3,4-oxadiazol-2-yl)-1H-indazol-6-yl]-2-(methyloxy)-3-pyridinyl]benzenesulfonamide;

N-[5-(4-{5-[(2-methyl-4-morpholinyl)methyl]-1,3,4-oxadiazol-2-yl}-1H-indazol-6-yl)-2-(methyloxy)-3-pyridinyl]methanesulfonamide;

6-(1H-indol-4-yl)-4-{5-[(2-methyl-4-morpholinyl)methyl]-1,3,4-oxadiazol-2-yl}-1H-indazole;

N-({5-[6-(1H-indol-4-yl)-1H-indazol-4-yl]-1,3,4-oxadiazol-2-yl}methyl)-3-(4-morpholinyl)-1-propanamine;

N-(2-(methyloxy)-5-{4-[5-(tetrahydro-1,4-oxazepin-4(5H)-ylmethyl)-1,3,4-oxadiazol-2-yl]-1H-indazol-6-yl}-3-pyridinyl)methanesulfonamide;

6-(1H-indol-4-yl)-4-[5-(tetrahydro-1,4-oxazepin-4(5H)-ylmethyl)-1,3,4-oxadiazol-2-yl]-1H-indazole;

N-[5-{4-[5-({[2-hydroxy-3-(4-morpholinyl)propyl]amino}methyl)-1,3,4-oxadiazol-2-yl]-1H-indazol-6-yl}-2-(methyloxy)-3-pyridinyl]methanesulfonamide;

2,4-difluoro-N-[5-{4-[5-({[2-hydroxy-3-(4-morpholinyl)propyl]amino}methyl)-1,3,4-oxadiazol-2-yl]-1H-indazol-6-yl}-2-(methyloxy)-3-pyridinyl]benzenesulfonamide;

N-[5-(4-{5-[(8aS)-hexahydropyrrolo[1,2-a]pyrazin-2(1H)-ylmethyl]-1,3,4-oxadiazol-2-yl}-1H-indazol-6-yl)-2-(methyloxy)-3-pyridinyl]methanesulfonamide;

2,4-difluoro-N-[5-(4-{5-[(8aS)-hexahydropyrrolo[1,2-a]pyrazin-2(1H)-ylmethyl]-1,3,4-oxadiazol-2-yl}-1H-indazol-6-yl)-2-(methyloxy)-3-pyridinyl]benzenesulfonamide;

N-[5-[4-(5-{[(2R,6S)-2,6-dimethyl-4-morpholinyl]methyl}-1,3,4-oxadiazol-2-yl)-1-methyl-1H-indazol-6-yl]-2-(methyloxy)-3-pyridinyl]-2,4-difluorobenzenesulfonamide;

N-[5-[4-(5-{[(2R,6S)-2,6-dimethyl-4-morpholinyl]methyl}-1,3,4-oxadiazol-2-yl)-1H-indazol-6-yl]-2-(methyloxy)-3-pyridinyl]-2-(methyloxy)benzenesulfonamide; or a salt thereof.

In another embodiment, the compound of the invention is:

6-(1H-indol-4-yl)-4-[5-(4-morpholinylmethyl)-1,3,4-oxadiazol-2-yl]-1H-indazole;

N-(2-chloro-5-{4-[5-(4-morpholinylmethyl)-1,3,4-oxadiazol-2-yl]-1H-indazol-6-yl}-3-pyridinyl)methanesulfonamide;

4-(5-{[(2R,6S)-2,6-dimethyl-4-morpholinyl]methyl}-1,3,4-oxadiazol-2-yl)-6-(1H-indol-4-yl)-1H-indazole;

6-(1H-indol-4-yl)-4-(5-{[4-(2-pyrimidinyl)-1-piperazinyl]methyl}-1,3,4-oxadiazol-2-yl)-1H-indazole;

4-{5-[(4,4-dimethyl-1-piperidinyl)methyl]-1,3,4-oxadiazol-2-yl}-6-(1H-indol-4-yl)-1H-indazole;

6-(1H-indol-4-yl)-4-(5-{[4-(2-methylpropyl)-1-piperazinyl]methyl}-1,3,4-oxadiazol-2-yl)-1H-indazole;

6-(1H-indol-4-yl)-4-(5-{[4-(1-methylethyl)-1-piperidinyl]methyl}-1,3,4-oxadiazol-2-yl)-1H-indazole;

6-(1H-indol-4-yl)-4-(5-{[2-(1-pyrrolidinylmethyl)-1-piperidinyl]methyl}-1,3,4-oxadiazol-2-yl)-1H-indazole;

4-(5-{[4-(4-fluorophenyl)-1-piperazinyl]methyl}-1,3,4-oxadiazol-2-yl)-6-(1H-indol-4-yl)-1H-indazole;

6-(1H-indol-4-yl)-4-(5-{[(1R,4R)-1,4,5-trimethyl-2,5-diazabicyclo[2.2.1]hept-2-yl]methyl}-1,3,4-oxadiazol-2-yl)-1H-indazole;

6-(1H-indol-4-yl)-4-(5-{[2-(1-pyrrolidinylmethyl)-4-morpholinyl]methyl}-1,3,4-oxadiazol-2-yl)-1H-indazole;

6-(1H-indol-4-yl)-4-[5-({4-[2-(4-morpholinyl)ethyl]-1-piperazinyl}methyl)-1,3,4-oxadiazol-2-yl]-1H-indazole;

6-(1H-indol-4-yl)-4-(5-{[4-(1-methylethyl)-1-piperazinyl]methyl}-1,3,4-oxadiazol-2-yl)-1 H-indazole;

4-(5-{[(2R,6S)-2,6-dimethyl-1-piperidinyl]methyl}-1,3,4-oxadiazol-2-yl)-6-(1H-indol-4-yl)-1H-indazole;

4-(5-{[(1S,4S)-1,4-dimethyl-7-azabicyclo[2.2.1]hept-7-yl]methyl}-1,3,4-oxadiazol-2-yl)-6-(1H-indol-4-yl)-1H-indazole;

4-({5-[6-(1H-indol-4-yl)-1H-indazol-4-yl]-1,3,4-oxadiazol-2-yl}methyl)octahydro-2H-1,4-benzoxazine;

6-(1H-indol-4-yl)-4-(5-{[2-(2-methylpropyl)-4-morpholinyl]methyl}-1,3,4-oxadiazol-2-yl)-1H-indazole;

N-{2-chloro-5-[4-(5-{[4-(1-methylethyl)-1-piperazinyl]methyl}-1,3,4-oxadiazol-2-yl)-1H-indazol-6-yl]-3-pyridinyl}methanesulfonamide;

N-{2-chloro-5-[4-(5-{[(2R,6S)-2,6-dimethyl-4-morpholinyl]methyl}-1,3,4-oxadiazol-2-yl)-1H-indazol-6-yl]-3-pyridinyl}methanesulfonamide;

N-(2-chloro-5-{4-[5-(4-morpholinylmethyl)-1,3,4-oxadiazol-2-yl]-1H-indazol-6-yl}-3-pyridinyl)methanesulfonamide;

N-[5-[4-(5-{[(2R,6S)-2,6-dimethyl-4-morpholinyl]methyl}-1,3,4-oxadiazol-2-yl)-1H-indazol-6-yl]-2-(methyloxy)-3-pyridinyl]methanesulfonamide;

N-[5-[4-(5-{[4-(1-methylethyl)-1-piperazinyl]methyl}-1,3,4-oxadiazol-2-yl)-1H-indazol-6-yl]-2-(methyloxy)-3-pyridinyl]methanesulfonamide;

4-(5-{[(2R,6S)-2,6-dimethyl-4-morpholinyl]methyl}-1,3,4-oxadiazol-2-yl)-6-(1H-indol-4-yl)-1-methyl-1H-indazole;

6-(1H-indol-4-yl)-1-methyl-4-(5-{[4-(1-methylethyl)-1-piperazinyl]methyl}-1,3,4-oxadiazol-2-yl)-1H-indazole;

N-[5-[1-methyl-4-(5-{[4-(1-methylethyl)-1-piperazinyl]methyl}-1,3,4-oxadiazol-2-yl)-1H-indazol-6-yl]-2-(methyloxy)-3-pyridinyl]methanesulfonamide;

N-[5-[4-(5-{[(2R,6S)-2,6-dimethyl-4-morpholinyl]methyl}-1,3,4-oxadiazol-2-yl)-1-methyl-1H-indazol-6-yl]-2-(methyloxy)-3-pyridinyl]methanesulfonamide;

N-[5-[4-(5-{[(2R,6S)-2,6-dimethyl-4-morpholinyl]methyl}-1,3,4-oxadiazol-2-yl)-1H-indazol-6-yl]-2-(m ethyloxy)-3-pyridinyl]-2,4-difluorobenzenesulfonamide;

N-[5-(4-{5-[(2,2-dimethyl-4-morpholinyl)methyl]-1,3,4-oxadiazol-2-yl}-1H-indazol-6-yl)-2-(methyloxy)-3-pyridinyl]methanesulfonamide; or a salt thereof.

In another embodiment, the compound of the invention is:

4-(5-{[(2R,6S)-2,6-dimethyl-4-morpholinyl]methyl}-1,3,4-oxadiazol-2-yl)-6-(1H-indol-4-yl)-1H-indazole;

N-[5-[4-(5-{[(2R,6S)-2,6-dimethyl-4-morpholinyl]methyl}-1,3,4-oxadiazol-2-yl)-1H-indazol-6-yl]-2-(methyloxy)-3-pyridinyl]methanesulfonamide;

N-[5-[4-(5-{[(2R,6S)-2,6-dimethyl-4-morpholinyl]methyl}-1,3,4-oxadiazol-2-yl)-1-methyl-1H-indazol-6-yl]-2-(methyloxy)-3-pyridinyl]methanesulfonamide;

N-[5-[4-(5-{[(2R,6S)-2,6-dimethyl-4-morpholinyl]methyl}-1,3,4-oxadiazol-2-yl)-1H-indazol-6-yl]-2-(methyloxy)-3-pyridinyl]-2,4-difluorobenzenesulfonamide; or a salt thereof.

In another embodiment, the compound of the invention is:

N-(2-chloro-5-{4-[5-(4-morpholinylmethyl)-1,3,4-oxadiazol-2-yl]-1H-indazol-6-yl}-3-pyridinyl)methanesulfonamide;

4-(5-{[(2R,6S)-2,6-dimethyl-4-morpholinyl]methyl}-1,3,4-oxadiazol-2-yl)-6-(1H-indol-4-yl)-1H-indazole;

4-{5-[(4,4-dimethyl-1-piperidinyl)methyl]-1,3,4-oxadiazol-2-yl}-6-(1H-indol-4-yl)-1H-indazole;

6-(1H-indol-4-yl)-4-(5-{[4-(2-methylpropyl)-1-piperazinyl]methyl}-1,3,4-oxadiazol-2-yl)-1H-indazole;

6-(1H-indol-4-yl)-4-(5-{[4-(1-methylethyl)-1-piperidinyl]methyl}-1,3,4-oxadiazol-2-yl)-1H-indazole;

6-(1H-indol-4-yl)-4-[5-({4-[2-(4-morpholinyl)ethyl]-1-piperazinyl}methyl)-1,3,4-oxadiazol-2-yl]-1H-indazole;

6-(1H-indol-4-yl)-4-(5-{[4-(1-methylethyl)-1-piperazinyl]methyl}-1,3,4-oxadiazol-2-yl)-1H-indazole;

4-({5-[6-(1H-indol-4-yl)-1H-indazol-4-yl]-1,3,4-oxadiazol-2-yl}methyl)octahydro-2H-1,4-benzoxazine;

N-{2-chloro-5-[4-(5-{[4-(1-methylethyl)-1-piperazinyl]methyl}-1,3,4-oxadiazol-2-yl)-1H-indazol-6-yl]-3-pyridinyl}methanesulfonamide;

N-{2-chloro-5-[4-(5-{[(2R,6S)-2,6-dimethyl-4-morpholinyl]methyl}-1,3,4-oxadiazol-2-yl)-1H-indazol-6-yl]-3-pyridinyl}methanesulfonamide;

N-[5-[4-(5-{[(2R,6S)-2,6-dimethyl-4-morpholinyl]methyl}-1,3,4-oxadiazol-2-yl)-1H-indazol-6-yl]-2-(methyloxy)-3-pyridinyl]methanesulfonamide;

N-[5-[1-methyl-4-(5-{[4-(1-methylethyl)-1-piperazinyl]methyl}-1,3,4-oxadiazol-2-yl)-1H-indazol-6-yl]-2-(methyloxy)-3-pyridinyl]methanesulfonamide;

N-[5-[4-(5-{[(2R,6S)-2,6-dimethyl-4-morpholinyl]methyl}-1,3,4-oxadiazol-2-yl)-1-methyl-1H-indazol-6-yl]-2-(methyloxy)-3-pyridinyl]methanesulfonamide;

N-[5-[4-(5-{[(2R,6S)-2,6-dimethyl-4-morpholinyl]methyl}-1,3,4-oxadiazol-2-yl)-1H-indazol-6-yl]-2-(m ethyloxy)-3-pyridinyl]-2,4-difluorobenzenesulfonamide;

N-[5-(4-{5-[(2,2-dimethyl-4-morpholinyl)methyl]-1,3,4-oxadiazol-2-yl}-1H-indazol-6-yl)-2-(methyloxy)-3-pyridinyl]methanesulfonamide;

N-{2-chloro-5-[4-(5-methyl-1,3,4-oxadiazol-2-yl)-1H-indazol-6-yl]-3-pyridinyl}methanesulfonamide;

N-(2-(methyloxy)-5-{4-[5-(6-oxa-9-azaspiro[4.5]dec-9-yl-methyl)-1,3,4-oxadiazol-2-yl]-1H-indazol-6-yl}-3-pyridinyl)methanesulfonamide;

N-[5-[4-(5-{[(3R,5S)-3,5-dimethyl-4-(1-methylethyl)-1-piperazinyl]methyl}-1,3,4-oxadiazol-2-yl)-1H-indazol-6-yl]-2-(methyloxy)-3-pyridinyl]methanesulfonamide;

N-[5-(4-{5-[(1,1-dioxido-4-thiomorpholinyl)methyl]-1,3,4-oxadiazol-2-yl}-1H-indazol-6-yl)-2-(methyloxy)-3-pyridinyl]methanesulfonamide;

N-[5-(4-{5-[(2-ethyl-4-morpholinyl)methyl]-1,3,4-oxadiazol-2-yl}-1H-indazol-6-yl)-2-(methyloxy)-3-pyridinyl]methanesulfonamide;

9-({5-[6-(1H-indol-4-yl)-1H-indazol-4-yl]-1,3,4-oxadiazol-2-yl}methyl)-6-oxa-9-azaspiro[4.5]decane;

4-{5-[(2,2-dimethyl-4-morpholinyl)methyl]-1,3,4-oxadiazol-2-yl}-6-(1H-indol-4-yl)-1H-indazole;

N-[5-[4-(5-{[(3R,5S)-3,5-dimethyl-4-(1-methylethyl)-1-piperazinyl]methyl}-1,3,4-oxadiazol-2-yl)-1H-indazol-6-yl]-2-(methyloxy)-3-pyridinyl]-2,4-difluorobenzenesulfonamide;

2,4-difluoro-N-[5-[4-(5-{[4-(1-methylethyl)-1-piperazinyl]methyl}-1,3,4-oxadiazol-2-yl)-1H-indazol-6-yl]-2-(methyloxy)-3-pyridinyl]benzenesulfonamide;

N-[5-(4-{5-[(2-methyl-4-morpholinyl)methyl]-1,3,4-oxadiazol-2-yl}-1H-indazol-6-yl)-2-(methyloxy)-3-pyridinyl]methanesulfonamide;

N-(2-(methyloxy)-5-{4-[5-(tetrahydro-1,4-oxazepin-4(5H)-ylmethyl)-1,3,4-oxadiazol-2-yl]-1H-indazol-6-yl}-3-pyridinyl)methanesulfonamide;

2,4-difluoro-N-[5-{4-[5-({[2-hydroxy-3-(4-morpholinyl)propyl]amino}methyl)-1,3,4-oxadiazol-2-yl]-1H-indazol-6-yl}-2-(methyloxy)-3-pyridinyl]benzenesulfonamide;

N-[5-(4-{5-[(8aS)-hexahydropyrrolo[1,2-a]pyrazin-2(1H)-ylmethyl]-1,3,4-oxadiazol-2-yl}-1H-indazol-6-yl)-2-(methyloxy)-3-pyridinyl]methanesulfonamide;

2,4-difluoro-N-[5-(4-{5-[(8aS)-hexahydropyrrolo[1,2-a]pyrazin-2(1H)-ylmethyl]-1,3,4-oxadiazol-2-yl}-1H-indazol-6-yl)-2-(methyloxy)-3-pyridinyl]benzenesulfonamide;

N-[5-[4-(5-{[(2R,6S)-2,6-dimethyl-4-morpholinyl]methyl}-1,3,4-oxadiazol-2-yl)-1-methyl-1H-indazol-6-yl]-2-(methyloxy)-3-pyridinyl]-2,4-difluorobenzenesulfonamide;
or a salt thereof.

In a further embodiment, the compound of the invention is:

4-(5-{[(2R,6S)-2,6-dimethyl-4-morpholinyl]methyl}-1,3,4-oxadiazol-2-yl)-6-(1H-indol-4-yl)-1H-indazole;

6-(1H-indol-4-yl)-4-(5-{[4-(1-methylethyl)-1-piperazinyl]methyl}-1,3,4-oxadiazol-2-yl)-1H-indazole;

N-[5-[4-(5-{[(2R,6S)-2,6-dimethyl-4-morpholinyl]methyl}-1,3,4-oxadiazol-2-yl)-1H-indazol-6-yl]-2-(methyloxy)-3-pyridinyl]methanesulfonamide;

N-[5-[1-methyl-4-(5-{[4-(1-methylethyl)-1-piperazinyl]methyl}-1,3,4-oxadiazol-2-yl)-1H-indazol-6-yl]-2-(methyloxy)-3-pyridinyl]methanesulfonamide;

N-[5-[4-(5-{[(2R,6S)-2,6-dimethyl-4-morpholinyl]methyl}-1,3,4-oxadiazol-2-yl)-1-methyl-1H-indazol-6-yl]-2-(methyloxy)-3-pyridinyl]methanesulfonamide; or
a salt thereof.

Terms and Definitions

"Alkyl" refers to a saturated hydrocarbon chain having the specified number of member atoms. For example, $C_{1-6}$alkyl refers to an alkyl group having from 1 to 6 member atoms, for example 1 to 4 member atoms. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

"Cycloalkyl" refers to a saturated hydrocarbon ring having the specified number of member atoms. Cycloalkyl groups are monocyclic ring systems. For example, $C_{3-6}$cycloalkyl refers to a cycloalkyl group having from 3 to 6 member atoms. In one embodiment, the cycloalkyl groups have 3 or 4 member atoms. In a further embodiment, the cycloalkyl groups have 5 or 6 member atoms. Cycloalkyl includes cyclopropyl, cyclobutyl, cyclopentyl, and cyclohexyl.

"Enantiomerically enriched" refers to products whose enantiomeric excess is greater than zero. For example, enantiomerically enriched refers to products whose enantiomeric excess is greater than 50% ee, greater than 75% ee, and greater than 90% ee.

"Enantiomeric excess" or "ee" is the excess of one enantiomer over the other expressed as a percentage. As a result, since both enantiomers are present in equal amounts in a racemic mixture, the enantiomeric excess is zero (0% ee). However, if one enantiomer was enriched such that it constitutes 95% of the product, then the enantiomeric excess would be 90% ee (the amount of the enriched enantiomer, 95%, minus the amount of the other enantiomer, 5%).

"Enantiomerically pure" refers to products whose enantiomeric excess is 99% ee or greater.

"Half-life" (or "half-lives") refers to the time required for half of a quantity of a substance to be converted to another chemically distinct species in vitro or in vivo.

"Halo" refers to the halogen radical fluoro, chloro, bromo, or iodo.

"Heteroaryl", unless otherwise defined, refers to an aromatic ring containing from 1 to 3 heteroatoms, for example 1 or 2 heteroatoms, as member atoms in the ring or rings. Heteroaryl groups containing more than one heteroatom may contain different heteroatoms. Heteroaryl groups may be optionally substituted with one or more substituents as defined herein. The heteroaryl groups herein are monocyclic ring systems or are fused bicyclic ring systems. The monocyclic heteroaryl rings have 6 member atoms. The bicyclic heteroaryl rings have 9 or 10 member atoms. Monocyclic heteroaryl includes pyridinyl, pyrimidinyl, pyridazinyl and pyrazinyl. In one embodiment, monocyclic heteroaryl is pyridinyl. Bicyclic heteroaryl includes indolyl, isoindolyl, indolizinyl, benzofuranyl, isobenzofuranyl, indazolyl, benzimidazolyl, pyrrolopyridinyl, pyrazolopyridinyl, pyrrolopyrimidinyl, quinolyl, isoquinolinyl, quinoxalinyl, quinazolinyl, cinnolinyl, benzopyranyl, benzoxazolyl, furopyridinyl and naphthridinyl.

"Heteroatom" refers to a nitrogen, sulphur, or oxygen atom.

"Heterocyclyl", unless otherwise defined, refers to a saturated or unsaturated ring containing 1 or 2 heteroatoms as member atoms in the ring. However, heterocyclyl rings are not aromatic. In certain embodiments, heterocyclyl is saturated. In other embodiments, heterocyclyl is unsaturated but not aromatic. Heterocyclyl groups containing more than one heteroatom may contain different heteroatoms. Heterocyclyl groups may be optionally substituted with one or more substituents as defined herein. The heterocyclyl groups herein are monocyclic ring systems having 6 or 7 member atoms, bicyclic ring systems having 9 or 10 member atoms, bridged ring systems having 7 member atoms, or spiro bicyclic ring systems having 10 member atoms. Monocyclic heterocyclyl includes piperidinyl, piperazinyl, morpholinyl, thiomorpholinyl and hexahydro-1,4-oxazepinyl. Bicyclic heterocyclyl includes octahydropyrrolo[1,2-a]pyrazinyl and octahydro-2H-1,4-benzoxazinyl. Bridged heterocyclyl includes 7-azabicylo[2.2.1]heptyl and 2,5-diazabicyclo[2.2.1]heptyl. Spiro bicyclic ring systems include 6-oxa-9-azaspiro[4.5]decyl.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Optionally substituted" indicates that a group, such as heteroaryl, may be unsubstituted or substituted with one or more substituents as defined herein.

"Substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination). In certain embodiments, a single atom may be substituted with more than one substituent as long as such substitution is in accordance with the permitted valence of the atom. Suitable substituents are defined herein for each substituted or optionally substituted group.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

| | |
|---|---|
| DCM | Dichloromethane |
| DIPEA | Diisopropylethylamine |
| DMSO | Dimethylsulfoxide |
| EtOAc | Ethyl acetate |
| g | Grams |
| h | Hour(s) |
| HCl | Hydrogen chloride |
| HPLC | High performance liquid chromatography |
| LCMS | Liquid chromatography mass spectroscopy |
| M | Molar |
| MDAP | Mass directed automated preparative HPLC |
| MeCN | Acetonitrile |
| MeOH | Methanol |
| mg | Milligrams |
| mins | Minutes |
| ml | Milliliters |
| mmol | Millimoles |
| Pd(dppf)Cl$_2$ | [1,1'-bis(diphenylphosphino)ferrocene] dichloropalladium(II) |
| Rt | Retention time |
| SCX | Strong Cation Exchange |
| SPE | Solid Phase Extraction |
| TFA | Trifluoroacetic acid |
| THF | Tetrahydrofuran |
| UPLC | Ultra high performance liquid chromatography |
| UV | Ultraviolet |

All references to brine are to a saturated aqueous solution of NaCl.

Included within the scope of the "compounds of the invention" are all solvates (including hydrates), complexes, polymorphs, prodrugs, radiolabelled derivatives, stereoisomers and optical isomers of the compounds of formula (I) and salts thereof.

The compounds of the invention may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. Solvates may involve nonaqueous solvents such as ethanol, isopropanol, DMSO, acetic acid, ethanolamine, and EtOAc, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs". The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The invention also includes isotopically-labelled compounds, which are identical to the compounds of formula (I) and salts thereof, but for the fact that one or more atoms are replaced by an atom having an atomic mass or mass number different from the atomic mass or mass number most commonly found in nature. Examples of isotopes that can be incorporated into the compounds of the invention include isotopes of hydrogen, carbon, nitrogen, oxygen and fluorine, such as 3H, 11C, 14C and 18F.

The compounds according to formula (I) may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in formula (I), or in any chemical structure illustrated herein, is not specified the structure is intended to encompass any stereoisomer and all mixtures thereof. Thus, compounds according to formula (I) containing one or more chiral center may be used as racemic mixtures, enantiomerically enriched mixtures, or as enantiomerically pure individual stereoisomers.

Individual stereoisomers of a compound according to formula (I) which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The compounds according to formula (I) may also contain centers of geometric asymmetry. Where the stereochemistry of a center of geometric asymmetry present in formula (I), or in any chemical structure illustrated herein, is not specified, the structure is intended to encompass the trans geometric isomer, the cis geometric isomer, and all mixtures thereof. Likewise, all tautomeric forms are also included in formula (I) whether such tautomers exist in equilibrium or predominately in one form.

It is to be understood that the references herein to compounds of formula (I) and salts thereof covers the compounds of formula (I) as free acids or free bases, or as salts thereof, for example as pharmaceutically acceptable salts thereof. Thus, in one embodiment, the invention is directed to compounds of formula (I) as the free acid or free base. In another embodiment, the invention is directed to compounds of formula (I) and salts thereof. In a further embodiment, the invention is directed to compounds of formula (I) and pharmaceutically acceptable salts thereof.

The skilled artisan will appreciate that pharmaceutically acceptable salts of the compounds according to formula (I) may be prepared. Indeed, in certain embodiments of the invention, pharmaceutically acceptable salts of the compounds according to formula (I) may be preferred over the respective free base or free acid because such salts impart greater stability or solubility to the molecule thereby facilitating formulation into a dosage form. Accordingly, the invention is further directed to compounds of formula (I) and pharmaceutically acceptable salts thereof.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form with a suitable base or acid, respectively.

Salts and solvates having non-pharmaceutically acceptable counter-ions or associated solvents are within the scope of the present invention, for example, for use as intermediates in the preparation of other compounds of formula (I) and their pharmaceutically acceptable salts. Thus one embodiment of the invention embraces compounds of formula (I) and salts thereof.

In certain embodiments, compounds according to formula (I) may contain an acidic functional group. Suitable pharmaceutically-acceptable salts include salts of such acidic functional groups. Representative salts include pharmaceutically acceptable metal salts such as sodium, potassium, lithium, calcium, magnesium, aluminum, and zinc salts; carbonates and bicarbonates of a pharmaceutically acceptable metal cation such as sodium, potassium, lithium, calcium, magnesium, aluminum, and zinc; pharmaceutically acceptable organic primary, secondary, and tertiary amines including aliphatic amines, aromatic amines, aliphatic diamines, and hydroxy alkylamines such as methylamine, ethylamine, 2-hydroxyethylamine, diethylamine, TEA, ethylenediamine, ethanolamine, diethanolamine, and cyclohexylamine.

In certain embodiments, compounds according to formula (I) may contain a basic functional group and are therefore capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, naphthoate, hydroxynaphthoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate.

Compound Preparation

The compounds of the invention may be made by a variety of methods, including standard chemistry. Any previously defined variable will continue to have the previously defined meaning unless otherwise indicated. Illustrative general synthetic methods are set out below and then specific compounds of the invention are prepared in the Examples section.

Compounds of formula (I), wherein $R^1$ and X are as defined above and $R^4$ is hydrogen, or salts thereof, may be prepared from compounds of formula (II)

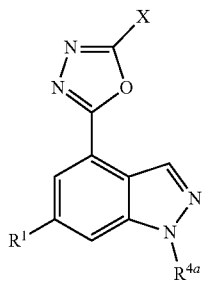

(II)

wherein $R^1$ and X are as defined above and $R^{4a}$ is a suitable protecting group, for example benzenesulphonyl, by treatment with a suitable aqueous inorganic base such as aqueous sodium hydroxide, in a suitable solvent such as isopropanol or 1,4-dioxane, at a suitable temperature such as room temperature, for example about 20° C.

Process 1

Compounds of formula (II), wherein $R^1$ and $R^{4a}$ are as defined above and X is —$CH_2NR^2R^3$, and compounds of formula (I) wherein $R^1$ is as defined above, X is —$CH_2NR^2R^3$ and $R^4$ is methyl, or salts thereof, may be prepared from compounds of formula (III)

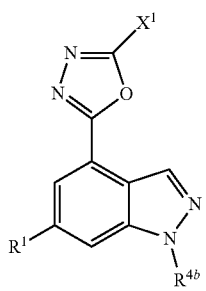

(III)

wherein $R^1$ is as defined above, $R^{4b}$ is methyl or $R^{4a}$ as defined above, and $X^1$ is $CH_2X^2$, where $X^2$ is a suitable leaving group for example CI, by treatment with a suitable amine of formula $HNR^2R^3$ as defined above such as morpholine, in a suitable solvent such as dichloromethane, and at a suitable temperature such as from 20 to 50° C., for example about 20° C. Alternatively, this process may be carried out in a suitable solvent such as acetonitrile, in the presence of a suitable amine such as 1-(1-methylethyl)piperazine, in the presence of a suitable base such as N,N-diisopropylethylamine, in the presence of a suitable iodide such as sodium iodide, and at a suitable temperature such as from 20 to 100° C., for example about 70° C. Alternatively, this process may be carried out in the presence of a suitable amine such as morpholine, with or without the presence of a suitable solvent such as acetonitrile, under microwave irradiation at a suitable temperature such as from 50 to 120° C., for example about 80° C.

Compounds of formula (III), wherein $R^1$, $X^1$ and $R^{4b}$ are as defined above, and compounds of formula (II), wherein $R^1$ and $R^{4a}$ are defined as above and X is $C_{1-6}$alkyl, —$CH_2$phenyl, —$(CH_2)_nOR^{10}$ or —$(CH_2)_pC_{3-6}$cycloalkyl, may be prepared from compounds of formula (IV)

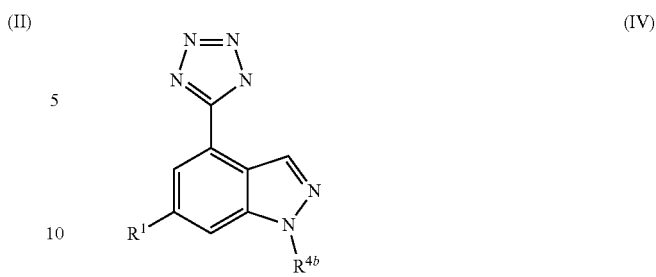

(IV)

wherein $R^1$ and $R^{4b}$ are as defined above, by treatment with a suitable acylating agent such as chloroacetyl chloride or 2-methylpropanoyl chloride, in a suitable solvent such as chloroform, under microwave irradiation at a suitable temperature such as from 50 to 120° C., for example about 100° C. Alternatively, this process may be carried out either thermally or under microwave irradiation, in a suitable solvent such as toluene, and at a suitable temperature such as from 60 to 200° C., for example about 100° C.

For compounds where $R^1$ contains a protecting group such as where $R^1$ is 1,1-dimethylethyl 1H-indole-1-carboxylate, an additional deprotection step is required, by treatment with a suitable acid such as acetic acid, at a suitable temperature such as from 50 to 130° C., for example about 100° C. Examples of suitable protection groups and the means of their removal can be found in T. W. Greene and P. G. M. Wuts 'Protective Groups in Organic Synthesis' ($3^{rd}$ Ed., J. Wiley and Sons, 1999).

Compounds of formula (IV), wherein $R^1$ and $R^{4b}$ are as defined above, may be prepared from compounds of formula (V)

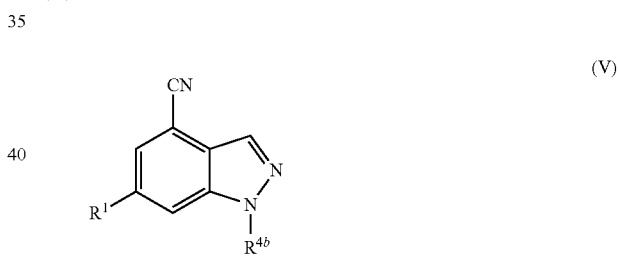

(V)

wherein $R^1$ and $R^{4b}$ are as defined above, by treatment with a suitable azide such as trimethylsilyl azide, in the presence of a suitable catalyst such as dibutyl(oxo)stannane, in a suitable solvent such as toluene, and at a suitable temperature such as from 50 to 120° C., for example about 110° C.

Compounds of formula (V), wherein $R^1$ and $R^{4b}$ are as defined above, may be prepared from compounds of formula (VI)

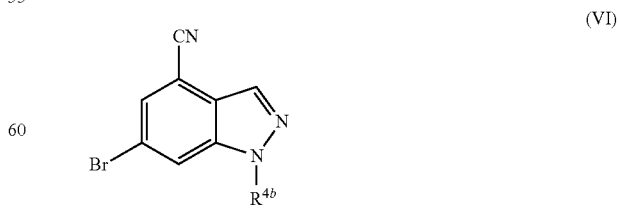

(VI)

wherein $R^{4b}$ is as defined above, by treatment with a suitable boronic acid or boronate ester such as 4-(4,4,5,5-tetramethyl-1,3,2-dioxaborolan-2-yl)-1H-indole (commercially available), in the presence of a suitable palladium catalyst such as 1,1'-bis(diphenylphosphino)ferrocene palladium dichloride, in a suitable solvent such as a mixture of 1,4-dioxane and water, in the presence of a suitable base such as tripotassium phosphate, and at a suitable temperature such as from 50 to 150° C., for example about 60° C. Alternatively, this process may be carried out under microwave irradiation, at a suitable temperature such as from 60 to 200° C., for example about 100° C.

The compound of formula (VI), wherein $R^{4b}$ is methyl, may be prepared from the compound of formula (VII)

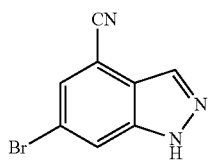

(VII)

by methylation using a suitable base such as sodium hydride, in a suitable solvent such as tetrahydrofuran, and at a suitable temperature such as about 0° C., followed by addition of an alkylating agent such as iodomethane and stirring at a suitable temperature such as room temperature. The compound of formula (VII) is commercially available.

Compounds of formula (VI), wherein $R^{4b}$ is a suitable protecting group, for example benzenesulphonyl, may be prepared from the compound of formula (VII) as defined above by treatment with a suitable sulphonylating agent such as benzenesulphonyl chloride, in the presence of a suitable base such as sodium hydride, in a suitable solvent such as N,N-dimethylformamide, and at a suitable temperature such as from 0° C. to 50° C., for example about 20° C.

Process 1b

Compounds of formula (II), wherein $R^1$ and $R^{4a}$ are as defined above and X is —$CH_2SO_2R^{11}$, and compounds of formula (I) wherein $R^1$ is as defined above, X is —$CH_2SO_2R^{11}$ and $R^4$ is methyl, or salts thereof, may be prepared from compounds of formula (III) as defined above, by treatment with a suitable sulfinate salt, such as sodium methanesulfinate, in a suitable solvent such as ethanol, and under microwave irradiation at a suitable temperature such as from 50° C. to 200° C., for example about 100° C.

Process 1c

Compounds of formula (II), wherein $R^1$ and $R^{4a}$ are as defined above and X is —$(CH_2)_nOR^{10}$, and compounds of formula (I) wherein $R^1$ is defined above, X is —$(CH_2)_nOR^{10}$ and $R^4$ is methyl, or salts thereof, may also be prepared from compounds of formula (III) as defined above, by treatment with a suitable alcohol such as methanol, in the presence of a suitable base such as potassium carbonate, under microwave irradiation at a suitable temperature such as from 80 to 150° C., for example about 110° C.

Process 2

For compounds of formula (II), wherein X and $R^{4a}$ are as defined above and $R^1$ is pyridinyl substituted by —$NHSO_2R^7$ as defined above and compounds of formula (I), wherein X is as defined above, $R^4$ is methyl and $R^1$ is pyridinyl substituted by —$NHSO_2R^7$ as defined above, or salts thereof, may be prepared from compounds of formula (XVI)

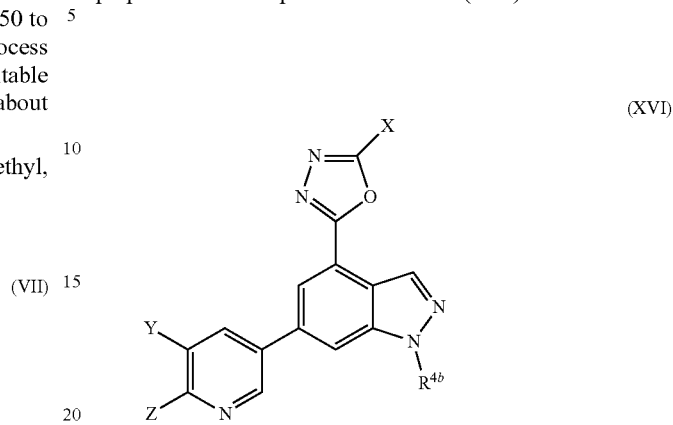

(XVI)

wherein X and $R^{4b}$ are as defined above, Y is $NH_2$ and Z is $C_{1-6}$alkyl, —$OR^6$ or halo, by treatment with a suitable sulfonyl chloride of formula $R^7SO_2Cl$ such as 2,4-difluorobenzenesulfonyl chloride in a suitable solvent such as chloroform, with a suitable base such as pyridine at a suitable temperature such as room temperature, for example about 20° C.

Compounds of formula (XVI), wherein X, $R^{4b}$ and Y are as defined above, compounds of formula (II), wherein $R^1$, X and $R^{4a}$ are as defined above, and compounds of formula (I) wherein $R^1$ and X are as defined above and $R^4$ is methyl, or salts thereof, may also be prepared from compounds of formula (VIII)

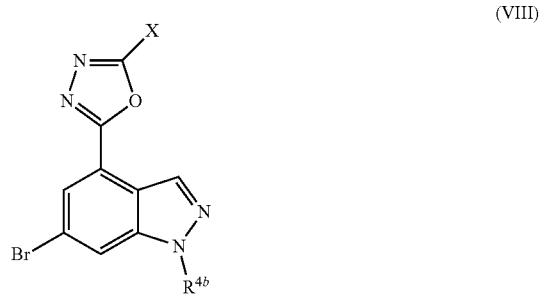

(VIII)

wherein X and $R^{4b}$ are as defined above, by treatment with a suitable boronic acid or boronate ester such as 4-(4,4,5,5-tetramethyl-1,3,2-dioxaborolan-2-yl)-1H-indole (commercially available), in the presence of a suitable palladium catalyst such as 1,1'-bis(diphenylphosphino)ferrocene palladium dichloride, in a suitable solvent such as a mixture of 1,4-dioxane and water, in the presence of a suitable base such as tripotassium phosphate or 2M sodium carbonate solution, under microwave irradiation, and at a suitable temperature such as from 50 to 200° C., for example about 85° C.

Compounds of formula (VIII), wherein $R^{4b}$ is as defined above and X is —$CH_2NR^2R^3$, may be prepared from compounds of formula (IX)

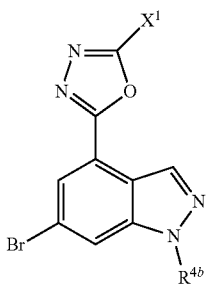

(IX)

wherein $R^{4b}$ is as defined above and $X^1$ is $CH_2X^2$, where $X^2$ is a suitable leaving group for example Cl, by treatment with an amine of formula $HNR^2R^3$ as defined above such as morpholine, in a suitable solvent such as dichloromethane and at a suitable temperature such as from 20 to 50° C., for example about 20° C. Alternatively, this process may be carried out in a suitable solvent such as acetonitrile, in the presence of a suitable amine such as 1-(1-methylethyl)piperazine, in the presence of a suitable base such as N,N-diisopropylethylamine, in the presence of a suitable iodide such as sodium iodide, and at a suitable temperature such as from 20 to 100° C., for example about 80° C.

Compounds of formula (IX), wherein $R^{4b}$ is as defined above and $X^1$ is —$CH_2Cl$ or $CH_2Br$, may be prepared from compounds of formula (X)

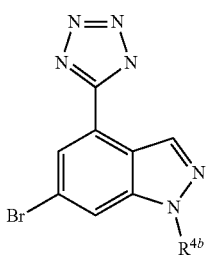

(X)

wherein $R^{4b}$ is as defined above, by treatment with a suitable acylating agent such as chloroacetyl chloride, in the presence of a suitable solvent such as toluene, under microwave irradiation, and at a suitable temperature such as from 60 to 200° C., for example about 115° C.

Compounds of formula (VIII) where $R^{4b}$ is defined as above and X is $C_{1-6}$alkyl, may be prepared directly from compounds of formula (X) wherein $R^{4b}$ is defined as above by treatment with a suitable acylating agent, such as acetyl chloride, in a suitable solvent such as toluene, under microwave irradiation at a suitable temperature such as from 80 to 150° C., for example about 130° C.

Compounds of formula (X), wherein $R^{4b}$ is as defined above, may be prepared from compounds of formula (VI), as defined above, by treatment with a suitable azide such as trimethylsilyl azide, in the presence of a suitable catalyst such as dibutyl(oxo)stannane, in a suitable solvent such as toluene, under microwave irradiation, and at a suitable temperature such as from 50 to 120° C., for example about 110° C.

Process 3

Compounds of formula (VIII), wherein $R^{4b}$ is as defined above and X is —$CH_2NR^2R^3$ as defined above, may be prepared from compounds of formula (XI)

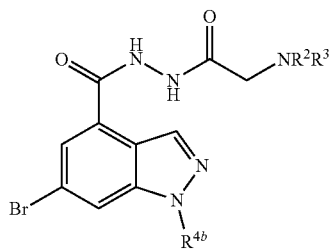

(XI)

wherein $R^2$, $R^3$ and $R^{4b}$ are as defined above, by treatment with a suitable dehydrating agent such as (methoxycarbonylsulfamoyl)triethylammonium hydroxide, inner salt (Burgess reagent), in a suitable solvent such as tetrahydrofuran, under microwave irradiation, and at a suitable temperature such as from 50 to 150° C., for example about 100° C.

Compounds of formula (XI), wherein $R^2$ and $R^3$ are as defined above and $R^{4b}$ is 2-tetrahydro-2H-pyran, may be prepared from compounds of formula (XII)

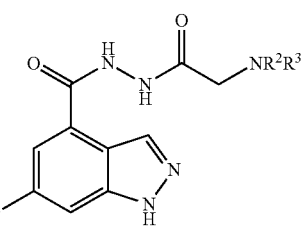

(XII)

wherein $R^2$ and $R^3$ are as defined above, by treatment with 3,4-dihydro-2H-pyran, in the presence of a suitable acid catalyst such as trifluoroacetic acid, in a suitable solvent such as ethyl acetate, and at a suitable temperature such as from 20 to 100° C., for example about 50° C.

Compounds of formula (XII), wherein $R^2$ and $R^3$ are as defined above, may be prepared from the compound of formula (XIII)

(XIII)

by treatment with a suitable $R^2R^3N$-acetic acid such as 4-morpholinylacetic acid, in the presence of a suitable amide coupling reagent such as O-(7-azabenzotriazol-1-yl)-N,N,N', N'-tetramethyluronium hexafluorophosphate, in the presence of a suitable base such as N,N-diisopropylethylamine, in a suitable solvent such as N,N-dimethylformamide, and at a suitable temperature such as from 20 to 50° C., for example about 20° C.

The compound of formula (XIII) may be prepared from the compound of formula (XIV)

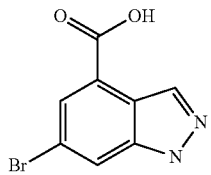
(XIV)

by treatment with a suitable hydrazide such as t-butylcarbazate in the presence of a suitable amide coupling reagent such as O-(7-azabenzotriazol-1-yl)-N,N,N',N'-tetramethyluronium hexafluorophosphate, in the presence of a suitable base such as N,N-diisopropylethylamine, in a suitable solvent such as N,N-dimethylformamide and at a suitable temperature such as room temperature, for example 20° C. Followed by deprotection, by treatment with a suitable acid such as hydrogen chloride, in a suitable solvent such as 1,4-dioxane and at a suitable temperature such as room temperature, for example 20° C. The compound of formula (XIV) is commercially available.

Process 4

Compounds of formula (V), wherein $R^1$ and $R^{4b}$ are as defined above may be prepared from compounds of formula (XV)

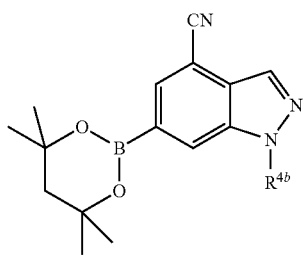
(XV)

wherein $R^{4b}$ is as defined above, by treatment with a suitable halide such as N-(5-bromo-2-chloro-3-pyridinyl)methanesulfonamide (commercially available), in the presence of a suitable palladium catalyst such as chloro(di-2-norbonylphosphino)(2'-dimethylamino-1,1'-biphenyl-2-yl)palladium (II), in a suitable solvent such as a mixture of 1,4-dioxane and water, in the presence of a suitable base such as tripotassium phosphate, under microwave irradiation, and at a suitable temperature such as from 50 to 200° C., for example about 100° C.

Compounds of formula (XV), wherein $R^{4b}$ is as defined above, may be prepared from compounds of formula (VI), as defined above, by treatment with a suitable borinane such as 4,4,4',4',6,6,6',6'-octamethyl-2,2'-bi-1,3,2-dioxaborinane (commercially available), in the presence of a suitable palladium catalyst such as 1,1'-bis(diphenylphosphino)ferrocene palladium dichloride, in a suitable solvent such as 1,4-dioxane, in the presence of a suitable base such as potassium acetate, under microwave irradiation, and at a suitable temperature such as from 50 to 150° C., for example about 80° C.

Process 5

Compounds of formula (VIII), wherein $R^{4b}$ is defined as above and X is $CH_2NR^2R^3$ as defined above, may be prepared from compounds of formula (XVII)

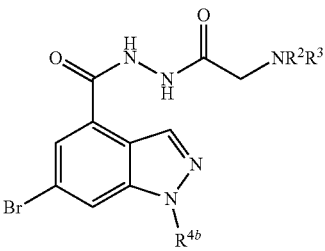
(XVII)

wherein $R^2$, $R^3$ and $R^{4b}$ are as defined above, by treatment with a suitable dehydrating agent such as (methoxycarbonylsulfamoyl)triethylaminonium hydroxide, in a suitable solvent such a tetrahydrofuran, at a suitable temperature such as from 50 to 150° C., for example 75° C.

Compounds of formula (XVII), wherein $R^2$, $R^3$ and $R^{4b}$ are defined as above, may be prepared from compounds of formula (XVIII)

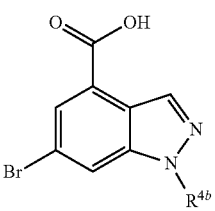
(XVIII)

wherein $R^{4b}$ is defined as above, by treatment with a suitable chlorinating agent such as thionyl chloride at a suitable temperature such as from 50 to 150° C., for example 100° C., followed by treatment with a suitable hydrazide such as 2-[(2R,6S)-2,6-dimethyl-4-morpholinyl]acetohydrazide and a suitable base such a N,N-diisopropylethylamine in a suitable solvent such as tetrahydrofuran at a suitable temperature such as from 20° C. to 100° C., for example 20° C.

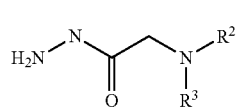
(XIX)

Hydrazides of formula (XIX), wherein $R^2$ and $R^3$ are defined as above, may be prepared from compounds of formula (XX)

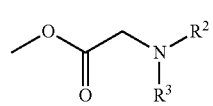
(XX)

wherein $R^2$ and $R^3$ are as defined above, by treatment with a suitable hydrazine such as hydrazine hydrate, in a suitable solvent such as methanol, at a suitable temperature such as from 50 to 150° C., for example about 70° C. Compounds of formula (XX) may be prepared as described in the literature. For the compound wherein and $NR^2R^3$ is (2R,6S)-2,6-dimethylmorpholine, see Journal of Fluorine Chemistry, 1998, 193-201).

Compounds of formula (XVIII), wherein R$^{4b}$ is defined as above, may be prepared from compounds of formula (XXI)

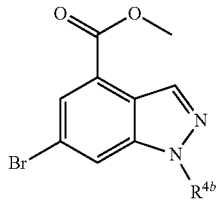
(XXI)

wherein R$^{4b}$ is defined as above, by treatment with a suitable base such as lithium hydroxide, in a suitable solvent such as a mixture of tetrahydrofuran and water, at a suitable temperature such as room temperature, for example about 20° C.

Compounds of formula (XXI), wherein R$^{4b}$ is methyl, may be prepared from the compound of formula (XXII)

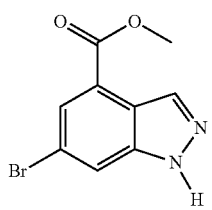
(XXII)

by methylation using a suitable base such as sodium hydride, in a suitable solvent such as tetrahydrofuran, and at a suitable temperature such as about 0° C., followed by addition of an alkylating agent such as iodomethane and stirring at a suitable temperature such as from 0° C. to room temperature.

Compounds of formula (XXI), wherein R$^{4b}$ is a suitable protecting group, for example benzenesulphonyl, may be prepared from compounds of formula (XXII) by treatment with a suitable sulphonylating agent such as benzenesulphonyl chloride, in the presence of a suitable base such as sodium hydride, in a suitable solvent such as N,N-dimethylformamide, and at a suitable temperature such as from 0° C. to 50° C., for example about 20° C.

The compound of formula (XXII) may be prepared from the compound of formula (XXIII)

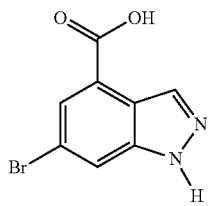
(XXIII)

by treatment with a suitable acid such as concentrated hydrochloric acid and a suitable alcohol such as methanol, at a suitable temperature such as from 50 to 150° C., for example about 70° C. The compound of formula (XXIII) is commercially available.

Process 6

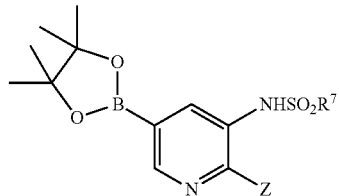
(XXIV)

Boronic esters of formula (XXIV), wherein R$^7$ is as defined above and Z is OR$^6$ as defined above or halo, may be prepared from compounds of formula (XXV)

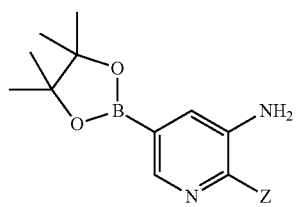
(XXV)

wherein Z is OR$^6$ as defined above or halo, by treatment with a suitable sulphonyl chloride such as methane sulfonyl chloride, in a suitable solvent such a pyridine, at a suitable temperature such as room temperature, for example about 20° C.

Compounds of formula (XXV) where Z is OR$^6$ as defined above or halo, may be prepared from compounds of formula (XXVI)

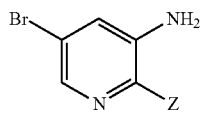
(XXIV)

wherein Z is OR$^6$ as defined above, or halo, by treatment with a suitable borolane such as 4,4,4',4',5,5,5',5'-octamethyl-2,2'-bi-1,3,2-dioxaborolane, in the presence of a suitable palladium catalyst such as dichloro[1,1'-bis(diphenylphosphino)ferrrocene]palladium (II) dichloromethane adduct, in the presence of a suitable base such as potassium acetate, in a suitable solvent such as 1,4-dioxane and at a suitable temperature such as from 50 to 120° C., for example about 80° C. Compounds of formula (XXIV) are commercially available.

Thus in one embodiment, the invention provides a process for preparing a compound of the invention comprising:

a) for a compound of formula (I) wherein R$^1$, R$^2$ and R$^3$ are as defined above and R$^4$ is hydrogen, or a salt thereof, reacting a compound of formula (II)

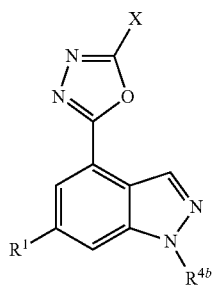
(II)

wherein $R^1$, $R^2$ and $R^3$ are as defined above and $R^{4a}$ is a suitable protecting group, with a suitable aqueous inorganic base;

b) for a compound of formula (I) wherein $R^1$, $R^2$ and $R^3$ are as defined above and $R^4$ is methyl, or a salt thereof, reacting a compound of formula (III)

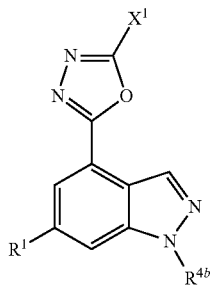

(III)

wherein $R^1$ is as defined above, $R^{4b}$ is methyl and $X^1$ is —CH$_2$X$^2$ wherein $X^2$ is a leaving group, with an amine of formula HNR$^2$R$^3$, wherein $R^2$ and $R^3$ are as defined above; or c) for a compound of formula (I) wherein $R^1$ and X are as defined above and $R^4$ is methyl, or a salt thereof, reacting a compound of formula (VIII)

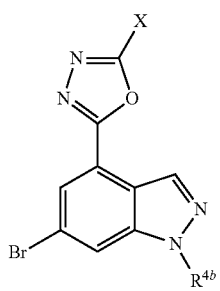

(VIII)

wherein X is as defined above and $R^{4b}$ is methyl, with a suitable boronic acid or boronate ester.

Methods of Use

The compounds of the invention are inhibitors of kinase activity, in particular PI3-kinase activity. Compounds which are PI3-kinase inhibitors may be useful in the treatment of disorders wherein the underlying pathology is (at least in part) attributable to inappropriate PI3-kinase activity, such as asthma and chronic obstructive pulmonary disease (COPD). "Inappropriate PI3-kinase activity" refers to any PI3-kinase activity that deviates from the normal PI3-kinase activity expected in a particular patient. Inappropriate PI3-kinase may take the form of, for instance, an abnormal increase in activity, or an aberration in the timing and or control of PI3-kinase activity. Such inappropriate activity may result then, for example, from overexpression or mutation of the protein kinase leading to inappropriate or uncontrolled activation. Accordingly, in another aspect the invention is directed to methods of treating such disorders.

Such disorders include respiratory diseases including asthma and chronic obstructive pulmonary disease (COPD); allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; cystic fibrosis; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trama), trigeminal neuralgia and Central pain.

The methods of treatment of the invention comprise administering a safe and effective amount of a compound of formula (I) or a pharmaceutically acceptable salt thereof to a patient in need thereof. Individual embodiments of the invention include methods of treating any one of the above-mentioned disorders by administering a safe and effective amount of a compound of formula (I) or a pharmaceutically acceptable salt thereof to a patient in need thereof.

As used herein, "treat" in reference to a disorder means: (1) to ameliorate or prevent the disorder or one or more of the biological manifestations of the disorder, (2) to interfere with (a) one or more points in the biological cascade that leads to or is responsible for the disorder or (b) one or more of the biological manifestations of the disorder, (3) to alleviate one or more of the symptoms or effects associated with the disorder, or (4) to slow the progression of the disorder or one or more of the biological manifestations of the disorder.

As indicated above, "treatment" of a disorder includes prevention of the disorder. The skilled artisan will appreciate that "prevention" is not an absolute term. In medicine, "prevention" is understood to refer to the prophylactic administration of a drug to substantially diminish the likelihood or severity of a disorder or biological manifestation thereof, or to delay the onset of such disorder or biological manifestation thereof.

As used herein, "safe and effective amount" in reference to a compound of formula (I) or a pharmaceutically acceptable salt thereof or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the disorder being treated; the severity of the disorder being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human (including adults and children) or other animal. In one embodiment, "patient" refers to a human.

The compounds of formula (I) or pharmaceutically acceptable salts thereof may be administered by any suitable route of administration, including both systemic administration and topical administration. Systemic administration includes oral administration, parenteral administration, transdermal administration and rectal administration. Parenteral administration refers to routes of administration other than enteral or transdermal, and is typically by injection or infusion. Parenteral administration includes intravenous, intramuscular, and subcutaneous injection or infusion. Topical administration includes application to the skin as well as intraocular, otic, intravaginal, inhaled and intranasal administration. Inhalation refers to administration into the patient's lungs whether inhaled through the mouth or through the nasal passages. In one embodiment, the compounds of formula (I) or pharmaceutically acceptable salts thereof may be administered orally. In another embodiment, the compounds of formula (I) or pharmaceutically acceptable salts thereof may be administered by inhalation. In a further embodiment, the compounds of formula (I) or pharmaceutically acceptable salts thereof may be administered intranasally.

The compounds of formula (I) or pharmaceutically acceptable salts thereof may be administered once or according to a dosing regimen wherein a number of doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for a compound of formula (I) or a pharmaceutically acceptable salt thereof depend on the pharmacokinetic properties of that compound, such as absorption, distribution, and half-life, which can be determined by the skilled artisan. In addition, suitable dosing regimens, including the duration such regimens are administered, for a compound of formula (I) or a pharmaceutically acceptable salt thereof depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical daily dosages for oral administration range from 0.001 mg to 50 mg per kg of total body weight, for example from 1 mg to 10 mg per kg of total body weight. For example, daily dosages for oral administration may be from 0.5 mg to 2 g per patient, such as 10 mg to 1 g per patient.

Additionally, the compounds of formula (I) may be administered as prodrugs. As used herein, a "prodrug" of a compound of formula (I) is a functional derivative of the compound which, upon administration to a patient, eventually liberates the compound of formula (I) in vivo. Administration of a compound of formula (I) as a prodrug may enable the skilled artisan to do one or more of the following: (a) modify the onset of the activity of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleavable in vivo. Such modifications, which include the preparation of phosphates, amides, esters, thioesters, carbonates, and carbamates, are well known to those skilled in the art.

The invention thus provides a method of treating a disorder mediated by inappropriate PI3-kinase activity comprising administering a safe and effective amount of a compound of formula (I) or a pharmaceutically acceptable salt thereof to a patient in need thereof.

In one embodiment, the disorder mediated by inappropriate PI3-kinase activity is selected from the group consisting of respiratory diseases (including asthma and chronic obstructive pulmonary disease (COPD)); allergic diseases (including allergic rhinitis and atopic dermatitis); autoimmune diseases (including rheumatoid arthritis and multiple sclerosis); inflammatory disorders (including inflammatory bowel disease); cardiovascular diseases (including thrombosis and atherosclerosis); hematologic malignancies; cystic fibrosis; neurodegenerative diseases; pancreatitis; multiorgan failure; kidney diseases; platelet aggregation; cancer; sperm motility; transplantation rejection; graft rejection; lung injuries; and pain (including pain associated with rheumatoid arthritis or osteoarthritis, back pain, general inflammatory pain, post hepatic neuralgia, diabetic neuropathy, inflammatory neuropathic pain (trama), trigeminal neuralgia and Central pain), In one embodiment, the disorder mediated by inappropriate PI3-kinase activity is a respiratory disease. In another embodiment, the disorder mediated by inappropriate PI3-kinase activity is asthma. In a further embodiment, the disorder mediated by inappropriate PI3-kinase activity is chronic obstructive pulmonary disease (COPD).

In one embodiment, the disorder mediated by inappropriate PI3-kinase activity is pain.

In one embodiment, the invention provides a compound of formula (I) or a pharmaceutically acceptable salt thereof for use in medical therapy. In another embodiment, the invention provides a compound of formula (I) or a pharmaceutically acceptable salt thereof for use in the treatment of a disorder mediated by inappropriate PI3-kinase activity. In a further embodiment, the invention provides the use of a compound of formula (I) or a pharmaceutically acceptable salt thereof in the manufacture of a medicament for use in the treatment of a disorder mediated by inappropriate PI3-kinase activity.

Compositions

The compounds of formula (I) and pharmaceutically acceptable salts thereof will normally, but not necessarily, be formulated into pharmaceutical compositions prior to administration to a patient. Accordingly, in another aspect the invention is directed to pharmaceutical compositions comprising a compound of formula (I) or a pharmaceutically acceptable salt thereof and one or more pharmaceutically-acceptable excipients. In a further aspect the invention is directed to pharmaceutical compositions for the treatment or prophylaxis of a disorder mediated by inappropriate PI3-kinase activity comprising a compound of formula (I) or a pharmaceutically acceptable salt thereof.

The pharmaceutical compositions of the invention may be prepared and packaged in bulk form wherein a safe and effective amount of a compound of formula (I) or a pharmaceutically acceptable salt thereof can be extracted and then given to the patient such as with powders or syrups. Alternatively, the pharmaceutical compositions of the invention may be prepared and packaged in unit dosage form wherein each physically discrete unit contains a compound of formula (I) or a pharmaceutically acceptable salt thereof. When prepared in unit dosage form, the pharmaceutical compositions of the invention typically may contain, for example, from 0.5 mg to 1 g, or from 1 mg to 700 mg, or from 5 mg to 100 mg of a compound of formula (I) or a pharmaceutically acceptable salt thereof.

The pharmaceutical compositions of the invention typically contain one compound of formula (I) or a pharmaceutically acceptable salt thereof.

As used herein, "pharmaceutically acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of formula (I) or a pharmaceutically acceptable salt thereof when administered to a patient and interactions which would result in pharmaceutical compositions that are not pharmaceutically acceptable are avoided. In addition, each excipient must of course be pharmaceutically-acceptable eg of sufficiently high purity.

The compound of formula (I) or a pharmaceutically acceptable salt thereof and the pharmaceutically acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of formula (I) or pharmaceutically acceptable salts thereof once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: Diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

Accordingly, in another aspect the invention is directed to process for the preparation of a pharmaceutical composition comprising a compound of formula (I) or a pharmaceutically acceptable salt thereof and one or more pharmaceutically acceptable excipients which comprises mixing the ingredients. A pharmaceutical composition comprising a compound of formula (I) or a pharmaceutically acceptable salt thereof may be prepared by, for example, admixture at ambient temperature and atmospheric pressure.

In one embodiment, the compounds of formula (I) or pharmaceutically acceptable salts thereof will be formulated for oral administration. In another embodiment, the compounds of formula (I) or pharmaceutically acceptable salts thereof will be formulated for inhaled administration. In a further embodiment, the compounds of formula (I) or pharmaceutically acceptable salts thereof will be formulated for intranasal administration.

In one aspect, the invention is directed to a solid oral dosage form such as a tablet or capsule comprising a safe and effective amount of a compound of formula (I) or a pharmaceutically acceptable salt thereof and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose.

The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as for example by coating or embedding particulate material in polymers, wax or the like.

The compounds of formula (I) or pharmaceutically acceptable salts thereof may also be coupled with soluble polymers as targetable drug carriers. Such polymers can include polyvinylpyrrolidone, pyran copolymer, polyhydroxypropyl-methacrylamide-phenol, polyhydroxyethylaspartamidephenol, or polyethyleneoxidepolylysine substituted with palmitoyl residues. Furthermore, the compounds of formula (I) or pharmaceutically acceptable salts thereof may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

In another aspect, the invention is directed to a liquid oral dosage form. Oral liquids such as solution, syrups and elixirs can be prepared in dosage unit form so that a given quantity contains a predetermined amount of a compound of formula (I) or a pharmaceutically acceptable salt thereof. Syrups can be prepared by dissolving the compound of formula (I) or a pharmaceutically acceptable salt thereof in a suitably flavored aqueous solution, while elixirs are prepared through the use of a non-toxic alcoholic vehicle. Suspensions can be formulated by dispersing the compound of formula (I) or a pharmaceutically acceptable salt thereof in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

In another aspect, the invention is directed to a dosage form adapted for administration to a patient by inhalation. For example, as a dry powder, an aerosol, a suspension, or a solution composition.

Dry powder compositions for delivery to the lung by inhalation typically comprise a compound of formula (I) or a pharmaceutically acceptable salt thereof as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (eg micronised) compound can be defined by a $D_{50}$ value of about 1 to about 10 microns (for example as measured using laser diffraction).

The dry powder may be administered to the patient via a reservoir dry powder inhaler (RDPI) having a reservoir suitable for storing multiple (un-metered doses) of medicament in dry powder form. RDPIs typically include a means for metering each medicament dose from the reservoir to a delivery position. For example, the metering means may comprise a metering cup, which is movable from a first position where the cup may be filled with medicament from the reservoir to a second position where the metered medicament dose is made available to the patient for inhalation.

Alternatively, the dry powder may be presented in capsules (e.g. gelatin or plastic), cartridges, or blister packs for use in a multi-dose dry powder inhaler (MDPI). MDPIs are inhalers wherein the medicament is comprised within a multi-dose pack containing (or otherwise carrying) multiple defined doses (or parts thereof) of medicament. When the dry powder is presented as a blister pack, it comprises multiple blisters for containment of the medicament in dry powder form. The blisters are typically arranged in regular fashion for ease of release of the medicament therefrom. For example, the blisters may be arranged in a generally circular fashion on a disc-form blister pack, or the blisters may be elongate in form, for example comprising a strip or a tape. Each capsule, cartridge, or blister may, for example, contain between 20 µg-10 mg of the compound of formula (I) or a pharmaceutically acceptable salt thereof.

Aerosols may be formed by suspending or dissolving a compound of formula (I) or a pharmaceutically acceptable salt thereof in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of formula (I) or a pharmaceutically acceptable salt thereof will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

There is thus provided as a further aspect of the invention a pharmaceutical aerosol formulation comprising a compound of formula (I) or a pharmaceutically acceptable salt thereof and a fluorocarbon or hydrogen-containing chlorofluorocarbon as propellant, optionally in combination with a surfactant and/or a cosolvent.

According to another aspect of the invention, there is provided a pharmaceutical aerosol formulation wherein the propellant is selected from 1,1,1,2-tetrafluoroethane, 1,1,1,2,3,3,3-heptafluoro-n-propane and mixtures thereof.

The formulations of the invention may be buffered by the addition of suitable buffering agents.

Capsules and cartridges for use in an inhaler or insufflator, of for example gelatine, may be formulated containing a powder mix for inhalation of a compound of formula (I) or a pharmaceutically acceptable salt thereof and a suitable powder base such as lactose or starch. Each capsule or cartridge may generally contain from 20 µg to 10 mg of the compound of formula (I) or pharmaceutically acceptable salt thereof. Alternatively, the compound of formula (I) or pharmaceutically acceptable salt thereof may be presented without excipients such as lactose.

The proportion of the active compound of formula (I) or pharmaceutically acceptable salt thereof in the local compositions according to the invention depends on the precise type of formulation to be prepared but will generally be within the range of from 0.001 to 10% by weight. Generally, for most types of preparations, the proportion used will be within the range of from 0.005 to 1%, for example from 0.01 to 0.5%. However, in powders for inhalation or insufflation the proportion used will normally be within the range of from 0.1 to 5%.

Aerosol formulations are preferably arranged so that each metered dose or "puff" of aerosol contains from 20 µg to 10 mg, preferably from 20 µg to 2000 µg, more preferably from about 20 µg to 500 µg of a compound of formula (I). Administration may be once daily or several times daily, for example 2, 3, 4 or 8 times, giving for example 1, 2 or 3 doses each time. The overall daily dose with an aerosol will be within the range from 100 µg to 10 mg, preferably from 200 µg to 2000 µg. The overall daily dose and the metered dose delivered by capsules and cartridges in an inhaler or insufflator will generally be double that delivered with aerosol formulations.

In the case of suspension aerosol formulations, the particle size of the particulate (e.g., micronised) drug should be such as to permit inhalation of substantially all the drug into the lungs upon administration of the aerosol formulation and will thus be less than 100 microns, desirably less than 20 microns, and in particular in the range of from 1 to 10 microns, such as from 1 to 5 microns, more preferably from 2 to 3 microns.

The formulations of the invention may be prepared by dispersal or dissolution of the medicament and a compound of formula (I) or a pharmaceutically acceptable salt thereof in the selected propellant in an appropriate container, for example, with the aid of sonication or a high-shear mixer. The process is desirably carried out under controlled humidity conditions.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The stability of the suspension aerosol formulations according to the invention may be measured by conventional techniques, for example, by measuring flocculation size distribution using a back light scattering instrument or by measuring particle size distribution by cascade impaction or by the "twin impinger" analytical process. As used herein reference to the "twin impinger" assay means "Determination of the deposition of the emitted dose in pressurised inhalations using apparatus A" as defined in British Pharmacopaeia 1988, pages A204-207, Appendix XVII C. Such techniques enable the "respirable fraction" of the aerosol formulations to be calculated. One method used to calculate the "respirable fraction" is by reference to "fine particle fraction" which is the amount of active ingredient collected in the lower impingement chamber per actuation expressed as a percentage of the total amount of active ingredient delivered per actuation using the twin impinger method described above.

The term "metered dose inhaler" or MDI means a unit comprising a can, a secured cap covering the can and a formulation metering valve situated in the cap. MDI system includes a suitable channelling device. Suitable channelling devices comprise for example, a valve actuator and a cylindrical or cone-like passage through which medicament may be delivered from the filled canister via the metering valve to the nose or mouth of a patient such as a mouthpiece actuator.

MDI canisters generally comprise a container capable of withstanding the vapour pressure of the propellant used such as a plastic or plastic-coated glass bottle or preferably a metal can, for example, aluminium or an alloy thereof which may optionally be anodised, lacquer-coated and/or plastic-coated (for example incorporated herein by reference WO96/32099 wherein part or all of the internal surfaces are coated with one or more fluorocarbon polymers optionally in combination with one or more non-fluorocarbon polymers), which container is closed with a metering valve. The cap may be secured onto the can via ultrasonic welding, screw fitting or crimping. MDIs taught herein may be prepared by methods of the art (e.g. see Byron, above and WO96/32099). Preferably the canister is fitted with a cap assembly, wherein a drug-metering valve is situated in the cap, and said cap is crimped in place.

In one embodiment of the invention the metallic internal surface of the can is coated with a fluoropolymer, more preferably blended with a non-fluoropolymer. In another embodiment of the invention the metallic internal surface of the can is coated with a polymer blend of polytetrafluoroethylene (PTFE) and polyethersulfone (PES). In a further embodiment of the invention the whole of the metallic internal surface of the can is coated with a polymer blend of polytetrafluoroethylene (PTFE) and polyethersulfone (PES).

The metering valves are designed to deliver a metered amount of the formulation per actuation and incorporate a gasket to prevent leakage of propellant through the valve. The gasket may comprise any suitable elastomeric material such as, for example, low density polyethylene, chlorobutyl, bromobutyl, EPDM, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK357) and 3M-Neotechnic Ltd, UK (e.g. Spraymiser™).

In various embodiments, the MDIs may also be used in conjunction with other structures such as, without limitation, overwrap packages for storing and containing the MDIs, including those described in U.S. Pat. Nos. 6,119,853; 6,179,118; 6,315,112; 6,352,152; 6,390,291; and 6,679,374, as well as dose counter units such as, but not limited to, those described in U.S. Pat. Nos. 6,360,739 and 6,431,168.

Conventional bulk manufacturing methods and machinery well known to those skilled in the art of pharmaceutical aerosol manufacture may be employed for the preparation of large-scale batches for the commercial production of filled canisters. Thus, for example, in one bulk manufacturing method for preparing suspension aerosol formulations a metering valve is crimped onto an aluminium can to form an empty canister. The particulate medicament is added to a charge vessel and liquefied propellant together with the optional excipients is pressure filled through the charge vessel into a manufacturing vessel. The drug suspension is mixed before recirculation to a filling machine and an aliquot of the drug suspension is then filled through the metering valve into the canister. In one example bulk manufacturing method for preparing solution aerosol formulations a metering valve is crimped onto an aluminium can to form an empty canister. The liquefied propellant together with the optional excipients and the dissolved medicament is pressure filled through the charge vessel into a manufacturing vessel.

In an alternative process, an aliquot of the liquefied formulation is added to an open canister under conditions which are sufficiently cold to ensure the formulation does not vaporise, and then a metering valve crimped onto the canister.

Typically, in batches prepared for pharmaceutical use, each filled canister is check-weighed, coded with a batch number and packed into a tray for storage before release testing.

Suspensions and solutions comprising a compound of formula (I) or a pharmaceutically acceptable salt thereof may also be administered to a patient via a nebulizer. The solvent or suspension agent utilized for nebulization may be any pharmaceutically-acceptable liquid such as water, aqueous saline, alcohols or glycols, e.g., ethanol, isopropylalcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically-acceptable excipients may be added to the suspension or solution. The compound of formula (I) or pharmaceutically acceptable salt thereof may be stabilized by the addition of an inorganic acid, e.g., hydrochloric acid, nitric acid, sulphuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of formula (I) or pharmaceutically acceptable salt thereof. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

In a further aspect, the invention is directed to a dosage form adapted for intranasal administration.

Formulations for administration to the nose may include pressurised aerosol formulations and aqueous formulations administered to the nose by pressurised pump. Formulations which are non-pressurised and adapted to be administered topically to the nasal cavity are of particular interest. Suitable formulations contain water as the diluent or carrier for this purpose. Aqueous formulations for administration to the lung or nose may be provided with conventional excipients such as buffering agents, tonicity modifying agents and the like. Aqueous formulations may also be administered to the nose by nebulisation.

The compounds of formula (I) or pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO05/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. In one embodiment, the fluid dispenser is of the general type illustrated in FIGS. 30-40 of WO05/044354.

Pharmaceutical compositions adapted for intranasal administration wherein the carrier is a solid include a coarse powder having a particle size for example in the range 20 to 500 microns which is administered by rapid inhalation through the nasal passage from a container of the powder held close up to the nose. Suitable compositions wherein the carrier is a liquid, for administration as a nasal spray or as nasal drops, include aqueous or oil solutions of the compound of formula (I) or a pharmaceutically acceptable salt thereof.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Topical preparations may be administered by one or more applications per day to the affected area; over skin areas occlusive dressings may advantageously be used. Continuous or prolonged delivery may be achieved by an adhesive reservoir system.

For treatments of the eye or other external tissues, for example mouth and skin, the compositions may be applied as a topical ointment or cream. When formulated in an ointment, the compound of formula (I) or a pharmaceutically acceptable salt thereof may be employed with either a paraffinic or a water-miscible ointment base. Alternatively, the compound of formula (I) or pharmaceutically acceptable salt thereof may be formulated in a cream with an oil-in-water cream base or a water-in-oil base.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The compound and pharmaceutical formulations according to the invention may be used in combination with or include one or more other therapeutic agents, for example selected from anti-inflammatory agents, anticholinergic agents (particularly an $M_1/M_2/M_3$ receptor antagonist), $\beta_2$-adrenoreceptor agonists, antiinfective agents, such as antibiotics or antivirals, or antihistamines. The invention thus provides, in a further aspect, a combination comprising a compound of formula (I) or a pharmaceutically acceptable salt thereof together with one or more other therapeutically active agents, for example selected from an anti-inflammatory agent, such as a corticosteroid or an NSAID, an anticholinergic agent, a $\beta_2$-adrenoreceptor agonist, an antiinfective agent, such as an antibiotic or an antiviral, or an antihistamine. One embodiment of the invention encompasses combinations comprising a compound of formula (I) or a pharmaceutically acceptable salt thereof together with a $\beta_2$-adrenoreceptor agonist, and/or an anticholinergic, and/or a PDE-4 inhibitor, and/or an antihistamine.

Certain compounds of the invention may show selectivity for PI3Kδ over other PI3-kinases. The invention thus provides, in a further aspect, a combination comprising a compound of formula (I) or a pharmaceutically acceptable salt thereof which is selective for PI3Kδ together with a compound or pharmaceutically acceptable salt thereof which is selective for another PI3-kinase, for example PI3Kγ.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimise the activity and/or stability and/or physical characteristics, such as solubility, of the therapeutic ingredient. It will be clear also that, where appropriate, the therapeutic ingredients may be used in optically pure form.

In one embodiment, the invention encompasses a combination comprising a compound of formula (I) or a pharmaceutically acceptable salt thereof together with a $\beta_2$-adrenoreceptor agonist.

Examples of $\beta_2$-adrenoreceptor agonists include salmeterol (which may be a racemate or a single enantiomer such as the R-enantiomer), salbutamol (which may be a racemate or a single enantiomer such as the R-enantiomer), formoterol (which may be a racemate or a single duastereomer such as the R,R-diastereomer), salmefamol, fenoterol carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt or free base of salbutamol or the fumarate salt of formoterol. In one embodiment, long-acting $\beta_2$-adrenoreceptor agonists, for example, compounds which provide effective bronchodilation for about 12 hrs or longer, are preferred.

Other $\beta_2$-adrenoreceptor agonists include those described in WO 02/066422, WO 02/070490, WO 02/076933, WO 03/024439, WO 03/072539, WO 03/091204, WO 04/016578, WO 2004/022547, WO 2004/037807, WO 2004/037773, WO 2004/037768, WO 2004/039762, WO 2004/039766, WO01/42193 and WO03/042160.

Examples of $\beta_2$-adrenoreceptor agonists include:
3-(4-{[6-({(2R)-2-hydroxy-2-[4-hydroxy-3-(hydroxymethyl)phenyl]ethyl}amino) hexyl]oxy}butyl)benzenesulfonamide;
3-(3-{[7-({(2R)-2-hydroxy-2-[4-hydroxy-3-hydroxymethyl)phenyl]ethyl}-amino) heptyl]oxy}propyl)benzenesulfonamide;
4-{(1R)-2-[(6-{2-[(2,6-dichlorobenzyl)oxy]ethoxy}hexyl) amino]-1-hydroxyethyl}-2-(hydroxymethyl)phenol;
4-{(1R)-2-[(6-{4-[3-(cyclopentylsulfonyl)phenyl] butoxy}hexyl)amino]-1-hydroxyethyl}-2-(hydroxymethyl)phenol;
N-[2-hydroxyl-5-[(1R)-1-hydroxy-2-[[2-4-[[(2R)-2-hydroxy-2-phenylethyl]amino]phenyl]ethyl]amino]ethyl] phenyl]formamide;
N-2{2-[4-(3-phenyl-4-methoxyphenyl)aminophenyl]ethyl}-2-hydroxy-2-(8-hydroxy-2(1H)-quinolinon-5-yl)ethylamine; and
5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

The $\beta_2$-adrenoreceptor agonist may be in the form of a salt formed with a pharmaceutically acceptable acid selected from sulphuric, hydrochloric, fumaric, hydroxynaphthoic (for example 1- or 3-hydroxy-2-naphthoic), cinnamic, substituted cinnamic, triphenylacetic, sulphamic, sulphanilic, naphthaleneacrylic, benzoic, 4-methoxybenzoic, 2- or 4-hydroxybenzoic, 4-chlorobenzoic and 4-phenylbenzoic acid.

Suitable anti-inflammatory agents include corticosteroids. Suitable corticosteroids which may be used in combination with the compounds of formula (I) or pharmaceutically acceptable salts thereof are those oral and inhaled corticosteroids and their pro-drugs which have anti-inflammatory activity. Examples include methyl prednisolone, prednisolone, dexamethasone, fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate), 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester, beclomethasone esters (for example the 17-propionate ester or the 17,21-dipropionate ester), budesonide, flunisolide, mometasone esters (for example mometasone furoate), triamcinolone acetonide, rofleponide, ciclesonide (16α,17-[[(R)-cyclohexylmethylene]bis(oxy)]-11β,21-dihydroxy-pregna-1,4-diene-3,20-dione), butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester. In one embodiment the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Examples of corticosteroids may include those described in WO2002/088167, WO2002/100879, WO2002/12265, WO2002/12266, WO2005/005451, WO2005/005452, WO2006/072599 and WO2006/072600.

Non-steroidal compounds having glucocorticoid agonism that may possess selectivity for transrepression over transactivation and that may be useful in combination therapy include those covered in the following patents: WO03/082827, WO98/54159, WO04/005229, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651 and WO03/08277. Further non-steroidal compounds are covered in: WO2006/000401, WO2006/000398 and WO2006/015870.

Examples of anti-inflammatory agents include non-steroidal anti-inflammatory drugs (NSAID's).

Examples of NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example montelukast), iNOS inhibitors, tryptase and elastase inhibitors, beta-2 integrin antagonists and adenosine receptor agonists or antagonists (e.g. adenosine 2a agonists), cytokine antagonists (for example chemokine antagonists, such as a CCR3 antagonist) or inhibitors of cytokine synthesis, or 5-lipoxygenase inhibitors. An iNOS (inducible nitric oxide synthase inhibitor) is preferably for oral administration. Examples of iNOS inhibitors include those disclosed in WO93/13055, WO98/30537, WO02/50021, WO95/34534 and WO99/62875. Examples of CCR3 inhibitors include those disclosed in WO02/26722.

In one embodiment, the invention provides the use of the compounds of formula (I) in combination with a phosphodiesterase 4 (PDE4) inhibitor, especially in the case of a formulation adapted for inhalation. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Compounds include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl) cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 3 Sep. 1996; this patent and the compounds it discloses are incorporated herein in full by reference.

Other compounds include AWD-12-281 from Elbion (Hofgen, N. et al. 15th EFMC Int Symp Med Chem (September 6-10, Edinburgh) 1998, Abst P. 98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further compounds are disclosed in the published international patent application WO04/024728 (Glaxo Group Ltd), WO04/056823 (Glaxo Group Ltd) and WO04/103998 (Glaxo Group Ltd) (e.g. Example 399 or 544 disclosed therein). Further compounds are also disclosed in WO2005/058892, WO2005/090348, WO2005/090353, and WO2005/090354, all in the name of Glaxo Group Limited.

Examples of anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Exemplary compounds for administration via inhalation include ipratropium (for example, as the bromide, CAS 22254-24-6, sold under the name Atrovent), oxitropium (for example, as the bromide, CAS 30286-75-0) and tiotropium (for example, as the bromide, CAS 136310-93-5, sold under the name Spiriva). Also of interest are revatropate (for example, as the hydrobromide, CAS 262586-79-8) and LAS-34273 which is disclosed in WO01/04118. Exemplary compounds for oral administration include pirenzepine (CAS 28797-61-7), darifenacin (CAS 133099-04-4, or CAS 133099-07-7 for the hydrobromide sold under the name Enablex), oxybutynin (CAS 5633-20-5, sold under the name Ditropan), terodiline (CAS 15793-40-5), tolterodine (CAS 124937-51-5, or CAS 124937-52-6 for the tartrate, sold under the name Detrol), otilonium (for example, as the bromide, CAS 26095-59-0, sold under the name Spasmomen), trospium chloride (CAS 10405-02-4) and solifenacin (CAS 242478-37-1, or CAS 242478-38-2 for the succinate also known as YM-905 and sold under the name Vesicare).

Additional compounds are disclosed in WO 2005/037280, WO 2005/046586 and WO 2005/104745, incorporated herein by reference. The present combinations include, but are not limited to:

(3-endo)-3-(2,2-di-2-thienylethenyl)-8,8-dimethyl-8-azoniabicyclo[3.2.1]octane iodide;

(3-endo)-3-(2-cyano-2,2-diphenylethyl)-8,8-dimethyl-8-azoniabicyclo[3.2.1]octane bromide;

4-[hydroxy(diphenyl)methyl]-1-{2-[(phenylmethyl)oxy]ethyl}-1-azoniabicyclo[2.2.2]octane bromide; and (1R,5S)-3-(2-cyano-2,2-diphenylethyl)-8-methyl-8-{2-[(phenylmethyl)oxy]ethyl}-8-azoniabicyclo[3.2.1]octane bromide.

Other anticholinergic agents include compounds which are disclosed in U.S. patent application 60/487,981 including, for example:

(3-endo)-3-(2,2-di-2-thienylethenyl)-8,8-dimethyl-8-azoniabicyclo[3.2.1]octane bromide;

(3-endo)-3-(2,2-diphenylethenyl)-8,8-dimethyl-8-azoniabicyclo[3.2.1]octane bromide;

(3-endo)-3-(2,2-diphenylethenyl)-8,8-dimethyl-8-azoniabicyclo[3.2.1]octane 4-methylbenzenesulfonate;

(3-endo)-8,8-dimethyl-3-[2-phenyl-2-(2-thienyl)ethenyl]-8-azoniabicyclo[3.2.1]octane bromide; and/or (3-endo)-8,8-dimethyl-3-[2-phenyl-2-(2-pyridinyl)ethenyl]-8-azoniabicyclo[3.2.1]octane bromide.

Further anticholinergic agents include compounds which are disclosed in U.S. patent application 60/511,009 including, for example:

(endo)-3-(2-methoxy-2,2-di-thiophen-2-yl-ethyl)-8,8-dimethyl-8-azonia-bicyclo[3.2.1]octane iodide;

3-((endo)-8-methyl-8-aza-bicyclo[3.2.1]oct-3-yl)-2,2-diphenyl-propionitrile;

(endo)-8-methyl-3-(2,2,2-triphenyl-ethyl)-8-aza-bicyclo [3.2.1]octane;

3-((endo)-8-methyl-8-aza-bicyclo[3.2.1]oct-3-yl)-2,2-diphenyl-propionamide;

3-((endo)-8-methyl-8-aza-bicyclo[3.2.1]oct-3-yl)-2,2-diphenyl-propionic acid;

(endo)-3-(2-cyano-2,2-diphenyl-ethyl)-8,8-dimethyl-8-azonia-bicyclo[3.2.1]octane iodide;

(endo)-3-(2-cyano-2,2-diphenyl-ethyl)-8,8-dimethyl-8-azonia-bicyclo[3.2.1]octane bromide;

3-((endo)-8-methyl-8-aza-bicyclo[3.2.1]oct-3-yl)-2,2-diphenyl-propan-1-ol;

N-benzyl-3-((endo)-8-methyl-8-aza-bicyclo[3.2.1]oct-3-yl)-2,2-diphenyl-propionamide;

(endo)-3-(2-carbamoyl-2,2-diphenyl-ethyl)-8,8-dimethyl-8-azonia-bicyclo[3.2.1]octane iodide;

1-benzyl-3-[3-((endo)-8-methyl-8-aza-bicyclo[3.2.1]oct-3-yl)-2,2-diphenyl-propyl]-urea;

1-ethyl-3-[3-((endo)-8-methyl-8-aza-bicyclo[3.2.1]oct-3-yl)-2,2-diphenyl-propyl]-urea;

N-[3-((endo)-8-methyl-8-aza-bicyclo[3.2.1]oct-3-yl)-2,2-diphenyl-propyl]-acetamide;

N-[3-((endo)-8-methyl-8-aza-bicyclo[3.2.1]oct-3-yl)-2,2-diphenyl-propyl]-benzamide;

3-((endo)-8-methyl-8-aza-bicyclo[3.2.1]oct-3-yl)-2,2-di-thiophen-2-yl-propionitrile;

(endo)-3-(2-cyano-2,2-di-thiophen-2-yl-ethyl)-8,8-dimethyl-8-azonia-bicyclo[3.2.1]octane iodide;

N-[3-((endo)-8-methyl-8-aza-bicyclo[3.2.1]oct-3-yl)-2,2-diphenyl-propyl]-benzenesulfonamide;
[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-methanesulfonamide; and/or
(endo)-3-{2,2-diphenyl-3-[(1-phenyl-methanoyl)-amino]-propyl}-8,8-dimethyl-8-azonia-bicyclo[3.2.1]octane bromide.

Further compounds include:
(endo)-3-(2-methoxy-2,2-di-thiophen-2-yl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
(endo)-3-(2-carbamoyl-2,2-diphenyl-ethyl)-8,8-dimethyl-8-azonia-bicyclo[3.2.1]octane iodide;
(endo)-3-(2-cyano-2,2-di-thiophen-2-yl-ethyl)-8,8-dimethyl-8-azonia-bicyclo[3.2.1]octane iodide; and/or
(endo)-3-{2,2-diphenyl-3-[(1-phenyl-methanoyl)-amino]-propyl}-8,8-dimethyl-8-azonia-bicyclo[3.2.1]octane bromide.

In one embodiment the invention provides a combination comprising a compound of formula (I) or a pharmaceutically acceptable salt thereof together with an H1 antagonist. Examples of H1 antagonists include, without limitation, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine. In a further embodiment the invention provides a combination comprising a compound of formula (I) or a pharmaceutically acceptable salt thereof together with an H3 antagonist (and/or inverse agonist). Examples of H3 antagonists include, for example, those compounds disclosed in WO2004/035556 and in WO2006/045416. Other histamine receptor antagonists which may be used in combination with the compounds of the present invention include antagonists (and/or inverse agonists) of the H4 receptor, for example, the compounds disclosed in Jablonowski et al., *J. Med. Chem.* 46:3957-3960 (2003).

The invention thus provides, in a further aspect, a combination comprising a compound of formula (I) or a pharmaceutically acceptable salt thereof together with a PDE4 inhibitor.

The invention thus provides, in a further aspect, a combination comprising a compound of formula (I) or a pharmaceutically acceptable salt thereof together with a $\beta_2$-adrenoreceptor agonist.

The invention thus provides, in a further aspect, a combination comprising a compound of formula (I) or a pharmaceutically acceptable salt thereof together with a corticosteroid.

The invention thus provides, in a further aspect, a combination comprising a compound of formula (I) or a pharmaceutically acceptable salt thereof together with a non-steroidal GR agonist.

The invention thus provides, in a further aspect, a combination comprising a compound of formula (I) or a pharmaceutically acceptable salt thereof together with an anticholinergic.

The invention thus provides, in a further aspect, a combination comprising a compound of formula (I) or a pharmaceutically acceptable salt thereof together with an antihistamine.

The invention thus provides, in a further aspect, a combination comprising a compound of formula (I) or a pharmaceutically acceptable salt thereof together with a PDE4 inhibitor and a $\beta_2$-adrenoreceptor agonist.

The invention thus provides, in a further aspect, a combination comprising a compound of formula (I) or a pharmaceutically acceptable salt thereof together with an anticholinergic and a PDE-4 inhibitor.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The individual compounds of such combinations may be administered either sequentially or simultaneously in separate or combined pharmaceutical formulations. In one embodiment, the individual compounds will be administered simultaneously in a combined pharmaceutical formulation. Appropriate doses of known therapeutic agents will readily be appreciated by those skilled in the art.

The invention thus provides, in a further aspect, a pharmaceutical composition comprising a combination of a compound of formula (I) or a pharmaceutically acceptable salt thereof together with another therapeutically active agent.

The invention thus provides, in a further aspect, a pharmaceutical composition comprising a combination of a compound of formula (I) or a pharmaceutically acceptable salt thereof together with a PDE4 inhibitor.

The invention thus provides, in a further aspect, a pharmaceutical composition comprising a combination of a compound of formula (I) or a pharmaceutically acceptable salt thereof together with a $\beta_2$-adrenoreceptor agonist.

The invention thus provides, in a further aspect, a pharmaceutical composition comprising a combination of a compound of formula (I) or a pharmaceutically acceptable salt thereof together with a corticosteroid.

The invention thus provides, in a further aspect, a pharmaceutical composition comprising a combination of a compound of formula (I) or a pharmaceutically acceptable salt thereof together with a non-steroidal GR agonist.

The invention thus provides, in a further aspect, a pharmaceutical composition comprising a combination of a compound of formula (I) or a pharmaceutically acceptable salt thereof together with an anticholinergic.

The invention thus provides, in a further aspect, a pharmaceutical composition comprising a combination of a compound of formula (I) or a pharmaceutically acceptable salt thereof together with an antihistamine.

The invention thus provides, in a further aspect, a pharmaceutical composition comprising a combination of a compound of formula (I) or a pharmaceutically acceptable salt thereof together with a PDE4 inhibitor and a $\beta_2$-adrenoreceptor agonist.

The invention thus provides, in a further aspect, a pharmaceutical composition comprising a combination of a compound of formula (I) or a pharmaceutically acceptable salt thereof together with an anticholinergic and a PDE4 inhibitor.

The invention will now be illustrated by way of the following non-limiting examples.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

When the name of a commercial supplier is given after the name of a compound or a reagent, for instance "compound X (Aldrich)" or "compound X/Aldrich", this means that compound X is obtainable from a commercial supplier, such as the commercial supplier named. If not referenced herein the compound or reagent can be purchased from a standard supplier such as Sigma Aldrich, Lancaster, Fluorochem, TCI etc.

Similarly, when a literature or a patent reference is given after the name of a compound, for instance compound Y (EP 0 123 456), this means that the preparation of the compound is described in the named reference.

The names of the Examples have been obtained using a compound naming programme which matches structure to name (e.g. ACD/Name Batch v 9.0).

General Experimental Details
Liquid Chromatography Mass Spectroscopy (LCMS) Methods LCMS analysis has been carried out using one of the methods listed below.
Method A
LCMS instrumentation consists of the following:
Column: Acquity HPLC BEH $C_{18}$ 1.7 μm 2.1 mm×50 mm.
Column oven set to 40 degrees centigrade
Solvent A: Water 0.1% Formic Acid+10 mM Ammonium Acetate
Solvent B: MeCN:Water 95:5+0.05% Formic Acid
Injection volume: 0.5 μl
Injection technique: Partial loop overfill
UV detection: 220 to 330 nm
UV sampling rate: 40 points per second
MS scan range: 100 to 1000 amu
MS scanning rate: 0.2 second scan with a 0.1 second inter scan delay
MS scan function: Electrospray with pos neg switching
Cycle time: 2 minutes and 30 seconds
Gradient:

| Time | Flow ml/min | % A | % B |
| --- | --- | --- | --- |
| 0 | 1 | 97 | 3 |
| 0.1 | 1 | 97 | 3 |
| 1.4 | 1 | 0 | 100 |
| 1.9 | 1 | 0 | 100 |
| 2 | 1 | 97 | 3 |

Method B
The HPLC analysis was conducted on a Sunfire C18 column (30 mm×4.6 mm i.d. 3.5 μm packing diameter) at 30 degrees centigrade.
Solvent A=0.1% v/v solution of Formic Acid in Water.
Solvent B=0.1% v/v solution of Formic Acid in Acetonitrile.

The gradient employed was:

| Time (min) | Flow Rate (ml/min) | % A | % B |
| --- | --- | --- | --- |
| 0 | 3 | 97 | 3 |
| 0.1 | 3 | 97 | 3 |
| 4.2 | 3 | 0 | 100 |
| 4.8 | 3 | 0 | 100 |
| 4.9 | 3 | 97 | 3 |
| 5.0 | 3 | 97 | 3 |

The UV detection was an averaged signal from wavelength of 210 nm to 350 nm and mass spectra were recorded on a mass spectrometer using alternate-scan positive and negative mode electrospray ionization.
Mass Directed Automated Preparative HPLC Methods
The methods for the mass-directed automated preparative HPLC used for the purification of compounds are described below:
Method A
Column
The column used is typically a Supelco LCABZ++ column whose dimensions are 20 mm internal diameter by 100 mm in length. The stationary phase particle size is 5 μm.
Solvents
A:. Aqueous solvent=Water+0.1% Formic Acid
B:. Organic solvent=MeCN:Water 95:5+0.05% Formic Acid
Make up solvent=MeOH:Water 80:20+50 mMol Ammonium Acetate
Needle rinse solvent=MeOH: Water:DMSO 80:10:10
Methods
There are five methods used depending on the analytical retention time of the compound of interest.
They all have a 15-minute runtime, which comprises of a 10-minute gradient followed by a 5-minute column flush and re-equilibration step.
MDP 1.5-2.2=0-30% B
MDP 2.0-2.8=5-30% B
MDP 2.5-3.0=15-55% B
MDP 2.8-4.0=30-80% B
MDP 3.8-5.5=50-90% B
Flow Rate
All of the above methods have a flow rate of 20 ml/min
It is thought that basic compounds isolated by this method are formate salts.
Method B
Columns
Small Scale Prep Column
Supelcosil ABZ+Plus column whose dimensions are 21.2 mm internal diameter by 100 mm in length. The stationary phase particle size is 5 μm.
Large Scale Prep Column
Supelcosil ABZ+Plus column whose dimensions are 30.0 mm internal diameter by 150 mm in length. The stationary phase particle size is 12 μm.
Solvents
A: Aqueous solvent=Water+0.1% Formic Acid
B: Organic solvent=MeCN:Water 95:5+0.05% Formic Acid
Make up solvent to ZQ=MeOH:Water 80:20+50 mMol Ammonium Acetate
2767 Needle rinse solvent=MeOH: Water:DMSO 80:10:10
Methods for Small Scale Prep for Up to 30 mg
There are ten methods available for use. The choice of method is dependant on the analytical retention time of the compound of interest (MDP=retention time as determined by LCMS Method A above).
Five methods have a 15-minute runtime, this comprises of a 10-minute gradient followed by a 5-minute column flush and re-equilibration step. The other five have a 25-minute runtime. Here the methods have the same starting and end points for the organic content of B but the gradients have been extended over a 20-minute period to provide greater chromatographic resolution.

MDP 1.5-2.2=00-30% B
MDP 2.0-2.8=10-40% B
MDP 2.5-3.0=15-55% B
MDP 2.8-4.0=30-80% B
MDP 3.8-5.5=60-90% B

Flow rates for the above methods are 20 ml/min
Methods for Large Scale Prep for Up to 90 mgs Due to the different column dimension and the phase particle size the percentage organic content varies slightly to the small scale methods. As for small scale there are ten methods available for use. The choice of method is dependant on the analytical retention time of the compound of interest interest (MDP=retention time as determined by LCMS Method A above).

Five methods have a 15-minute runtime, which comprises of a 10-minute gradient followed by a 5-minute column flush and re-equilibration step. The other five have a 25-minute runtime. Here the methods have the same starting and end points for the organic content of B but the gradients have been extended over a 20-minute period to provide greater chromatographic resolution.

MDP 1.5-2.2=00-30% B
MDP 2.0-2.8=10-40% B
MDP 2.5-3.0=25-55% B
MDP 2.8-4.0=40-75% B
MDP 3.8-5.5=60-90% B

Flow rates for the above methods are 40 ml/min

It is thought that basic compounds isolated by this method are formate salts.

Method C

Column details: Zorbax Eclipse XDB-C18 prep HT (dimensions 212×100 mm, 5 um packing)

Software/hardware: Agilent 1100 series LC/MSD hardware, chemstation 32 purification software. Collects on uv/mass ion trigger Solvents:
A=0.1% v/v solution of Trifluoroacetic Acid in Water.
B=0.1% v/v solution of Trifluoroacetic Acid in Acetonitrile.
20 ml/min solvent speed, gradient elution:
1 min 90% Water (0.1% TFA):10% MECN (0.1% TFA) increasing over 9 mins to 5% Water (0.1% TFA):95% MECN (0.1% TFA) to elute compounds.

Method D

Column Details: XBRIDGE C18 column (100 mm×19 mm id 5 uM packing diameter)

Solvents
A=10 mM ammonium bicarbonate in water adjusted to pH 10 with aq. ammonia solution
B=Acetonitrile The UV detection was an averaged signal from wavelength of 210 nm to 350 nm and mass spectra were recorded on a mass spectrometer using an alternate-scan positive and negative mode electrospray ionization.

Method E—High pH

Column Details: Waters_XBRIDGE Prep C18 column 5 um OBD (19×100 mm)

The solvents employed were:
A=10 mM Ammonium Bicarbonate in water adjusted to pH 10 with aq. Ammonia solution
B=Acetonitrile+0.1% aq. Ammonia Collection was triggered by uv, ms or a combination of the two. The UV detection was at a selected wavelength generally 230 nm, 210 nm or 254 nm. Mass spectra were recorded on a mass spectrometer using an alternate-scan positive and negative mode electrospray ionization.

Collection was triggered by uv, ms or a combination of the two.

The UV detection was at a selected wavelength generally 230 nm, 210 nm or 254 nm. Mass spectra were recorded on a mass spectrometer using an alternate-scan positive and negative mode electrospray ionization.

Method F—Low pH

Column Details: SUNFIRE C18 column (100 mm×19 mm id 5 uM packing diameter)

The solvents employed were:
A=0.1% v/v solution of Trifluoroacetic Acid in Water.
B=0.1% v/v solution of Trifluoroacetic Acid in Acetonitrile.

Collection was triggered by uv, ms or a combination of the two.

The UV detection was at a selected wavelength generally 230 nm, 210 nm or 254 nm. Mass spectra were recorded on a mass spectrometer using an alternate-scan positive and negative mode electrospray ionization.

Method G

The HPLC purification was conducted on a Sunfire C18 column (100 mm×19 mm i.d. 5 μm packing diameter) at ambient temperature.

The solvents employed were:
A=0.1% v/v solution of Formic Acid in Water.
B=0.1% v/v solution of Formic Acid in Acetonitrile.

The gradient employed was:

| Time (min) | Flow Rate (ml/min) | % A | % B |
| --- | --- | --- | --- |
| 0 | 20 | 85 | 15 |
| 1 | 20 | 85 | 15 |
| 10 | 20 | 45 | 55 |
| 10.5 | 20 | 1 | 99 |
| 15 | 20 | 1 | 99 |

The UV detection was an averaged signal from wavelength of 210 nm to 350 nm.

Intermediates and Examples

Intermediate 1

6-Bromo-1-[(4-methylphenyl)sulfonyl]-1H-indazole-4-carbonitrile

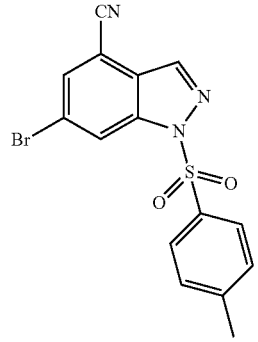 [SMILES: Cc1ccc(S(=O)(=O)n2ncc3c(C#N)cc(Br)cc32)cc1]

Sodium hydride (0.108 g, 4.50 mmol) was added to a stirred solution of 6-bromo-1H-indazole-4-carbonitrile (0.5 g, 2.252 mmol) in N,N-dimethylformamide (10 ml) at room temperature. The mixture was stirred at room temperature for 10 mins when p-toluenesulphonyl chloride (0.558 g, 2.93 mmol) was then added. The pale yellow suspension was stirred for 20 mins at room temperature. The mixture was poured into stirring water (100 ml) and the precipitated product collected by filtration. The cream coloured solid was dried in vacuo at 65° C. to give the title compound (0.794 g).
LCMS (Method B): Rt 3.38 mins, MH+377.8.

Intermediate 2a

6-Bromo-1-[(4-methylphenyl)sulfonyl]-4-(1H-tetrazol-5-yl)-1H-indazole

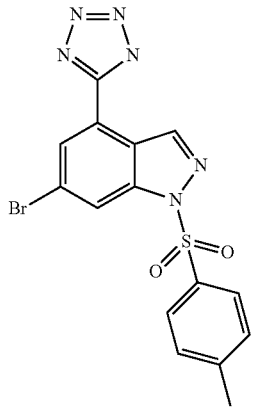 [SMILES: Cc1ccc(S(=O)(=O)n2ncc3c(-c4nnn[nH]4)cc(Br)cc32)cc1]

A stirred solution of 6-bromo-1-[(4-methylphenyl)sulfonyl]-1H-indazole-4-carbonitrile (0.79 g, 2.1 mmol), trimethylsilyl azide (0.484 g, 4.20 mmol) and dibutyltin oxide (0.105 g, 0.420 mmol) in toluene (10 ml) was heated at 110° C. for 1 h in the microwave (biotage initiator). The resulting cream coloured solid was collected by filtration, washed with toluene and dried in vacuo at 65° C. to give the title compound as a near colourless solid (0.3 g). The mother liquor was evaporated and the residue triturated with cyclohexane (10 ml) to give a further quantity of the title compound as a pale yellow solid (0.38 g).
LCMS (Method B): Rt 3.48 mins, MH$^+$ 420.

Intermediate 2b 6-bromo-1-(phenylsulfonyl)-4-(1H-tetrazol-5-yl)-1H-indazole

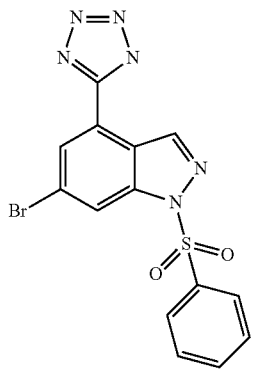 [SMILES: O=S(=O)(c1ccccc1)n1ncc2c(-c3nnn[nH]3)cc(Br)cc21]

To 6-Bromo-1-(phenylsulfonyl)-1H-indazole-4-carbonitrile (18.34 g, 50.6 mmol) in toluene (700 ml) was added dibutyl(oxo)stannane (2.52 g, 10.13 mmol) and trimethylsilyl azide (13.32 ml, 101 mmol) over 2 mins. The mixture was stirred at 110° C., under nitrogen for 4 h. The reaction was cooled, then evaporated to solid and dried under vacuum overnight. The solid was triturated with diethyl ether (50 ml) and ground up then filtered under vacuum to give a beige solid (18.07 g). This solid was re-combined with the filtrate, triturated in methanol (45 ml), filtered and washed with methanol to give a pale peach solid. This was re-combined with the filtrate and stirred in methanol (300 ml) for ~20 mins, then filtered to give the title compound as a pale peach solid (17.9 g).
LCMS (Method A): Rt 1.16 mins, MH+ 407.

Intermediate 3a

6-Bromo-4-[5-(chloromethyl)-1,3,4-oxadiazol-2-yl]-1-[(4-methylphenyl)sulfonyl]-1H-indazole

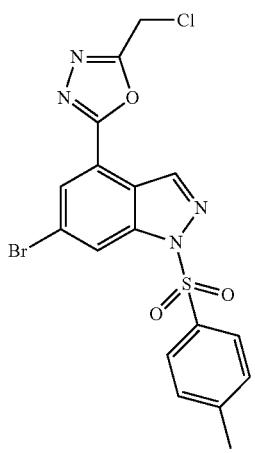 [SMILES: Cc1ccc(S(=O)(=O)n2ncc3c(-c4nnc(CCl)o4)cc(Br)cc32)cc1]

A stirred mixture of 6-bromo-1-[(4-methylphenyl)sulfonyl]-4-(1H-tetrazol-5-yl)-1H-indazole (0.237 g, 0.565 mmol) and chloroacetyl chloride (0.136 ml, 1.696 mmol) in toluene (3 ml) was heated at 130° C. in the microwave (biotage initiator) for 20 mins. The solvent was removed in vacuo and triturated with ether (10 ml) to give the title compound as a colourless solid (0.18 g).
LCMS (Method B): Rt 3.52 mins, MH$^+$ 468.
Similarly prepared was:

Intermediate 3b

6-Bromo-4-[5-(chloromethyl)-1,3,4-oxadiazol-2-yl]-1-(phenylsulfonyl)-1H-indazole

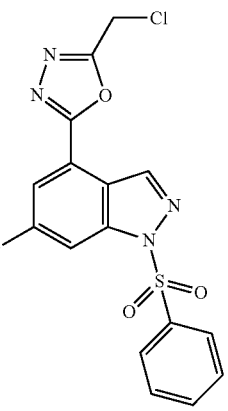

LCMS (Method A) Rt 1.38 mins, MH+ 454.

Intermediate 4

6-Bromo-1-[(4-methylphenyl)sulfonyl]-4-[5-(4-morpholinylmethyl)-1,3,4-oxadiazol-2-yl]-1H-indazole

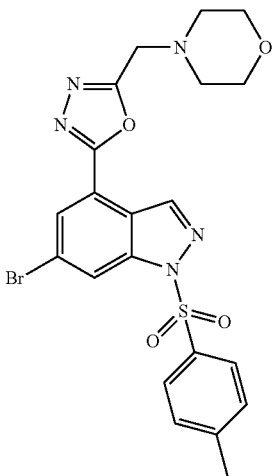 [SMILES: Cc1ccc(S(=O)(=O)n2ncc3c(-c4nnc(CN5CCOCC5)o4)cc(Br)cc32)cc1]

A stirred mixture of 6-bromo-4-[5-(chloromethyl)-1,3,4-oxadiazol-2-yl]-1-[(4-methylphenyl)sulfonyl]-1H-indazole (0.1 g, 0.214 mmol) and morpholine (0.056 ml, 0.641 mmol) in acetonitrile (2.5 ml) was heated at 80° C. in the microwave (biotage initiator) for 45 mins. The mixture was evaporated and the residual solid triturated with ether (10 ml) to afford the title compound as a cream coloured solid which was collected by filtration (0.07 g).

LCMS (Method B): Rt 2.90 mins, MH+ 520.

Intermediate 5

6-(1H-Indol-4-yl)-1-[(4-methylphenyl)sulfonyl]-4-[5-(4-morpholinylmethyl)-1,3,4-oxadiazol-2-yl]-1H-indazole

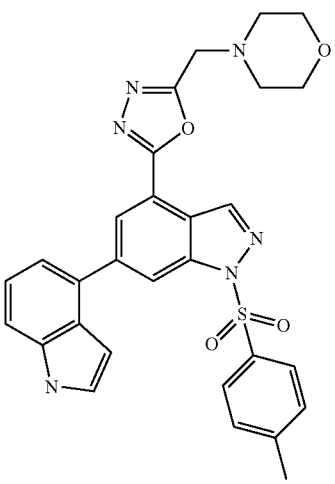 [SMILES: Cc1ccc(S(=O)(=O)n2ncc3c(-c4nnc(CN5CCOCC5)o4)cc(-c4cccc5[nH]ccc45)cc32)cc1]

A stirred mixture of 6-bromo-1-[(4-methylphenyl)sulfonyl]-4-[5-(4-morpholinylmethyl)-1,3,4-oxadiazol-2-yl]-1H-indazole (75 mg, 0.145 mmol), 4-(4,4,5,5-tetramethyl-1,3,2-dioxaborolan-2-yl)-1H-indole (52.8 mg, 0.217 mmol), 1,1'-bis(diphenylphosphino)-ferrocene palladium dichloride (5.29 mg, 7.23 μmol) and tripotassium phosphate (92 mg, 0.434 mmol) in 1,4-dioxane (2 ml) and water (0.2 ml) was heated at 100° C. in the microwave (Biotage initiator) for 30 mins. The mixture was poured into water (40 ml) and extracted into ethyl acetate (2×30 ml). The combined extracts were washed with water (30 ml), dried (frit) and evaporated. The residual solid was purified on a silica (5 g) cartridge using ether and ethyl acetate/ether (2:1) as the eluent. The appropriate fractions were evaporated to dryness to give the title compound as a cream coloured solid (24 mg).

LCMS (Method B): Rt 2.85 mins, MH+ 555.

Intermediate 6

6-Bromo-1-(phenylsulfonyl)-1H-indazole-4-carbonitrile

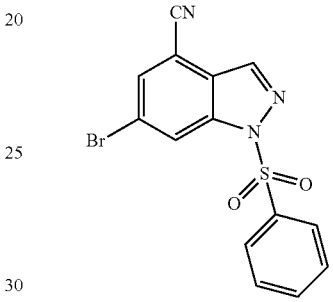

To a solution of 6-bromo-1H-indazole-4-carbonitrile (5 g, 22.52 mmol) in N,N-dimethylformamide (50 ml) was added, in portions, sodium hydride (1.351 g, 33.8 mmol) and the mixture stirred at 20° C. for 15 mins then cooled to 0° C. when benzenesulfonyl chloride (3.16 ml, 24.77 mmol) was added dropwise. The mixture was stirred at 20° C. for 18 h then concentrated in vacuo and the residue partitioned between water (100 ml) and dichloromethane (100 ml). The organic layer was separated by hydrophobic frit and evaporated in vacuo to give the title compound as a yellow solid (7.94 g).

LCMS (Method A): Rt 1.25 mins. H$^1$ NMR: (400 MHz, CDCl$_3$)—δ ppm: 8.7 (1H, s), 8.3 (1H, s), 8.05 (2H, m), 7.8 (1H, s), 7.65 (1H, t), 7.55 (2H, m).

Intermediate 7

6-(1H-Indol-4-yl)-1-(phenylsulfonyl)-1H-indazole-4-carbonitrile

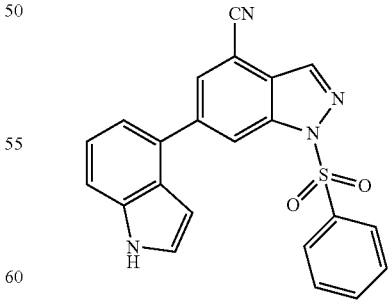

To a solution of 6-bromo-1-(phenylsulfonyl)-1H-indazole-4-carbonitrile (5 g, 13.80 mmol) in 1,4-dioxane (50 ml) and water (20 ml) was added 4-(4,4,5,5-tetramethyl-1,3,2-dioxaborolan-2-yl)-1H-indole (4.03 g, 16.57 mmol), 1,1'-bis(diphenylphosphino)ferrocene palladium dichloride (1.010 g, 1.380 mmol) and potassium phosphate tribasic (8.79 g, 41.4 mmol). The mixture was heated at 60° C. for 1 h, cooled and evaporated in vacuo. The residue was partitioned between water (50 ml) and dichloromethane (100 ml). The suspended solid was collected and the organics were separated by hydrophobic frit and concentrated to approx 50 ml. The precipitated solid was collected as a beige solid (1.93 g) and the filtrate purified by silica (300 g) cartridge using a gradient of ethyl acetate and cyclohexane, to give the title compound as a pale yellow solid (0.91 g). The solid collected during partitioning was purified by pre-absorbing onto florisil and purification by silica (100 g) cartridge on Flashmaster 11 using a gradient of dichloromethane and ethyl acetate to give a further quantity of the title compound as a pale yellow solid (0.45 g).

LCMS (Method A): Rt 1.24 mins, MH+399.

Intermediate 8

6-(1H-Indol-4-yl)-1-(phenylsulfonyl)-4-(1H-tetrazol-5-yl)-1H-indazole

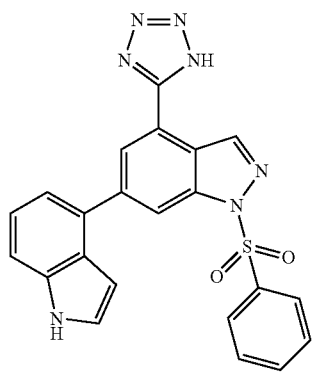 [SMILES: O=S(=O)(c1ccccc1)n1ncc2c(-c3nnn[nH]3)cc(-c3cccc4[nH]ccc34)cc21]

6-(1H-Indol-4-yl)-1-(phenylsulfonyl)-1H-indazole-4-carbonitrile (1.93 g, 4.84 mmol) as a slurry in toluene (90 ml) was treated with trimethylsilyl azide (1.241 ml, 9.35 mmol) and dibutyl(oxo)stannane (0.217 g, 0.872 mmol) and heated at ~120° C. for 5.75 h then left to stand at 20° C. for 18 h. The heterogeneous solution was evaporated to dryness then taken up in dichloromethane (200 ml), and this was heated in a waterbath at 40° C. to assist dissolving of the solid. This solution was then filtered and loaded directly onto a silica (100 g) cartridge which was eluted with a gradient of 0-50% methanol/dichloromethane over 60 mins using the Flashmaster II. Appropriate fractions were combined and evaporated to dryness to give the following products:

A yellow solid (0.257 g) consistent with impure desired tetrazole which was dissolved in DCM/methanol and absorbed onto silica. This was eluted with 0-25% methanol in DCM over 30 mins to give the title compound as a pale yellow solid (0.09 g).

LCMS (Method A): Rt 1.10 mins, MH+442.

A pale yellow solid (0.25 g) consistent with the title compound.

LCMS (Method B): Rt 2.99 mins, MH+442.

The original residue from the filtration [see above] was dissolved in a mixture of DCM/methanol (~250 ml) and adsorbed onto Florisil. This was eluted with 0-25% methanol over 60 min on a silica (100 g) cartridge to give a further quantity of the title compound as a pale yellow solid (1.07 g).

LCMS (Method A): 1.10 mins, MH+442.

Intermediate 9

4-[5-(Chloromethyl)-1,3,4-oxadiazol-2-yl]-6-(1H-indol-4-yl)-1-(phenylsulfonyl)-1H-indazole

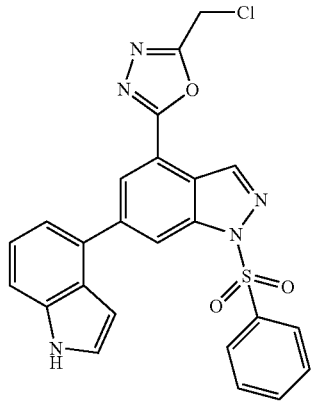 [SMILES: O=S(=O)(c1ccccc1)n1ncc2c(-c3nnc(CCl)o3)cc(-c3cccc4[nH]ccc34)cc21]

6-(1H-Indol-4-yl)-1-(phenylsulfonyl)-4-(1H-tetrazol-5-yl)-1H-indazole (1.41 g, 3.19 mmol) was slurried into anhydrous chloroform (20 ml), treated with chloroacetyl chloride (1.023 ml, 12.78 mmol) and heated at 100° C. in a Biotage Initiator microwave for 30 mins, the mixture was split into 4 batches for the microwave reaction. The mixtures were allowed to cool to room temperature and the resultant precipitate collected by filtration to give the title compound as a yellow/brown solid (0.237 g). LCMS (Method A): Rt 1.25 mins, MH+490.

The filtrate was concentrated in vacuo to give a yellow/brown solid. This was triturated with chloroform (~7 ml) and the resultant yellow precipitate collected by filtration and washed with chloroform (2 ml) and the solid air dried overnight to afford the title compound (0.562 g). LCMS (Method A): Rt 1.25 mins, MH+490.

The filtrate was evaporated in vacuo and then dissolved in chloroform (5 ml) and left to stand overnight the mixture was loaded onto a silica (100 g) cartridge and eluted with 0-100% ethyl acetate in cyclohexane over 60 mins to give the title compound (0.213 g).

LCMS (Method A): Rt 1.25 mins, MH+490.

Intermediate 10

N-(2-Chloro-5-{4-cyano-1-[(4-methylphenyl)sulfonyl]-1H-indazol-6-yl}-3-pyridinyl)methanesulfonamide

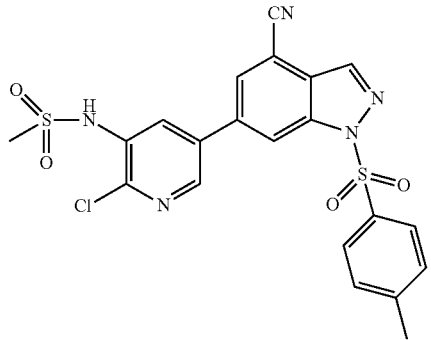 [SMILES: Cc1ccc(S(=O)(=O)n2ncc3c(C#N)cc(-c4cnc(Cl)c(NS(C)(=O)=O)c4)cc32)cc1]

Method 1

{6-Chloro-5-[(methylsulfonyl)amino]-3-pyridinyl}boronic acid (4.9 g, 19.56 mmol), 6-bromo-1-[(4-methylphenyl)sulfonyl]-1H-indazole-4-carbonitrile (5.89 g, 15.65 mmol), 1,1'-bis(diphenylphosphino)ferrocene palladium dichloride (1.431 g, 1.956 mmol) and tripotassium phosphate (12.46 g, 58.7 mmol) were placed in 1,4-dioxane (100 ml) and water (33.3 ml) and the mixture heated at 85° C. for 2 h. The mixture was cooled to room temperature and the solvent removed. The residue was partitioned between water (200 ml) and dichloromethane (200 ml). The organic layer was collected using a hydrophobic frit and the solvent removed in vacuo. The residue was purified by chromatography on silica (3×100 g) cartridges eluting with 0-100% ethyl acetate in cyclohexane over 40 mins to a give the title compound as a pale yellow solid (0.92 g).

LCMS (Method A): Rt 1.16 min MH+502/504.

The column was eluted with 0-25% methanol in dichloromethane over 30 mins, and was purified further, eluting with 0-100% ethyl acetate in cyclohexane over 40 mins to give a further quantity of the title compound (0.59 g).

LCMS (Method A): Rt 1.16 mins, MH+502.

Method 2

Alternatively, 1-[(4-methylphenyl)sulfonyl]-6-(4,4,6,6-tetramethyl-1,3,2-dioxaborinan-2-yl)-1H-indazole-4-carbonitrile (50 mg, 0.114 mmol), N-(5-bromo-2-chloro-3-pyridinyl)methanesulfonamide (35.9 mg), tripotassium phosphate (72.8 mg, 0.343 mmol) and chloro(di-2-norbonylphosphino)(2'-dimethylamino-1,1'-biphenyl-2-yl)palladium (II) (12.82 mg, 0.023 mmol) were placed in 1,4-dioxane (2 ml) and water (0.667 ml) and the mixture heated under microwave irradiation at 80° C. for 5 mins. Additional chloro(di-2-norbonylphosphino)(2'-dimethylamino-1,1'-biphenyl-2-yl)palladium (II) (10 mg) was added and the mixture heated under microwave irradiation at 100° C. for 5 mins. Additional chloro(di-2-norbonylphosphino)(2'-dimethylamino-1,1'-biphenyl-2-yl)palladium (II) (5 mg) was added and the mixture was heated at 100° C. for a further 10 mins. The solvent was removed in vacuo and the residue partitioned between water (50 ml) and dichloromethane (50 ml). The organic layer was collected and concentrated, then the residue purified by column chromatography on silica gel, eluting with 0-100% ethyl acetate in cyclohexane to give the title compound as a pale yellow gum (10 mg).

LCMS (Method B): Rt 3.0 mins, MH+ 502.

Intermediate 11

N-{2-Chloro-5-[1-[(4-methylphenyl)sulfonyl]-4-(1H-tetrazol-5-yl)-1H-indazol-6-yl]-3-pyridinyl}methanesulfonamide

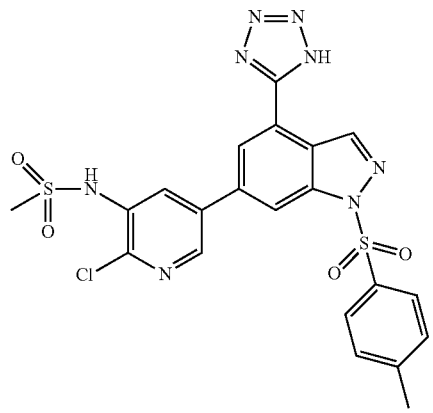 [SMILES: Cc1ccc(S(=O)(=O)n2ncc3c(-c4nnn[nH]4)cc(-c4cnc(Cl)c(NS(C)(=O)=O)c4)cc32)cc1]

N-(2-Chloro-5-{4-cyano-1-[(4-methylphenyl)sulfonyl]-1H-indazol-6-yl}-3-pyridinyl)methanesulfonamide (1.6 g, 3.19 mmol), trimethylsilyl azide azide (0.734 g, 6.37 mmol) and dibutyl(oxo)stannane (0.079 g, 0.319 mmol) were placed in toluene (30 ml) and the mixture heated at 100° C. for 16 h. The mixture was stirred at this temperature over the weekend. The mixture was cooled to room temperature and the solvent removed in vacuo. The residue was adsorbed onto florisil and chromatographed on silica (100 g cartridge) eluting with 0-100% ethyl acetate in cyclohexane followed by 0-20% methanol to give the title compound (1.3 g).

LCMS (Method A): Rt 1.06 mins, MH+545.

Intermediate 12

N-(2-Chloro-5-{4-[5-(chloromethyl)-1,3,4-oxadiazol-2-yl]-1-[(4-methylphenyl)sulfonyl]-1H-indazol-6-yl}-3-pyridinyl)methanesulfonamide

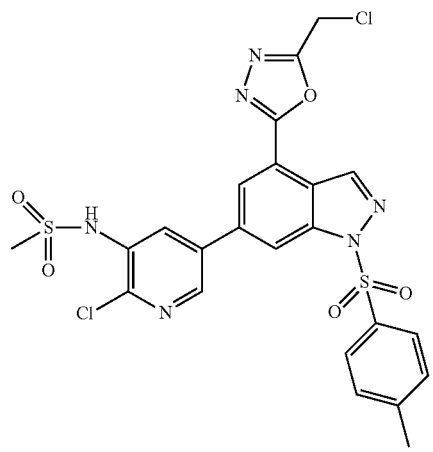 [SMILES: Cc1ccc(S(=O)(=O)n2ncc3c(-c4nnc(CCl)o4)cc(-c4cnc(Cl)c(NS(C)(=O)=O)c4)cc32)cc1]

N-{2-Chloro-5-[1-[(4-methylphenyl)sulfonyl]-4-(1H-tetrazol-5-yl)-1H-indazol-6-yl]-3-pyridinyl}methanesulfonamide (1.3 g, 2.385 mmol) and chloro acetylchloride (0.285 ml, 3.58 mmol) were placed in toluene (35 ml) and the mixture heated at 105° C. for 30 mins. The temperature was increased to 115° C. and the mixture heated for 1 h. The mixture was cooled to room temperature and the solvent removed in vacuo. This was purified by chromatography on a silica (100 g) cartridge eluting with 0-100% ethyl acetate in cyclohexane followed by 0-20% methanol in dichloromethane, to give the title compound as a yellow solid (0.332 g).

LCMS (Method B): Rt 3.06 mins, MH+593/595.

Intermediate 13

N-(2-Chloro-5-{1-[(4-methylphenyl)sulfonyl]-4-[5-(4-morpholinylmethyl)-1,3,4-oxadiazol-2-yl]-1H-indazol-6-yl}-3-pyridinyl)methanesulfonamide

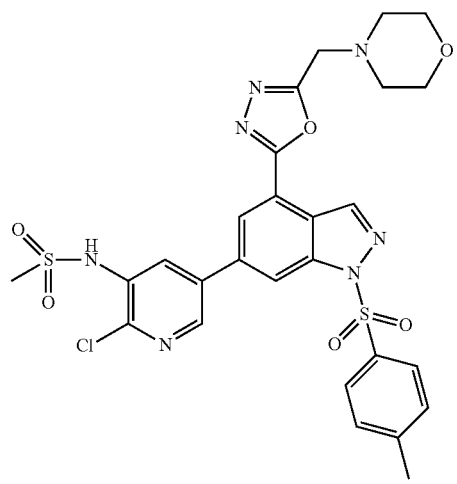 [SMILES: Cc1ccc(S(=O)(=O)n2ncc3c(-c4nnc(CN5CCOCC5)o4)cc(-c4cnc(Cl)c(NS(C)(=O)=O)c4)cc32)cc1]

N-(2-Chloro-5-{4-[5-(chloromethyl)-1,3,4-oxadiazol-2-yl]-1-[(4-methylphenyl)sulfonyl]-1H-indazol-6-yl}-3-pyridinyl)methanesulfonamide (50 mg, 0.084 mmol) and morpholine (0.015 ml, 0.169 mmol) were placed in acetonitrile (5 ml) and the mixture heated at 80° C. for 4 h. Further morpholine (150 was added and the reaction was continued to heat overnight. The mixture was cooled to room temperature and the mixture loaded onto an SCX (5 g) cartridge. The cartridge was washed with methanol and then eluted with 2M ammonia in methanol. The mixture was purified by chromatography on silica (20 g) cartridge eluting with 0-100% ethyl acetate in cyclohexane followed by 0-20% methanol to give the title compound (52 mg).

LCMS (Method A): Rt 1.04 mins, MH+644.

Intermediate 14

N-(5-Bromo-2-chloro-3-pyridinyl)methanesulfonamide

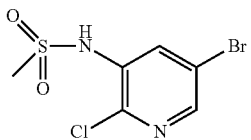

5-Bromo-2-chloro-3-pyridinamine [commercially available] (10 g, 48.2 mmol) was dissolved in pyridine (75 ml) and methanesulfonyl chloride (7.46 ml, 96 mmol) added, and the mixture stirred overnight. Further methanesulfonyl chloride (2.1 ml) was added and the reaction stirred at room temperature for 5 h. A further portion of methanesulfonyl chloride (2.1 ml) was added and the mixture stirred at room temperature overnight. The pH was adjusted to ~pH6 by the addition of 2M hydrochloric acid. The mixture was then extracted with dichloromethane (2×150 ml) the combined organic layers were dried using a hydrophobic frit and the solvent removed in vacuo. The residue was suspended in methanol (200 ml) and 2M sodium hydroxide (50 ml) added. The mixture was stirred for 1 h and then the solvent removed in vacuo. The residue was dissolved in water (250 ml) and extracted with dichloromethane (150 ml). The aqueous layer was then acidified and the resulting precipitate collected by filtration. The solid was air dried overnight to give the title compound as an off white solid (13.45 g).

LCMS (Method A): 0.81 mins, MH− 285.

Intermediate 15

{6-Chloro-5-[(methylsulfonyl)amino]-3-pyridinyl}boronic acid

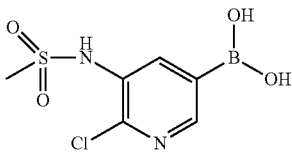

N-(5-Bromo-2-chloro-3-pyridinyl)methanesulfonamide (5 g, 17.51 mmol), potassium acetate (5.16 g, 52.5 mmol), 4,4,4',4',5,5,5',5'-octamethyl-2,2'-bi-1,3,2-dioxaborolane (4.89 g, 19.26 mmol) and 1,1'-bis(diphenylphosphino)ferrocene palladium dichloride (1.281 g, 1.751 mmol) were placed in 1,4-dioxane (51 ml) and the mixture heated for 16 h at 90° C. The reaction was left stirring at 90° C. for a further 5 h. Further catalyst (0.3 g), potassium acetate (1.7 g) and 4,4,4',4',5,5,5',5'-octamethyl-2,2'-bi-1,3,2-dioxaborolane (1.5 g) were added and the mixture stirred at 95° C. overnight. The mixture was cooled to room temperature then the mixture was filtered through a hydrophobic frit and the solvent removed in vacuo. The residue was partitioned between water (250 ml) and dichloromethane (250 ml). the organic layer was collected and the solvent removed in vacuo. The residue was columned on silica (3×100 g) cartridges eluting with 0-25% methanol in dichloromethane over 40 mins gave the title compound as a dark brown oil (4.9 g).

LCMS (Method A): Rt 0.46 mins, MH+251.

Intermediate 16

1,1-Dimethylethyl 2-[(6-bromo-1H-indazol-4-yl)carbonyl]hydrazinecarboxylate

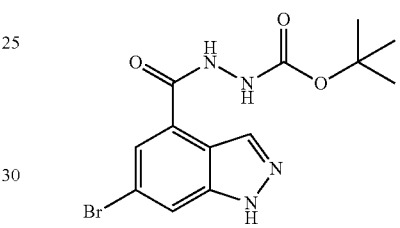

To 6-bromo-1H-indazole-4-carboxylic acid (5 g, 20.74 mmol) in N,N-dimethylformamide (20 ml) was added 0-(7-azabenzotriazol-1-yl)-N,N,N'N'-tetramethyluronium hexafluorophosphate (8.68 g, 22.82 mmol) followed by N,N-diisopropyethylamine (5.42 ml, 31.1 mmol), and the clear solution was stirred for 10 mins at 20° C. To this was added t-butylcarbazate (3.29 g, 24.89 mmol) and the heterogeneous reaction was stirred for 24 h at 20° C. under nitrogen. The mixture was left to stand for 7 days. Dichloromethane (200 ml) and saturated aqueous sodium hydrogen carbonate (50 ml) were added. Ethyl acetate (100 ml) added and the monophasic mixture was left to stand for 30 mins then the mixture was filtered through a filter paper under vacuum to give a biphasic filtrate. The organic phase was separated, passed through a hydrophobic frit, then evaporated to dryness to give a yellow liquid containing N,N-dimethylformamide. The solid collected on the filter paper was dried in air to give a beige solid (6 g) which was treated with methanol (75 ml) and chloroform (75 ml) and the mixture stirred at room temperature for 2 h. The mixture was left to stand for 10 mins, then the supernatant was decanted off and loaded directly onto an aminopropyl (70 g) cartridge which had been pre-eluted with methanol. A further quantity of methanol (30 ml) and chloroform (30 ml) was added to the remaining slurry, stirred for 10 mins and heated for a couple of minutes with a heat gun. The mixture was left to stand for 10 mins and the supernatant added to the cartridge. The cartridge was then eluted with methanol, and the eluant evaporated to give the title compound as a yellow solid (3.47 g).

LCMS (Method B): Rt 2.78 mins, MH+355.

The aqueous was further extracted with dichloromethane (2×100 ml), the combined organics were passed through a hydrophobic frit, then evaporated to dryness to give light yellow liquid containing N,N-dimethylformamide. The two liquids from above were combined and loaded equally onto silica (2×100 g) cartridges which had been pre-eluted with cyclohexane. The cartridges were eluted with 0-100% ethyl acetate/cyhexane over 40 mins using the Flashmaster II to give further quantities of the title compound as a beige solid (0.693 g).

LCMS (Method B): Rt 2.78 mins, MH+355.

Intermediate 17

6-Bromo-1H-indazole-4-carbohydrazide

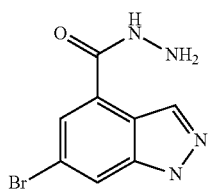 [SMILES: NNC(=O)c1cc(Br)cc2[nH]ncc12]

1,1-Dimethylethyl 2-[(6-bromo-1H-indazol-4-yl)carbonyl]hydrazinecarboxylate.

(3.45 g, 4.63 mmol) was treated with 4M hydrogen chloride in 1,4-dioxane (30 ml, 120 mmol) and stirred at 20° C. for 24 h under nitrogen. The solvent was blown off to leave a white solid which was azeotroped with dichloromethane (10 ml) followed by methanol (10 ml) to give a white solid (2.34 g). A portion of this material (0.505 g) was dissolved in methanol (10 ml) and purified on a SCX (10 g) cartridge which had been pre-conditioned with methanol. Methanol was eluted followed by 2M ammonia in ethanol. Basic fractions were combined and evaporated to dryness to give the title compound as a beige solid (0.180 g).

LCMS (Method B): Rt 2.06 mins, MH+257.

The remaining material (1.82 g) was dissolved in methanol (20 ml) and purified on an SCX (50 g) cartridge which had been pre-conditioned with methanol. Methanol was eluted followed by 2M ammonia in ethanol. Basic fractions were combined and evaporated to dryness to a further quantity of the title compound as a beige solid (0.477 g).

LCMS (Method B): Rt 2.06 mins, MH+255.

Intermediate 18

6-Bromo-N'-(4-morpholinylacetyl)-1H-indazole-4-carbohydrazide

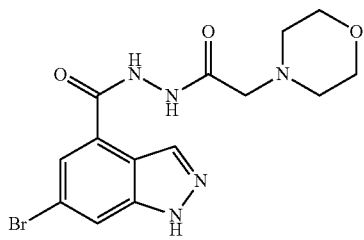 [SMILES: O=C(CN1CCOCC1)NNC(=O)c1cc(Br)cc2[nH]ncc12]

O-(7-Azabenzotriazol-1-yl)-N,N,N'N'-tetramethyluronium hexafluorophosphate (0.841 g, 2.212 mmol) was dissolved in N,N-dimethylformamide (5 ml) then treated with 4-morpholinylacetic acid (0.304 g, 2.092 mmol) and then N,N-diisopropyethylamine (0.386 ml, 2.212 mmol). The clear solution was stirred at 20° C. for 10 mins then to this was added 6-bromo-1H-indazole-4-carbohydrazide (0.513 g, 2.011 mmol) as a partial solution in N,N-dimethylformamide (8 ml). The clear solution was stirred at 20° C. for 72 h under nitrogen. It was then reduced in volume to ~1 ml, diluted with methanol (5 ml) and loaded onto an aminopropyl cartridge which had been pre-conditioned with methanol. The fully-loaded cartridge was left to stand for 2 h then eluted with methanol and the eluant evaporated to give an orange oil. This was diluted with dichloromethane (3 ml) and loaded onto a silica (10 g) cartridge. This was eluted with a gradient of methanol and ethyl acetate to give the title compound as a beige solid (0.792 g).

LCMS (Method B): Rt 1.96 mins, MH+ 384.

Intermediate 19

6-Bromo-N'-(4-morpholinylacetyl)-1-(tetrahydro-2H-pyran-2-yl)-1H-indazole-4-carbohydrazide

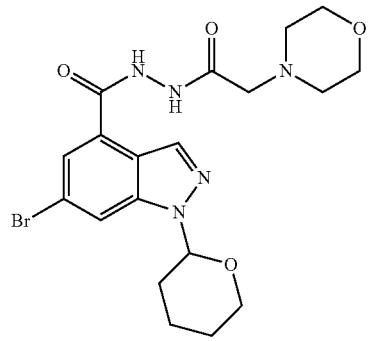 [SMILES: O=C(CN1CCOCC1)NNC(=O)c1cc(Br)cc2c1cnn2C1CCCCO1]

6-Bromo-N'-(4-morpholinylacetyl)-1H-indazole-4-carbohydrazide (0.232 g, 0.607 mmol) in ethyl acetate (3 ml) was treated with 3,4-dihydro-2H-pyran (0.111 ml, 1.214 mmol) then heated to 50° C. under nitrogen. Trifluoroacetic acid (4 drops) was added and heating continued for 1.5 h at 50° C. A further portion of 3,4-dihydro-2H-pyran (0.111 ml, 1.214 mmol) and trifluoroacetic acid (0.047 ml, 0.607 mmol) were added and heating continued for a further 1.5 h. The solution was left to stand at room temperature for 18 h. The clear solution was diluted with ethyl acetate (5 ml), washed with saturated aqueous sodium bicarbonate (2×10 ml), filtered through a phase separator cartridge then blown to dryness and left under vacuum. The crude product was dissolved in dichloromethane (2 ml) and purified on a silica (5 g) cartridge which was eluted with a gradient of methanol and chloroform and the appropriate fractions evaporated to give the title compound as a beige gummy solid (0.199 g).

LCMS Method (B): Rt 1.39 mins, MH+468.

Intermediate 20

6-Bromo-4-[5-(4-morpholinylmethyl)-1,3,4-oxadiazol-2-yl]-1-(tetrahydro-2H-pyran-2-yl)-1H-indazole

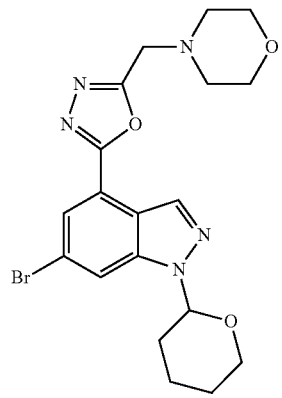 [SMILES: Brc1cc(-c2nnc(CN3CCOCC3)o2)c2cnn(C3CCCCO3)c2c1]

6-Bromo-N'-(4-morpholinylacetyl)-1-(tetrahydro-2H-pyran-2-yl)-1H-indazole-4-carbohydrazide (0.053 g, 0.114 mmol) in a microwave vial was treated with tetrahydrofuran (1 ml) and (methoxycarbonylsulfamoyl)triethylammonium hydroxide, inner salt (Burgess reagent) (0.054 g, 0.227 mmol). The mixture was heated in a Biotage Initiator microwave at 100° C. for 30 mins on high power. The solution was diluted with water (4 ml) and the product extracted with dichloromethane (2×10 ml). The combined organics were filtered through a hydrophobic frit then blown to dryness to give a yellow gum (60 mg). This material was dissolved in dichloromethane (1 ml) and purified on a silica (2 g) cartridge which was eluted with a gradient of methanol and chloroform to give a yellow gum (44 mg). This was dissolved in dichloromethane (2 ml) and loaded onto an SCX (1 g) cartridge which had been pre-conditioned with methanol. Methanol then 2M ammonia in ethanol was eluted. The basic fractions were blown to dryness to give the title compound (25 mg).

LCMS (Method B): Rt 2.37 mins, MH+450.

Intermediate 21

2-(Methyloxy)-5-(4,4,5,5-tetramethyl-1,3,2-dioxaborolan-2-yl)-3-pyridinamine

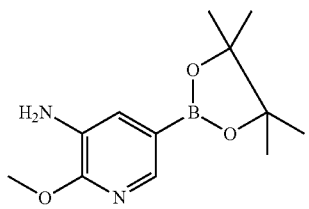

To 5-bromo-2-(methyloxy)-3-pyridinamine (18.93 g, 93 mmol, available from Asymchem) in a 1 L round-bottom flask was added nitrogen-purged 1,4-Dioxane (500 mL) followed by 4,4,4',4',5,5,5',5'-octamethyl-2,2'-bi-1,3,2-dioxaborolane (47.4 g, 186 mmol), potassium acetate (27.5 g, 280 mmol) (0.402 g, 0.493 mmol) and PdCl2(dppf)-CH2Cl2 adduct (7.61 g, 9.32 mmol). The mixture was then stirred at 80° C. under nitrogen. The reaction mixture was allowed to cool then partitioned between ethyl acetate and water. The mixture was filtered through a celite pad and the aqueous layer extracted further with ethyl acetate (2×). The combined organics were washed with water, brine and dried over magnesium sulphate overnight. The residue was purified on 1.5 Kg Silica cartridge, eluting a 0-50% ethyl acetate/dichloromethane over 10 column volumes. The appropriate fractions were combined and evaporated to dryness. The residue was triturated with cyclohexane, the solid filtered off and dried in vacuo to leave the title compound as a light pink solid (1.1 g).

LCMS (Method A) Rt 0.91 mins, MH+ 251

A second crop was obtained from the above filtrate and after drying gave a further portion of the title compound as a light pink solid (2.95 g).

Intermediate 22

N-[2-(Methyloxy)-5-(4,4,5,5-tetramethyl-1,3,2-dioxaborolan-2-yl)-3-pyridinyl]methanesulfonamide

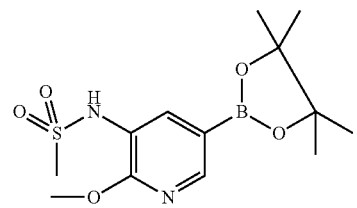 [SMILES: COc1ncc(B2OC(C)(C)C(C)(C)O2)cc1NS(C)(=O)=O]

To a solution of 2-(methyloxy)-5-(4,4,5,5-tetramethyl-1,3,2-dioxaborolan-2-yl)-3-pyridinamine (0.5 g, 1.999 mmol) in pyridine (5 ml) was added methanesulphonyl chloride (0.309 ml, 4.00 mmol) and the mixture stirred at 20° C. for 18 hr when the solvent was removed in vacuo. The residue was partitioned between saturated sodium bicarbonate solution (10 ml) and dichloromethane (20 ml), separated by hydrophobic frit and purified by silica (70 g) cartridge on Flashmaster II using a gradient of dichloromethane and methanol to give the title compound as a brown solid (0.46 g).

LCMS (Method A) Rt 0.98 mins, MH+ 329.

Intermediate 23

6-Bromo-4-(5-{[(2R,6S)-2,6-dimethyl-4-morpholinyl]methyl}-1,3,4-oxadiazol-2-yl)-1-(phenylsulfonyl)-1H-indazole

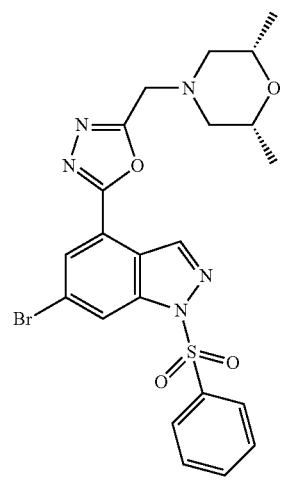 [SMILES: C[C@@H]1CN(Cc2nnc(-c3cc(Br)cc4c3cnn4S(=O)(=O)c3ccccc3)o2)C[C@H](C)O1]

To a solution of 6-bromo-4-[5-(chloromethyl)-1,3,4-oxadiazol-2-yl]-1-(phenylsulfonyl)-1H-indazole (1.7 g, 3.75 mmol) in dichloromethane (50 ml) was added (2R,6S)-2,6-dimethylmorpholine (0.863 g, 7.49 mmol) and the mixture stirred at 50° C. for 18 hr. The crude product was purified by silica (100 g) cartridge on Flashmaster II using a gradient of dichloromethane and methanol to give the title compound as a pale yellow solid (1.79 g).

LCMS (Method A) Rt 1.22 mins, MH+ 534.

Similarly prepared was:

Intermediate 24

6-Bromo-4-(5-{[4-(1-methylethyl)-1-piperazinyl]methyl}-1,3,4-oxadiazol-2-yl)-1-(phenylsulfonyl)-1H-indazole

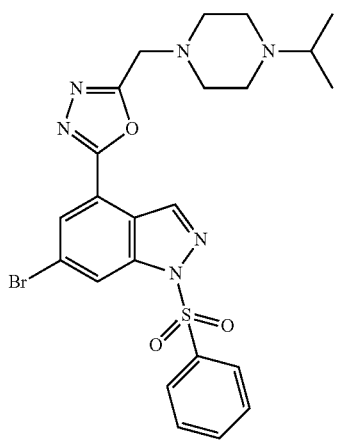 [SMILES: CC(C)N1CCN(Cc2nnc(-c3cc(Br)cc4c3cnn4S(=O)(=O)c3ccccc3)o2)CC1]

LCMS (Method A) Rt 0.93 mins, MH+ 547.

Intermediate 25

5-[4-(5-{[(2R,6S)-2,6-Dimethyl-4-morpholinyl]methyl}-1,3,4-oxadiazol-2-yl)-1-(phenylsulfonyl)-1H-indazol-6-yl]-2-(methyloxy)-3-pyridinamine

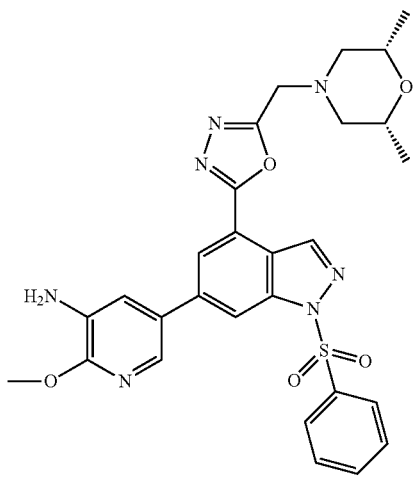

To a solution of 6-bromo-4-(5-{[(2R,6S)-2,6-dimethyl-4-morpholinyl]methyl}-1,3,4-oxadiazol-2-yl)-1-(phenylsulfonyl)-1H-indazole (0.82 g, 1.540 mmol) in 1,4-dioxane (15 ml) and water (1.5 ml) was added 2-(methyloxy)-5-(4,4,5,5-tetramethyl-1,3,2-dioxaborolan-2-yl)-3-pyridinamine (0.501 g, 2.002 mmol), 1,1'-bis(diphenylphosphino)ferrocene palladium dichloride (0.225 g, 0.308 mmol) and potassium phosphate tribasic (0.981 g, 4.62 mmol). The mixture was heated at 80° C. for 2 hr, cooled and concentrated in vacuo and the residue partitioned between dichloromethane and water (20 ml), separated by hydrophobic frit and purified by silica (100 g) cartridge on Flashmaster II, using a gradient of dichloromethane and methanol (1% triethylamine) to give the title compound as an orange solid (0.88 g).

LCMS (Method A) Rt 1.08 mins, MH+ 576.

Intermediate 26

N-[5-[4-(5-{[(2R,6S)-2,6-Dimethyl-4-morpholinyl]methyl}-1,3,4-oxadiazol-2-yl)-1-(phenylsulfonyl)-1H-indazol-6-yl]-2-(methyloxy)-3-pyridinyl]methanesulfonamide

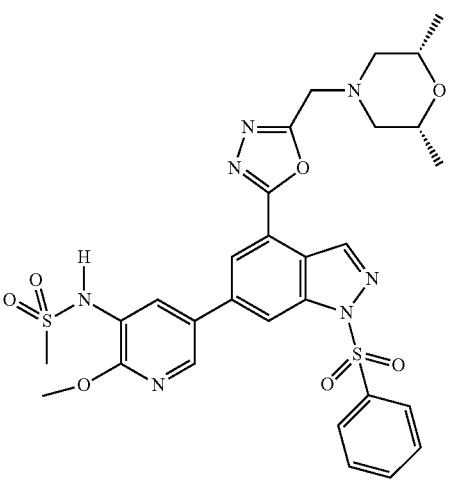 [SMILES: COc1ncc(-c2cc(-c3nnc(CN4C[C@@H](C)O[C@@H](C)C4)o3)c3cnn(S(=O)(=O)c4ccccc4)c3c2)cc1NS(C)(=O)=O]

To a solution of 5-[4-(5-{[(2R,6S)-2,6-dimethyl-4-morpholinyl]methyl}-1,3,4-oxadiazol-2-yl)-1-(phenylsulfonyl)-1H-indazol-6-yl]-2-(methyloxy)-3-pyridinamine (200 mg, 0.347 mmol) in pyridine (1 ml) was added, dropwise, methanesulphonyl chloride (0.054 ml, 0.695 mmol) and the mixture stirred at 20° C. for 18 hr. Water (10 ml) was added and the title compound was collected by filtration as a brown solid (106 mg).

LCMS (Method A) Rt 1.05 mins, MH+ 654.

Intermediate 27

N-[5-[4-(5-{[4-(1-Methylethyl)-1-piperazinyl]methyl}-1,3,4-oxadiazol-2-yl)-1-(phenylsulfonyl)-1H-indazol-6-yl]-2-(methyloxy)-3-pyridinyl]methanesulfonamide

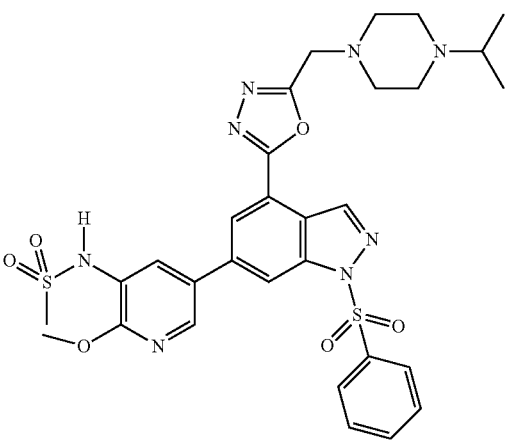 [SMILES: COc1ncc(-c2cc(-c3nnc(CN4CCN(C(C)C)CC4)o3)c3cnn(S(=O)(=O)c4ccccc4)c3c2)cc1NS(C)(=O)=O]

To a solution of 6-bromo-4-(5-{[4-(1-methylethyl)-1-piperazinyl]methyl}-1,3,4-oxadiazol-2-yl)-1-(phenylsulfonyl)-1H-indazole (100 mg, 0.183 mmol) in 1,4-dioxane (2.5 ml) and water (0.250 ml) was added N-[2-(methyloxy)-5-(4,4,5,5-tetramethyl-1,3,2-dioxaborolan-2-yl)-3-pyridinyl]methanesulfonamide (78 mg, 0.238 mmol), 1,1'-bis(diphenylphosphino)ferrocene palladium dichloride (26.8 mg, 0.037 mmol) and potassium phosphate tribasic (117 mg, 0.550 mmol). The mixture was heated under microwave irradiation at 60° C. for 10 min, then the solvent was removed in vacuo and the residue partitioned between dichloromethane (5 ml) and water (5 ml), separated by hydrophobic frit and purified by silica (5 g) cartridge using a gradient of dichloromethane and methanol to give the title compound as a brown solid (122 mg).

LCMS (Method A) Rt 0.87 mins, MH+ 667.

Intermediate 28

N-[5-Bromo-2-(methyloxy)-3-pyridinyl]-2,4-difluorobenzenesulfonamide

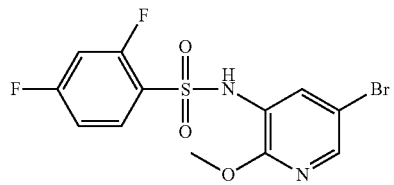 [SMILES: COc1ncc(Br)cc1NS(=O)(=O)c1ccc(F)cc1F]

To a cooled (0° C.) solution of 5-bromo-2-(methyloxy)-3-pyridinamine (13.7 g, 67.5 mmol) in pyridine (200 ml) was added slowly 2,4-difluorobenzenesulfonyl chloride (14.37 g, 67.6 mmol) over 15 min (reaction became heterogeneous). The ice bath was removed and the reaction was stirred at ambient temperature for 16 h. Most of the pyridine was removed in vacuo and the residue diluted with water (500 mL). The solids were filtered off and washed with copious amounts of water to give 21 g of crude desired product. More solid appeared in the mother liquor and was filtered and washed with water to give an additional 1.5 g of desired material. The two batches were combined, triturated with 70 ml of methylene chloride, and dried in a vacuum oven at 50° C. to give the title compound (15 g).

LCMS (Method B) Rt=1.11 min, MH+=378/380.

Intermediate 29

2,4-Difluoro-N-[2-(methyloxy)-5-(4,4,5,5-tetramethyl-1,3,2-dioxaborolan-2-yl)-3-pyridinyl]benzenesulfonamide

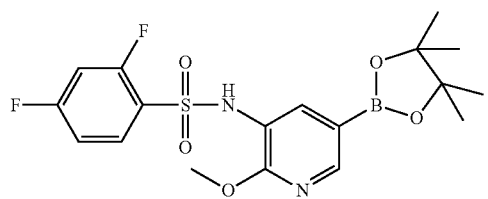 [SMILES: COc1ncc(B2OC(C)(C)C(C)(C)O2)cc1NS(=O)(=O)c1ccc(F)cc1F]

To a stirred solution of 2-(methyloxy)-5-(4,4,5,5-tetramethyl-1,3,2-dioxaborolan-2-yl)-3-pyridinamine (3 g, 12.00 mmol) in pyridine (12 ml), 2,4-difluorobenzenesulfonyl chloride (1.774 ml, 13.19 mmol) was added and the reaction mixture stirred at room temperature for 2 hours. 2 N HCl (aq) solution (20 ml) and DCM (20 ml) were added and the layers separated. The aqueous layer was washed with additional DCM (2×15 ml). Then the organic layers were combined, dried (hydrophobic frit) and evaporated in vacuo to give a brown oil. There was still some pyridine in the reaction mixture so 2M HCl was added and 15 ml DCM to extract one more time. The solvent was removed in vacuo to give the title compound as an orange solid (4.3 g).

LCMS (Method A) Rt=1.20 min, MH+=426 [NB. also observe Rt=0.73 min, MH+=344 consistent with boronic acid (hydrolysis product due to HPLC eluent)].

Intermediate 30

6-Bromo-1-methyl-1H-indazole-4-carbonitrile

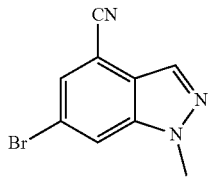

Tetrahydrofuran (27 ml) was added to a flask containing sodium hydride (0.275 g, 6.89 mmol) and the mixture was stirred for 10 minutes at 0° C. 6-Bromo-1H-indazole-4-carbonitrile (1.39 g, 6.26 mmol) was added portionwise and the mixture was stirred for 10 mins until no further effervescence was seen. Iodomethane (0.431 ml, 6.89 mmol) was added and the mixture stirred at 0° C. for 1 h. The ice bath was removed and the flask was placed in a water bath at room temperature. The reaction remained stirring for 19 h and the mixture was then evaporated in vacuo. The residual solid purified by silica (100 g) cartridge using a gradient of ethyl acetate and cyclohexane to give the title compound as a white solid (370 mg).

LCMS (Method B): Rt 2.60 mins, MH+237.

Intermediate 31

6-Bromo-1-methyl-4-(1H-tetrazol-5-yl)-1H-indazole

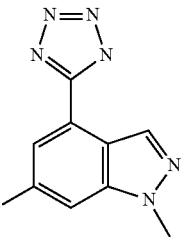

6-Bromo-1-methyl-1H-indazole-4-carbonitrile (514 mg, 2.177 mmol) was dissolved in toluene (20 mL) and dibutyl (oxo)stannane (108 mg, 0.435 mmol) and trimethylsilyl azide (0.573 mL, 4.35 mmol) were added over 2 mins. The mixture was then stirred at 110° C. under nitrogen for 28 h. Further trimethylsilyl azide (0.03 mL, 0.228 mmol) was added and the mixture continued stirring at 110° C. under nitrogen for 44 h. The solvent was removed in vacuo to give a white solid. 2M sodium hydroxide in methanol was added and the mixture heated to 50° C. and then filtered whilst hot to remove insoluble impurities. The filtrate was cooled and then acidified via dropwise addition of 2M hydrochloric acid. The resultant precipitate was filtered and dried in a vacuum oven to give the title compound as a white solid (604 mg).

LCMS (Method B): Rt 2.12 mins, MH+279.

Intermediate 32

6-Bromo-4-[5-(chloromethyl)-1,3,4-oxadiazol-2-yl]-1-methyl-1H-indazole

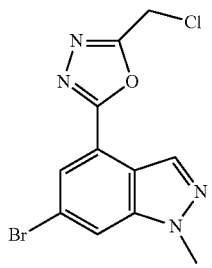 [SMILES: Cn1ncc2c(-c3nnc(CCl)o3)cc(Br)cc21]

6-Bromo-1-methyl-4-(1H-tetrazol-5-yl)-1H-indazole (604.6 mg, 2.166 mmol) was dissolved in chloroform (20 ml). Chloroacetyl chloride (0.520 ml, 6.49 mmol) was added and the mixture stirred at 110° C. for 46 h. Further chloroacetyl chloride (0.174 ml, 2.166 mmol) was added and the reaction continued stirred at 110° C. for 26 h. The reaction mixture was cooled and the solvent removed in vacuo. The resultant white solid was washed with DCM, the solvent removed under vacuum and the solid dried under high vacuum for 18 h to give the title compound as a white solid (528 mg).

LCMS (Method B): Rt 2.67 mins, MH+329.

Intermediate 33

6-Bromo-4-(5-{[(2R,6S)-2,6-dimethyl-4-morpholinyl]methyl}-1,3,4-oxadiazol-2-yl)-1-methyl-1H-indazole

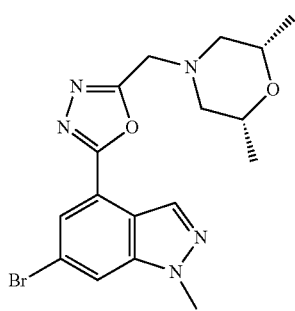 [SMILES: C[C@@H]1CN(Cc2nnc(-c3cc(Br)cc4c3cnn4C)o2)C[C@H](C)O1]

Method 1

6-Bromo-4-[5-(chloromethyl)-1,3,4-oxadiazol-2-yl]-1-methyl-1H-indazole (260 mg, 0.794 mmol) and (2R,6S)-2,6-dimethylmorpholine (1.5 ml, 0.794 mmol) were added to a microwave vial. The reaction mixture was heated under microwave irradiation at 90° C. for 15 mins. The reaction mixture was evaporated under a stream of nitrogen, dissolved in DCM (20 ml) and washed with a 10% solution of 2M hydrochloric acid in water. The organic layer was collected and the solvent removed in vacuo to give the title compound as an orange solid (240 mg).

LCMS (Method A): Rt 0.90 mins, MH+408.

Method 2

6-Bromo-N'-{[(2R,6S)-2,6-dimethyl-4-morpholinyl]acetyl}-1-methyl-1H-indazole-4-carbohydrazide (485 mg, 1.143 mmol) was dried on high vacuum line then added with Burgess reagent (methoxycarbonylsulfamoyl)triethylammonium hydroxide, inner salt) (409 mg, 1.715 mmol) in suspension in anhydrous Tetrahydrofuran (THF) (10 ml) and heated to 75° C. for 2 h. The solvent was then removed in vacuo and the residue partitioned between dichloromethane (10 ml) and saturated sodium bicarbonate solution (10 ml). The layers were separated, the aqueous washed with further dichloromethane (5 ml) and the combined organics concentrated in vacuo. The resultant solid was purified by column chromatography, loading in dichloromethane and purified on Flashmaster II silica (Si) 20 g using a 0-100% ethyl acetate-cyclohexane over 20 min. The appropriate fractions were combined and concentrated in vacuo to give the title compound as a white solid (200 mg).

LCMS (Method A) Rt=0.88 min, MH+=408.

Intermediate 34

6-Bromo-1-methyl-4-(5-{[4-(1-methylethyl)-1-piperazinyl]methyl}-1,3,4-oxadiazol-2-yl)-1H-indazole

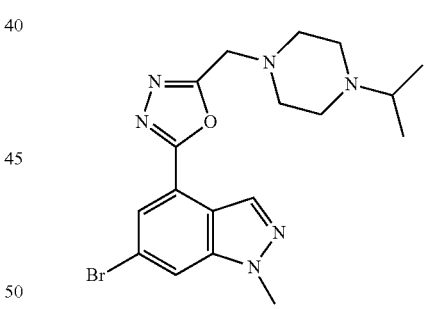

6-Bromo-4-[5-(chloromethyl)-1,3,4-oxadiazol-2-yl]-1-methyl-1H-indazole (260 mg, 0.794 mmol) and 1-(1-methylethyl)piperazine (1.5 ml, 0.794 mmol) were added to a microwave vial. The reaction mixture was heated under microwave irradiation at 90° C. for 15 mins. The reaction mixture was evaporated under a stream of nitrogen, dissolved in DCM (20 ml) and washed with a 10% solution of 2M hydrochloric acid in water. The layers were separated by hydrophobic frit and the aqueous layer was neutralised to pH=7 with 2M sodium hydroxide then extracted with DCM (20 ml). The organic layer was collected and the solvent removed in vacuo to give the title compound as an orange solid (310 mg).

LCMS (Method A): Rt 0.64 mins, MH+ 421.

Intermediate 35

6-Bromo-4-{5-[(2,2-dimethyl-4-morpholinyl)methyl]-1,3,4-oxadiazol-2-yl}-1-(phenylsulfonyl)-1H-indazole

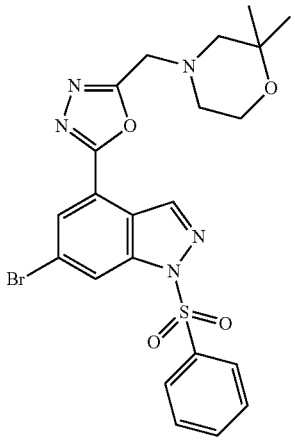 [SMILES: CC1(C)CN(Cc2nnc(-c3cc(Br)cc4c3cnn4S(=O)(=O)c3ccccc3)o2)CCO1]

To a solution of 6-bromo-4-[5-(chloromethyl)-1,3,4-oxadiazol-2-yl]-1-(phenylsulfonyl)-1H-indazole (200 mg, 0.441 mmol) in acetonitrile (2 ml) was added 2,2-dimethylmorpholine (102 mg, 0.882 mmol, available from Chembridge Corporation) and the mixture heated at 70° C. for 18 hr. The mixture was cooled to room temperature and a further portion of 2,2-dimethylmorpholine (102 mg, 0.882 mmol), DIPEA (0.154 mL, 0.882 mmol) and sodium iodide (66.1 mg, 0.441 mmol) were added. The mixture was then heated again at 70° C. for 2 hours. The mixture was cooled to room temperature, diluted with DCM and washed with water. The organic layer was separated through a hydrophobic frit and the solvent removed in vacuo. The resulting yellow oil was dried in a vacuum oven at 60° C. overnight to give a pale yellow solid, which was dissolved in DCM (10 ml) and washed with dilute HCl (10 ml) followed by water (10 ml), separating the layers using a hydrophobic frit. The DCM was removed in vacuo to give the title compound as a cream solid (214 mg).

LCMS (Method A) $R_t$=1.25 min, MH+ 534.

Intermediate 36

N-[5-[4-(5-{[(2R,6S)-2,6-Dimethyl-4-morpholinyl]methyl}-1,3,4-oxadiazol-2-yl)-1-(phenylsulfonyl)-1H-indazol-6-yl]-2-(methyloxy)-3-pyridinyl]-2,4-difluorobenzenesulfonamide

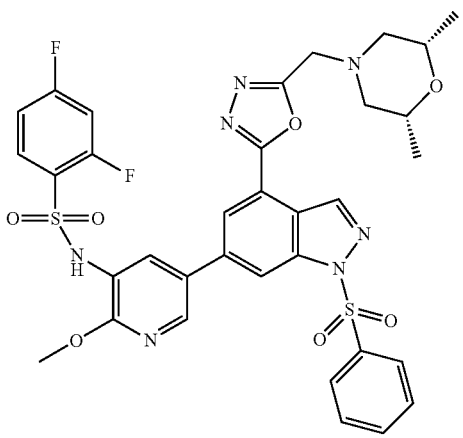 [SMILES: COc1ncc(-c2cc(-c3nnc(CN4C[C@@H](C)O[C@@H](C)C4)o3)c3cnn(S(=O)(=O)c4ccccc4)c3c2)cc1NS(=O)(=O)c1ccc(F)cc1F]

2,4-Difluorobenzenesulfonyl chloride (0.048 mL, 0.354 mmol) was added dropwise to a solution of 5-[4-(5-{[(2R,6S)-2,6-dimethyl-4-morpholinyl]methyl}-1,3,4-oxadiazol-2-yl)-1-(phenylsulfonyl)-1H-indazol-6-yl]-2-(methyloxy)-3-pyridinamine (185 mg, 0.321 mmol) in pyridine (1 ml). The mixture was stirred at room temperature for 2 h. 2,4-Difluorobenzenesulfonyl chloride (0.048 mL, 0.354 mmol) was added dropwise and the mixture continued stirring at room temperature for 1 h. Water (10 ml) was added and the resultant brown precipitate collected by filtration and dried in the vacuum oven for 72 h to give the title compound as a brown solid (194 mg).

LCMS (Method A): Rt 1.19 mins, MH+752.

Intermediate 37

6-(1H-Indol-4-yl)-1-[(4-methylphenyl)sulfonyl]-1H-indazole-4-carbonitrile

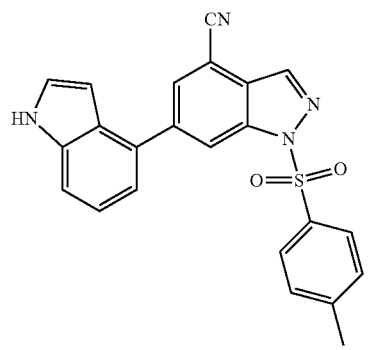 [SMILES: Cc1ccc(S(=O)(=O)n2ncc3c(C#N)cc(-c4cccc5[nH]ccc45)cc32)cc1]

To a suspension of 6-bromo-1-[(4-methylphenyl)sulfonyl]-1H-indazole-4-carbonitrile in 1,4-dioxane (100 ml) was added 4-(4,4,5,5-tetramethyl-1,3,2-dioxaborolan-2-yl)-1H-indole (4.79 g, 10.72 mmol, available from Frontier Scientific Europe), 1,1'-bis(diphenylphosphino)ferrocene palladium dichloride (2.061 g, 2.82 mmol) and potassium phosphate tribasic (8.97 g, 42.3 mmol). Water (20 ml) was added and the reaction mixture heated to 80° C. for 1 h. The solvent was removed and the residue partitioned between water (50 ml) and ethyl acetate (100 ml). The layers were filtered and the filtrate partitioned and concentrated, then purified by column chromatography, on a silica cartridge (300 g), eluting with a gradient of cyclohexane and ethyl acetate to give the title compound as a pale yellow solid (2.5 g).

LCMS (Method B): Rt 3.39 mins, MH+ 413.

Intermediate 38

6-(1H-Indol-4-yl)-1-[(4-methylphenyl)sulfonyl]-4-(1H-tetrazol-5-yl)-1H-indazole-6-(1H-indol-4-yl)-1-(phenylsulfonyl)-4-(1H-tetrazol-5-yl)-1H-indazole (1:1)

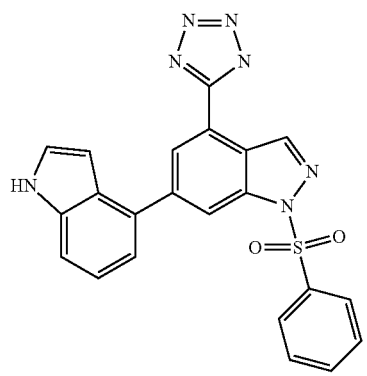

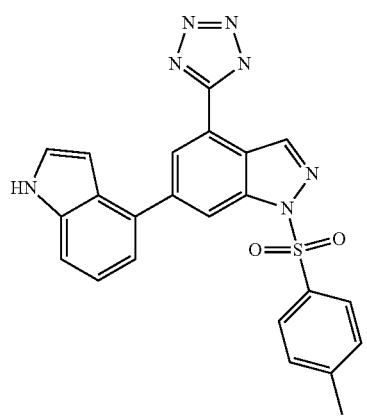

6-(1H-Indol-4-yl)-1-(phenylsulfonyl)-1H-indazole-4-carbonitrile (0.669 g, 1.679 mmol) and 6-(1H-indol-4-yl)-1-[(4-methylphenyl)sulfonyl]-1H-indazole-4-carbonitrile (0.561 g, 1.360 mmol) were slurried in toluene (60 ml) and treated with trimethylsilyl azide (0.887 ml, 6.68 mmol) and dibutyl(oxo)stannane (0.151 g, 0.608 mmol). The reaction mixture was heated, under nitrogen at 120° C. for 16 h, then additional trimethylsilyl azide (0.221 ml, 1.67 mmol) was added. After heating for a further 2 h, the solution was evaporated to dryness, treated with methanol (30 ml) and absorbed onto Florisil. The Florisil was loaded onto a silica cartridge (100 g) which was eluted with 0-30% methanol+1% triethylamine/dichloromethane. The appropriate fractions were combined and concentrated to give the title compound as a brown solid (1.724 g).

LCMS (Method B): Rt 3.08 mins, MH+ 442 and Rt 3.22 mins, MH+ 456.

Intermediate 39

1,1-Dimethylethyl 4-[4-cyano-1-(phenylsulfonyl)-1H-indazol-6-yl]-1H-indole-1-carboxylate

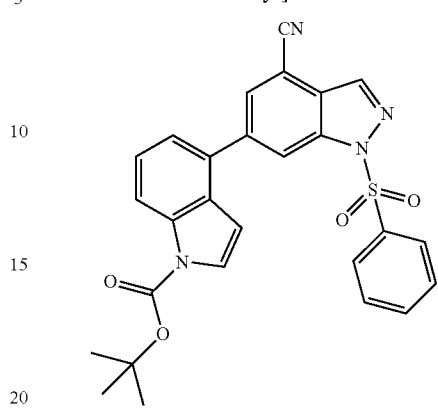

To a round bottomed flask was charged 6-bromo-1-(phenylsulfonyl)-1H-indazole-4-carbonitrile (10 g, 27.6 mmol), 1,1-dimethylethyl 4-(4,4,5,5-tetramethyl-1,3,2-dioxaborolan-2-yl)-1H-indole-1-carboxylate (14.21 g, 41.4 mmol) and potassium phosphate tribasic (17.58 g, 83 mmol). The resulting mixture was treated with 1,4-dioxane (120 ml) and water (12 ml) that had previously been purged with nitrogen. The mixture was then treated with 1'-bis(diphenylphosphino)ferrocene palladium dichloride (1.547 g, 2.76 mmol) and heated to reflux, under nitrogen for 2 h. Additional 1'-bis(diphenylphosphino)ferrocene palladium dichloride (1.547 g, 2.76 mmol) was added and the mixture heated at reflux for a further 1 h. The hot reaction mixture was filtered through Celite, washed well with chloroform and the filtrate concentrated in vacuo. The residue was dissolved in DCM/cyclohexane (1:1, 50 ml) and purified by column chromatography on silica (750 g cartridge), eluting with 0-40% ethyl acetate/cyclohexane. The pure fractions were combined and concentrated to give the title compound as a yellow solid (6.16 g).

LCMS (Method A): Rt 1.50 mins, MH+ 499.

Intermediate 40

6-(1H-Indol-4-yl)-1-(phenylsulfonyl)-4-(1H-tetrazol-5-yl)-1H-indazole

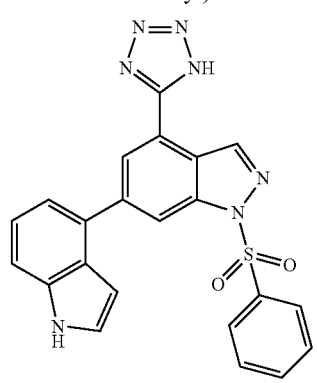

To a round bottomed flask was charged 1,1-dimethylethyl 4-[4-cyano-1-(phenylsulfonyl)-1H-indazol-6-yl]-1H-indole- 1-carboxylate (6.16 g, 12.36 mmol) followed by toluene (250 ml). The resulting solution was then treated with dibutyl(oxo)stannane (0.554 g, 2.224 mmol) and trimethylsilyl azide (3.3 ml, 25.09 mmol). The mixture was heated to 90° C. overnight, then cooled to room temperature and concentrated in vacuo. The residue was dissolved in methanol/DCM and preabsorbed onto silica (20 g). This was placed on the top of a silica cartridge (750 g) and eluted with 0-40% methanol in DCM. The product containing fraction was evaporated to give a green foam which was placed into acetic acid (50 ml) and the mixture heated to 100° C. overnight. The mixture was heated for a further 24 h, then cooled to room temperature and water (250 ml) added. A precipitate formed, which was collected by filtration and air dried over the weekend to give the title compound as a pale grey solid (1.8 g).

LCMS (Method A): Rt 1.07 min, MH– 440.

An off white precipitate had formed in the filtrate, which was collected by filtration and dried in a vacuum oven at 45° C. overnight to afford a further quantity of the title compound as an off white solid (454 mg).

LCMS (Method A): Rt 1.07 mins, MH– 440.

Intermediate 41

6-Bromo-4-(5-methyl-1,3,4-oxadiazol-2-yl)-1-[(4-methylphenyl)sulfonyl]-1H-indazole

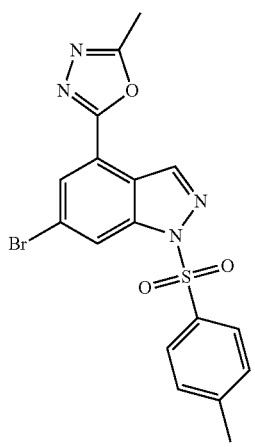 [SMILES: Cc1ccc(S(=O)(=O)n2ncc3c(-c4nnc(C)o4)cc(Br)cc32)cc1]

A stirred mixture of 6-Bromo-1-[(4-methylphenyl)sulphonyl]-4-(1H-tetrazol-5-yl)-1H-indazole (300 mg, 0.615 mmol) and acetyl chloride (0.722 ml, 10.15 mmol) in toluene (10 ml) were heated under microwave irradiation at 130° C. for 20 mins. The reaction mixture was heated for a further 20 mins at 130° C. then evaporated to dryness. The resultant yellow solid was treated with methanol (10 ml), to give a beige solid and supernatant. The supernatant was pipetted off, the process repeated twice and the resultant solid dried under vacuum to give the title compound as a beige solid (75 mg).

LCMS (Method B): Rt 3.28 mins, MH+ 433/435.

Intermediate 42

1-[(4-Methyl phenyl)sulfonyl]-6-(4,4,6,6-tetramethyl-1,3,2-dioxaborinan-2-yl)-1H-indazole-4-carbonitrile

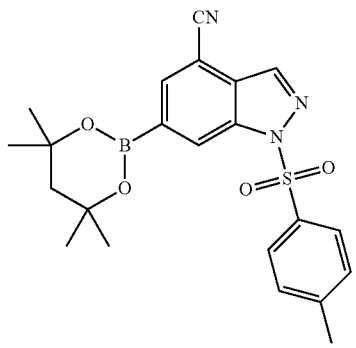 [SMILES: Cc1ccc(S(=O)(=O)n2ncc3c(C#N)cc(B4OC(C)(C)CC(C)(C)O4)cc32)cc1]

6-Bromo-1-[(4-methylphenyl)sulfonyl]-1H-indazole-4-carbonitrile (1 g, 2.66 mmol), 4,4,4',4',6,6,6',6'-octamethyl-2-2'-bi-1,3,2-dioxaborinane (0.899 g, 3.19 mmol), potassium acetate (0.783 g, 7.97 mmol) and 1,1'-bis(diphenylphosphino)ferrocene palladium (0.389 g, 0.532 mmol) were heated under microwave irradiation with 1,4-dioxane (15 ml) at 80° C. for 30 mins. The solvent was removed in vacuo and the residue partitioned between dichloromethane (100 ml) and water (100 ml). The organic layer was collected and the solvent removed in vacuo. The residue was purified by column chromatography on silica gel (100 g cartridge), eluting with 0-50% ethyl acetate in cyclohexane. The resultant residue was azeotroped in toluene and dried on the vacuum line to give the title compound as a cream solid (0.99 g).

LCMS (Method A): Rt 1.53 mins, MH+ 438.

Intermediate 43

N-(2-Chloro-5-{4-(5-methyl-1,3,4-oxadiazol-2-yl)-1[(4-methylphenyl)sulfonyl]-1H-indazol-6-yl}-3-pyridinyl)methanesulfonamide

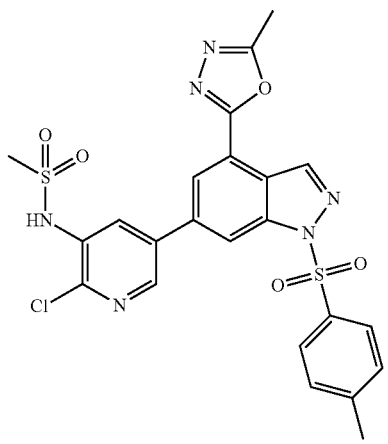 [SMILES: Cc1ccc(S(=O)(=O)n2ncc3c(-c4nnc(C)o4)cc(-c4cnc(Cl)c(NS(C)(=O)=O)c4)cc32)cc1]

N-{2-Chloro-5-[1-[(4-methylphenyl)sulfonyl]-4-(1H-tetrazol-5-yl)-1H-indazol-6-yl]-3-pyridinyl}methanesulfonamide (50 mg, 0.092 mmol) and acetyl chloride (8.48 µl, 0.119 mmol) were placed in toluene (2 ml) and left to stand for 10 mins before heating under microwave irradiation at 120° C. for 40 mins. Additional acetyl chloride (8.48 µl, 0.119 mmol) was added and the reaction mixture heated for a further 40 mins at 120° C. The solvent was removed and the residue purified by column chromatography, on a silica cartridge (20 g) eluting with 0-100% ethyl acetate/cyclohexane followed by 0-20% methanol to give the title compound as a white solid (16 mg).

LCMS (Method A): Rt 1.11 mins, MH+ 559 and [M+CH$_3$CN]$^+$ 600.

Intermediate 44

6-Oxa-9-azaspiro[4.5]decane

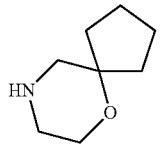

To a of solution 1,1-dimethylethyl 6-oxa-9-azaspiro[4.5]decane-9-carboxylate (200 mg, 0.829 mmol, available from Tyger Scientific Inc) in DCM (3 ml) was added trifluoroacetic acid (TFA) (0.5 ml). The resulting colourless yellow solution was stirred at room temperature for 24 hr. The solvent was evaporated to give the title compound as a grey oil (203 mg).

$^1$NMR (400 MHz, DMSO-d$_6$) δ=8.91 (2H, br. S), 3.73 (2H, dd), 2.98-3.11 (4H, m), 1.52-1.70 (6H, m)

Intermediate 45

9-({5-[6-Bromo-1-(phenylsulfonyl)-1H-indazol-4-yl]-1,3,4-oxadiazol-2-yl}methyl)-6-oxa-9-azaspiro[4.5]decane

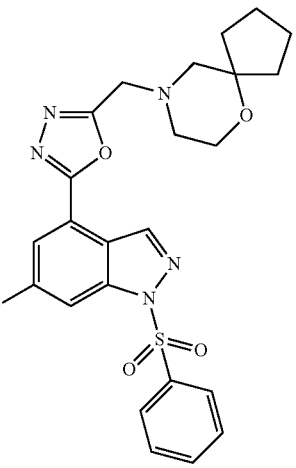

6-Bromo-4-[5-(chloromethyl)-1,3,4-oxadiazol-2-yl]-1-(phenylsulfonyl)-1H-indazole (200 mg, 0.441 mmol) in acetonitrile (2 ml) was treated with 6-oxa-9-azaspiro[4.5]decane (160 mg, 0.793 mmol), DIPEA (0.154 ml, 0.8825 mmol) and sodium iodide (66 mg, 0.44 mmol). The reaction mixture was heated at 70° C. for 5 h, then cooled, diluted with DCM and washed with aqueous HCl. The organic layer was separated using a hydrophobic frit, washed with water and the solvent removed under a stream of nitrogen. The resulting residue was purified by loading onto a silica cartridge (20 g) and eluting with 0-100% ethyl acetate/cyclohexane over 40 mins. The appropriate fractions were combined and evaporated to give the title compound as a yellow solid (74 mg).

LCMS (Method A): Rt 1.32 mins, MH+ 558/560.

The compounds listed below were synthesised using the general method above. For each of the compounds listed below column chromatography was not required.

| Intermediate | Starting Material | Structure | Rt mins | MH+ | Name |
|---|---|---|---|---|---|
| 46 | 2-methylmorpholine (available from Enamine Ltd) | 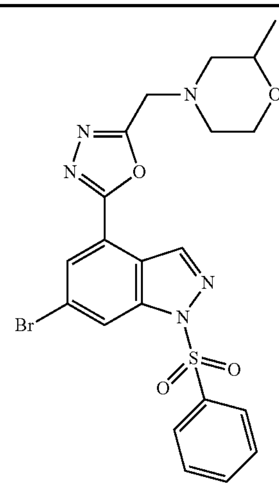 | 1.11 | 518/520 | 6-bromo-4-{5-[(2-methyl-4-morpholinyl)methyl]-1,3,4-oxadiazol-2-yl}-1-(phenylsulfonyl)-1H-indazole |

| Intermediate | Starting Material | Structure | Rt mins | MH+ | Name |
|---|---|---|---|---|---|
| 47 | Hexahydro-1,4-oxazepine, hydrochloride (Available from Alfa Aesar) | 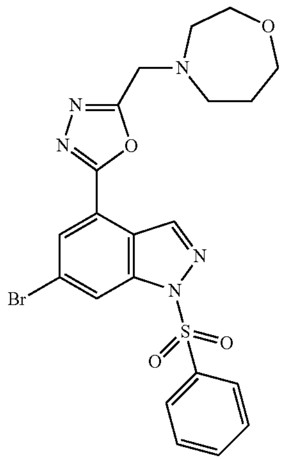 [SMILES: O=S(=O)(c1ccccc1)n1ncc2c(-c3nnc(CN4CCCOCC4)o3)cc(Br)cc21] | 0.89 | 518/520 | 6-bromo-1-(phenylsulfonyl)-4-[5-(tetrahydro-1,4-oxazepin-4(5H)-ylmethyl)-1,3,4-oxadiazol-2-yl]-1H-indazole |

Intermediate 48

6-Bromo-4-(5-{[(3R,5S)-3,5-dimethyl-4-(1-methyl-ethyl)-1-piperazinyl]methyl}-1,3,4-oxadiazol-2-yl)-1-(phenylsulfonyl)-1H-indazole

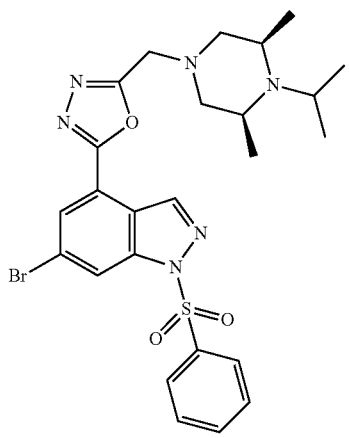 [SMILES: CC(C)N1[C@H](C)CN(Cc2nnc(-c3cc(Br)cc4c3cnn4S(=O)(=O)c3ccccc3)o2)C[C@@H]1C]

6-Bromo-4-[5-(bromomethyl)-1,3,4-oxadiazol-2-yl]-1-(phenylsulfonyl)-1H-indazole (200 mg, 0.441 mmol) in acetonitrile (2 ml) was treated with (2R,6S)-2,6-dimethyl-1-(1-methylethyl)piperazine (138 mg, 0.883 mmol, see *J. Med. Chem.*, 1999, 42, 1123-1144 for literature preparation), DIPEA (0.154 ml, 0.8825 mmol) and sodium iodide (66 mg, 0.44 mmol). The reaction mixture was heated at 70° C. for 5 h. The reaction mixture was then cooled, diluted with DCM and washed with an aqueous 2M HCl solution (5 ml). The organic layer was separated using a hydrophobic frit, washed with water and the solvent removed under a stream of nitrogen to give the title compound as a brown oil.

LCMS (Method A): Rt 0.80 mins, MH+ 573/575.

The compounds listed below were synthesised using the general method above.

| Intermediate | Starting Material | Structure | Rt mins | MH+ | Name |
|---|---|---|---|---|---|
| 49 | thiomorpholine, 1,1-dioxide (available from Sigma-Aldrich) | 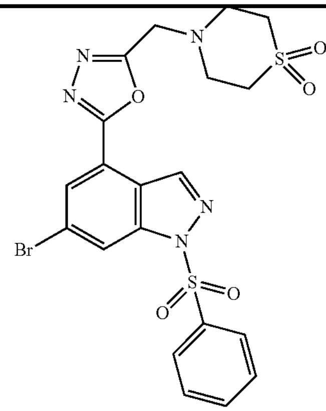 | 1.07 | 552/554 | 6-bromo-4-{5-[(1,1-dioxido-4-thiomorpholinyl)methyl]-1,3,4-oxadiazol-2-yl}-1-(phenylsulfonyl)-1H-indazole |

-continued

| Intermediate | Starting Material | Structure | Rt mins | MH+ | Name |
|---|---|---|---|---|---|
| 50 | 2-Ethylmorpholine (available from BioFarma UK) | 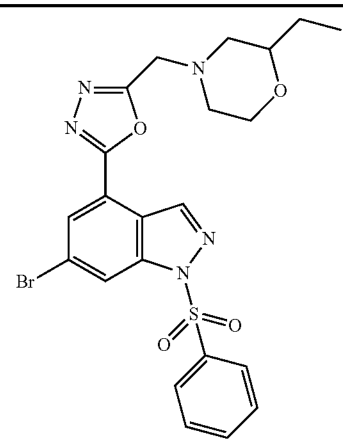 | 1.21 | 532/534 | 6-bromo-4-{5-[(2-ethyl-4-morpholinyl)methyl]-1,3,4-oxadiazol-2-yl}-1-(phenylsulfonyl)-1H-indazole |

Intermediate 51

N-{[5-(6-Bromo-1H-indazol-4-yl)-1,3,4-oxadiazol-2-yl]methyl}-3-(4-morpholinyl)-1-propanamine

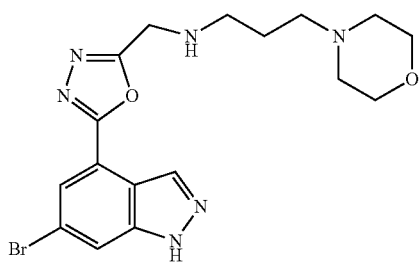 [SMILES: Brc1cc(-c2nnc(CNCCCN3CCOCC3)o2)c2cn[nH]c2c1]

6-Bromo-4-[5-(chloromethyl)-1,3,4-oxadiazol-2-yl]-1-(phenylsulfonyl)-1H-indazole (300 mg, 0.661 mmol) and sodium iodide (99 mg, 0.661 mmol) were weighed into a round-bottomed flask and dissolved in acetonitrile (2 ml) before [3-(4-morpholinyl)propyl]amine (191 mg, 1.322 mmol, available from Sigma-Aldrich) and DIPEA (0.231 ml, 1.322 mmol) were added. The mixture was heated to 70° C. for 2 h, then cooled and the solvent removed under a stream of nitrogen. The crude residue was dissolved in DCM/MeOH (1:1) and preadsorbed onto silica which was then added to the top of a 20 g silica cartridge that was subsequently eluted with 0-15% MeOH(+1% triethylamine)/DCM over 20 mins. The appropriate fractions were combined and the solvent removed in vacuo to give the title compound as a yellow oily solid (328 mg).

LCMS (Method A): Rt 0.35 mins, MH+ 421/423.

Intermediate 52

N-(2-(Methyloxy)-5-{1-(phenylsulfonyl)-4-[5-(tetrahydro-1,4-oxazepin-4(5H)-ylmethyl)-1,3,4-oxadiazol-2-yl]-1H-indazol-6-yl}-3-pyridinyl)methanesulfonamide

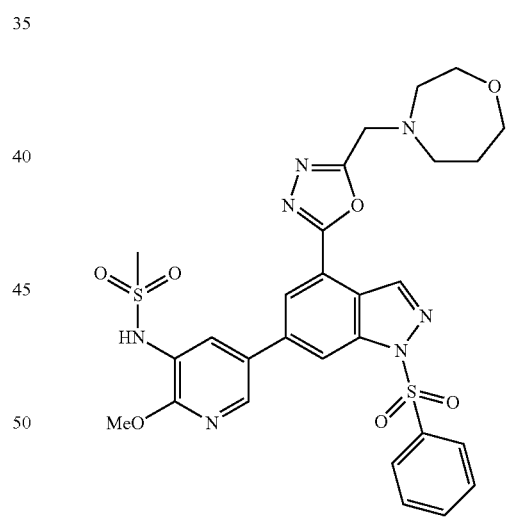

6-Bromo-1-(phenylsulfonyl)-4-[5-(tetrahydro-1,4-oxazepin-4(5H)-ylmethyl)-1,3,4-oxadiazol-2-yl]-1H-indazole (279 mg, 0.538 mmol) was dissolved in 1,4-dioxane (5 ml) and half of the resulting solution was charged to a reaction vessel. N-[2-(methyloxy)-5-(4,4,5,5-tetramethyl-1,3,2-dioxaborolan-2-yl)-3-pyridinyl]methanesulfonamide (114 mg, 0.347 mmol), 1,1'-bis(diphenylphosphino)ferrocene palladium dichloride (39.5 mg, 0.054 mmol), potassium phosphate tribasic (171.5 mg, 0.808 mmol) and water (0.25 ml) were added. The reaction mixture was heated at 100° C. for 20 mins. The mixture was passed through a 1 g silica SPE cartridge, washing with MeOH. The solvent was removed under a stream of nitrogen and the residue was partitioned between DCM (10 ml) and water (10 ml), separated with a hydrophobic frit and the solvent again removed under a stream of nitrogen. The residue was purified by preparative HPLC using the following method:

| | |
|---|---|
| Column Packing | Waters Sunfire c18 |
| Column Particle Size | 5.0 μm |
| Column Dimensions | 100 × 19 mmID |
| Solvent A | 0.1% v/v formic acid in water |
| Solvent B | MeCN + 0.1% v/v of formic acid |
| Temperature | ambient |
| Flow Rate | 20 ml/min |
| Injection Volume | 500 μL |
| Injection Vehicle | 1:1 DMSO/MeCN |
| UV detection | Diode-array 210-400 nm (averaged) |
| MS detection | Electrospray, +ve/−ve switching, 100-1000 amu, centroid mode |
| MS scan function | Electrospray, +ve/−ve switching, centroid mode |

| Time (mins) | % A | % B | Flow rate (ml/min) |
|---|---|---|---|
| 0 | 75 | 25 | 20 |
| 1 | 75 | 25 | 20 |
| 15 | 68 | 32 | 20 |
| 15.5 | 1 | 99 | 20 |
| 18 | 1 | 99 | 20 |
| 18.5 | 75 | 25 | 20 |
| 20 | 75 | 25 | 20 |

The appropriate fractions were dried down to give the title compound as a cream solid (50 mg).

LCMS (Method A): Rt 0.78, MH+ 640

The compound listed below was synthesised using the general method above.

Intermediate 54

1-[({5-[6-Bromo-1-(phenylsulfonyl)-1H-indazol-4-yl]-1,3,4-oxadiazol-2-yl}methyl)amino]-3-(4-morpholinyl)-2-propanol

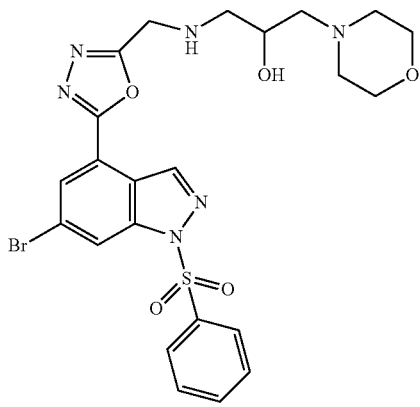 [SMILES: O=S(=O)(c1ccccc1)n1ncc2c(-c3nnc(CNCC(O)CN4CCOCC4)o3)cc(Br)cc21]

6-Bromo-4-[5-(chloromethyl)-1,3,4-oxadiazol-2-yl]-1-(phenylsulfonyl)-1H-indazole (300 mg, 0.661 mmol) and sodium iodide (138 mg, 0.921 mmol) were weighed into a round-bottomed flask and dissolved in acetonitrile (2 ml) before 1-amino-3-morpholin-4-ylpropan-2-ol (212 mg, 1.322 mmol, available from Enamine Ltd) and DIPEA (0.231 ml, 1.322 mmol) were added. The mixture was heated to 70° C. for 2 h, then cooled, diluted with DCM and washed with 2 M aqueous HCl (5 ml). The organic layer was separated with a hydrophobic frit and the aqueous layer was neutralised to

| Intermediate | Starting Material | Structure | Rt mins | MH+ | Name |
|---|---|---|---|---|---|
| 53 | 4-(4,4,5,5-tetramethyl-1,3,2-dioxaborolan-2-yl)-1H-indole (85 mg, 0.350 mmol) | | 0.88 | 555 | 6-(1H-indol-4-yl)-1-(phenylsulfonyl)-4-[5-(tetrahydro-1,4-oxazepin-4(5H)-ylmethyl)-1,3,4-oxadiazol-2-yl]-1H-indazole | pH 7 by addition of 2M NaOH resulting in the formation of a solid precipitate. This was filtered off under vacuum and dried in air for 2 h to give the title compound as a cream solid (220 mg).

LCMS (Method A): Rt 0.63 mins, MH+ 577/579.

Intermediate 55

N-[5-[4-{5-[(8aS)-Hexahydropyrrolo[1,2-a]pyrazin-2(1H)-ylmethyl]-1,3,4-oxadiazol-2-yl}-1-(phenylsulfonyl)-1H-indazol-6-yl]-2-(methyloxy)-3-pyridinyl]methanesulfonamide

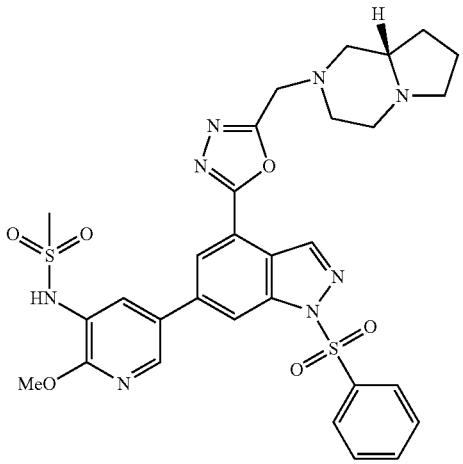 [SMILES: COc1ncc(-c2cc(-c3nnc(CN4CCN5CCC[C@H]5C4)o3)c3cnn(S(=O)(=O)c4ccccc4)c3c2)cc1NS(C)(=O)=O]

To a solution of 6-bromo-4-{5-[(8aS)-hexahydropyrrolo[1,2-a]pyrazin-2(1H)-ylmethyl]-1,3,4-oxadiazol-2-yl}-1-(phenylsulfonyl)-1H-indazole (100 mg, 0.184 mmol) was added N-[2-(methyloxy)-5-(4,4,5,5-tetramethyl-1,3,2-dioxaborolan-2-yl)-3-pyridinyl]methanesulfonamide (72.5 mg, 0.221 mmol), 1,1'-bis(diphenylphosphino)ferrocene palladium dichloride (36 mg, 0.049 mmol) and potassium phosphate tribasic (126 mg, 0.594 mmol). The mixture was heated under microwave irradiation at 100° C. for 20 mins. The mixture was passed through a 1 g silica SPE cartridge, washing with MeOH. The solvent was removed under a stream of nitrogen and the residue was partitioned between DCM (10 ml) and water (10 ml), separated with a hydrophobic frit and the solvent again removed under a stream of nitrogen. The residue was dissolved in DCM and added to the top of a 10 g silica SPE cartridge that was subsequently eluted with 0-15% MeOH/DCM over 20 mins. The product-containing fractions were combined and the solvent removed in vacuo to give the title compound as an orange oil (95 mg).

LCMS (Method A). Product Rt 0.69, MH+ 665.

The compound listed below was synthesised using the general method above.

| Intermediate | Starting Material | Structure | Rt mins | MH+ | Name |
|---|---|---|---|---|---|
| 56 | 2,4-difluoro-N-[2-(methyloxy)-5-(4,4,5,5-tetramethyl-1,3,2-dioxaborolan-2-yl)-3-pyridinyl]benzenesulfonamide | 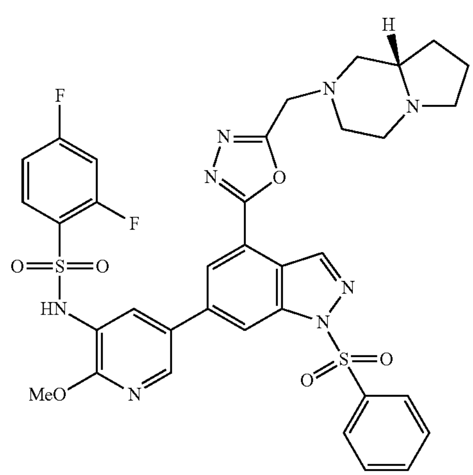 [SMILES: COc1ncc(-c2cc(-c3nnc(CN4CCN5CCC[C@H]5C4)o3)c3cnn(S(=O)(=O)c4ccccc4)c3c2)cc1NS(=O)(=O)c1ccc(F)cc1F] | 0.82 | 763 | 2,4-difluoro-N-[5-[4-{5-[(8aS)-hexahydropyrrolo[1,2-a]pyrazin-2(1H)-ylmethyl]-1,3,4-oxadiazol-2-yl}-1-(phenylsulfonyl)-1H-indazol-6-yl]-2-(methyloxy)-3-pyridinyl]benzenesulfonamide |

Intermediate 57

6-Bromo-4-{5-[(8aS)-hexahydropyrrolo[1,2-a]pyrazin-2(1H)-ylmethyl]-1,3,4-oxadiazol-2-yl}-1-(phenylsulfonyl)-1H-indazole

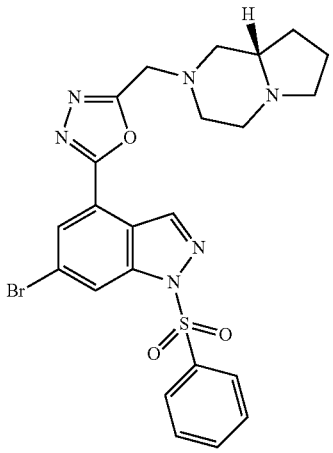 [SMILES: O=S(=O)(c1ccccc1)n1ncc2c(-c3nnc(CN4CCN5CCC[C@H]5C4)o3)cc(Br)cc21]

6-Bromo-4-[5-(chloromethyl)-1,3,4-oxadiazol-2-yl]-1-(phenylsulfonyl)-1H-indazole (300 mg, 0.661 mmol) and sodium iodide (99 mg, 0.661 mmol) were weighed into a round-bottomed flask and dissolved in acetonitrile (2 ml) before (S)-1,4-diazabicyclo[4.3.0]nonane (167 mg, 1.322 mmol, available from ABCR GmbH & CO.KG) and DIPEA (0.231 ml, 1.322 mmol) were added. The mixture was heated to 70° C. for 2 h. The mixture was cooled, diluted with DCM and washed with 2 M aqueous HCl (2 ml). The organic layer was separated by hydrophobic frit. The aqueous extracts were combined and neutralised to pH 7 with NaOH then extracted with more DCM (2×10 ml) which was combined with the other organic extracts and evaporated under a stream of nitrogen to give an orange oil. This was dissolved in DCM and loaded onto the top of a 10 g silica cartridge that was subsequently eluted with 0-15% MeOH(+1% triethylamine)/DCM over 15 mins. The appropriate fractions were combined and the solvent removed in vacuo to give the title compound as a cream solid (220 mg).

LCMS (Method A): Rt=0.73, MH+ 543/545.

Intermediate 58

5-[4-(5-{[(2R,6S)-2,6-Dimethyl-4-morpholinyl]methyl}-1,3,4-oxadiazol-2-yl)-1-methyl-1H-indazol-6-yl]-2-(methyloxy)-3-pyridinamine

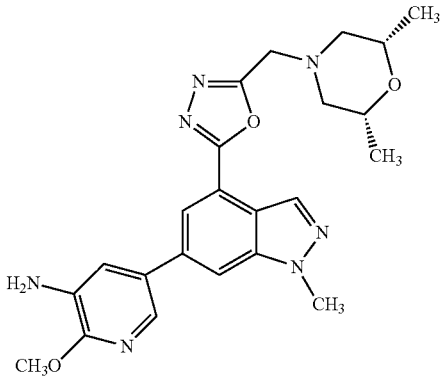

6-Bromo-4-(5-{[(2R,6S)-2,6-dimethyl-4-morpholinyl]methyl}-1,3,4-oxadiazol-2-yl)-1-methyl-1H-indazole (200 mg, 0.492 mmol), 2-(methyloxy)-5-(4,4,5,5-tetramethyl-1,3,2-dioxaborolan-2-yl)-3-pyridinamine (123 mg, 0.492 mmol), 1,1'-bis(diphenylphosphino)ferrocene palladium dichloride (72.0 mg, 0.098 mmol) and tripotassium phosphate (313 mg, 1.477 mmol) were added to 1,4-dioxane (4 ml) and water (1 ml) then heated under microwave irradiation for 20 mins at 100° C. The solvent was removed under nitrogen and the crude residue purified by chromatography (20 g Si cartridge, gradient: 0-100% EtOAc/DCM +0-20% MeOH). The appropriate fractions were combined and the solvent was removed to give the title compound as a brown solid (130 mg).

LCMS (Method A): Rt 0.76 mins, MH+ 450.

Intermediate 59

Methyl 6-bromo-1H-indazole-4-carboxylate

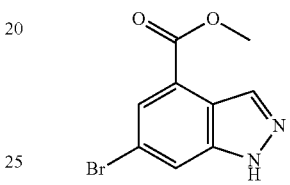

Concentrated hydrochloric acid (46.9 ml, 1543 mmol) was added to a stirred suspension of 6-bromo-1H-indazole-4-carboxylic acid (4.65 g, 19.29 mmol, available from Sinova) in methanol (100 ml) and the reaction mixture was heated to 70° C. for 18 h. The reaction mixture was allowed to cool to RT resulting in the precipitation of a solid. The mixture was cooled in ice and the yellow precipitate filtered off and washed with methanol to give the title compound as a yellow solid (2.54 g).

LCMS (Method A): Rt=0.90 mins, MH+ 255/257.

Intermediate 60

Methyl 6-bromo-1-[(4-methylphenyl)sulfonyl]-1H-indazole-4-carboxylate

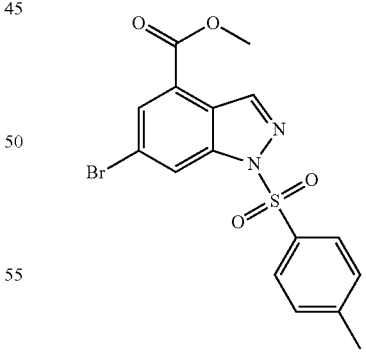

Sodium hydride (1.289 g, 32.2 mmol) was added portion wise to a solution of methyl 6-bromo-1H-indazole-4-carboxylate (4.11 g, 16.11 mmol) in N,N-dimethylformamide (50 ml) at 0° C. The dark orange mixture was stirred at 0° C. for 10 mins, then treated with 4-methylbenzenesulfonyl chloride (3.38 g, 17.72 mmol). The resultant pale cream mixture was stirred for 30 mins at 0° C. then poured into water (1000 ml). The cream precipitate was filtered off under vacuum and

Intermediate 61

6-Bromo-1-[(4-methylphenyl)sulfonyl]-1H-indazole-4-carboxylic acid

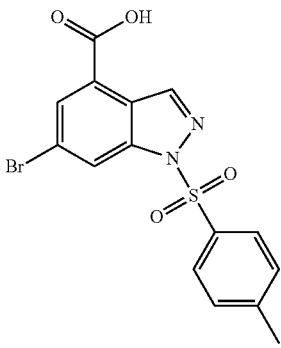 [SMILES: Cc1ccc(S(=O)(=O)n2ncc3c(C(=O)O)cc(Br)cc32)cc1]

Lithium hydroxide (0.774 g, 32.3 mmol) was added to a stirred suspension of methyl 6-bromo-1-[(4-methylphenyl)sulfonyl]-1H-indazole-4-carboxylate (5.51 g, 13.46 mmol) in tetrahydrofuran (50 ml) and water (15 ml) and the reaction mixture was stirred at RT for 1 h. The reaction mixture was poured onto 2N HCl (800 ml) with stirring. The precipitate formed was filtered off under vacuum and dried at 50° C. in a vacuum oven for 18 h to give the title compound as a yellow solid (3.5 g).

LCMS (Method B): Rt 3.10 mins, MH+ 395/397.

Intermediate 62

2-[(2R,6S)-2,6-Dimethyl-4-morpholinyl]acetohydrazide

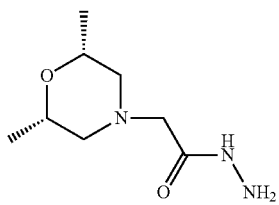

Methyl[(2R,6S)-2,6-dimethyl-4-morpholinyl]acetate (5.05 g, 27.0 mmol, see Journal of Fluorine Chemistry (1998) 193-201 for literature preparation) was dissolved in methanol (20 ml) and hydrazine hydrate (2.013 ml, 27.0 mmol) added. The reaction mixture was heated to 70° C. for 18 h. The solvent was partially concentrated in vacuo to remove the methanol and extracted with ethyl acetate (3×20 ml). The combined organic layers were dried and concentrated to afford the title compound as a yellow solid (3.35 g).

$^{1}$H NMR (400 MHz, chloroform-d) δ=8.06 (1H, br. S.) 3.75-3.98 (2H, m), 3.60-3.71 (2H, m), 1.88-1.96 (2H, m), 1.15 (6H, d)

Intermediate 63

6-Bromo-N'-{[(2R,6S)-2,6-dimethyl-4-morpholinyl]acetyl}-1-[(4-methylphenyl)sulfonyl]-1H-indazole-4-carbohydrazide

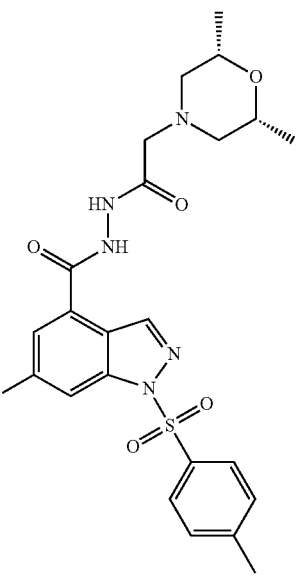

6-Bromo-1-[(4-methylphenyl)sulfonyl]-1H-indazole-4-carboxylic acid (1.5 g, 3.80 mmol) was suspended in thionyl chloride (8.31 ml, 114 mmol) and heated to 100° C. for 30 mins. The thionyl chloride was removed in vacuo and excess aziotroped with dry diethyl ether to give a yellow solid. This was dissolved in dry tetrahydrofuran (40 ml) and 2-[(2R,6S)-2,6-dimethyl-4-morpholinyl]acetohydrazide (1.066 g, 5.69 mmol) and DIPEA (2.65 ml, 15.18 mmol) added. The reaction mixture was heated to 60° C. for 20 mins. The solvent was removed in vacuo and the residue partitioned between dichloromethane (50 ml) and water (50 ml). The layers were separated and the organic concentrated in vacuo to give a yellow foam. This was purified by column chromatography, loading in dichloromethane onto a silica cartridge (50 g), eluting with 0-100% ethyl acetate-cyclohexane over 30 mins. The appropriate fractions were combined and evaporated in vacuo to give the title compound as a yellow solid (950 mg).

LCMS (Method B): Rt 2.06 mins, MH+ 564/566.

Intermediate 64

6-Bromo-4-(5-{[(2R,6S)-2,6-dimethyl-4-morpholinyl]methyl}-1,3,4-oxadiazol-2-yl)-1-[(4-methylphenyl)sulfonyl]-1H-indazole

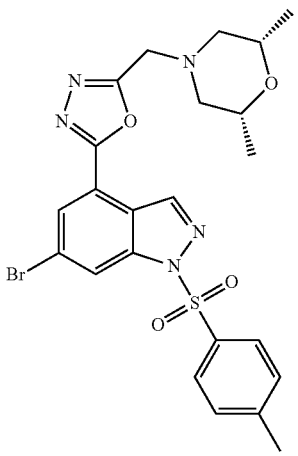 [SMILES: Cc1ccc(S(=O)(=O)n2ncc3c(-c4nnc(CN5C[C@@H](C)O[C@@H](C)C5)o4)cc(Br)cc32)cc1]

6-Bromo-N'-{[(2R,6S)-2,6-dimethyl-4-morpholinyl]acetyl}-1-[(4-methylphenyl)sulfonyl]-1H-indazole-4-carbohydrazide (950 mg, 1.683 mmol) was dried over phosphorus pentoxide in a desicator overnight. 6-bromo-N'-{[(2R,6S)-2,6-dimethyl-4-morpholinyl]acetyl}-1-[(4-methylphenyl)sulfonyl]-1H-indazole-4-carbohydrazide (950 mg, 1.683 mmol) and methoxycarbonylsulfamoyl)triethylammonium hydroxide (602 mg, 2.52 mmol) were suspended in anhydrous tetrahydrofuran (20 ml) and heated to 75° C. for 2 h. The solvent was removed in vacuo and the residue partitioned between dichloromethane (15 ml) and saturated sodium bicarbonate solution (15 ml). The layers were separated (hydrophobic frit), the aqueous washed with further dichloromethane (5 ml) and the combined organics concentrated in vacuo to give a yellow solid. This was purified by column chromatography, loading in dichloromethane onto a silica cartridge 50 g, using a 0-100% ethyl acetate-cyclohexane over 40 mins. The appropriate fractions were combined and evaporated in vacuo to give the title compound as a white solid (680 mg).

LCMS (Method A): Rt 1.25 mins, MH+ 546/548.

Intermediate 65

5-{4-(5-{[(2R,6S)-2,6-Dimethyl-4-morpholinyl]methyl}-1,3,4-oxadiazol-2-yl)-1-[(4-methyl phenyl)sulfonyl]-1H-indazol-6-yl}-2-(methyloxy)-3-pyridinamine

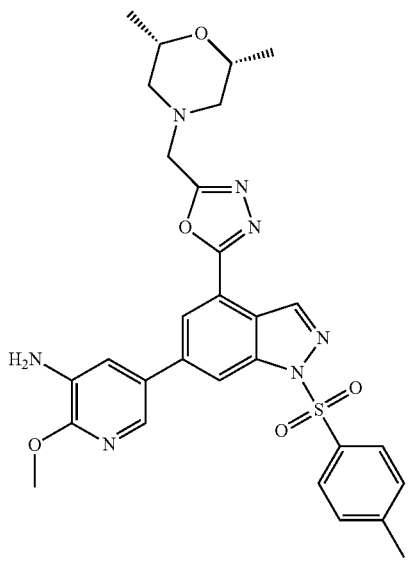 [SMILES: COc1ncc(-c2cc(-c3nnc(CN4C[C@@H](C)O[C@@H](C)C4)o3)c3cnn(S(=O)(=O)c4ccc(C)cc4)c3c2)cc1N]

6-Bromo-4-(5-{[(2R,6S)-2,6-dimethyl-4-morpholinyl]methyl}-1,3,4-oxadiazol-2-yl)-1-[(4-methylphenyl)sulfonyl]-1H-indazole (680 mg, 1.244 mmol) was dissolved in 1,4-dioxane (15 ml) and water (1.5 ml). 2-(methyloxy)-5-(4,4,5,5-tetramethyl-1,3,2-dioxaborolan-2-yl)-3-pyridinamine (311 mg, 1.244 mmol), bis(diphenylphosphino)ferrocene palladium dichloride (182 mg, 0.249 mmol) and tripotassium phosphate monohydrate (860 mg, 3.73 mmol) were added and the reaction mixture heated at 80° C. for 2 h. 2-(methoxy)-5-(4,4,5,5-tetramethyl-1,3,2-dioxaborolan-2-yl)-3-pyridinamine (0.1 eq, 31 mg) was added and the reaction mixture heated at 80° C. for a further 18 h. The solvent was removed in vacuo and the residue partitioned between DCM (50 ml) and water (50 ml). The layers were separated (hydrophobic frit), the organic concentrated in vacuo and the residue purified by column chromatography, loading in dichloromethane and purified on a silica cartridge (100 g), using a 0-30% methanol(+1% triethylamine)-dichloromethane over 40 mins. The appropriate fractions were combined and concentrated in vacuo to a brown gum. This was purified again by column chromatography, loading in dichloromethane and purified on a silica cartridge (50 g) using a 0-100% ethyl acetate-cyclohexane+0-20% methanol over 40 mins. The appropriate fractions were combined and evaporated in vacuo to give the title compound as a yellow solid (320 mg).

LCMS (Method A): Rt 1.10 mins, MH+ 590.

Intermediate 66

Methyl 6-bromo-1-methyl-1H-indazole-4-carboxylate

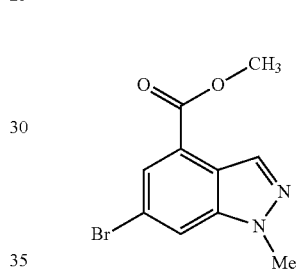

Sodium hydride (0.690 g, 17.25 mmol) was added to a 250 ml round bottom flask and tetrahydrofuran (THF) (60 mL) was added. The mixture was stirred for 10 minutes in an ice bath then methyl 6-bromo-1H-indazole-4-carboxylate (4 g, 15.68 mmol) was added portionwise and stirred until no further effervescence was seen (10 minutes). Iodomethane (5 mL, 80 mmol) was then added to the flask and the mixture stirred at 0° C. for 1 hour, then the ice bath was removed and a water bath at room temperature used and the reaction left overnight (30 hours). The solvent was removed in vacuo to give a yellow cream. The crude was partitioned between water (20 mL) and DCM (20 mL) then the solvent was removed in vacuo to give a yellow solid (2.2 g) This was purified by chromatography on silica using a 50 g Si cartridge and run on Flash Master 11 using a gradient of 0-100% EtOAc/cyclohexane over 30 min. The resultant fractions were analysed by HPLC and fractions containing the two regioisomers were independently combined and the solvent removed in vacuo. The title compound methyl 6-bromo-1-methyl-1H-indazole-4-carboxylate was isolated as white solid (730 mg). LCMS (Method A): $R_t$ 1.03 min, MH+ 270. Regiochemistry confirmed by NMR.

Methyl 6-bromo-2-methyl-1H-indazole-4-carboxylate was also isolated as white solid (750 mg).

LCMS (Method A): Rt 0.97 min, MH+ 270. Regiochemistry confirmed by NMR.

Intermediate 67

6-Bromo-1-methyl-1H-indazole-4-carboxylic acid

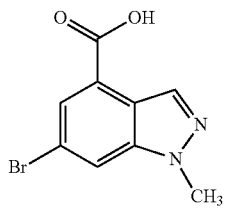

Lithium hydroxide (156 mg, 6.51 mmol) was added to a stirred suspension of methyl 6-bromo-1-methyl-1H-indazole-4-carboxylate (730 mg, 2.71 mmol) in tetrahydrofuran (THF) (25 ml) and water (5 ml) and the reaction mixture was stirred at room temperature for 1 h. During this time the cream suspension turned to a pale brown solution. The reaction mixture was poured onto 2N HCl (100 ml) with stirring. The precipitate formed was filtered off under vacuum and dried at 50° C. in a vacuum oven for 18 h to give the title compound as a white solid (480 mg).

LCMS (Method A) Rt 0.79 min, MH+ 255.

Intermediate 68

6-Bromo-N'-{[(2R,6S)-2,6-dimethyl-4-morpholinyl]acetyl}-1-methyl-1H-indazole-4-carbohydrazide

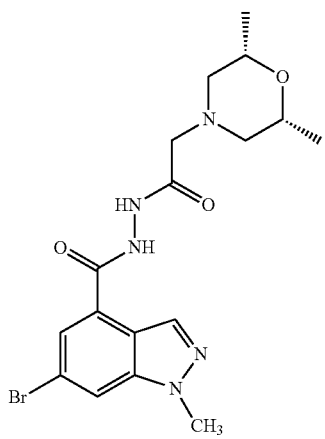 [SMILES: C[C@@H]1CN(CC(=O)NNC(=O)c2cc(Br)cc3c2cnn3C)C[C@H](C)O1]

6-Bromo-1-methyl-1H-indazole-4-carboxylic acid (480 mg, 1.882 mmol) was suspended in thionyl chloride (4.12 ml, 56.5 mmol) and heated to 100° C. for 30 mins. The thionyl chloride was removed in vacuo and excess azeotroped with dry diethyl ether to give a yellow solid. This was dissolved in dry tetrahydrofuran (THF) (15 ml) and 2-[(2R,6S)-2,6-dimethyl-4-morpholinyl]acetohydrazide (529 mg, 2.82 mmol) and DIPEA (1.315 ml, 7.53 mmol) were added. The reaction mixture was heated to 60° C. for 20 mins. Solvent was removed in vacuo and the residue partitioned between dichloromethane (15 ml) and water (15 ml). The layers were separated and the organic phase concentrated in vacuo to give a green solid which was purified by column chromatography, loading in dichloromethane and purified on Flashmaster 11 silica (Si) 20 g using a 0-100% ethyl acetate-cyclohexane+0-20% MeOH over 30 mins. The appropriate fractions were combined and evaporated in vacuo to afford the title compound as a yellow solid (485 mg). LCMS (Method A) Rt 0.49 min, MH+ 424.

Example 1

6-(1H-Indol-4-yl)-4-[5-(4-morpholinylmethyl)-1,3,4-oxadiazol-2-yl]-1H-indazole

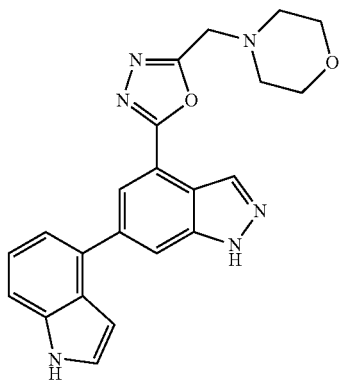 [SMILES: c1cc(-c2cc(-c3nnc(CN4CCOCC4)o3)c3cn[nH]c3c2)c2cc[nH]c2c1]

A stirred solution of 6-(1H-indol-4-yl)-1-[(4-methylphenyl)sulfonyl]-4-[5-(4-morpholinylmethyl)-1,3,4-oxadiazol-2-yl]-1H-indazole (25 mg, 0.045 mmol) and 2M sodium hydroxide (3 ml) in isopropanol (10 ml) was stirred at room temperature for 1 h. The solution was treated with 2M hydrochloric acid (3 ml) and evaporated to low bulk until the product was precipitated. The resulting solid was collected by filtration and washed with water to give the title compound as a cream coloured solid (15 mg).

LCMS (Method B): Rt 1.84 mins, MH+401.

Example 2

N-(2-Chloro-5-{4-[5-(4-morpholinylmethyl)-1,3,4-oxadiazol-2-yl]-1H-indazol-6-yl}-3-pyridinyl)methanesulfonamide

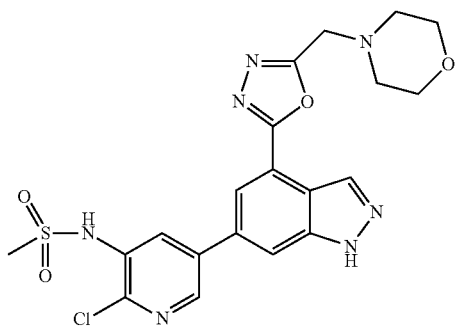 [SMILES: CS(=O)(=O)Nc1cc(-c2cc(-c3nnc(CN4CCOCC4)o3)c3cn[nH]c3c2)cnc1Cl]

N-(2-Chloro-5-{1-[(4-methylphenyl)sulfonyl]-4-[5-(4-morpholinylmethyl)-1,3,4-oxadiazol-2-yl]-1H-indazol-6-yl}-3-pyridinyl)methanesulfonamide (52 mg, 0.081 mmol) was placed in isopropanol (3 ml) and 2M sodium hydroxide (1 ml, 2.0 mmol) added. The mixture was stirred at room temperature overnight and blown to dryness under a stream of nitrogen. The mixture was dissolved in water (10 ml) and washed with dichloromethane (10 ml). The organic layer was acidified by the addition of 2M hydrochloric acid and the solvent removed. The residue was purified by Mass Directed Automated Preparative HPLC (Method B) to give the title compound (8 mg).

LCMS (Method B): Rt 0.66 mins, MH+490.

Example 3

4-(5-{[(2R,6S)-2,6-Dimethyl-4-morpholinyl]methyl}-1,3,4-oxadiazol-2-yl)-6-(1H-indol-4-yl)-1H-indazole

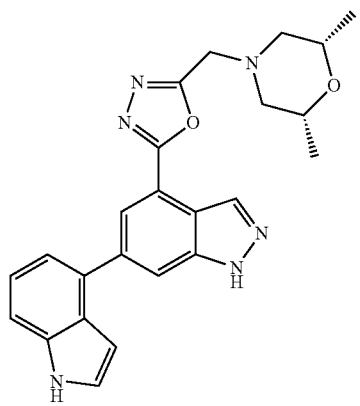 [SMILES: C[C@@H]1CN(Cc2nnc(-c3cc(-c4cccc5[nH]ccc45)cc4[nH]ncc34)o2)C[C@H](C)O1]

(2R,6S)-2,6-Dimethylmorpholine (12.57 mg, 0.11 mmol) and 4-[5-(chloromethyl)-1,3,4-oxadiazol-2-yl]-6-(1H-indol-4-yl)-1-(phenylsulfonyl)-1H-indazole (51 mg, 0.104 mmol) were dissolved in acetonitrile (0.5 ml) and N,N-diisopropylethylamine (0.0262 ml, 0.15 mmol) was added, followed by sodium iodide (14.99 mg, 0.1 mmol). The solution was stirred at 70° C. for 18 h and blown to dryness under a stream of nitrogen. Isopropanol (0.5 ml) was added followed by 2M sodium hydroxide (0.5 ml) and stirred for 18 h when the mixture was neutralised and the solvent removed under a stream of nitrogen. The crude product was dissolved in dimethylsulphoxide (0.5 ml) and purified by Mass Directed Automated Preparative HPLC (Method F) and the solvent was evaporated in vacuo using Genevac to give the title compound (4 mg).

LCMS (Method B): Rt 2.11, MH+429.

The compounds listed below were synthesised using the general method above.

| Example Number | Monomer | Structure | Rt min | MH+ | Name |
|---|---|---|---|---|---|
| Example 4 | 2-(1-piperazinyl)pyrimidine dihydrochloride (available from Fluka) | 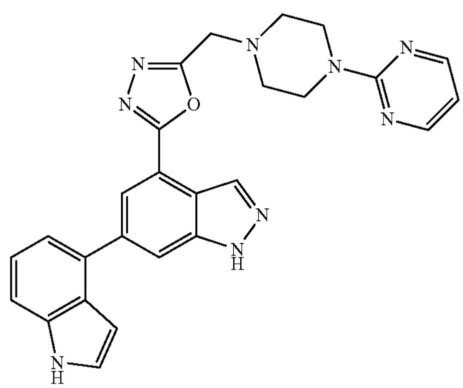 [SMILES: c1cnc(N2CCN(Cc3nnc(-c4cc(-c5cccc6[nH]ccc56)cc5[nH]ncc45)o3)CC2)nc1] | 2.11 | 478 | 6-(1H-indol-4-yl)-4-(5-{[4-(2-pyrimidinyl)-1-piperazinyl]methyl}-1,3,4-oxadiazol-2-yl)-1H-indazole |
| Example 5 | 4,4-dimethyl-piperidine hydrochloride (available from MicroChemistry Ltd) | 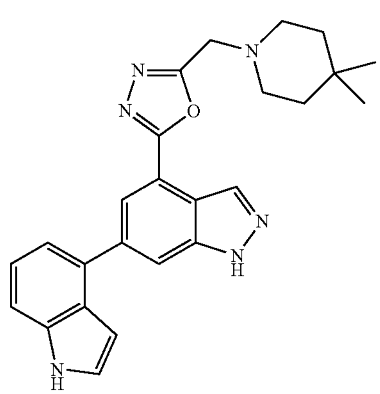 [SMILES: CC1(C)CCN(Cc2nnc(-c3cc(-c4cccc5[nH]ccc45)cc4[nH]ncc34)o2)CC1] | 1.71 | 427 | 4-{5-[(4,4-dimethyl-1-piperidinyl)methyl]-1,3,4-oxadiazol-2-yl}-6-(1H-indol-4-yl)-1H-indazole |

-continued

| Example Number | Monomer | Structure | Rt min | MH+ | Name |
|---|---|---|---|---|---|
| Example 6 | 1-(2-methylpropyl)piperazine (available from Fluorochem) | 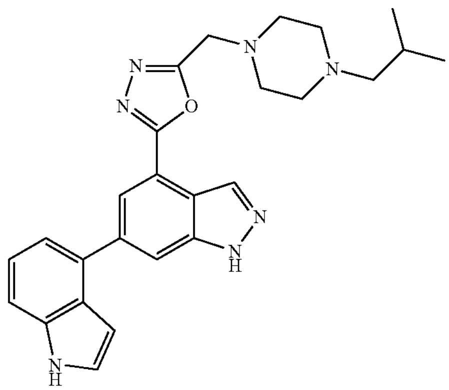 [SMILES: CC(C)CN1CCN(Cc2nnc(-c3cc(-c4cccc5[nH]ccc45)cc4[nH]ncc34)o2)CC1] | 1.55 | 456 | 6-(1H-indol-4-yl)-4-(5-{[4-(2-methylpropyl)-1-piperazinyl]methyl}-1,3,4-oxadiazol-2-yl)-1H-indazole |
| Example 7 | 4-(1-methylethyl)piperidine (available from ChemBridge Building Block Library) | 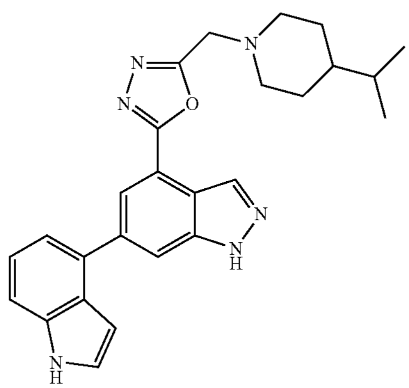 | 1.86 | 441 | 6-(1H-indol-4-yl)-4-(5-{[4-(1-methylethyl)-1-piperidinyl]methyl}-1,3,4-oxadiazol-2-yl)-1H-indazole |
| Example 8 | 2-(1-pyrrolidinylmethyl)piperidine (available from Fluorochem) | 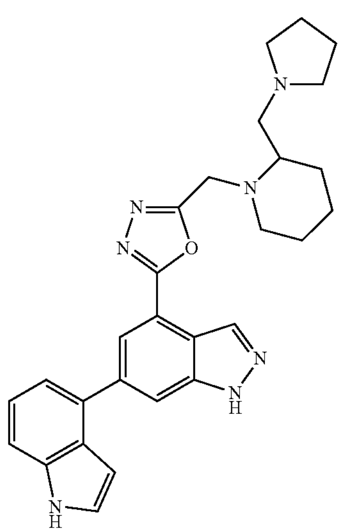 [SMILES: c1cc(-c2cc(-c3nnc(CN4CCCCC4CN4CCCC4)o3)c3cn[nH]c3c2)c2cc[nH]c2c1] | 1.69 | 482 | 6-(1H-indol-4-yl)-4-(5-{[2-(1-pyrrolidinylmethyl)-1-piperidinyl]methyl}-1,3,4-oxadiazol-2-yl)-1H-indazole |

The following examples were synthesised as above with additional purification steps as follows:

The solutions from the previous purification were neutralised and the solvent removed then purified by Mass Directed Automated Preparative HPLC (Method G) and the solvent was evaporated in vacuo using Genevac to give the following title compounds. (LCMS Method B)

| Example Number | Monomer | Structure | Rt min | MH+ | Name |
|---|---|---|---|---|---|
| Example 9 | 1-(4-fluorophenyl)piperazine hydrochloride (available from Aldrich) | 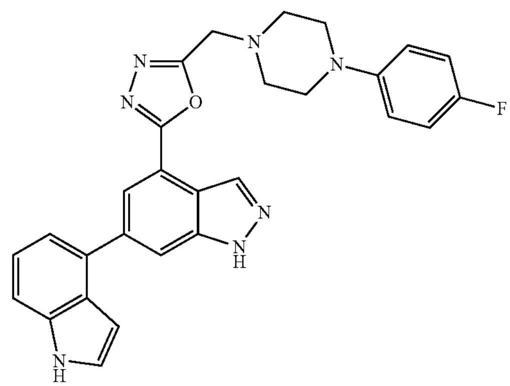 [SMILES: Fc1ccc(N2CCN(Cc3nnc(-c4cc(-c5cccc6[nH]ccc56)cc5[nH]ncc45)o3)CC2)cc1] | 2.48 | 494 | 4-(5-{[4-(4-fluorophenyl)-1-piperazinyl]methyl}-1,3,4-oxadiazol-2-yl)-6-(1H-indol-4-yl)-1H-indazole |
| Example 10 | (1S,4S)-2-methyl-2,5-diazabicyclo[2.2.1]heptane hydrobromide (available from Aldrich) | 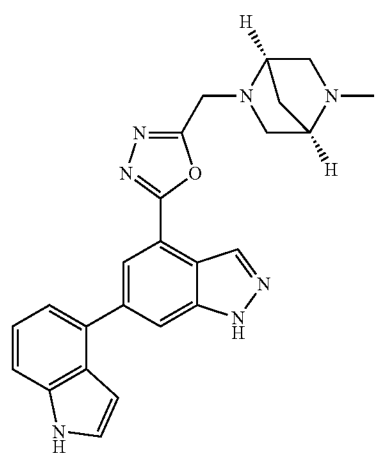 [SMILES: CN1C[C@H]2C[C@@H]1CN2Cc1nnc(-c2cc(-c3cccc4[nH]ccc34)cc3[nH]ncc23)o1] | 1.39 | 426 | 6-(1H-indol-4-yl)-4-(5-{[(1R,4R)-5-methyl-2,5-diazabicyclo[2.2.1]hept-2-yl]methyl}-1,3,4-oxadiazol-2-yl)-1H-indazole |
| Example 11 | 2-(1-pyrrolidinylmethyl)morpholine (available from AB Chemicals Inc.) | 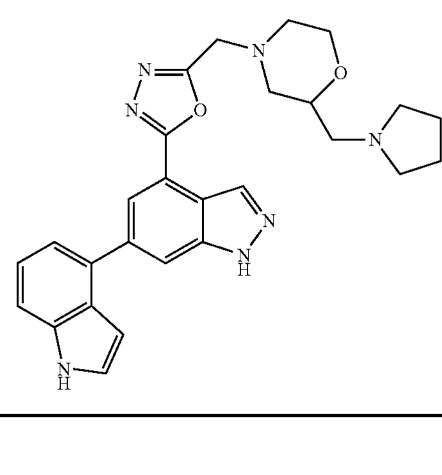 | 1.41 | 484 | 6-(1H-indol-4-yl)-4-(5-{[2-(1-pyrrolidinylmethyl)-4-morpholinyl]methyl}-1,3,4-oxadiazol-2-yl)-1H-indazole |

Example 12

6-(1H-Indol-4-yl)-4-[5-({4-[2-(4-morpholinyl) ethyl]-1-piperazinyl}methyl)-1,3,4-oxadiazol-2-yl]-1H-indazole

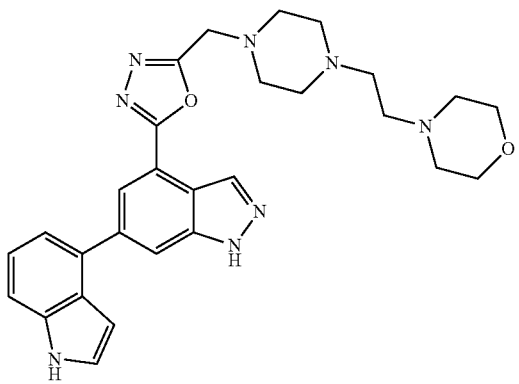 [SMILES: c1cc(-c2cc(-c3nnc(CN4CCN(CCN5CCOCC5)CC4)o3)c3cn[nH]c3c2)c2cc[nH]c2c1]

4-[2-(1-piperazinyl)ethyl]morpholine (14.1 mg, 0.11 mmol) and 4-[5-(chloromethyl)-1,3,4-oxadiazol-2-yl]-6-(1H-indol-4-yl)-1-(phenylsulfonyl)-1H-indazole (50 mg, 0.102 mmol) were dissolved in acetonitrile (0.5 ml) and N,N-diisopropylethylamine (0.026 ml, 0.15 mmol) was added, followed by sodium iodide (15.3 mg, 0.102 mmol). The solution was stirred at 70° C. for 18 h and blown to dryness under a stream of nitrogen. Isopropanol (0.3 ml) was added followed by 2M sodium hydroxide (0.3 ml) and stirred for 5 h when the mixture was neutralised and the solvent removed under a stream of nitrogen. The crude product was dissolved in dimethylsulphoxide (0.3 ml) and methanol (0.15 ml) with formic acid (0.05 ml) then purified by Mass Directed Automated Preparative HPLC (Method F) to give the title compound (26.4 mg).

LCMS (Method B): Rt 1.30, MH+513.

The following examples were synthesised as above with additional deprotection and purification steps as follows:

Isopropanol (0.3 ml) was added followed by 2M sodium hydroxide (0.3 ml) and stirred overnight when the mixture was neutralised and applied onto a Bicarbonate SPE (0.5 g) cartridge pre-conditioned with methanol (1 ml) then eluted with methanol (2 ml). The solvent was removed under a stream of nitrogen to give the following title compounds. (LCMS Method B)

| Example Number | Monomer | Structure | Rt min | MH+ | Name |
|---|---|---|---|---|---|
| Example 13 | 4-(1-methylethyl)piperazine (available from Aldrich) | 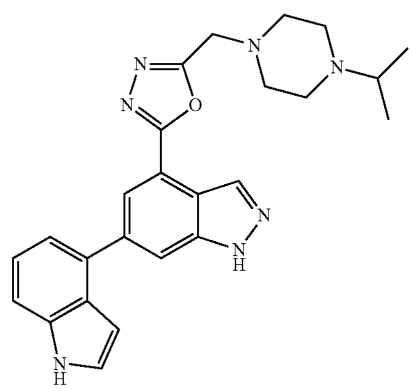 [SMILES: CC(C)N1CCN(Cc2nnc(-c3cc(-c4cccc5[nH]ccc45)cc4[nH]ncc34)o2)CC1] | 1.45 | 442 | 6-(1H-indol-4-yl)-4-(5-{[4-(1-methylethyl)-1-piperazinyl]methyl}-1,3,4-oxadiazol-2-yl}-1H-indazole. |
| Example 14 | (2R,6S)-2,6-Dimethylpiperidine (available from Aldrich) | 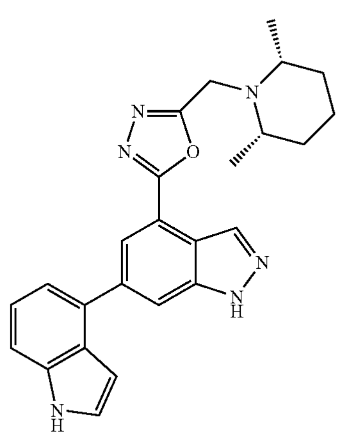 [SMILES: C[C@@H]1CCC[C@H](C)N1Cc1nnc(-c2cc(-c3cccc4[nH]ccc34)cc3[nH]ncc23)o1] | 1.62 | 427 | 4-(5-{[(2R,6S)-2,6-dimethyl-1-piperidinyl]methyl}-1,3,4-oxadiazol-2-yl)-6-(1H-indol-4-yl)-1H-indazole |

-continued

| Example Number | Monomer | Structure | Rt min | MH+ | Name |
|---|---|---|---|---|---|
| Example 15 | (1s,4s)-7-azabicyclo[2.2.1]heptane hydrochloride (available from Enamine Ltd | 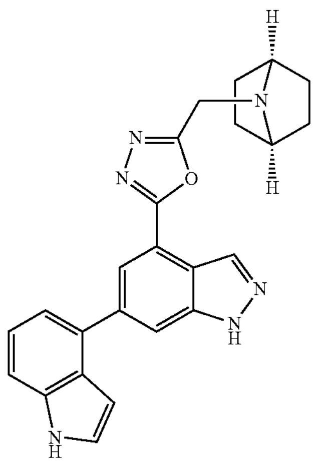 [SMILES: c1cc(-c2cc(-c3nnc(CN4[C@H]5CC[C@@H]4CC5)o3)c3cn[nH]c3c2)c2cc[nH]c2c1] | 1.46 | 411 | 4-{5-[(1s,4s)-7-azabicyclo[2.2.1]hept-7-ylmethyl]-1,3,4-oxadiazol-2-yl}-6-{1H-indol-4-yl)-1H-indazole |
| Example 16 | Octahydro-2H-1,4-benzoxazine (available from Chemical Block Ltd | 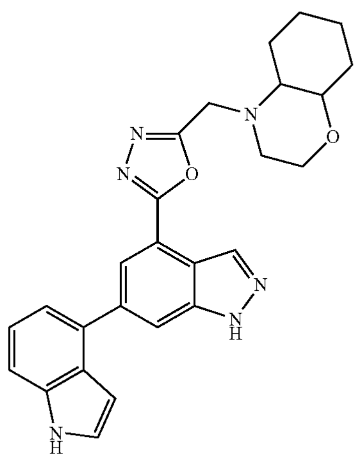 [SMILES: c1cc(-c2cc(-c3nnc(CN4CCOC5CCCCC54)o3)c3cn[nH]c3c2)c2cc[nH]c2c1] | 2.24 | 455 | 4-({5-[6-(1H-indol-4-yl)-1H-indazol-4-yl]-1,3,4-oxadiazol-2-yl}methyl)octahydro-2H-1,4-benzoxazine |
| Example 17 | 2-(2-methylpropyl)morpholine (available from ChemBridge Corp. | 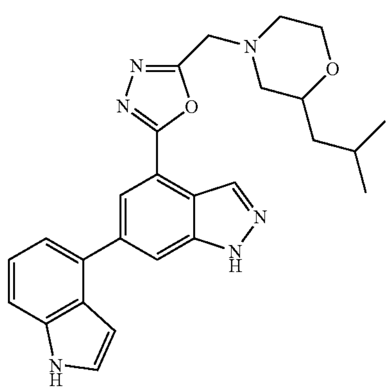 [SMILES: CC(C)CC1CN(Cc2nnc(-c3cc(-c4cccc5[nH]ccc45)cc4[nH]ncc34)o2)CCO1] | 2.55 | 457 | 6-(1H-indol-4-yl)-4-(5-{[2-(2-methylpropyl)-4-morpholinyl]methyl}-1,3,4-oxadiazol-2-yl)-1H-indazole |

Example 18

N-{2-Chloro-5-[4-(5-{[4-(1-methylethyl)-1-piperazinyl]methyl}-1,3,4-oxadiazol-2-yl)-1H-indazol-6-yl]-3-pyridinyl}methanesulfonamide

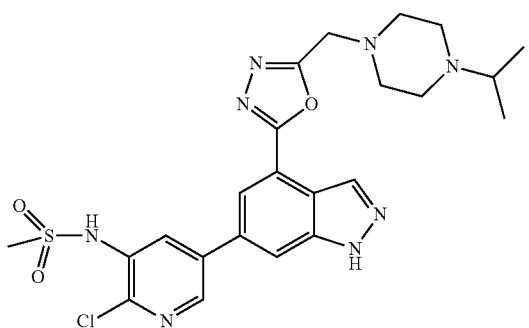 [SMILES: CC(C)N1CCN(Cc2nnc(-c3cc(-c4cnc(Cl)c(NS(C)(=O)=O)c4)cc4[nH]ncc34)o2)CC1]

N-(2-Chloro-5-{4-[5-(chloromethyl)-1,3,4-oxadiazol-2-yl]-1-[(4-methylphenyl)sulfonyl]-1H-indazol-6-yl}-3-pyridinyl)methanesulfonamide (25 mg, 0.042 mmol) and 1-(1-methylethyl)piperazine (500 mg, 3.90 mmol) were placed a vial and heated in a microwave at 90° C. for 15 mins. The 1-(1-methylethyl)piperazine was blown off under a stream of nitrogen and the residue suspended in isopropanol (2 ml) and 2M sodium hydroxide (1 ml) added. The mixture was stirred at room temperature for 2 h. The solvent was blown off under a stream of nitrogen and the residue purified by Mass Directed Automated Preparative HPLC (Method B) to give the title compound as a pale yellow gum (4 mg).

LCMS (Method A): Rt 0.63 mins, MH+531.

Example 19

N-{2-Chloro-5-[4-(5-{[(2R,6S)-2,6-dimethyl-4-morpholinyl]methyl}-1,3,4-oxadiazol-2-yl)-1H-indazol-6-yl]-3-pyridinyl}methanesulfonamide

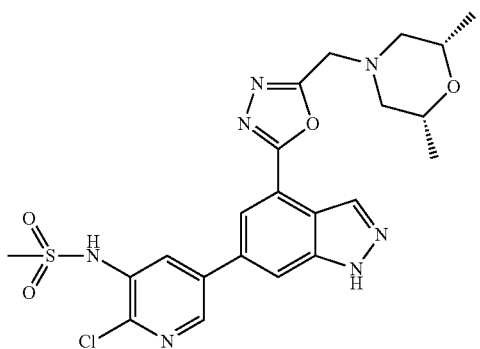

N-(2-Chloro-5-{4-[5-(chloromethyl)-1,3,4-oxadiazol-2-yl]-1-[(4-methylphenyl)sulfonyl]-1H-indazol-6-yl}-3-pyridinyl)methanesulfonamide (50 mg, 0.084 mmol) and (2R,6S)-2,6-dimethylmorpholine (0.5 ml, 0.084 mmol) were placed a vial and heated in a microwave at 90° C. for 15 mins. The reaction was heated in the microwave for a further 20 mins. The (2R,6S)-2,6-dimethylmorpholine was removed and the residue placed into isopropanol (3 ml) and 2M sodium hydroxide (1 ml) and the mixture stirred at room temperature for 3 h. The solvent was removed and the residue purified by Mass Directed Automated Preparative HPLC (Method B). The desired product was not collected so the waste was concentrated in vacuo and the residue purified by Mass Directed Automated Preparative HPLC (Method B) to give the title compound as white solid (12 mg).

LCMS (Method A): Rt 0.72 mins, MH+ 518.

Example 20

N-(2-Chloro-5-{4-[5-(4-morpholinylmethyl)-1,3,4-oxadiazol-2-yl]-1H-indazol-6-yl}-3-pyridinyl)methanesulfonamide

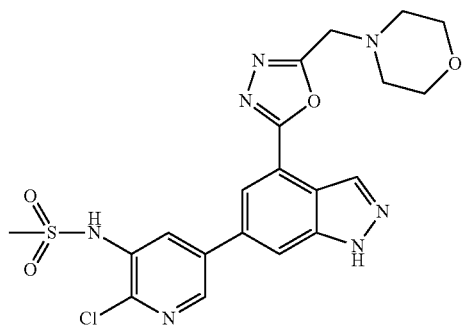 [SMILES: CS(=O)(=O)Nc1cc(-c2cc(-c3nnc(CN4CCOCC4)o3)c3cn[nH]c3c2)cnc1Cl]

N-(2-Chloro-5-{4-[5-(chloromethyl)-1,3,4-oxadiazol-2-yl]-1-[(4-methylphenyl)sulfonyl]-1H-indazol-6-yl}-3-pyridinyl)methanesulfonamide (30 mg, 0.051 mmol) and morpholine (1 ml, 11.48 mmol) were placed a vial and heated in a microwave at 90° C. for 15 mins. The morpholine was blown off under a stream of nitrogen and the residue suspended in isopropanol (2 ml) and 2M sodium hydroxide (1 ml) added. The mixture was stirred at room temperature for 2 h. The solvent was blown off and the residue purified by chromatography on a silica gel (20 g) cartridge, eluting with 0-25% methanol in dichloromethane over 30 mins. The solvent was removed in vacuo and the residue loaded onto a SCX (10 g) cartridge and eluted with methanol and then 2M ammonia in methanol. The residue was purified by Mass Directed Automated Preparative HPLC (Method B) to give the title compound as a white solid (5 mg).

LCMS (Method A): Rt 0.67 mins, MH+ 490.

Example 21

N-[5-[4-(5-{[(2R,6S)-2,6-Dimethyl-4-morpholinyl]methyl}-1,3,4-oxadiazol-2-yl)-1H-indazol-6-yl]-2-(methyloxy)-3-pyridinyl]methanesulfonamide

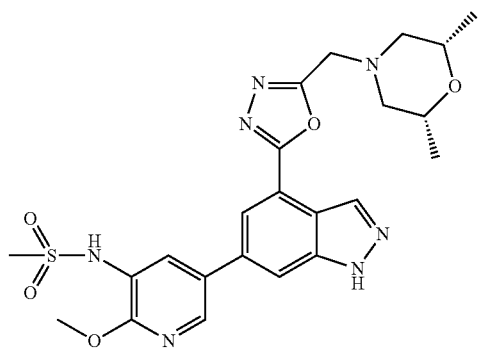

To a solution of N-[5-[4-(5-{[(2R,6S)-2,6-dimethyl-4-morpholinyl]methyl}-1,3,4-oxadiazol-2-yl)-1-(phenylsulfonyl)-1H-indazol-6-yl]-2-(methyloxy)-3-pyridinyl]methanesulfonamide (106 mg, 0.162 mmol) in 1,4-dioxane (1 ml) was added 2M sodium hydroxide (1 ml, 2.000 mmol) and the mixture stirred at 20° C. for 18 h. The mixture was evaporated in vacuo and the residue partitioned between ethyl acetate (10 ml) and saturated ammonium chloride (5 ml), separated by hydrophilic frit and purified by silica (5 g) cartridge using a gradient of dichloromethane and methanol to give a pale brown solid 50 mg which was purified by MDAP to give the title compound as a white solid (32 mg).

LCMS (Method A) Rt 0.73 mins, MH+ 514.

Similarly prepared was lan-2-yl)-1H-indole (32.9 mg, 0.135 mmol), sodium carbonate (39.1 mg, 0.369 mmol) and 1,1-bis(diphenylphosphino)ferrocene palladium dichloride) (9.00 mg, 0.012 mmol) were added to a microwave vial and dissolved in 1,4-dioxane (0.5 ml) and water (0.5 ml). The reaction mixture was heated under microwave irradiation at 110° C. for 15 mins. The reaction mixture was passed through a 2 g silica cartridge that was then washed with methanol. The solvent was evaporated under a stream of nitrogen and the residual solid was purified by silica (20 g) cartridge using a gradient of ethyl acetate and cyclohexane to give the title compound as a white solid (5.5 mg).

LCMS (Method A): Rt 0.89 min, MH+ 443.

| Example Number | Starting Material | Structure | Rt min | MH+ | Name |
|---|---|---|---|---|---|
| Example 22 | N-[5-[4-(5-{[4-(1-methylethyl)-1-piperazinyl]methyl}-1,3,4-oxadiazol-2-yl)-1-(phenylsulfonyl)-1H-indazol-6-yl]-2-(methyloxy)-3-pyridinyl]methanesulfonamide | 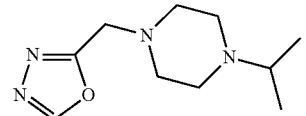 | 0.55 | 527 | N-[5-[4-(5-{[4-(1-methylethyl)-1-piperazinyl]methyl}-1,3,4-oxadiazol-2-yl)-1H-indazol-6-yl]-2-(methyloxy)-3-pyridinyl]methanesulfonamide |

Example 23

4-(5-{[(2R,6S)-2,6-Dimethyl-4-morpholinyl]methyl}-1,3,4-oxadiazol-2-yl)-6-(1H-indol-4-yl)-1-methyl-1H-indazole Example 24

6-(1H-Indol-4-yl)-1-methyl-4-(5-{[4-(1-methylethyl)-1-piperazinyl]methyl}-1,3,4-oxadiazol-2-yl)-1H-indazole

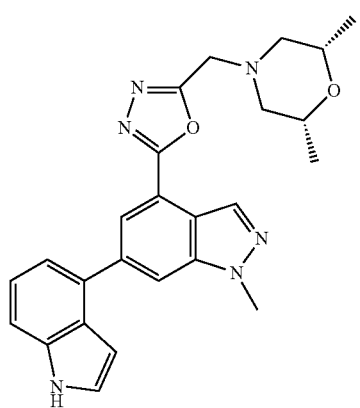 [SMILES: C[C@@H]1CN(Cc2nnc(-c3cc(-c4cccc5[nH]ccc45)cc4c3cnn4C)o2)C[C@H](C)O1]

6-Bromo-4-(5-{[(2R,6S)-2,6-dimethyl-4-morpholinyl]methyl}-1,3,4-oxadiazol-2-yl)-1-methyl-1H-indazole (50 mg, 0.123 mmol), 4-(4,4,5,5-tetramethyl-1,3,2-dioxaboro- 6-Bromo-1-methyl-4-(5-{[4-(1-methylethyl)-1-piperazinyl]methyl}-1,3,4-oxadiazol-2-yl)-1H-indazole (45 mg, 0.107 mmol), 4-(4,4,5,5-tetramethyl-1,3,2-dioxaborolan-2-yl)-1H-indole (26.1 mg, 0.107 mmol), sodium carbonate (34.1 mg, 0.322 mmol) and 1,1-bis(diphenylphosphino)ferrocene palladium dichloride (7.85 mg, 10.73 μmol) were added to a microwave vial and dissolved in 1,4-dioxane (0.5 ml) and water (0.5 ml). The reaction mixture was heated under microwave irradiation at 110° C. for 15 mins. The reaction mixture was passed through a 2 g silica cartridge that was then washed with methanol. The solvent was evaporated under a stream of nitrogen and the residual solid was purified firstly by silica (20 g) cartridge using a gradient of ethyl acetate and cyclohexane then by Mass Directed Automated Preparative HPLC (Method B). The solvent was evaporated under a stream of nitrogen to give the title compound as a white solid (20 mg).

LCMS (Method A): Rt 0.63 min, MH+456.

Example 25

N-[5-[1-Methyl-4-(5-{[4-(1-methylethyl)-1-piperazinyl]methyl}-1,3,4-oxadiazol-2-yl)-1H-indazol-6-yl]-2-(methyloxy)-3-pyridinyl]methanesulfonamide

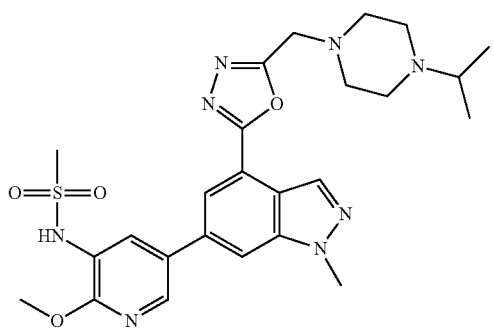 [SMILES: COc1ncc(-c2cc(-c3nnc(CN4CCN(C(C)C)CC4)o3)c3cnn(C)c3c2)cc1NS(C)(=O)=O]

6-Bromo-1-methyl-4-(5-{[4-(1-methylethyl)-1-piperazinyl]methyl}-1,3,4-oxadiazol-2-yl)-1H-indazole (40 mg, 0.095 mmol), N-[2-(methyloxy)-5-(4,4,5,5-tetramethyl-1,3,2-dioxaborolan-2-yl)-3-pyridinyl]methanesulfonamide (31.3 mg, 0.095 mmol), sodium carbonate (30.3 mg, 0.286 mmol) and 1,1-bis(diphenylphosphino)ferrocene palladium dichloride (6.98 mg, 9.54 μmol) were added to a microwave vial and dissolved in 1,4-dioxane (0.5 ml) and water (0.5 ml). The reaction mixture was heated under microwave irradiation at 110° C. for 15 mins. The reaction mixture was evaporated under a stream of nitrogen and the residual solid was dissolved in DMSO (1 ml), filtered through a frit and purified by Mass Directed Automated Preparative HPLC (Method B). The solvent was evaporated under a stream of nitrogen and the residue was dissolved in 1,4-dioxane (1 ml) and water (1 ml), frozen in a cardice bath and placed on the freeze-drier for 18 h to afford the title compound as a white solid (20 mg).

LCMS (Method A): Rt 0.56 min, MH+ 541.

Example 26

N-[5-[4-(5-{[(2R,6S)-2,6-Dimethyl-4-morpholinyl]methyl}-1,3,4-oxadiazol-2-yl)-1-methyl-1H-indazol-6-yl]-2-(methyloxy)-3-pyridinyl]methanesulfonamide

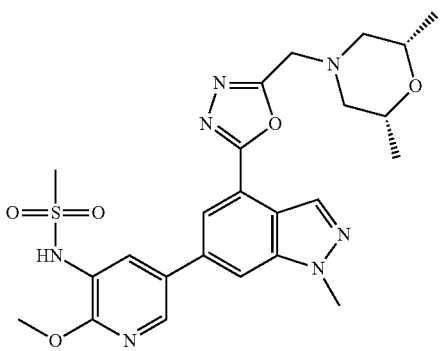 [SMILES: COc1ncc(-c2cc(-c3nnc(CN4C[C@@H](C)O[C@@H](C)C4)o3)c3cnn(C)c3c2)cc1NS(C)(=O)=O]

6-Bromo-4-(5-{[(2R,6S)-2,6-dimethyl-4-morpholinyl]methyl}-1,3,4-oxadiazol-2-yl)-1-methyl-1H-indazole (45 mg, 0.111 mmol), N-[2-(methyloxy)-5-(4,4,5,5-tetramethyl-1,3,2-dioxaborolan-2-yl)-3-pyridinyl]methanesulfonamide (36.4 mg, 0.111 mmol), sodium carbonate (35.2 mg, 0.332 mmol) and 1,1-bis(diphenylphosphino)ferrocene palladium dichloride (8.10 mg, 0.011 mmol) were added to a microwave vial and dissolved in 1,4-dioxane (0.5 ml) and water (0.5 ml). The reaction mixture was heated under microwave irradiation at 110° C. for 15 mins. The reaction mixture was passed through a 2 g silica cartridge that was then washed with methanol. The solvent was evaporated under a stream of nitrogen and the residual solid was purified by Mass Directed Automated Preparative HPLC (Method B) and the solvent was evaporated under a stream of nitrogen to give the title compound as a white solid (10 mg).

LCMS (Method A): Rt 0.77 min, MH+ 528.

Example 27

N-[5-[4-(5-{[(2R,6S)-2,6-Dimethyl-4-morpholinyl]methyl}-1,3,4-oxadiazol-2-yl)-1H-indazol-6-yl]-2-(methyloxy)-3-pyridinyl]-2,4-difluorobenzenesulfonamide

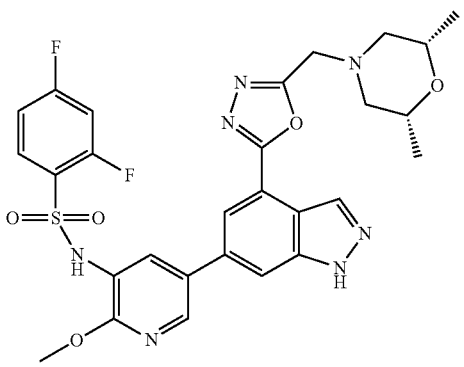 [SMILES: COc1ncc(-c2cc(-c3nnc(CN4C[C@@H](C)O[C@@H](C)C4)o3)c3cn[nH]c3c2)cc1NS(=O)(=O)c1ccc(F)cc1F]

Sodium hydroxide (2 ml, 4.00 mmol) was added to a solution of N-[5-[4-(5-{[(2R,6S)-2,6-dimethyl-4-morpholinyl]

methyl}-1,3,4-oxadiazol-2-yl)-1-(phenylsulfonyl)-1H-indazol-6-yl]-2-(methyloxy)-3-pyridinyl]-2,4-difluorobenzenesulfonamide (194 mg, 0.212 mmol) in 1,4-dioxane (2 ml). The mixture was stirred at room temperature for 2 h. The solvent was evaporated under a stream of nitrogen and the residue partitioned between ethyl acetate (10 ml) and saturated ammonium chloride (5 ml). The organic layer was separated by hydrophobic frit, washed with water and the solvent removed in vacuo. The residual solid was purified by Mass Directed Automated Preparative HPLC (Method B) and the solvent was evaporated under a stream of nitrogen to give the title compound as a cream coloured solid (10 mg).

LCMS (Method A): Rt 0.89 mins, MH+612.

Example 28

N-[5-(4-{5-[(2,2-Dimethyl-4-morpholinyl)methyl]-1,3,4-oxadiazol-2-yl}-1H-indazol-6-yl)-2-(methyloxy)-3-pyridinyl]methanesulfonamide

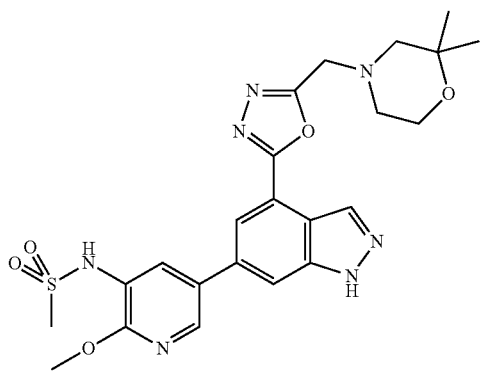 [SMILES: COc1ncc(-c2cc(-c3nnc(CN4CCOC(C)(C)C4)o3)c3cn[nH]c3c2)cc1NS(C)(=O)=O]

To a solution of 6-bromo-4-{5-[(2,2-dimethyl-4-morpholinyl)methyl]-1,3,4-oxadiazol-2-yl}-1-(phenylsulfonyl)-1H-indazole (112 mg, 0.210 mmol) was added N-[2-(methyloxy)-5-(4,4,5,5-tetramethyl-1,3,2-dioxaborolan-2-yl)-3-pyridinyl]methanesulfonamide (69.0 mg, 0.210 mmol), 1,1'-bis(diphenylphosphino)ferrocene palladium dichloride (30.8 mg, 0.042 mmol) and potassium phosphate tribasic (134 mg, 0.631 mmol). The mixture was heated under microwave irradiation at 100° C. for 20 min, then concentrated in vacuo and the residue partitioned between DCM (10 ml) and water (5 ml). The layers were separated by hydrophobic frit and the organics were concentrated, then re-dissolved in DCM and loaded on the top of a 20 g silica SPE cartridge, which was then eluted with 0-100% EtOAc/cyclohexane followed by 0-20% MeOH/EtOAc on the FlashMaster II. The desired fractions were combined and the solvent removed in vacuo to give a pale orange solid (80 mg), which was dissolved in 1,4-dioxane (0.5 ml), treated with 2M sodium hydroxide (0.5 ml, 1.000 mmol) and stirred at 20° C. for 18 h. The mixture was evaporated to dryness under a stream of nitrogen and the residue partitioned between ethyl acetate (5 ml) and saturated ammonium chloride (2 ml) and separated by hydrophilic frit. The solvent was removed under a stream of nitrogen and the residue was dissolved in DMSO (1 ml) and purified by MDAP (Method B). The product-containing fractions were evaporated to dryness under a stream of nitrogen to afford the title compound as a white solid (24 mg).

LCMS (Method A) Rt=0.75 min, MH+ 514.

Example 29

6-(1H-Indol-4-yl)-4-[5-(1-methylethyl)-1,3,4-oxadiazol-2-yl]-1H-indazole

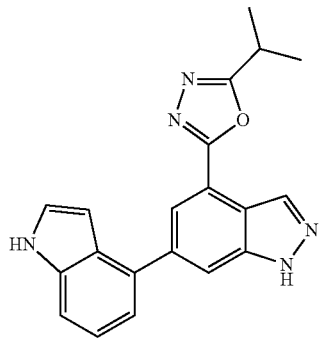 [SMILES: CC(C)c1nnc(-c2cc(-c3cccc4[nH]ccc34)cc3[nH]ncc23)o1]

6-(1H-Indol-4-yl)-1-[(4-methylphenyl)sulfonyl]-4-(1H-tetrazol-5-yl)-1H-indazole-6-(1H-indol-4-yl)-1-(phenylsulfonyl)-4-(1H-tetrazol-5-yl)-1H-indazole (1:1) (100 mg, 0.084 mmol) and 2-methylpropanoyl chloride (0.175 ml, 1.672 mmol) in chloroform (4 ml), were heated under microwave irradiation at 100° C. for 30 mins, followed by 100° C. for 30 mins, followed by 100° C. for 1 h. The reaction mixture was treated with isopropanol (1 ml) then blown to dryness. The solid was dissolved in isopropanol (2 ml) and dichloromethane (2 ml) and absorbed onto Florisil. The Florisil was placed on top of a silica cartridge (10 g) and eluted with 0-100% ethyl acetate/cyclohexane. The appropriate fractions combined and concentrated to give a yellow solid, 35 mg. The solid was treated with isopropanol (1 ml) and 2M aqueous sodium hydroxide (1.003 ml) and stirred at 20° C. for 20 h. The mixture was then treated with 2M aqueous hydrochloric acid (1 ml), blown to dryness and slurried in isopropanol (2 ml) and dichloromethane (1 ml) with soniction. The mixture was absorbed onto Florisil, loaded onto a silica cartridge (10 g) and eluted with 0-100% ethyl acetate/cyclohexane. Fractions did not collect, so the waste was evaporated to dryness, the residue dissolved in dichloromethane (2 ml) and loaded onto a silica cartridge (10 g) and purified by column chromatography, eluting with 0-100% ethyl acetate/cyclohexane. Appropriate fractions were combined and evaporated to give the title compound as a white film (11 mg).

LCMS (Method B): Rt 2.63 mins, MH+ 344.

Example 30

4-(5-Cyclohexyl-1,3,4-oxadiazol-2-yl)-6-(1H-indol-4-yl)-1H-indazole

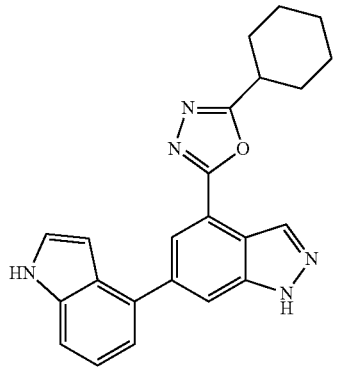 [SMILES: c1cc(-c2cc(-c3nnc(C4CCCCC4)o3)c3cn[nH]c3c2)c2cc[nH]c2c1]

6-(1H-Indol-4-yl)-1-[(4-methylphenyl)sulfonyl]-4-(1H-tetrazol-5-yl)-1H-indazole-6-(1H-indol-4-yl)-1-(phenylsulfonyl)-4-(1H-tetrazol-5-yl)-1H-indazole (1:1) (100 mg, 0.084 mmol) and cyclohexanecarbonyl chloride (0.224 ml, 1.672 mmol) in chloroform (4 ml), were heated under microwave irradiation at 100° C. for 30 mins, followed by 100° C. for 30 mins, followed by 100° C. for 1 h. Additional cyclohexanecarbonyl chloride (0.114 ml, 0.849 mmol) was added and the reaction heated under microwave irradiation at 100° C. for a further 1 h. The reaction mixture was treated with isopropanol (2 ml), the solvent reduced to 2 ml by blowing down and absorbed onto Florisil. The Florisil was placed on top of a silica cartridge (10 g) and eluted with 0-100% ethyl acetate/cyclohexane. Appropriate fractions combined and concentrated to give a beige solid, 15 mg. The solid was treated with isopropanol (0.5 ml) and 2M aqueous sodium hydroxide (0.498 ml) and stirred at 20° C. for 20 h. The mixture was then treated with 2M aqueous hydrochloric acid (1 ml), blown to dryness and slurried in isopropanol (2 ml) and dichloromethane (1 ml) with soniction. The mixture was absorbed onto Florisil, loaded onto a silica cartridge (10 g) and eluted with 0-100% ethyl acetate/cyclohexane. Appropriate fractions were combined and evaporated to give the title compound as a colourless film (3 mg).

LCMS (Method B): Rt 3.06 mins, MH+ 384.

Example 31

4-[5-(Cyclohexylmethyl)-1,3,4-oxadiazol-2-yl]-6-(1H-indol-4-yl)-1H-indazole

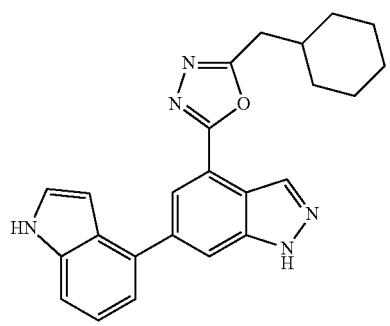 [SMILES: c1cc(-c2cc(-c3nnc(CC4CCCCC4)o3)c3cn[nH]c3c2)c2cc[nH]c2c1]

6-(1H-Indol-4-yl)-1-[(4-methylphenyl)sulfonyl]-4-(1H-tetrazol-5-yl)-1H-indazole-6-(1H-indol-4-yl)-1-(phenylsulfonyl)-4-(1H-tetrazol-5-yl)-1H-indazole (1:1) (100 mg, 0.084 mmol) and cyclohexylacetyl chloride (0.257 ml, 1.672 mmol) in chloroform (4 ml) were heated under microwave irradiation at 100° C. for 1 h. The reaction mixture was treated with isopropanol (2 ml), the solvent reduced by blowing down to ~2 ml and absorbed onto Florisil. The Florisil was placed on top of a silica cartridge (10 g) and eluted with 0-100% ethyl acetate/cyclohexane. Appropriate fractions combined and concentrated to give a yellow solid, 17 mg. The solid was treated with isopropanol (0.5 ml) and 2M aqueous sodium hydroxide (0.498 ml, 0.995 mmol) and stirred at 20° C. for 20 h. The mixture was then treated with 2M aqueous hydrochloric acid (1 ml), blown to dryness and slurried in isopropanol (2 ml) and dichloromethane (1 ml) with soniction. The mixture was absorbed onto Florisil, then loaded onto a silica cartridge (10 g) and eluted with 0-100% ethyl acetate/cyclohexane. Appropriate fractions were combined and evaporated to give the title compound as an off-white solid (3.2 mg).

LCMS (Method A): Rt 1.25 min, MH+ 398 and [M+CH$_3$CN]$^+$ 439.

Example 32

6-(1H-Indol-4-yl)-4-[5-(phenylmethyl)-1,3,4-oxadiazol-2-yl]-1H-indazole

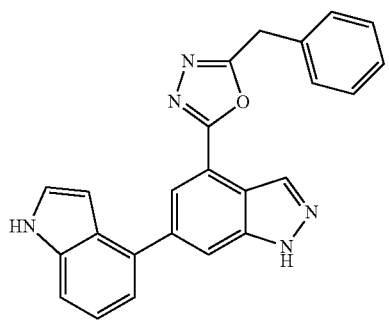 [SMILES: c1ccc(Cc2nnc(-c3cc(-c4cccc5[nH]ccc45)cc4[nH]ncc34)o2)cc1]

6-(1H-Indol-4-yl)-1-[(4-methylphenyl)sulfonyl]-4-(1H-tetrazol-5-yl)-1H-indazole-6-(1H-indol-4-yl)-1-(phenylsulfonyl)-4-(1H-tetrazol-5-yl)-1H-indazole (1:1) (100 mg, 0.084 mmol) and phenylacetyl chloride (0.224 ml, 1.699 mmol) in chloroform (4 ml), were heated under microwave irradiation at 100° C. for 30 mins, followed by 100° C. for a further 30 mins. The reaction mixture was treated with methanol (5 ml) and evaporated to dryness. The residue was then dissolved in dichloromethane, loaded onto a silica cartridge (10 g) and purified by column chromatography, eluting with 0-25% methanol/dichloromethane. The appropriate fractions were combined and concentrated to give a brown solid. The solid was treated with isopropanol (0.5 ml) and 2M aqueous sodium hydroxide (0.510 ml, 1.019 mmol) and stirred at 20° C. for 1 h. Additional isopropanol (0.5 ml) and 2M aqueous sodium hydroxide (0.510 ml) were added, the mixture sonicated and then stirred at 20° C. for a further 18 h. The mixture was neutralised with 2M aqueous hydrochloric acid, evaporated to dryness and azeotroped with isopropanol (5 ml). The residue was dissolved in isopropanol (5 ml), absorbed onto Florisil, then placed on top of a silica cartridge (10 g) and eluted with 0-100% ethyl acetate/cyclohexane. Appropriate fractions were combined and evaporated to give the title compound as an off-white solid (9 mg).

LCMS (Method B): Rt 2.82 mins, MH+ 392.

Example 33

6-(1H-Indol-4-yl)-4-{5-[2-(methyloxy)ethyl]-1,3,4-oxadiazol-2-yl}-1H-indazole

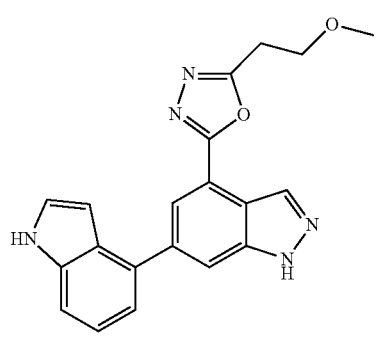 [SMILES: COCCc1nnc(-c2cc(-c3cccc4[nH]ccc34)cc3[nH]ncc23)o1]

6-(1H-Indol-4-yl)-1-[(4-methylphenyl)sulfonyl]-4-(1H-tetrazol-5-yl)-1H-indazole-6-(1H-indol-4-yl)-1-(phenylsulfonyl)-4-(1H-tetrazol-5-yl)-1H-indazole (1:1) (75 mg, 0.127 mmol) and 3-(methyloxy)propanoyl chloride (31.2 mg, 0.255 mmol, available from Fluorochem) in chloroform (2 ml), were heated under microwave irradiation at 100° C. for 1 h. The solvent was blown off and the residue dissolved in isopropanol (2 ml) and 2M sodium hydroxide (1 ml) and stirred at RT for 2 h. The solvent was removed and the residue purified by column chromatography, on silica (20 g cartridge), eluting with 0-100% ethylacetate/cyclohexane followed by 0-25% methanol/dichloromethane. Further purification by Mass Directed Automated Preparative HPLC afforded the title compound (3 mg).

LCMS (Method A): Rt 0.91 mins, MH+ 360 and [M+CH$_3$CN]$^+$ 401.

Example 34

6-(1H-Indol-4-yl)-4-(5-{[(phenylmethyl)oxy]methyl}-1,3,4-oxadiazol-2-yl)-1H-indazole

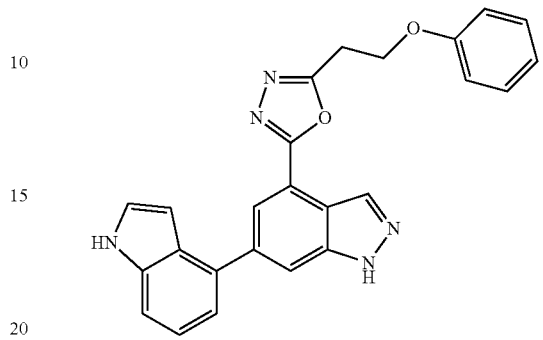

6-(1H-Indol-4-yl)-1-[(4-methylphenyl)sulfonyl]-4-(1H-tetrazol-5-yl)-1H-indazole-6-(1H-indol-4-yl)-1-(phenylsulfonyl)-4-(1H-tetrazol-5-yl)-1H-indazole (1:1) (100 mg, 0.170 mmol) and benzyloxyacetyl chloride (62.7 mg, 0.340 mmol) in chloroform (2 ml), were heated under microwave irradiation at 100° C. for 1 h. The solvent was blown off and the residue dissolved in isopropanol (2 ml) and 2M sodium hydroxide (1 ml) and stirred at RT for 2 h. The solvent was removed and the residue purified by column chromatography, on silica (20 g cartridge), eluting with 0-100% ethylacetate/cyclohexane to give the title compound as a clear gum (5.8 mg).

LCMS (Method A): Rt 1.11 mins, MH+ 421 and [M+CH$_3$CN]$^+$ 463.

Similarly prepared with {[(1R,2S,5R)-5-methyl-2-(1-methylethyl)cyclohexyl]oxy}acetyl chloride (available from Sigma-Aldrich) was:

| Example Number | Starting Material | Structure | Rt mins | MH+ | Name |
|---|---|---|---|---|---|
| 35 | Intermediate 37 6-Bromo-1-[(4-methylphenyl)sulfonyl]-4-(1H-tetrazol-5-yl)-1H-indazole/6-(1H-Indol-4-yl)-1-(phenylsulfonyl)-4-(1H-tetrazol-5-yl)-1H-indazole (approx 1:1) | 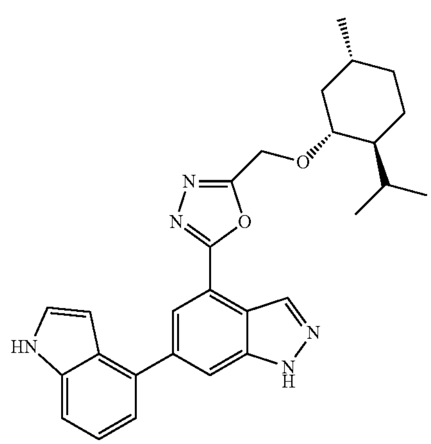 [SMILES: CC(C)[C@@H]1CC[C@@H](C)C[C@H]1OCc1nnc(-c2cc(-c3cccc4[nH]ccc34)cc3[nH]ncc23)o1] | 1.42 | 470 | 6-(1H-indol-4-yl)-4-[5-({[(1R,2S,5R)-5-methyl-2-(1-methylethyl)cyclohexyl]oxy}methyl)-1,3,4-oxadiazol-2-yl]-1H-indazole |

Example 36

{5-[6-(1H-Indol-4-yl)-1H-indazol-4-yl]-1,3,4-oxadiazol-2-yl}methanol

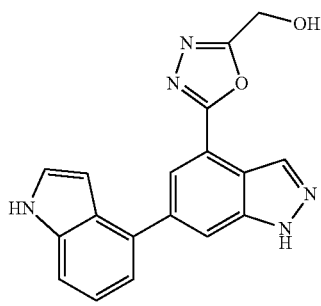 [SMILES: OCc1nnc(-c2cc(-c3cccc4[nH]ccc34)cc3[nH]ncc23)o1]

4-[5-(Chloromethyl)-1,3,4-oxadiazol-2-yl]-6-(1H-indol-4-yl)-1-(phenylsulfonyl)-1H-indazole (25 mg, 0.051 mmol), cyclohexylmethanol (17.48 mg, 0.153 mmol) and potassium carbonate (21.16 mg, 0.153 mmol) were placed in N-methyl-2-pyrrolidone (1 ml) and the mixture heated under microwave irradiation at 100° C. for 20 mins. Additional cyclohexylmethanol (17.48 mg, 0.153 mmol) was added and the mixture heated at 110° C. for 20 mins, followed by 110° C. for a further 20 mins. The solvent was removed and the residue purified by Mass Directed Automated Preparative HPLC to give the title compound as a white solid (5 mg).

LCMS (Method A): Rt 0.77 mins, MH+ 332.

Example 37

6-(1H-Indol-4-yl)-4-{5-[(methyloxy)methyl]-1,3,4-oxadiazol-2-yl}-1H-indazole

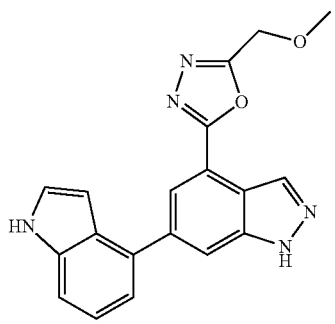 [SMILES: COCc1nnc(-c2cc(-c3cccc4[nH]ccc34)cc3[nH]ncc23)o1]

4-[5-(Chloromethyl)-1,3,4-oxadiazol-2-yl]-6-(1H-indol-4-yl)-1-(phenylsulfonyl)-1H-indazole (25 mg, 0.051 mmol) was placed in methanol (1.5 ml, 37.1 mmol) and potassium carbonate (7.05 mg, 0.051 mmol) added. The mixture was heated under microwave irradiation at 110° C. for 20 mins. The solvent was removed and the residue purified by Mass Directed Automated Preparative HPLC to give the title compound as a white solid (3 mg).

LCMS (Method A): Rt 0.91 mins, MH+ 346 and [M+CH$_3$CN]+ 387.

Example 38

6-(1H-Indol-4-yl)-4-(5-methyl-1,3,4-oxadiazol-2-yl)-1H-indazole

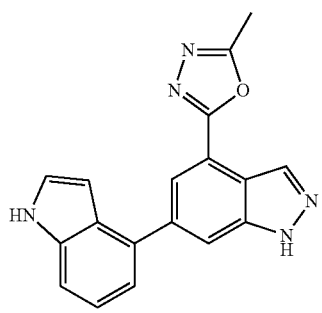 [SMILES: Cc1nnc(-c2cc(-c3cccc4[nH]ccc34)cc3[nH]ncc23)o1]

6-Bromo-4-(5-methyl-1,3,4-oxadiazol-2-yl)-1-[(4-methylphenyl)sulfonyl]-1H-indazole (70 mg, 0.162 mmol) was dissolved in 1,4-dioxane (1.2 ml) and 4-(4,4,5,5-tetramethyl-1,3,2-dioxaborolan-2-yl)-1H-indole (47.1 mg, 0.194 mmol, available from Frontier Scientific Europe), 1,1-bis(diphenylphosphino)ferrocenedichloropalladium(II) (5.91 mg, 8.08 μmol), water (0.8 ml) and 2M aqueous sodium bicarbonate (0.242 ml, 0.485 mmol) were added. The reaction mixture was heated under microwave irradiation at 150° C. for 15 mins. The solution was loaded onto a silica cartridge (0.5 g) and eluted with methanol. The eluant was concentrated, the residue dissolved in methanol and absorbed onto Florisil. This was placed on top of a silica cartridge (10 g) and eluted with 25-50% ethyl acetate/cyclohexane. Appropriate fractions were evaporated to give the title compound as a yellow solid (27 mg).

LCMS (Method B): Rt 2.22 mins, MH+ 316.

Example 39

N-{2-Chloro-5-[4-(5-methyl-1,3,4-oxadiazol-2-yl)-1H-indazol-6-yl]-3-pyridinyl}methanesulfonamide

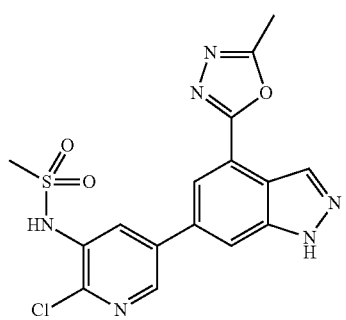 [SMILES: Cc1nnc(-c2cc(-c3cnc(Cl)c(NS(C)(=O)=O)c3)cc3[nH]ncc23)o1]

N-(2-chloro-5-{4-(5-methyl-1,3,4-oxadiazol-2-yl)-1-[(4-methylphenyl)sulfonyl]-1H-indazol-6-yl}-3-pyridinyl)methanesulfonamide (16 mg, 0.029 mmol) and 2M sodium hydroxide (1 ml, 2.0 mmol) were placed in isopropanol (5 ml) and the mixture stirred at room temperature overnight. The solvent was removed and the residue partitioned between water (5 ml) and dichloromethane (5 ml). The aqueous was acidified to ~pH 1 with 2M hydrogen chloride, then extracted with dichloromethane (20 ml). The organic layer was concentrated to give the title compound as a white solid (10 mg).

LCMS (Method A): Rt 0.76 mins, MH+ 405 and [M+CH$_3$CN]$^+$ 446.

Example 40

6-(1H-Indol-4-yl)-4-{5-[(methylsulfonyl)methyl]-1,3,4-oxadiazol-2-yl}-1H-indazole

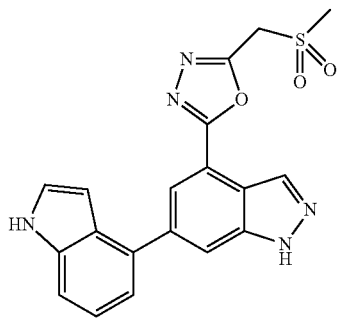 [SMILES: CS(=O)(=O)Cc1nnc(-c2cc(-c3cccc4[nH]ccc34)cc3[nH]ncc23)o1]

4-[5-(Chloromethyl)-1,3,4-oxadiazol-2-yl]-6-(1H-indol-4-yl)-1-(phenylsulfonyl)-1H-indazole (50 mg, 0.102 mmol) and sodium methanesulfinate (10.42 mg, 0.102 mmol) in ethanol (0.8 ml) were heated under microwave irradiation to 100° C. for 30 mins then 150° C. for 30 min, followed by 150° C. for a further 30 mins. Additional sodium methanesulfinate (10.42 mg, 0.102 mmol) was added and the reaction heated to 150° C. for a further 30 mins. The solvent was removed and the resultant beige solid treated with isopropanol (1 ml) and 2M aqueous sodium hydroxide (1.003 ml, 2.006 mmol) and stirred at 20° C. for 20 h. The mixture was neutralised with 2M aqueous hydrogen chloride, evaporated to dryness and azeotroped with isopropanol (2 ml). The residue was partitioned between dichloromethane (5 ml) and water (5 ml) and shaken vigorously. The aqueous phase was pipetted off, then the heterogeneous solution was treated with methanol (5 ml), absorbed onto Florisil and the solvents removed. The Florisil was placed on top of a silica cartridge (10 g) and eluted with 0-3% methanol/dichloromethane. Appropriate fractions were combined and concentrated to give a beige solid, 16 mg. Further purification by Mass Directed Automated Preparative HPLC afforded the title compound as a white solid (5 mg).

LCMS (Method A): Rt 0.79 mins, [M-H]$^-$ 392.

Example 41

6-(1H-Indol-4-yl)-4-{5-[(phenylsulfonyl)methyl]-1,3,4-oxadiazol-2-yl}-1H-indazole

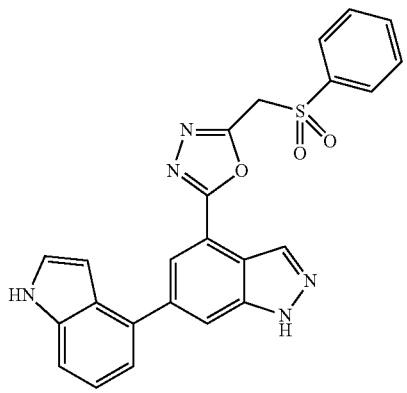 [SMILES: O=S(=O)(Cc1nnc(-c2cc(-c3cccc4[nH]ccc34)cc3[nH]ncc23)o1)c1ccccc1]

4-[5-(Chloromethyl)-1,3,4-oxadiazol-2-yl]-6-(1H-indol-4-yl)-1-(phenylsulfonyl)-1H-indazole (60 mg, 0.110 mmol) and sodium benzenesulfinate dihydrate (33.1 mg, 0.165 mmol, available from TCI Europe) in ethanol (0.8 ml) were heated under microwave irradiation to 100° C. for 30 mins then 150° C. for 20 mins. The mixture was treated with dichloromethane (3 ml) and methanol (3 ml) and absorbed onto Florisil. This was placed on top a silica cartridge (10 g) and eluted with 0-100% ethyl acetate/cyclohexane and then 0-20% methanol/ethyl acetate. Appropriate fractions were combined and concentrated to give a yellow solid, 33 mg. The solid was treated with isopropanol (1 ml) and 2M aqueous sodium hydroxide (0.999 ml, 1.998 mmol) and stirred at 20° C. for 22 h. The mixture was neutralised with 2M aqueous hydrochloric acid, blown to dryness and purified by Mass Directed Automated Preparative HPLC. Appropriate fraction was evaporated, then azeotroped with methanol to give the title compound as a white solid (8 mg).

LCMS (Method A): Rt 0.95 mins, MH+ 456.

Example 42

N-(2-(Methyloxy)-5-{4-[5-(6-oxa-9-azaspiro[4.5]dec-9-ylmethyl)-1,3,4-oxadiazol-2-yl]-1H-indazol-6-yl}-3-pyridinyl)methanesulfonamide

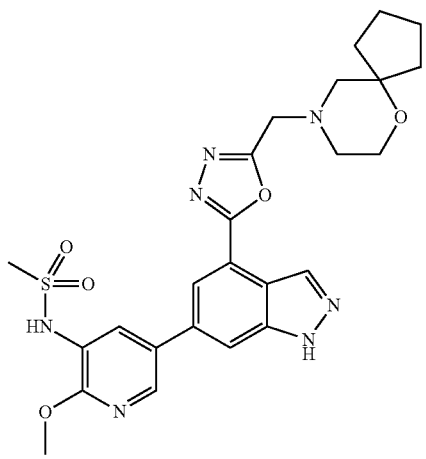 [SMILES: COc1ncc(-c2cc(-c3nnc(CN4CCOC5(CCCC5)C4)o3)c3cn[nH]c3c2)cc1NS(C)(=O)=O]

To a solution of 9-({5-[6-bromo-1-(phenylsulfonyl)-1H-indazol-4-yl]-1,3,4-oxadiazol-2-yl}methyl)-6-oxa-9-azaspiro[4.5]decane (74 mg, 0.133 mmol) in 1,4 dioxane (2.5 ml) and water (1 ml) was added N-[2-(methyloxy)-5-(4,4,5,5-tetramethyl-1,3,2-dioxaborolan-2-yl)-3-pyridinyl]methanesulfonamide (47.8 mg, 0.146 mmol), 1,1'-bis(diphenylphosphino)ferrocene palladium dichloride (19.39 mg, 0.027 mmol) and potassium phosphate tribasic (84 mg, 0.398 mmol). The mixture was heated under microwave irradiation at 100° C. for 20 mins. The mixture was passed through a 1 g silica SPE cartridge, washing with MeOH. The solvent was removed under a stream of nitrogen and the residue was partitioned between DCM (10 ml) and water (10 ml), separated with a hydrophobic frit and the solvent again removed under a stream of nitrogen. The protected compound was dissolved in 1,4-dioxane (1 ml) and sodium hydroxide (1 ml, 2.000 mmol) and stirred at room temperature for 4 h. The mixture was evaporated to dryness under a stream of nitrogen. The residue was partitioned between ethyl acetate (5 ml) and saturated ammonium chloride (2 ml) and separated with a hydrophilic frit. The solvent was removed under a stream of nitrogen and the crude residue was dissolved in DMSO (1 ml) and purified by Mass Directed Automated Preparative HPLC.

The appropriate fraction was blown down under a stream of nitrogen to give the title compound as a white solid (71.5 mg).
LCMS (Method A): Rt 0.82 mins, MH+ 540.

Example 43

2-[({5-[6-(1H-Indol-4-yl)-1H-indazol-4-yl]-1,3,4-oxadiazol-2-yl}methyl)amino]ethanol

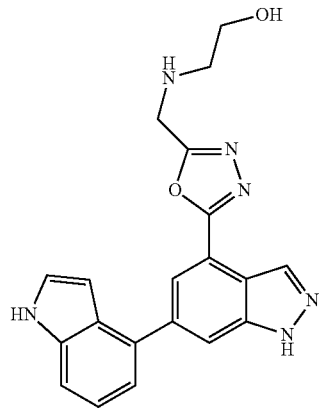 [SMILES: OCCNCc1nnc(-c2cc(-c3cccc4[nH]ccc34)cc3[nH]ncc23)o1]

4-[5-(Chloromethyl)-1,3,4-oxadiazol-2-yl]-6-(1H-indol-4-yl)-1-(phenylsulfonyl)-1H-indazole (100 mg, 0.184 mmol) in acetonitrile (2 ml) was treated with 2-aminoethanol (0.055 ml, 0.918 mmol) and heated in a microwave at 100° C. for 30 mins. The acetonitrile supernatant was pipetted off, and the solid washed with further acetonitrile (5 ml). The solid was dissolved in methanol and DMSO (1:1, 3 ml) and loaded onto a 2 g SCX cartridge. Methanol was eluted, then 2M ammonia in ethanol. Basic fractions were blown to dryness to give a brown solid. The fully-protected intermediate was treated with isopropanol (1.000 ml) followed by 2M aqueous sodium hydroxide (1.001 ml, 2.002 mmol) and stirred for 20 h at 20° C. The solution was neutralised by addition of 2M hydrochloric acid, then blown to dryness to give a brown solid. This was transferred into a small vial, and treated with DMSO/MeOH (1:1, 1 ml) then filtered and purified on MDAP (Method E). The appropriate fraction was blown to dryness to give the title compound as a beige solid (10 mg).
LCMS (Method A): Rt 0.57 mins, MH+ 375.

Example 44

1-[({5-[6-(1H-Indol-4-yl)-1H-indazol-4-yl]-1,3,4-oxadiazol-2-yl}methyl)amino]-3-(4-morpholinyl)-2-propanol

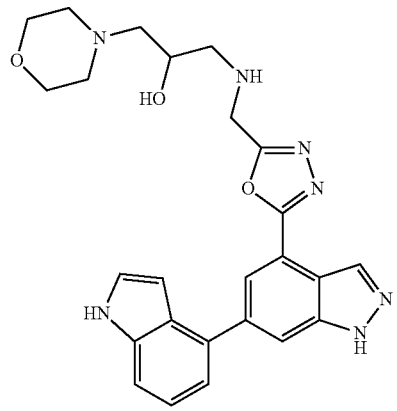 [SMILES: OC(CNCc1nnc(-c2cc(-c3cccc4[nH]ccc34)cc3[nH]ncc23)o1)CN1CCOCC1]

4-[5-(Chloromethyl)-1,3,4-oxadiazol-2-yl]-6-(1H-indol-4-yl)-1-(phenylsulfonyl)-1H-indazole (100 mg, 0.184 mmol) in acetonitrile (2 ml) was treated with 1-amino-3-(4-morpholinyl)-2-propanol (147 mg, 0.918 mmol, available from Enamine Ltd) and heated in a microwave at 100° C. for 30 mins. The solution was pipetted off the solid, then the solid was dissolved in DMSO (ml) and loaded onto a 5 g SCX cartridge. Methanol was eluted, then 2M ammonia in ethanol. Basic fractions were blown to dryness. The fully-protected intermediate was treated with isopropanol (1.000 ml) followed by 2M aqueous sodium hydroxide (1.001 ml, 2.002 mmol) and stirred for 20 h at 20° C. The solution was neutralised by addition of 2M hydrochloric acid then blown to dryness to give a brown solid. The material was purified MDAP (Method E). The appropriate fraction was blown to dryness to give the title compound as a brown film (27 mg).
LCMS (Method B): Rt 1.96 mins, MH+ 474.

Example 45

N-[5-[4-(5-{[(3R,5S)-3,5-Dimethyl-4-(1-methylethyl)-1-piperazinyl]methyl}-1,3,4-oxadiazol-2-yl)-1H-indazol-6-yl]-2-(methyloxy)-3-pyridinyl]methanesulfonamide

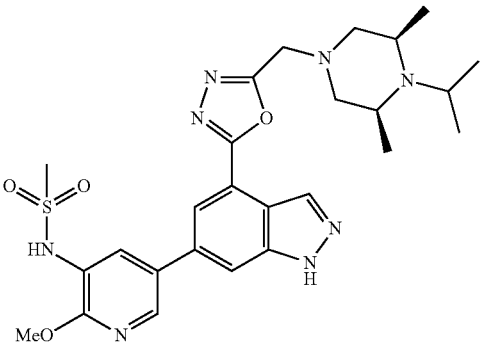 [SMILES: COc1ncc(-c2cc(-c3nnc(CN4C[C@@H](C)N(C(C)C)[C@@H](C)C4)o3)c3cn[nH]c3c2)cc1NS(C)(=O)=O]

6-Bromo-4-(5-{[(3R,5S)-3,5-dimethyl-4-(1-methylethyl)-1-piperazinyl]methyl}-1,3,4-oxadiazol-2-yl)-1-(phenylsulfonyl)-1H-indazole (172 mg, 0.300 mmol), N-[2-(methyloxy)-5-(4,4,5,5-tetramethyl-1,3,2-dioxaborolan-2-yl)-3-pyridinyl]methanesulfonamide (108 mg, 0.330 mmol), 1,1'-bis(diphenylphosphino)ferrocene palladium dichloride (43.9 mg, 0.060 mmol) and potassium phosphate tribasic (191 mg, 0.900 mmol) were added to a microwave vial and dissolved in 1,4-dioxane (2.5 ml) and water (0.25 ml). The mixture was heated under microwave irradiation at 100° C. for 20 mins. The mixture was passed through a 1 g silica SPE cartridge, washing with MeOH. The solvent was removed under a stream of nitrogen and the residue was partitioned between DCM (10 ml) and water (10 ml), separated with a hydrophobic frit and the solvent again removed under a stream of nitrogen. The protected compound was dissolved in 1,4-dioxane (1 ml) and sodium hydroxide (1 ml, 2.000 mmol) and stirred at room temperature for 4 h. The mixture was evaporated to dryness under a stream of nitrogen. The residue was partitioned between ethyl acetate (5 ml) and saturated ammonium chloride (2 ml) and separated with a hydrophilic frit. The solvent was removed under a stream of nitrogen and the crude residue was dissolved in DMSO (1 ml) and purified by high pH MDAP (Method E). The appropriate fraction was blown to dryness to give the title compound as a white solid (40 mg).
LCMS (Method A): Rt 0.76 mins, MH+ 555.

The compounds listed below were synthesised using the general method above:

| Example Number | Starting Material | Structure | Rt mins | MH+ | Name |
|---|---|---|---|---|---|
| 46 | prepared with 6-bromo-4-{5-[(1,1-dioxido-4-thiomorpholinyl)methyl]-1,3,4-oxadiazol-2-yl}-1-(phenylsulfonyl)-1H-indazole) | 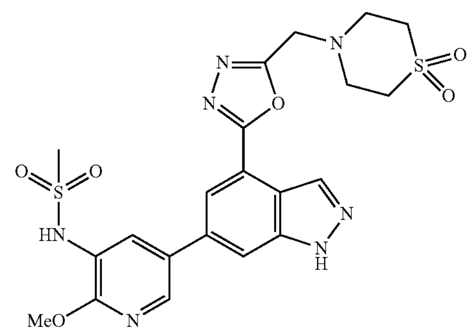 [SMILES: COc1ncc(-c2cc(-c3nnc(CN4CCS(=O)(=O)CC4)o3)c3cn[nH]c3c2)cc1NS(C)(=O)=O] | 0.82 | 534 | N-[5-(4-{5-[(1,1-dioxido-4-thiomorpholinyl)methyl]-1,3,4-oxadiazol-2-yl}-1H-indazol-6-yl)-2-(methyloxy)-3-pyridinyl]methanesulfonamide |

Example 47

N-[5-(4-{5-[(2-Ethyl-4-morpholinyl)methyl]-1,3,4-oxadiazol-2-yl}-1H-indazol-6-yl)-2-(methyloxy)-3-pyridinyl]methanesulfonamide

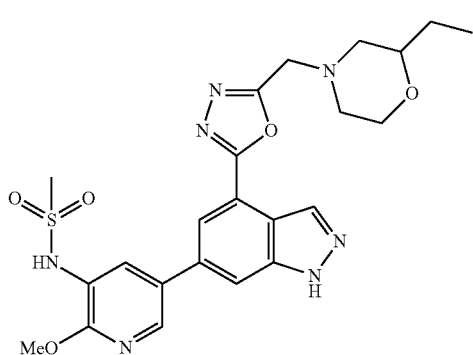 [SMILES: CCC1CN(Cc2nnc(-c3cc(-c4cnc(OC)c(NS(C)(=O)=O)c4)cc4[nH]ncc34)o2)CCO1]

6-Bromo-4-{5-[(2-ethyl-4-morpholinyl)methyl]-1,3,4-oxadiazol-2-yl}-1-(phenylsulfonyl)-1H-indazole (170 mg, 0.319 mmol), N-[2-(methyloxy)-5-(4,4,5,5-tetramethyl-1,3,2-dioxaborolan-2-yl)-3-pyridinyl]methanesulfonamide (115 mg, 0.351 mmol), 1,1'-bis(diphenylphosphino)ferrocene palladium dichloride (46.7 mg, 0.064 mmol) and potassium phosphate tribasic (203 mg, 0.958 mmol) were added to a microwave vial and dissolved in 1,4-dioxane (5 ml) and water (0.5 ml). The mixture was heated under microwave irradiation at 100° C. for 20 mins. The solvent was removed under a stream of nitrogen and the residue was partitioned between DCM (10 ml) and water (10 ml), separated with a hydrophobic frit and the solvent again removed under a stream of nitrogen. The protected compound was dissolved in 1,4-dioxane (1 ml) and sodium hydroxide (1 ml, 2.000 mmol) and stirred at room temperature for 4 h. The mixture was evaporated to dryness under a stream of nitrogen. The residue was partitioned between ethyl acetate (5 ml) and saturated ammonium chloride (2 ml) and separated with a hydrophilic frit. The solvent was removed under a stream of nitrogen and the crude residue was dissolved in DMSO (2 ml) and purified by Mass Directed Automated Preparative HPLC. The appropriate fraction was blown down under a stream of nitrogen to give a yellow solid. The solid was purified further by high pH MDAP (Method E) and the appropriate fraction was blown down under a stream of nitrogen to give the title compound as a white solid (12 mg).

LCMS (Method A): Rt 0.90 mins, MH+ 514.

Example 48

9-({5-[6-(1H-Indol-4-yl)-1H-indazol-4-yl]-1,3,4-oxadiazol-2-yl}methyl)-6-oxa-9-azaspiro[4.5]decane

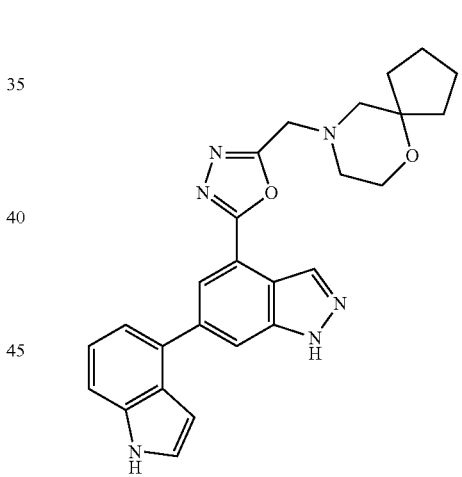

To a solution of 9-({5-[6-bromo-1-(phenylsulfonyl)-1H-indazol-4-yl]-1,3,4-oxadiazol-2-yl}methyl)-6-oxa-9-azaspiro[4.5]decane (100 mg, 0.179 mmol) in 1,4 dioxane (2.5 ml) and water (0.25 ml) was added 4-(4,4,5,5-tetramethyl-1,3,2-dioxaborolan-2-yl)-1H-indole (56.6 mg, 0.233 mmol, available from Frontier Scientific Europe), 1,1'-bis(diphenylphosphino)ferrocene palladium dichloride (26.2 mg, 0.036 mmol) and potassium phosphate tribasic (114 mg, 0.537 mmol). The mixture was heated under microwave irradiation at 100° C. for 20 mins. The mixture was passed through a 1 g silica SPE cartridge, washing with MeOH. The solvent was removed under a stream of nitrogen and the residue was partitioned between DCM (10 ml) and water (10 ml), separated with a hydrophobic frit and the solvent again removed under a stream of nitrogen. The residue was dissolved in DMSO (2 ml) and purified by Mass Directed Automated Preparative HPLC. The appropriate fractions were blown down under a stream of nitrogen to give a yellow solid. The solid was dissolved in 1,4-dioxane (1 ml) and sodium hydroxide (1 ml, 2.000 mmol) and stirred at room temperature for 3 h. The mixture was evaporated to dryness under a stream of nitrogen. The residue was partitioned between ethyl acetate (5 ml) and saturated ammonium chloride (2 ml) and separated with a hydrophilic frit. The solvent was removed under a stream of nitrogen and the residue was freeze dried from 1,4-dioxane/water (1:1, 2 ml) overnight to give the title compound as a cream solid (21 mg).

LCMS (Method A): Rt 0.93 mins, MH+ 455.

Example 49

4-{5-[(2,2-Dimethyl-4-morpholinyl)methyl]-1,3,4-oxadiazol-2-yl}-6-(1H-indol-4-yl)-1H-indazole

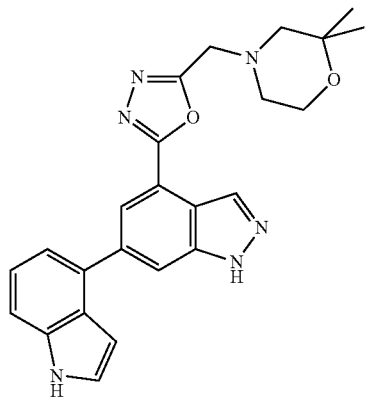 [SMILES: CC1(C)CN(Cc2nnc(-c3cc(-c4cccc5[nH]ccc45)cc4[nH]ncc34)o2)CCO1]

To a solution of 6-bromo-4-{5-[(2,2-dimethyl-4-morpholinyl)methyl]-1,3,4-oxadiazol-2-yl}-1-(phenylsulfonyl)-1H-indazole (176 mg, 0.298 mmol) in dioxane (2.5 ml) and water (0.25 ml) was added 4-(4,4,5,5-tetramethyl-1,3,2-dioxaborolan-2-yl)-1H-indole (102 mg, 0.420 mmol, available from Frontier Scientific Europe), 1,1'-bis(diphenylphosphino)ferrocene palladium dichloride (43.5 mg, 0.060 mmol) and potassium phosphate tribasic (198 mg, 0.933 mmol). The mixture was heated under microwave irradiation at 100° C. for 20 mins. The mixture was passed through a 1 g silica SPE cartridge, washing with MeOH. The solvent was removed under a stream of nitrogen and the residue was partitioned between DCM (10 ml) and water (10 ml), separated with a hydrophobic frit and the solvent again removed under a stream of nitrogen. The crude residue was dissolved in DMSO (2 ml) and purified by Mass Directed Automated Preparative HPLC. The product-containing fractions were blown down under a stream of nitrogen to give a yellow solid. The protected compound was dissolved in 1,4-dioxane (1 ml) and sodium hydroxide (1 ml, 2.000 mmol) and stirred at room temperature for 3 h. The mixture was evaporated to dryness under a stream of nitrogen. The residue was partitioned between ethyl acetate (5 ml) and saturated ammonium chloride (2 ml) and separated with a hydrophilic frit. The solvent was removed under a stream of nitrogen to give a brown solid (31 mg) that was dissolved in DMSO (750 µL) and purified by Mass Directed Automated Preparative HPLC. The solvent was removed under a stream of nitrogen. The appropriate fraction was blown down under a stream of nitrogen to give the title compound as a pale yellow gum (2.4 mg).

LCMS (Method A): Rt 0.86 mins, MH+ 429.

Example 50

N-[5-[4-(5-{[(3R,5S)-3,5-Dimethyl-4-(1-methylethyl)-1-piperazinyl]methyl}-1,3,4-oxadiazol-2-yl)-1H-indazol-6-yl]-2-(methyloxy)-3-pyridinyl]-2,4-difluorobenzenesulfonamide

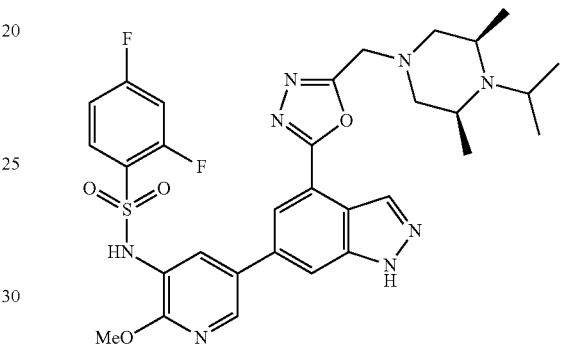

6-Bromo-4-(5-{[(3R,5S)-3,5-dimethyl-4-(1-methylethyl)-1-piperazinyl]methyl}-1,3,4-oxadiazol-2-yl)-1-(phenylsulfonyl)-1H-indazole (172 mg, 0.300 mmol), 2,4-difluoro-N-[2-(methyloxy)-5-(4,4,5,5-tetramethyl-1,3,2-dioxaborolan-2-yl)-3-pyridinyl]benzenesulfonamide (128 mg, 0.300 mmol), 1,1'-bis(diphenylphosphino)ferrocene palladium dichloride (43.9 mg, 0.060 mmol) and potassium phosphate tribasic (191 mg, 0.900 mmol) were added to a microwave vial and dissolved in 1,4-dioxane (2.5 ml) and water (0.25 ml). The mixture was heated under microwave irradiation at 100° C. for 20 mins. The mixture was passed through a 1 g silica SPE cartridge, washing with MeOH. The solvent was removed under a stream of nitrogen and the residue was partitioned between DCM (10 ml) and water (10 ml), separated with a hydrophobic frit and the solvent again removed under a stream of nitrogen. The protected compound was dissolved in 1,4-dioxane (1 ml) and sodium hydroxide (1 ml, 2.000 mmol) and stirred at room temperature for 4 h. The mixture was evaporated to dryness under a stream of nitrogen. The residue was partitioned between ethyl acetate (5 ml) and saturated ammonium chloride (2 ml) and separated with a hydrophilic frit. The solvent was removed under a stream of nitrogen and the residue was dissolved in DMSO (1 ml) and purified by purified by Mass Directed Automated Preparative HPLC. The appropriate fraction was blown down under a stream of nitrogen to give the title compound as a pale yellow solid (4.9 mg).

LCMS (Method A): Rt 0.65 mins, MH+ 653.

The compounds listed below were synthesised using the general method above:

| Example Number | Starting Material | Structure | Rt mins | MH+ | Name |
|---|---|---|---|---|---|
| 51 | 6-bromo-4-(5-{[4-(1-methylethyl)-1-piperazinyl]methyl}-1,3,4-oxadiazol-2-yl)-1-(phenyl-sulfonyl)-1H-indazole | 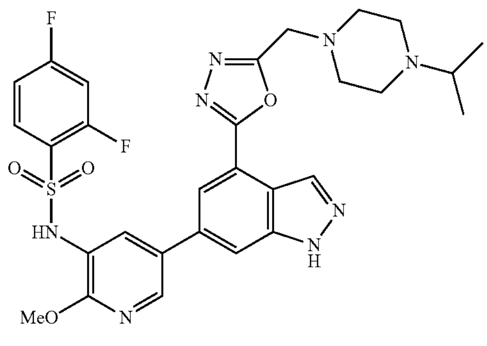 [SMILES: COc1ncc(-c2cc(-c3nnc(CN4CCN(C(C)C)CC4)o3)c3cn[nH]c3c2)cc1NS(=O)(=O)c1ccc(F)cc1F] | 0.62 | 625 | 2,4-difluoro-N-[5-[4-(5-{[4-(1-methylethyl)-1-piperazinyl]methyl}-1,3,4-oxadiazol-2-yl)-1H-indazol-6-yl]-2-(methyloxy)-3-pyridinyl]benzene-sulfonamide |

Example 52

N-[5-(4-{5-[(2-Methyl-4-morpholinyl)methyl]-1,3,4-oxadiazol-2-yl}-1H-indazol-6-yl)-2-(methyloxy)-3-pyridinyl]methanesulfonamide

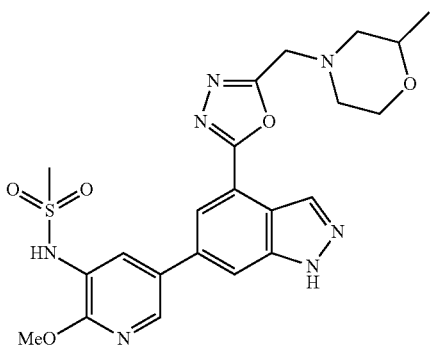 [SMILES: COc1ncc(-c2cc(-c3nnc(CN4CCOC(C)C4)o3)c3cn[nH]c3c2)cc1NS(C)(=O)=O]

6-Bromo-4-{5-[(2-methyl-4-morpholinyl)methyl]-1,3,4-oxadiazol-2-yl]-1-(phenylsulfonyl)-1H-indazole (269 mg, 0.519 mmol) was dissolved in 1,4-dioxane (5 ml) and half of this stock solution was charged to a reaction vessel. N-[2-(methyloxy)-5-(4,4,5,5-tetramethyl-1,3,2-dioxaborolan-2-yl)-3-pyridinyl]methanesulfonamide (110 mg, 0.335 mmol), 1,1'-bis(diphenylphosphino)ferrocene palladium dichloride (38 mg, 0.052 mmol), potassium phosphate tribasic (165 mg, 0.779 mmol) and water (0.25 ml) were added. The reaction mixture was heated under microwave irradiation at 100° C. for 20 mins, then 100° C. for 40 mins and lastly 100° C. for 20 mins. More N-[2-(methyloxy)-5-(4,4,5,5-tetramethyl-1,3,2-dioxaborolan-2-yl)-3-pyridinyl]methanesulfonamide (34.1 mg, 0.104 mmol), 1,1'-bis(diphenylphosphino)ferrocene palladium dichloride (7.59 mg, 10.38 μmol) and potassium phosphate tribasic (33.0 mg, 0.156 mmol) were added and the mixture was heated under microwave irradiation at 100° C. for 20 mins. The mixture was passed through a 1 g silica SPE cartridge, washing with MeOH. The solvent was removed under a stream of nitrogen and the residue was partitioned between DCM (10 ml) and water (10 ml), separated with a hydrophobic frit and the solvent again removed under a stream of nitrogen. The crude was purified using preparative HPLC as follows:

| Column Packing | Waters Sunfire c18 |
|---|---|
| Column Particle Size | 5.0 μm |
| Column Dimensions | 100 × 19 mmID |
| Solvent A | 0.1% v/v formic acid in water |
| Solvent B | MeCN + 0.1% v/v of formic acid |
| Temperature | ambient |
| Flow Rate | 20 ml/min |
| Injection Volume | 500 μL |
| Injection Vehicle | 1:1 DMSO/MeCN |
| UV detection | Diode-array 210-400 nm (averaged) |
| MS detection | Electrospray, +ve/−ve switching, 100-1000 amu, centroid mode |
| MS scan function | Electrospray, +ve/−ve switching, centroid mode |

| Time (mins) | % A | % B | Flow rate (ml/min) |
|---|---|---|---|
| 0 | 65 | 35 | 20 |
| 1 | 65 | 35 | 20 |
| 15 | 65 | 35 | 20 |
| 15.5 | 100 | 0 | 20 |
| 18 | 100 | 0 | 20 |
| 18.5 | 65 | 35 | 20 |
| 20 | 65 | 35 | 20 |

The appropriate fraction were blown to dryness. 1,4-Dioxane (1 ml) was added and 2M sodium hydroxide (1 ml, 2.000 mmol) and the mixture stirred at 20° C. for 2 h. The mixture was partitioned between ethyl acetate (5 ml) and saturated ammonium chloride solution (2 ml), separated with a hydrophilic frit. The organic layer was evaporated to dryness under a stream of nitrogen to give the title compound as a cream solid (27 mg).

LCMS (Method A): Rt 0.63 mins, MH+ 500.

Example 53

6-(1H-Indol-4-yl)-4-{5-[(2-methyl-4-morpholinyl)methyl]-1,3,4-oxadiazol-2-yl}-1H-indazole

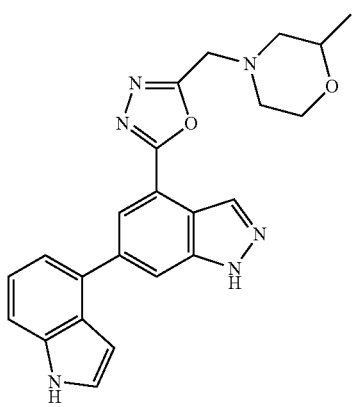 [SMILES: CC1CN(Cc2nnc(-c3cc(-c4cccc5[nH]ccc45)cc4[nH]ncc34)o2)CCO1]

6-Bromo-4-{5-[(2-methyl-4-morpholinyl)methyl]-1,3,4-oxadiazol-2-yl]-1-(phenylsulfonyl)-1H-indazole (269 mg, 0.519 mmol) was dissolved in 1,4-dioxane (5 ml) and half of this stock solution was charged to a reaction vessel. 4-(4,4,5,5-tetramethyl-1,3,2-dioxaborolan-2-yl)-1H-indole (82 mg, 0.337 mmol), 1,1'-bis(diphenylphosphino)ferrocene palladium dichloride (38 mg, 0.052 mmol), potassium phosphate tribasic (165 mg, 0.779 mmol) and water (0.25 ml) were added. The reaction mixture was heated under microwave irradiation at 100° C. for 20 mins. The mixture was passed through a 1 g silica SPE cartridge, washing with MeOH. The solvent was removed under a stream of nitrogen and the residue was partitioned between DCM (10 ml) and water (10 ml), separated with a hydrophobic frit and the solvent again removed under a stream of nitrogen. The crude residue was purified using preparative HPLC as follows:

| | |
|---|---|
| Column Packing | Waters Sunfire C18 |
| Column Particle Size | 5.0 μm |
| Column Dimensions | 100 × 19 mmID |
| Solvent A | 0.1% v/v formic acid in water |
| Solvent B | MeCN + 0.1% v/v of formic acid |
| Temperature | ambient |
| Flow Rate | 20 ml/mins |
| Injection Volume | 200 μL |
| Injection Vehicle | 1:1 DMSO/MeCN |
| UV detection | Diode-array 210-400 nm (averaged) |
| MS detection | Electrospray, +ve/−ve switching, 100-1000 amu, centroid mode |
| MS scan function | Electrospray, +ve/−ve switching, centroid mode |

| Time (mins) | % A | % B | Flow rate (ml/min) |
|---|---|---|---|
| 0 | 60 | 40 | 20 |
| 1 | 60 | 40 | 20 |
| 25 | 60 | 40 | 20 |
| 25.5 | 100 | 0 | 20 |
| 27 | 100 | 0 | 20 |
| 27.5 | 60 | 40 | 20 |
| 30 | 60 | 40 | 20 |

The appropriate fractions were dried down. 1,4-Dioxane (1 ml) and 2M sodium hydroxide (1 ml, 2.000 mmol) was added and the mixture stirred at 20° C. for 2 h. The mixture was partitioned between ethyl acetate (5 ml) and saturated ammonium chloride solution (2 ml), separating the layers with a hydrophilic frit. The organic layer was evaporated to dryness under a stream of nitrogen. The residue was taken up again in 1,4-dioxane (1 ml) and 2M sodium hydroxide (1 ml, 2.000 mmol) and stirred at room temperature for 3 h. The mixture was evaporated under a stream of nitrogen. The residue was partitioned between ethyl acetate and saturated ammonium chloride solution, the organic layer was separated with a hydrophilic frit and the solvent removed under a stream of nitrogen to give the title compound as a cream solid (18 mg).

LCMS (Method A): Rt 0.75 mins, MH+ 415.

Example 54

N-({5-[6-(1H-Indol-4-yl)-1H-indazol-4-yl]-1,3,4-oxadiazol-2-yl}methyl)-3-(4-morpholinyl)-1-propanamine

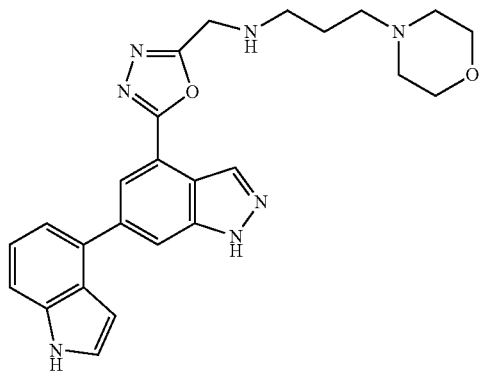 [SMILES: c1cc(-c2cc(-c3nnc(CNCCCN4CCOCC4)o3)c3cn[nH]c3c2)c2cc[nH]c2c1]

To a solution of N,N-{[5-(6-bromo-1H-indazol-4-yl)-1,3,4-oxadiazol-2-yl]methyl}-3-(4-morpholinyl)-1-propanamine (100 mg, 0.237 mmol) was added 4-(4,4,5,5-tetramethyl-1,3,2-dioxaborolan-2-yl)-1H-indole (57.7 mg, 0.237 mmol, available from Frontier Scientific Europe), 1,1'-bis(diphenylphosphino)ferrocene palladium dichloride (34.7 mg, 0.047 mmol) and potassium phosphate tribasic (151 mg, 0.712 mmol). The mixture was heated under microwave irradiation at 100° C. for 20 mins, 120° C. for 20 mins and finally 150° C. for 20 mins. The reaction mixture was filtered through a 1 g silica SPE cartridge, washing with MeOH. The solvent was evaporated under a stream of nitrogen and the residue partitioned between DCM and water, the organic layer was separated with a hydrophobic frit and the solvent again removed under a stream of nitrogen to give a brown oil (75 mg). The crude residue was purified by Mass Directed Automated Preparative HPLC and the appropriate fraction was blown down under a stream of nitrogen to give the title compound as a colourless gum (109 mg).

LCMS (Method A): Rt 0.43 mins, 458.

Example 55

N-(2-(Methyloxy)-5-{4-[5-(tetrahydro-1,4-oxazepin-4(5H)-ylmethyl)-1,3,4-oxadiazol-2-yl]-1H-indazol-6-yl}-3-pyridinyl)methanesulfonamide

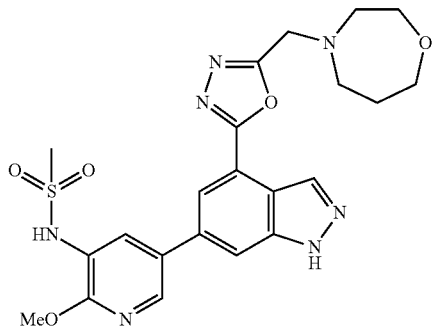 [SMILES: COc1ncc(-c2cc(-c3nnc(CN4CCCOCC4)o3)c3cn[nH]c3c2)cc1NS(C)(=O)=O]

To a solution of N-(2-(methyloxy)-5-{1-(phenylsulfonyl)-4-[5-(tetrahydro-1,4-oxazepin-4(5H)-ylmethyl)-1,3,4-oxadiazol-2-yl]-1H-indazol-6-yl}-3-pyridinyl)methanesulfonamide (50 mg, 0.078 mmol) in 1,4-dioxane (1 ml) was added 2M sodium hydroxide (1 ml, 2.000 mmol) and the mixture stirred at 20° C. for 2 h. The mixture was partitioned between ethyl acetate (5 ml) and saturated ammonium chloride solution (2 ml), separating the layers with a hydrophilic frit. The organic layer was evaporated to dryness under a stream of nitrogen to give the title compound as a pale brown solid (35 mg).

LCMS (Method A): Rt 0.51 mins, MH+ 500.

The compound listed below was synthesised using the general method above:

Example 57

N-[5-{4-[5-({[2-Hydroxy-3-(4-morpholinyl)propyl]amino}methyl)-1,3,4-oxadiazol-2-yl]-1H-indazol-6-yl}-2-(methyloxy)-3-pyridinyl]methanesulfonamide

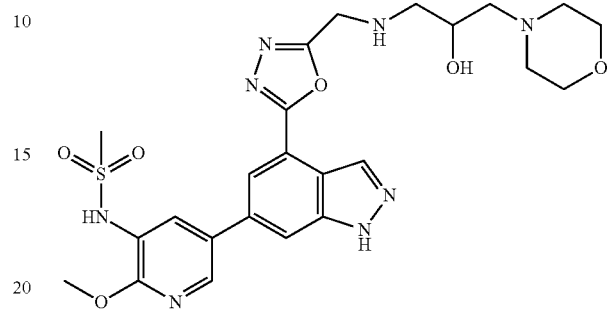

1-[({5-[6-Bromo-1-(phenylsulfonyl)-1H-indazol-4-yl]-1,3,4-oxadiazol-2-yl}methyl)amino]-3-(4-morpholinyl)-2-propanol (100 mg, 0.346 mmol), N-[2-(methyloxy)-5-(4,4,5,5-tetramethyl-1,3,2-dioxaborolan-2-yl)-3-pyridinyl]methanesulfonamide (81 mg, 0.247 mmol), 1,1'-bis(diphenylphosphino)ferrocene palladium dichloride (25.35 mg, 0.0345 mmol) and potassium phosphate tribasic (110.5 mg, 0.5195 mmol) were added to a mixture of 1,4-dioxane (2.5 ml) and water (0.25 ml). The reaction mixture was heated under microwave irradiation at 80° C. for 30 mins and then 100° C. for 10 mins. The mixture was then passed through a 1 g silica SPE cartridge, washing with MeOH. The solvent was removed under a stream of nitrogen and the residue was partitioned between DCM (10 ml) and water (10 ml), separated by a hydrophobic frit and the solvent again removed under a stream of nitrogen. The protected compound was dissolved in 1,4-dioxane (1 ml) and sodium hydroxide (1 ml) and stirred at room temperature for 1 h. The mixture was neutralised with addition of 2M HCl, dissolved in DMSO,

| Example Number | Starting Material | Structure | Rt mins | MH+ | Name |
|---|---|---|---|---|---|
| 56 | 6-(1H-indol-4-yl)-1-(phenylsulfonyl)-4-[5-(tetrahydro-1,4-oxazepin-4(5H)-ylmethyl)-1,3,4-oxadiazol-2-yl]-1H-indazole | | 0.58 | 415 | 6-(1H-indol-4-yl)-4-[5-(tetrahydro-1,4-oxazepin-4(5H)-ylmethyl)-1,3,4-oxadiazol-2-yl]-1H-indazole | filtered through a filter tube and purified by high pH MDAP (Method E). The appropriate fractions and waste were evaporated to dryness in vacuo. The residue was dissolved in 1:1 DMSO/water and purified by preparative HPLC using the following method:

The appropriate fractions were dried down give the title compound as a pale yellow solid (12 mg).
LCMS (Method A): 0.40 mins, MH+ 559.
The compound listed below was synthesised using the general method above:

| Example Number | Starting Material | Structure | Rt mins | MH+ | Name |
|---|---|---|---|---|---|
| 58 | 2,4-difluoro-N-[2-(methyloxy)-5-(4,4,5,5-tetramethyl-1,3,2-dioxaborolan-2-yl)-3-pyridinyl]benzenesulfonamide | 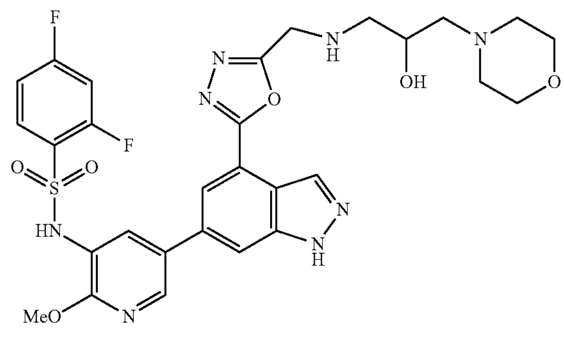 [SMILES: COc1ncc(-c2cc(-c3nnc(CNCC(O)CN4CCOCC4)o3)c3cn[nH]c3c2)cc1NS(=O)(=O)c1ccc(F)cc1F] | 0.54 | 657 | 2,4-difluoro-N-[5-{4-[5-({[2-hydroxy-3-(4-morpholinyl)propyl]amino}methyl)-1,3,4-oxadiazol-2-yl]-1H-indazol-6-yl}-2-(methyloxy)-3-pyridinyl]benzenesulfonamide |

| Column Packing | Waters Atlantis |
|---|---|
| Column Particle Size | 5.0 μm |
| Column Dimensions | 100 × 19 mmID |
| Solvent A | 0.1% v/v TFA in water |
| Solvent B | MeOH + 0.1% v/v TFA |
| Temperature | ambient |
| Flow Rate | 20 ml/min |
| Injection Volume | 500 μL |
| UV detection | Diode-array 210-400 nm (averaged) |
| MS detection | Electrospray, +ve/−ve switching, 100-1000 amu, centroid mode |
| MS scan function | Electrospray, +ve/−ve switching, centroid mode |

| Time (mins) | % A | % B | Flow rate (ml/min) |
|---|---|---|---|
| 0 | 75 | 25 | 20 |
| 1 | 75 | 25 | 20 |
| 25 | 25 | 75 | 20 |
| 26 | 1 | 99 | 20 |
| 28.5 | 1 | 99 | 20 |
| 29 | 75 | 25 | 20 |
| 30 | 75 | 25 | 20 |

The crude residue was collected and re-purified using a similar method but using 10-30% MeCN/TFA and the following gradient.

| Time (mins) | % A | % B | Flow rate (ml/min) |
|---|---|---|---|
| 0 | 90 | 10 | |
| 1 | 90 | 10 | 20 |
| 25 | 70 | 30 | 20 |
| 26 | 1 | 99 | 20 |
| 28.5 | 1 | 99 | 20 |
| 29 | 90 | 10 | 20 |
| 30 | 90 | 10 | 20 |

Example 59

N-[5-(4-{5-[(8aS)-Hexahydropyrrolo[1,2-a]pyrazin-2(1H)-ylmethyl]-1,3,4-oxadiazol-2-yl}-1H-indazol-6-yl)-2-(methyloxy)-3-pyridinyl]methanesulfonamide

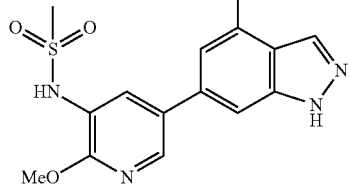

N-[5-[4-{5-[(8aS)-Hexahydropyrrolo[1,2-a]pyrazin-2(1H)-ylmethyl]-1,3,4-oxadiazol-2-yl}-1-(phenylsulfonyl)-1H-indazol-6-yl]-2-(methyloxy)-3-pyridinyl]methanesulfonamide (95 mg, 0.143 mmol) was dissolved in 1,4-dioxane (1 ml) and sodium hydroxide (1 ml, 0.143 mmol) was added. The mixture was stirred at room temperature for 1 h. The mixture was dried down under a stream of nitrogen and the residue partitioned between ethyl acetate (5 ml) and saturated ammonium chloride (2 ml). The organic layer was separated, dried by passing through a hydrophobic frit and the solvent removed in vacuo to give an orange oil. This was triturated with cyclohexane to give the title compound as an orange solid (26 mg).
LCMS (K4101903-1). Rt 0.49 mins, MH+ 525.

Example 60

2,4-Difluoro-N-[5-(4-{5-[(8aS)-hexahydropyrrolo[1,2-a]pyrazin-2(1H)-ylmethyl]-1,3,4-oxadiazol-2-yl}-1H-indazol-6-yl)-2-(methyloxy)-3-pyridinyl]benzenesulfonamide

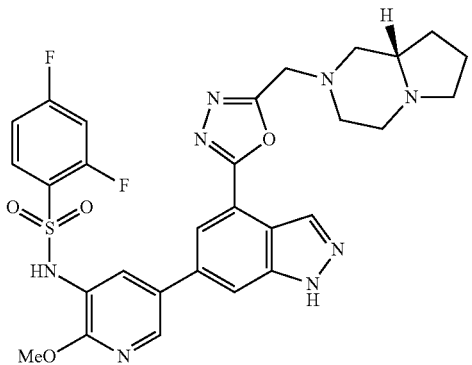 [SMILES: COc1ncc(-c2cc(-c3nnc(CN4CCN5CCC[C@H]5C4)o3)c3cn[nH]c3c2)cc1NS(=O)(=O)c1ccc(F)cc1F]

2,4-Difluoro-N-[5-[4-{5-[(8aS)-hexahydropyrrolo[1,2-a]pyrazin-2(1H)-ylmethyl]-1,3,4-oxadiazol-2-yl}-1-(phenylsulfonyl)-1H-indazol-6-yl]-2-(methyloxy)-3-pyridinyl]benzenesulfonamide (84 mg, 0.110 mmol) was dissolved in 1,4-dioxane (1 ml) and sodium hydroxide (1 ml, 0.110 mmol) was added. The mixture was stirred at room temperature for 1 h. The mixture was dried down under a stream of nitrogen and the residue partitioned between ethyl acetate (5 ml) and saturated ammonium chloride (2 ml). The organic layer was separated, dried by passing through a hydrophobic frit and the solvent removed in vacuo to give a brown gum. This was dissolved in DMSO (1 ml) and purified by high pH MDAP (Method E, extended run). The product-containing fraction was dried under a stream of nitrogen to give the title compound as a cream solid (2.4 mg).

LCMS (Method A): Rt 0.63 mins, MH+ 623.

Example 61

N-[5-[4-(5-{[(2R,6S)-2,6-Dimethyl-4-morpholinyl]methyl}-1,3,4-oxadiazol-2-yl)-1-methyl-1H-indazol-6-yl]-2-(methyloxy)-3-pyridinyl]-2,4-difluorobenzenesulfonamide

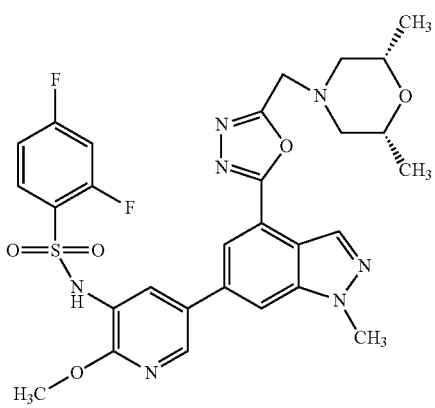 [SMILES: COc1ncc(-c2cc(-c3nnc(CN4C[C@@H](C)O[C@@H](C)C4)o3)c3cnn(C)c3c2)cc1NS(=O)(=O)c1ccc(F)cc1F]

5-[4-(5-{[(2R,6S)-2,6-Dimethyl-4-morpholinyl]methyl}-1,3,4-oxadiazol-2-yl)-1-methyl-1H-indazol-6-yl]-2-(methyloxy)-3-pyridinamine (130 mg, 0.289 mmol) was dissolved in chloroform (3 ml) then 2,4-difluorobenzenesulfonyl chloride (0.058 ml, 0.434 mmol) was added. Pyridine (0.094 ml, 1.157 mmol) was added to the reaction mixture and it was stirred at room temperature (25° C.) for 18 h. The solvent was blown down under nitrogen for 24 h to give a brown oil. Half of material was purified by column chromatography with a gradient of 0-25% MeOH/DCM over 20 mins. Fractions containing product were combined and the solvent removed to give a brown oil which was triturated in ether. The solvent was removed under nitrogen to give an orange solid. This solid was dissolved in DMSO and purified by Mass Directed Automated Preparative HPLC. The solvent was removed under nitrogen to give a white solid (5 mg). The other half of the crude material was purified by Mass Directed Automated Preparative HPLC and the appropriate fractions were combined and solvent was removed under nitrogen to give a white solid (25 mg). The two batches were combined to give the title compound as a white solid (30 mg). LCMS (Method A): Rt 0.99 mins, MH+ 626.

Example 62

N-[5-[4-(5-{[(2R,6S)-2,6-Dimethyl-4-morpholinyl]methyl}-1,3,4-oxadiazol-2-yl)-1H-indazol-6-yl]-2-(methyloxy)-3-pyridinyl]-2-(methyloxy)benzenesulfonamide

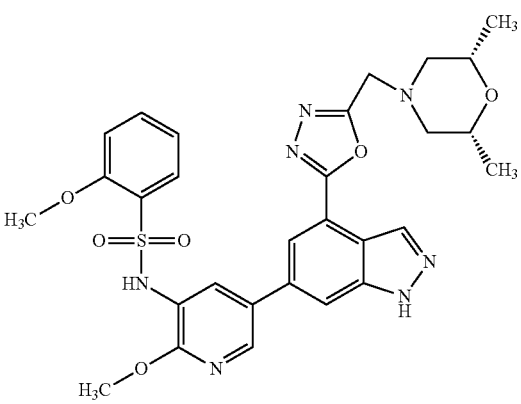

5-{4-(5-{[(2R,6S)-2,6-Dimethyl-4-morpholinyl]methyl}-1,3,4-oxadiazol-2-yl)-1-[(4-methylphenyl)sulfonyl]-1H-indazol-6-yl}-2-(methyloxy)-3-pyridinamine (150 mg, 0.254 mmol) was dissolved in chloroform (3 ml) then 2-(methyloxy)benzenesulfonyl chloride (79 mg, 0.382 mmol) was added. Pyridine (0.082 ml, 1.018 mmol) was added to the reaction mixture and it was stirred at room temperature for 5 h. The compound was dissolved in 1,4-dioxane (2 ml) and 2M sodium hydroxide (2 ml) and stirred at room temperature for 3 h. The reaction mixture was neutralized to pH 7 with 2M HCl, then the solvent was removed under a stream of nitrogen. The solid was dissolved in DMSO then filtered through a filter tube and purified by Mass Directed Automated Preparative HPLC. The solvent was removed under nitrogen to give the title compound as a white solid (60 mg).

LCMS (Method A): Rt 0.88 mins, MH+ 606.

Biological Data
PI3K Alpha, Beta, Delta and Gamma Assays
Assay Principle

The assay readout exploits the specific and high affinity binding of PIP3 to an isolated pleckstrin homology (PH) domain in the generation of a signal. Briefly, the PIP3 product is detected by displacement of biotinylated PIP3 from an energy transfer complex consisting of Europium (Eu)-labelled anti-GST monoclonal antibody, a GST-tagged PH domain, biotin-PIP3 and Streptavidin-APC. Excitation of Eu leads to a transfer of energy to APC and a sensitized fluorescence emission at 665 nm. PIP3 formed by PI3 kinase activity competes for the binding site on the PH domain, resulting in a loss of energy transfer and a decrease in signal.

Assay Protocol

Solid compounds are typically plated with 0.1 μl of 100% DMSO in all wells (except column 6 and 18) of a 384-well, v bottom, low volume Greiner plate. The compounds are serially diluted (4-fold in 100% DMSO) across the plate from column 1 to column 12 and column 13 to column 24 and leave column 6 and 18 containing only DMSO to yield 11 concentrations for each test compound.

The assays are run using specific PI3 kinase kits from Millipore (Cat#33-001)

The assay kit consist of the following:
4×PI3K reaction buffer (Contains 200 mM Hepes pH 7, 600 mM NaCl, 40 mM Mgcl$_2$, <1% Cholate (w/v), <1% Chaps (w/v), 0.05% Sodium Azide (w/v))
PIP2 (1 mM)
3×Biotin PIP3 (50 μM)
Detection Mix C (Contains 267 mM KF)
Detection Mix A (Contains 60 μg/ml streptavadin-APC)
Detection Mix B (Contains 36 μg/ml Europium-anti-GST (Anti-GST-K) and 90 μg/ml GST-GRP1-PH-Domain and 1 mM DTT)
Stop Solution (Contains 150 mM EDTA)

Manually add 3 μl of Reaction buffer (contains 1 mM DTT) to column 18 only for 100% inhibition control (no activity)

Manually add 3 μl of 2× Enzyme solution to all wells except column 18. Preincubate with compound for 15 minutes.

Manually add 3 μl of 2× Substrate solution to all wells. (column 6 represents 0% inhibition control)

Leave plate for 1 hr (cover from light) (In the case of Gamma only a 50 min incubation is required)

Manually add 3 μl Stop/Detection solution to all wells
Leave plate for 1 hour (cover from light)

The assay is read upon the BMG Rubystar and the ratio data is utilised to calculate 11 point curves.

NB The substrate solution (concentrations) differ with each isoform (see below)

Alpha
2× substrate solution containing 500 μM ATP, 16 μM PIP2 and 0.030 μM 3× biotin-PIP3.

Beta
2× substrate solution containing 800 μM ATP, 16 μM PIP2 and 0.030 μM 3× biotin-PIP3.

Delta
2× substrate solution containing 160 μM ATP, 10 μM PIP2 and 0.030 μM 3× biotin-PIP3.

Gamma
2× substrate solution containing 30 μM ATP, 16 μM PIP2 and 0.030 μM 3× biotin-PIP3.

Analysis Method

Data processed through the XC50 4-parameter logistic curve fit algorithm in Activity Base.

Normalise to % inhibition between the high and low controls (0% and 100% inhibition respectively)

Primary Module fit: Slope, Min and Max asymptotes varies
Secondary Module fits: (1) Fix Min asymptote, (2) Fix Max asymptote, (3) Fix Min and Max asymptotes
Curve Fit QC: pXC50 95% CL ratio>10
−20<Min asymptote<20
80<Max asymptote<120

The compounds of Examples 1 to 62 were tested in one or more of the PI3K Alpha, Beta, Delta and/or Gamma assays above or similar assays and were found to have a mean pIC$_{50}$ of 5 or greater.

What is claimed is:

1. A compound of formula (I):

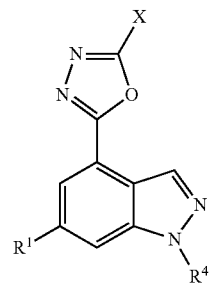

(I)

wherein
$R^1$ is 9- or 10-membered bicyclic heteroaryl wherein the 9- or 10-membered bicyclic heteroaryl contains from one to three heteroatoms independently selected from oxygen and nitrogen and is optionally substituted by $C_{1-6}$alkyl, $C_{3-6}$cycloalkyl, halo, —CN or —NHSO$_2$R$^5$, or pyridinyl optionally substituted by one or two substituents independently selected from $C_{1-6}$alkyl, —OR$^6$, halo and —NHSO$_2$R$^7$;

X is —CH$_2$NR$^2$R$^3$, $C_{1-6}$alkyl, —CH$_2$phenyl, —(CH$_2$)$_n$OR$^{10}$, —CH$_2$SO$_2$R$^{11}$ or —(CH$_2$)$_p$C$_{3-6}$cycloalkyl;

$R^2$ and $R^3$, together with the nitrogen atom to which they are attached, are linked to form a 6- or 7-membered heterocyclyl or a 9- or 10-membered bicyclic heterocyclyl wherein the 6- or 7-membered heterocyclyl or the 9- or 10-membered bicyclic heterocyclyl optionally contains an oxygen atom, a sulphur atom or a further nitrogen atom and is optionally substituted by from one to three substituents independently selected from oxo, $C_{1-6}$alkyl, —(CH$_2$)$_m$NR$^8$R$^9$, phenyl optionally substituted by halo, and 6-membered heteroaryl wherein the 6-membered heteroaryl contains one or two nitrogen atoms, a 7-membered bridged heterocyclyl wherein the 7-membered bridged heterocyclyl optionally contains a further nitrogen atom and is optionally substituted by from one to three substituents independently selected from $C_{1-6}$alkyl, or a 10-membered spiro bicyclic heterocyclyl wherein the 10-membered spiro bicyclic heterocyclyl optionally contains an oxygen atom, or $R^2$ is hydrogen and $R^3$ is $C_{1-6}$alkyl optionally substituted by one or two substituents independently selected from —OR$^{12}$ and —NR$^{13}$R$^{14}$;

$R^4$ is hydrogen or methyl;
$R^6$, $R^{12}$ and $R^{15}$ are each independently hydrogen or $C_{1-4}$alkyl;

R$^5$ and R$^7$ are each independently C$_{1-6}$alkyl or phenyl wherein the phenyl is optionally substituted by one or two substituents independently selected from halo and —OR$^{15}$;

R$^8$ and R$^9$, together with the nitrogen atom to which they are attached, are linked to form a 5- or 6-membered heterocyclyl optionally containing an oxygen atom;

R$^{19}$ is hydrogen, C$_{1-6}$alkyl, —(CH$_2$)$_q$phenyl or C$_{3-6}$cycloalkyl wherein the C$_{3-6}$cycloalkyl is optionally substituted by one or two substituents independently selected from C$_{1-6}$alkyl;

R$^{11}$ is C$_{1-6}$alkyl or phenyl;

R$^{13}$ and R$^{14}$, together with the nitrogen atom to which they are attached, are linked to form a 6-membered heterocyclyl optionally containing an oxygen atom;

m, p and q are each independently 0, 1 or 2; and n is 1 or 2;

or a pharmaceutically acceptable salt thereof.

2. A compound according to claim 1, or a salt thereof, wherein R$^1$ is 9- or 10-membered bicyclic heteroaryl wherein the 9- or 10-membered bicyclic heteroaryl contains one or two nitrogen atoms and is optionally substituted by C$_{1-6}$alkyl or halo.

3. A compound according to claim 1, or a salt thereof, wherein R$^1$ is pyridinyl optionally substituted by one or two substituents independently selected from C$_{1-6}$alkyl, —OR$^6$, halo and —NHSO$_2$R$^7$.

4. A compound according to claim 1, or a salt thereof, wherein X is —CH$_2$NR$^2$R$^3$.

5. A compound according to claim 1, or a salt thereof, wherein R$^4$ is hydrogen.

6. A compound which is selected from the group consisting of:
4-(5-{[(2R,6S)-2,6-dimethyl-4-morpholinyl]methyl}-1,3,4-oxadiazol-2-yl)-6-(1H-indol-4-yl)-1H-indazole;
6-(1H-indol-4-yl)-4-(5-{[4-(1-methylethyl)-1-piperazinyl]methyl}-1,3,4-oxadiazol-2-yl)-1H-indazole;
N-[5-[4-(5-{[(2R,6S)-2,6-dimethyl-4-morpholinyl]methyl}-1,3,4-oxadiazol-2-yl)-1H-indazol-6-yl]-2-(methyloxy)-3-pyridinyl]methanesulfonamide;
N-[5-[1-methyl-4-(5-{[4-(1-methylethyl)-1-piperazinyl]methyl}-1,3,4-oxadiazol-2-yl)-1H-indazol-6-yl]-2-(methyloxy)-3-pyridinyl]methanesulfonamide;
N-[5-[4-(5-{[(2R,6S)-2,6-dimethyl-4-morpholinyl]methyl}-1,3,4-oxadiazol-2-yl)-1-methyl-1H-indazol-6-yl]-2-(methyloxy)-3-pyridinyl]methanesulfonamide; and
a salt thereof.

7. A compound according to claim 1 in the form of a pharmaceutically acceptable salt thereof.

8. A pharmaceutical composition comprising a compound as defined in claim 1, or a pharmaceutically acceptable salt thereof, and one or more pharmaceutically acceptable excipients.

9. A compound which is selected from the group consisting of:
6-(1H-indol-4-yl)-4-[5-(4-morpholinylmethyl)-1,3,4-oxadiazol-2-yl]-1H-indazole;
N-(2-chloro-5-{4-[5-(4-morpholinylmethyl)-1,3,4-oxadiazol-2-yl]-1H-indazol-6-yl}-3-pyridinyl)methanesulfonamide;
4-(5-{[(2R,6S)-2,6-dimethyl-4-morpholinyl]methyl}-1,3,4-oxadiazol-2-yl)-6-(1H-indol-4-yl)-1H-indazole;
6-(1H-indol-4-yl)-4-(5-{[4-(2-pyrimidinyl)-1-piperazinyl]methyl}-1,3,4-oxadiazol-2-yl)-1H-indazole;
4-{5-[(4,4-dimethyl-1-piperidinyl)methyl]-1,3,4-oxadiazol-2-yl}-6-(1H-indol-4-yl)-1H-indazole;
6-(1H-indol-4-yl)-4-(5-{[4-(2-methylpropyl)-1-piperazinyl]methyl}-1,3,4-oxadiazol-2-yl)-1H-indazole;
6-(1H-indol-4-yl)-4-(5-{[4-(1-methylethyl)-1-piperidinyl]methyl}-1,3,4-oxadiazol-2-yl)-1H-indazole;
6-(1H-indol-4-yl)-4-(5-{[2-(1-pyrrolidinylmethyl)-1-piperidinyl]methyl}-1,3,4-oxadiazol-2-yl)-1H-indazole;
4-(5-{[4-(4-fluorophenyl)-1-piperazinyl]methyl}-1,3,4-oxadiazol-2-yl)-6-(1H-indol-4-yl)-1H-indazole;
6-(1H-indol-4-yl)-4-(5-{[(1R,4R)-1,4,5-trimethyl-2,5-diazabicyclo[2.2.1]hept-2-yl]methyl}-1,3,4-oxadiazol-2-yl)-1H-indazole;
6-(1H-indol-4-yl)-4-(5-{[2-(1-pyrrolidinylmethyl)-4-morpholinyl]methyl}-1,3,4-oxadiazol-2-yl)-1H-indazole;
6-(1H-indol-4-yl)-4-[5-({4-[2-(4-morpholinyl)ethyl]-1-piperazinyl}methyl)-1,3,4-oxadiazol-2-yl]-1H-indazole;
6-(1H-indol-4-yl)-4-(5-{[4-(1-methylethyl)-1-piperazinyl]methyl}-1,3,4-oxadiazol-2-yl)-1H-indazole;
4-(5-{[(2R,6S)-2,6-dimethyl-1-piperidinyl]methyl}-1,3,4-oxadiazol-2-yl)-6-(1H-indol-4-yl)-1H-indazole;
4-(5-{[(1S,4S)-1,4-dimethyl-7-azabicyclo[2.2.1]hept-7-yl]methyl}-1,3,4-oxadiazol-2-yl)-6-(1H-indol-4-yl)-1H-indazole;
4-({5-[6-(1H-indol-4-yl)-1H-indazol-4-yl]-1,3,4-oxadiazol-2-yl}methyl)octahydro-2H-1,4-benzoxazine;
6-(1H-indol-4-yl)-4-(5-{[2-(2-methylpropyl)-4-morpholinyl]methyl}-1,3,4-oxadiazol-2-yl)-1H-indazole;
N-{2-chloro-5-[4-(5-{[4-(1-methylethyl)-1-piperazinyl]methyl}-1,3,4-oxadiazol-2-yl)-1H-indazol-6-yl]-3-pyridinyl}methanesulfonamide;
N-{2-chloro-5-[4-(5-{[(2R,6S)-2,6-dimethyl-4-morpholinyl]methyl}-1,3,4-oxadiazol-2-yl)-1H-indazol-6-yl]-3-pyridinyl}methanesulfonamide;
N-(2-chloro-5-{4-[5-(4-morpholinylmethyl)-1,3,4-oxadiazol-2-yl]-1H-indazol-6-yl}-3-pyridinyl)methanesulfonamide;
N-[5-[4-(5-{[(2R,6S)-2,6-dimethyl-4-morpholinyl]methyl}-1,3,4-oxadiazol-2-yl)-1H-indazol-6-yl]-2-(methyloxy)-3-pyridinyl]methanesulfonamide;
N-[5-[4-(5-{[4-(1-methylethyl)-1-piperazinyl]methyl}-1,3,4-oxadiazol-2-yl)-1H-indazol-6-yl]-2-(methyloxy)-3-pyridinyl]methanesulfonamide;
4-(5-{[(2R,6S)-2,6-dimethyl-4-morpholinyl]methyl}-1,3,4-oxadiazol-2-yl)-6-(1H-indol-4-yl)-1-methyl-1H-indazole;
6-(1H-indol-4-yl)-1-methyl-4-(5-{[4-(1-methylethyl)-1-piperazinyl]methyl}-1,3,4-oxadiazol-2-yl)-1H-indazole;
N-[5-[1-methyl-4-(5-{[4-(1-methylethyl)-1-piperazinyl]methyl}-1,3,4-oxadiazol-2-yl)-1H-indazol-6-yl]-2-(methyloxy)-3-pyridinyl]methanesulfonamide;
N-[5-[4-(5-{[(2R,6S)-2,6-dimethyl-4-morpholinyl]methyl}-1,3,4-oxadiazol-2-yl)-1-methyl-1H-indazol-6-yl]-2-(methyloxy)-3-pyridinyl]methanesulfonamide;
N-[5-[4-(5-{[(2R,6S)-2,6-dimethyl-4-morpholinyl]methyl}-1,3,4-oxadiazol-2-yl)-1H-indazol-6-yl]-2-(methyloxy)-3-pyridinyl]-2,4-difluorobenzenesulfonamide;
N-[5-(4-{5-[(2,2-dimethyl-4-morpholinyl)methyl]-1,3,4-oxadiazol-2-yl}-1H-indazol-6-yl)-2-(methyloxy)-3-pyridinyl]methanesulfonamide;
6-(1H-indol-4-yl)-4-[5-(1-methylethyl)-1,3,4-oxadiazol-2-yl]-1H-indazole;
4-(5-cyclohexyl-1,3,4-oxadiazol-2-yl)-6-(1H-indol-4-yl)-1H-indazole;

4-[5-(cyclohexylmethyl)-1,3,4-oxadiazol-2-yl]-6-(1H-indol-4-yl)-1H-indazole;
6-(1H-indol-4-yl)-4-[5-(phenylmethyl)-1,3,4-oxadiazol-2-yl]-1H-indazole;
6-(1H-indol-4-yl)-4-{5-[2-(methyloxy)ethyl]-1,3,4-oxadiazol-2-yl}-1H-indazole;
6-(1H-indol-4-yl)-4-(5-{[(phenylmethyl)oxy]methyl}-1,3,4-oxadiazol-2-yl)-1H-indazole;
6-(1H-indol-4-yl)-4-[5-({[(1R,2S,5R)-5-methyl-2-(1-methylethyl)cyclohexyl]oxy}methyl)-1,3,4-oxadiazol-2-yl]-1H-indazole;
{5-[6-(1H-indol-4-yl)-1H-indazol-4-yl]-1,3,4-oxadiazol-2-yl}methanol;
6-(1H-Indol-4-yl)-4-{5-[(methyloxy)methyl]-1,3,4-oxadiazol-2-yl}-1H-indazole;
6-(1H-indol-4-yl)-4-(5-methyl-1,3,4-oxadiazol-2-yl)-1H-indazole;
N-{2-chloro-5-[4-(5-methyl-1,3,4-oxadiazol-2-yl)-1H-indazol-6-yl]-3-pyridinyl}methanesulfonamide;
6-(1H-indol-4-yl)-4-{5-[(methylsulfonyl)methyl]-1,3,4-oxadiazol-2-yl}-1H-indazole;
6-(1H-indol-4-yl)-4-{5-[(phenylsulfonyl)methyl]-1,3,4-oxadiazol-2-yl}-1H-indazole;
N-(2-(methyloxy)-5-{4-[5-(6-oxa-9-azaspiro[4.5]dec-9-ylmethyl)-1,3,4-oxadiazol-2-yl]-1H-indazol-6-yl}-3-pyridinyl)methanesulfonamide;
2-[({5-[6-(1H-indol-4-yl)-1H-indazol-4-yl]-1,3,4-oxadiazol-2-yl}methyl)amino]ethanol;
1-[({5-[6-(1H-indol-4-yl)-1H-indazol-4-yl]-1,3,4-oxadiazol-2-yl}methyl)amino]-3-(4-morpholinyl)-2-propanol;
N-[5-[4-(5-{[(3R,5S)-3,5-dimethyl-4-(1-methylethyl)-1-piperazinyl]methyl]-1,3,4-oxadiazol-2-yl)-1H-indazol-6-yl]-2-(methyloxy)-3-pyridinyl}methanesulfonamide;
N-[5-(4-{5-[(1,1-dioxido-4-thiomorpholinyl)methyl]-1,3,4-oxadiazol-2-yl}-1H-indazol-6-yl)-2-(methyloxy)-3-pyridinyl}methanesulfonamide;
N-[5-(4-{5-[(2-ethyl-4-morpholinyl)methyl]-1,3,4-oxadiazol-2-yl}-1H-indazol-6-yl)-2-(methyloxy)-3-pyridinyl}methanesulfonamide;
9-({5-[6-(1H-indol-4-yl)-1H-indazol-4-yl]-1,3,4-oxadiazol-2-yl}methyl)-6-oxa-9-azaspiro[4.5]decane;
4-{5-[(2,2-dimethyl-4-morpholinyl)methyl]-1,3,4-oxadiazol-2-yl}-6-(1H-indol-4-yl)-1H-indazole;
N-[5-[4-(5-{[(3R,5S)-3,5-dimethyl-4-(1-methylethyl)-1-piperazinyl]methyl]-1,3,4-oxadiazol-2-yl)-1H-indazol-6-yl]-2-(methyloxy)-3-pyridinyl}-2,4-difluorobenzenesulfonamide;
2,4-difluoro-N-[5-[4-(5-{[4-(1-methylethyl)-1-piperazinyl]methyl}-1,3,4-oxadiazol-2-yl)-1H-indazol-6-yl]-2-(methyloxy)-3-pyridinyl]benzenesulfonamide;
N-[5-(4-{5-[(2-methyl-4-morpholinyl)methyl]-1,3,4-oxadiazol-2-yl]-1H-indazol-6-yl)-2-(methyloxy)-3-pyridinyl}methanesulfonamide;
6-(1H-indol-4-yl)-4-{5-[(2-methyl-4-morpholinyl)methyl]-1,3,4-oxadiazol-2-yl}-1H-indazole;
N-({5-[6-(1H-indol-4-yl)-1H-indazol-4-yl]-1,3,4-oxadiazol-2-yl}methyl)-3-(4-morpholinyl)-1-propanamine;
N-(2-(methyloxy)-5-{4-[5-(tetrahydro-1,4-oxazepin-4(5H)-ylmethyl)-1,3,4-oxadiazol-2-yl]-1H-indazol-6-yl}-3-pyridinyl)methanesulfonamide;
6-(1H-indol-4-yl)-4-[5-(tetrahydro-1,4-oxazepin-4(5H)-ylmethyl)-1,3,4-oxadiazol-2-yl]-1H-indazole;
N-[5-{4-[5-({[2-hydroxy-3-(4-morpholinyl)propyl]amino}methyl)-1,3,4-oxadiazol-2-yl]-1H-indazol-6-yl]-2-(methyloxy)-3-pyridinyl}methanesulfonamide;
2,4-difluoro-N-[5-{4-[5-({[2-hydroxy-3-(4-morpholinyl)propyl]amino}methyl)-1,3,4-oxadiazol-2-yl]-1H-indazol-6-yl]-2-(methyloxy)-3-pyridinyl}benzenesulfonamide;
N-[5-(4-{5-[(8aS)-hexahydropyrrolo[1,2-a]pyrazin-2(1H)-ylmethyl]-1,3,4-oxadiazol-2-yl}-1H-indazol-6-yl)-2-(methyloxy)-3-pyridinyl}methanesulfonamide;
2,4-difluoro-N-[5-(4-{5-[(8aS)-hexahydropyrrolo[1,2-a]pyrazin-2(1H)-ylmethyl]-1,3,4-oxadiazol-2-yl}-1H-indazol-6-yl)-2-(methyloxy)-3-pyridinyl]benzenesulfonamide;
N-[5-[4-(5-{[(2R,6S)-2,6-dimethyl-4-morpholinyl]methyl}-1,3,4-oxadiazol-2-yl)-1-methyl-1H-indazol-6-yl]-2-(methyloxy)-3-pyridinyl]-2,4-difluorobenzenesulfonamide;
N-[5-[4-(5-{[(2R,6S)-2,6-dimethyl-4-morpholinyl]methyl}-1,3,4-oxadiazol-2-yl)-1H-indazol-6-yl]-2-(methyloxy)-3-pyridinyl]-2-(methyloxy)benzenesulfonamide;
and a pharmaceutically acceptable salt thereof.

\* \* \* \* \*